(12) United States Patent
Cha et al.

(10) Patent No.: US 11,718,606 B2
(45) Date of Patent: Aug. 8, 2023

(54) POLYCYCLIC COMPOUND AND ORGANIC LIGHT EMITTING ELEMENT COMPRISING SAME

(71) Applicant: LG CHEM, LTD., Seoul (KR)

(72) Inventors: Yongbum Cha, Daejeon (KR); Jin Joo Kim, Daejeon (KR); Sung Kil Hong, Daejeon (KR); Seong So Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 576 days.

(21) Appl. No.: 16/088,406

(22) PCT Filed: Oct. 20, 2017

(86) PCT No.: PCT/KR2017/011639
§ 371 (c)(1),
(2) Date: Sep. 25, 2018

(87) PCT Pub. No.: WO2018/074881
PCT Pub. Date: Apr. 26, 2018

(65) Prior Publication Data
US 2020/0048232 A1    Feb. 13, 2020

(30) Foreign Application Priority Data

Oct. 20, 2016  (KR) .................. 10-2016-0136746
Oct. 18, 2017  (KR) .................. 10-2017-0135383

(51) Int. Cl.
*C07D 407/10*   (2006.01)
*C07C 211/54*   (2006.01)
(Continued)

(52) U.S. Cl.
CPC .......... *C07D 407/10* (2013.01); *C07C 211/54* (2013.01); *C07C 211/57* (2013.01);
(Continued)

(58) Field of Classification Search
CPC ... C07C 211/54; C07C 211/57; C07D 209/82; C07D 209/88; C07D 213/16;
(Continued)

(56) References Cited

U.S. PATENT DOCUMENTS

2004/0124766 A1*  7/2004  Nakagawa .......... H01L 51/5234
                                                        313/504
2006/0273714 A1* 12/2006  Forrest ................ H01L 51/5044
                                                        313/504
(Continued)

FOREIGN PATENT DOCUMENTS

CN   106033801 A   10/2016
JP   11-204262 A   7/1999
(Continued)

OTHER PUBLICATIONS

Patentscope machine translation for WO 2015/162912A (publication date Oct. 2015). (Year: 2015).*
(Continued)

*Primary Examiner* — Dawn L Garrett
(74) *Attorney, Agent, or Firm* — Dentons US LLP

(57) ABSTRACT

The present application relates to a compound of Chemical Formula 1 and an organic light emitting device including the same.

11 Claims, 1 Drawing Sheet

| 4 |
|---|
| 7 |
| 3 |
| 6 |
| 5 |
| 2 |
| 1 |

(51) Int. Cl.
| | |
|---|---|
| *C07C 211/57* | (2006.01) |
| *C07D 209/82* | (2006.01) |
| *C07D 239/26* | (2006.01) |
| *C07D 251/24* | (2006.01) |
| *C07D 307/91* | (2006.01) |
| *C07D 333/76* | (2006.01) |
| *C07D 401/10* | (2006.01) |
| *C07D 403/04* | (2006.01) |
| *C07D 407/04* | (2006.01) |
| *C07D 409/04* | (2006.01) |
| *C07D 409/10* | (2006.01) |
| *C07D 491/048* | (2006.01) |
| *C07D 495/04* | (2006.01) |
| *C07F 9/53* | (2006.01) |
| *H10K 85/60* | (2023.01) |
| *H10K 50/15* | (2023.01) |
| *H10K 50/16* | (2023.01) |
| *H10K 50/17* | (2023.01) |

(52) U.S. Cl.
CPC ......... *C07D 209/82* (2013.01); *C07D 239/26* (2013.01); *C07D 251/24* (2013.01); *C07D 307/91* (2013.01); *C07D 333/76* (2013.01); *C07D 401/10* (2013.01); *C07D 403/04* (2013.01); *C07D 407/04* (2013.01); *C07D 409/04* (2013.01); *C07D 409/10* (2013.01); *C07D 491/048* (2013.01); *C07D 495/04* (2013.01); *C07F 9/5325* (2013.01); *H10K 85/615* (2023.02); *H10K 85/622* (2023.02); *H10K 85/631* (2023.02); *H10K 85/633* (2023.02); *H10K 85/636* (2023.02); *H10K 85/649* (2023.02); *H10K 85/653* (2023.02); *H10K 85/654* (2023.02); *H10K 85/655* (2023.02); *H10K 85/657* (2023.02); *H10K 85/6572* (2023.02); *H10K 85/6574* (2023.02); *H10K 85/6576* (2023.02); *H10K 50/15* (2023.02); *H10K 50/16* (2023.02); *H10K 50/171* (2023.02)

(58) Field of Classification Search
CPC .. C07D 239/26; C07D 251/24; C07D 307/91; C07D 333/46; C07D 333/76; C07D 401/10; C07D 403/04; C07D 403/10; C07D 405/10; C07D 407/04; C07D 407/10; C07D 409/04; C07D 409/10; C07D 491/048; C07D 495/04; C07F 9/5325; C09K 11/06; C09K 2211/1088; C09K 2211/1092; H01L 51/0018; H01L 51/0052; H01L 51/0054; H01L 51/0059; H01L 51/006; H01L 51/0061; H01L 51/0062; H01L 51/0065; H01L 51/0067; H01L 51/0068; H01L 51/0071; H01L 51/0072; H01L 51/0073; H01L 51/0074; H01L 51/5016; H01L 51/5056; H01L 51/5072; H01L 51/5092; H01L 51/5096; H10K 85/615; H10K 85/622; H10K 85/631; H10K 85/633; H10K 85/636; H10K 85/649; H10K 85/653; H10K 85/654; H10K 85/655; H10K 85/657; H10K 85/6572; H10K 85/6574; H10K 85/6576; H10K 50/15; H10K 50/16; H10K 50/171; H10K 50/11; H10K 50/18; H10K 2101/10; H10K 71/233; H10K 50/12

See application file for complete search history.

(56) References Cited

U.S. PATENT DOCUMENTS

| | | |
|---|---|---|
| 2010/0072885 A1 | 3/2010 | Watanabe et al. |
| 2011/0121274 A1* | 5/2011 | Parham .............. H01L 51/0067 257/40 |
| 2012/0181922 A1 | 7/2012 | Kawamura et al. |
| 2013/0221338 A1* | 8/2013 | Kawamura ............ H05B 33/14 257/40 |
| 2016/0064669 A1 | 3/2016 | Kato |
| 2017/0018718 A1 | 1/2017 | Jang et al. |
| 2017/0033294 A1 | 2/2017 | Jang et al. |
| 2017/0084845 A1 | 3/2017 | Kim et al. |
| 2017/0222157 A1 | 8/2017 | Jatsch et al. |
| 2017/0317285 A1 | 11/2017 | Mujica-Fernaud et al. |
| 2018/0047910 A1 | 2/2018 | Low et al. |

FOREIGN PATENT DOCUMENTS

| | | | |
|---|---|---|---|
| JP | 2008290991 A | | 12/2008 |
| JP | 2009203176 A | | 9/2009 |
| JP | 2011222831 A | | 11/2011 |
| KR | 1020120084238 A | | 7/2012 |
| KR | 1020150006722 A | | 1/2015 |
| KR | 20150061174 A | * | 6/2015 |
| KR | 1020150065944 A | | 6/2015 |
| KR | 1020150115622 A | | 10/2015 |
| KR | 10-2016-0149527 A | * | 12/2016 |
| KR | 1020170034586 A | | 3/2017 |
| KR | 1020170040735 A | | 4/2017 |
| KR | 1020170077283 A | | 7/2017 |
| KR | 1020170088313 A | | 8/2017 |
| KR | 1020170092097 A | | 8/2017 |
| WO | 2015162912 A1 | | 10/2015 |
| WO | 2016/012075 A1 | | 1/2016 |

OTHER PUBLICATIONS

Machine translation for KR 20160149527A (publication date Dec. 2016). (Year: 2016).*

Machine translation of KR 20150061174 A (publication date Jun. 2015). (Year: 2015).*

Hsu, F.M., Chien, C.H., Shih, P.I. and Shu, C.F., 2009. Phosphine-oxide-containing bipolar host material for blue electrophosphorescent devices. Chemistry of Materials, 21(6), pp. 1017-1022. (Year: 2009).*

Chemical Abstract Compounds, STN express, RN 22815-16-3, date: 1984.

"Reactions with cyclopentadienones XVI. Reaction products of 1,1-diaryl-2-propyn-1-ols and 1-methoxy-1,1-diaryl-2-propynes with cyclopentadienones", Chemische Berichte (1969), 102(6), pp. 1904-1916.

Reid, et al.: "Ringschlubreaktionen von Acetylenketonen mit zweifach CH-aciden Verbindungen zu Phenolen", XP55251253, Liebigs Annalen der Chemie, vol. 757, 1972, pp. 153-169.

* cited by examiner

[Figure 1]
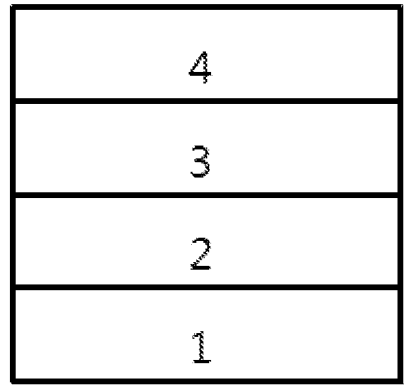
[Figure 2]
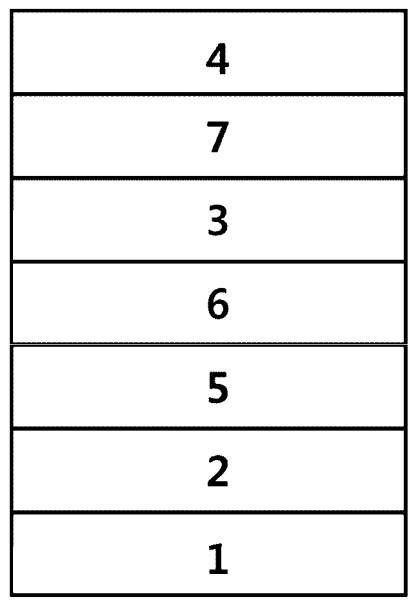

POLYCYCLIC COMPOUND AND ORGANIC LIGHT EMITTING ELEMENT COMPRISING SAME

This application is a National Stage Application of International Application No. PCT/KR2017/011639, filed Oct. 20, 2017, and claims the benefit of Korean Patent Application No. 10-2016-0136746 filed on Oct. 20, 2016, and Korean Patent Application No. 10-2017-0135383 filed on Oct. 18, 2017, the entire contents of which are incorporated herein by reference.

TECHNICAL FIELD

This application claims priority to and the benefit of Korean Patent Application No. 10-2016-0136746 filed in the Korean Intellectual Property Office on Oct. 20, 2016, the entire contents of which are incorporated herein by reference.

This application claims priority to and the benefit of Korean Patent Application No. 10-2017-0135383 filed in the Korean Intellectual Property Office on Oct. 18, 2017, the entire contents of which are incorporated herein by reference.

The present specification relates to a polycyclic compound and an organic light emitting device including the same.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have in many cases a multi-layered structure composed of different materials in order to improve the efficiency and stability of an organic light emitting device, and for example, may be composed of a hole injection layer, a hole transporting layer, a light emitting layer, an electron transporting layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

REFERENCES OF THE RELATED ART

[Patent Document] WO2003012890 A2

DISCLOSURE

Technical Problem

The present specification provides a polycyclic compound and an organic light emitting device including the same.

Technical Solution

An exemplary embodiment of the present specification provides a compound represented by the following Chemical Formula 1.

[Chemical Formula 1]

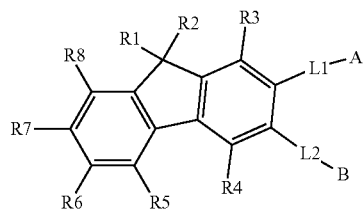

In Chemical Formula 1,

R1 and R2 are the same as or different from each other, and are each independently an aryl group, R3 to R8 are the same as or different from each other, and are each independently hydrogen; deuterium; a nitrile group; a substituted or unsubstituted alkyl group; a substituted or unsubstituted cycloalkyl group; a substituted or unsubstituted alkoxy group; a substituted or unsubstituted aryloxy group; a substituted or unsubstituted alkenyl group; a substituted or unsubstituted silyl group; a substituted or unsubstituted amine group; a substituted or unsubstituted aryl group; or a substituted or unsubstituted heteroaryl group, L1 and L2 are the same as or different from each other, and are each independently a single bond; a substituted or unsubstituted arylene group; or a substituted or unsubstituted heteroarylene group, and A and B are the same as or different from each other, and are each independently a substituted or unsubstituted aryl group; a substituted or unsubstituted heteroaryl group; a substituted or unsubstituted phosphine oxide group; or a substituted or unsubstituted amine group.

Further, an exemplary embodiment of the present specification provides an organic light emitting device including: a first electrode; a second electrode disposed to face the first electrode; and an organic material layer having one or more layers disposed between the first electrode and the second electrode, in which one or more layers of the organic material layer include the compound represented by Chemical Formula 1.

Advantageous Effects

A compound according to an exemplary embodiment of the present specification may be used as a material for an organic material layer of an organic light emitting device, and it is possible to improve efficiency, achieve low driving voltage, and/or improve service life characteristics in the organic light emitting device by using the same.

DESCRIPTION OF DRAWINGS

FIG. 1 illustrates an organic light emitting device according to an exemplary embodiment of the present specification.

FIG. 2 illustrates an organic light emitting device according to another exemplary embodiment of the present specification.

MODE FOR INVENTION

Hereinafter, the present specification will be described in more detail.

An exemplary embodiment of the present specification provides the compound represented by Chemical Formula 1. Specifically, an exemplary embodiment of the present specification provides a polycyclic compound having a specific substituent at Nos. 2 and 3 positions of fluorene.

When one part "includes" one constituent element in the present specification, unless otherwise specifically described, this does not mean that another constituent element is excluded, but means that another constituent element may be further included.

When one member is disposed "on" another member in the present specification, this includes not only a case where the one member is brought into contact with another member, but also a case where still another member is present between the two members.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or more substituents selected from the group consisting of deuterium; a nitrile group; a substituted or unsubstituted alkyl group; a substituted or unsubstituted cycloalkyl group; a substituted or unsubstituted alkoxy group; a substituted or unsubstituted aryloxy group; a substituted or unsubstituted alkenyl group; a substituted or unsubstituted silyl group; a substituted or unsubstituted boron group; a substituted or unsubstituted amine group; a substituted or unsubstituted aryl group; and a substituted or unsubstituted heterocyclic group or being substituted with a substituent to which two or more substituents are linked among the substituents exemplified above, or having no substituent. For example, "the substituent to which two or more substituents are linked" may be an aryl group substituted with an aryl group, an aryl group substituted with a heteroaryl group, a heterocyclic group substituted with an aryl group, an aryl group substituted with an alkyl group, and the like.

In the present specification, the alkyl group may be straight or branched, and the number of carbon atoms thereof is not particularly limited, but is preferably 1 to 30. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, a cycloalkyl group is not particularly limited, but has preferably 3 to 30 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, a heteroaryl group includes one or more atoms other than carbon, that is, one or more heteroatoms, and specifically, the heteroatom may include one or more atoms selected from the group consisting of O, N, Se, and S, and the like. The number of carbon atoms thereof is not particularly limited, but is preferably 2 to 30, and the heteroaryl group may be monocyclic or polycyclic. Examples of a heterocyclic group include a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a qinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzoimidazolyl group, a benzothiazolyl group, a benzocarbazolyl group, a dibenzopyrrole group, an indole group, a benzothiophene group, a dibenzothiophene group, a benzofuranyl group, a phenanthrolinyl group (phenanthroline), a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the alkoxy group may be straight, branched, or cyclic. The number of carbon atoms of the alkoxy group is not particularly limited, but is preferably 1 to 30. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, an amine group may be selected from the group consisting of —NH$_2$; an alkylamine group; an N-alkylarylamine group; an arylamine group; an N-arylheteroarylamine group; an N-alkylheteroarylamine group; and a heteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, an N-phenylnaphthylamine group, a ditolylamine group, an N-phenyltolylamine group, a triphenylamine group, an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenyl terphenylamine group; an N-phenanthrenylfluorenylamine group; an N-biphenylfluorenylamine group, and the like, but are not limited thereto.

In the present specification, an N-alkylarylamine group means an amine group in which an alkyl group and an aryl group are substituted with N of the amine group.

In the present specification, an N-arylheteroarylamine group means an amine group in which an aryl group and a heteroaryl group are substituted with N of the amine group.

In the present specification, an N-alkylheteroarylamine group means an amine group in which an alkyl group and a heteroaryl group are substituted with N of the amine group.

In the present specification, the alkyl group in the alkylamine group, the N-arylalkylamine group, the alkylthioxy group, the alkylsulfoxy group, and the N-alkylheteroarylamine group is the same as the above-described examples of the alkyl group.

In the present specification, the alkenyl group may be straight or branched, and the number of carbon atoms thereof is not particularly limited, but is preferably 2 to 30. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, specific examples of a silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, an aryl group is not particularly limited, but has preferably 6 to 30 carbon atoms, and the aryl group may be monocyclic or polycyclic.

When the aryl group is a monocyclic aryl group, the number of carbon atoms thereof is not particularly limited, but is preferably 6 to 30. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 30. Specific examples of the polycyclic aryl group include a naphthyl group, an anthracenyl group, a phenanthryl group, a triphenyl group, a pyrenyl group, a phenalenyl group, a perylenyl group, a chrysenyl group, a fluorenyl group, and the like, but are not limited thereto.

In the present specification, the fluorenyl group may be substituted, and adjacent substituents may be bonded to each other to form a ring.

When the fluorenyl group is substituted, the fluorenyl group may be

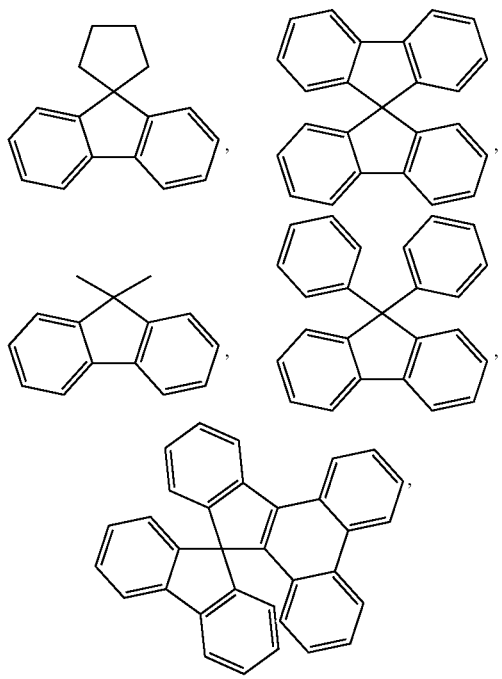

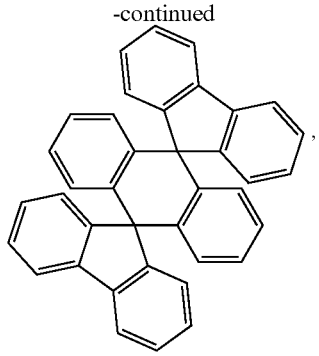

and the like. However, the fluorenyl group is not limited thereto.

In the present specification, the aryl group in the aryloxy group, the N-arylalkylamine group, and the N-arylheteroarylamine group is the same as the above-described examples of the aryl group. Specifically, examples of the aryloxy group include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group, and the like.

In the present specification, a heteroaryl group includes one or more atoms other than carbon, that is, one or more heteroatoms, and specifically, the heteroatom may include one or more atoms selected from the group consisting of O, N, Se, and S, and the like. The number of carbon atoms thereof is not particularly limited, but is preferably 2 to 30, and the heteroaryl group may be monocyclic or polycyclic. Examples of a heterocyclic group include a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a qinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzoimidazolyl group, a benzothiazolyl group, a benzocarbazolyl group, a dibenzopyrrole group, an indole group, a benzothiophene group, a dibenzothiophene group, a benzofuranyl group, a phenanthrolinyl group (phenanthroline), a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups may include a monocyclic heteroaryl group, a polycyclic heteroaryl group, or both a monocyclic heteroaryl group and a polycyclic heteroaryl group. For example, the heteroaryl group in the heteroarylamine group may be selected from the above-described examples of the heteroaryl group.

According to an exemplary embodiment of the present specification, A and B of Chemical Formula 1 are the same as or different from each other, and are each independently a substituted or unsubstituted aryl group; a substituted or unsubstituted alkyl group; a substituted or unsubstituted amine group; a substituted or unsubstituted heteroaryl group; a substituted or unsubstituted silyl group; or a substituted or unsubstituted phosphine oxide group.

According to an exemplary embodiment of the present specification, A and B of Chemical Formula 1 are the same as or different from each other, and are each independently a substituted or unsubstituted aryl group having 6 to 30 carbon atoms; a substituted or unsubstituted alkyl group having 1 to 10 carbon atoms; an amine group which is substituted with an aryl group unsubstituted or substituted with an alkyl group, or a heteroaryl group including one or more of N, O and S and substituted or unsubstituted with an aryl group; a substituted or unsubstituted monocyclic or polycyclic heteroaryl group including one or more of N, O and S; a silyl group which is unsubstituted or substituted with an aryl group; or a phosphine oxide group which is unsubstituted or substituted with an aryl group.

According to an exemplary embodiment of the present specification, A and B of Chemical Formula 1 are the same as or different from each other, and are each independently an alkyl group; a silyl group which is substituted with an alkyl group; a heteroaryl group which is unsubstituted or substituted with an aryl group; an aryl group which is unsubstituted or substituted with an alkyl group; an amine group which is substituted with an aryl group unsubstituted or substituted with an alkyl group; or an aryl group having 6 to 30 carbon atoms, which is unsubstituted or substituted with a phosphine oxide group substituted with an aryl group.

According to an exemplary embodiment of the present specification, A and B of Chemical Formula 1 are the same as or different from each other, and are each independently an alkyl group having 1 to 10 carbon atoms; a silyl group substituted with a methyl group; an amine group which is substituted with an aryl group unsubstituted or substituted with an alkyl group, or a heteroaryl group unsubstituted or substituted with an aryl group; a phosphine oxide group substituted with an aryl group; or an aryl group having 6 to 30 carbon atoms, which is unsubstituted or substituted with a nitrile group or an alkyl group, or an aryl group having 6 to 30 carbon atoms, which is unsubstituted or substituted with a heteroaryl group including one or more of N, O and S, which is unsubstituted or substituted with an aryl group.

According to an exemplary embodiment of the present specification, A and B of Chemical Formula 1 are the same as or different from each other, and are each independently a methyl group; a tert-butyl group; a silyl group which is substituted with a methyl group; an amine group which is substituted with an aryl group unsubstituted or substituted with a methyl group, or a heteroaryl group unsubstituted or substituted with an aryl group having 6 to 30 carbon atoms; a phosphine oxide group which is substituted with an aryl group having 6 to 30 carbon atoms; a phenyl group which is unsubstituted or substituted with a nitrile group or an alkyl group; a phenanthrene group; a triphenylene group; a fluorene group which is substituted with a methyl group; a naphthyl group; a dibenzofuran group; a dibenzothiophene group; a monocyclic or polycyclic N-containing heterocyclic group which is unsubstituted or substituted with a phenyl group or a biphenyl group;

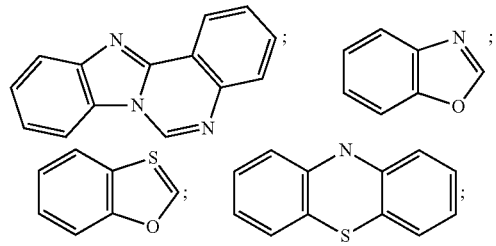

or an aryl group having 6 to 30 carbon atoms, which is unsubstituted or substituted with

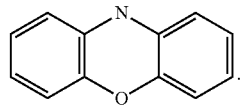 [SMILES: c1ccc2c(c1)Nc1ccccc1O2]

According to an exemplary embodiment of the present specification, A and B of Chemical Formula 1 are the same as or different from each other, and are each independently a methyl group; a tert-butyl group; a trimethylsilyl group (TMS); an amine group which is substituted with a phenyl group, a biphenyl group, a terphenyl group, a dimethylfluorene group, a dibenzothiophene group, a dibenzofuran group, or a carbazole group substituted with a phenyl group; a diphenylphosphine oxide group; a phenyl group which is unsubstituted or substituted with a nitrile group; a phenanthrene group; a triphenylene group; a dimethylfluorene group; a naphthyl group; a dibenzofuran group; a dibenzothiophene group; a benzocarbazole group; a carbazole group; a triazine group which is unsubstituted or substituted with a phenyl group or a biphenyl group; a pyrimidine group which is unsubstituted or substituted with a phenyl group; a pyridine group which is unsubstituted or substituted with a phenyl group; a quinoline group; which is unsubstituted or substituted with a phenyl group; a benzimidazole group which is unsubstituted or substituted with a phenyl group;

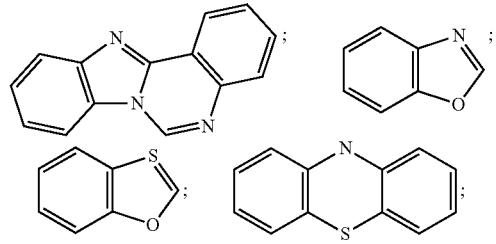

or an aryl group having 6 to 30 carbon atoms, which is substituted with

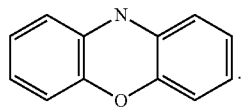

According to an exemplary embodiment of the present specification, the substituted or unsubstituted aryl group having 6 to 30 carbon atoms is a phenyl group; a biphenyl group; a terphenyl group; a tetraphenyl group; a naphthyl group; a phenanthrene group; a triphenylene group; or a fluorene group.

According to an exemplary embodiment of the present specification, A and B of Chemical Formula 1 are the same as or different from each other, and are each independently a substituted or unsubstituted alkyl group having 1 to 10 carbon atoms; an amine group which is substituted with an aryl group unsubstituted or substituted with an alkyl group, or a heteroaryl group including one or more of N, O and S and substituted or unsubstituted with an aryl group; a substituted or unsubstituted monocyclic or polycyclic heteroaryl group including one or more of N, O and S; a silyl group which is unsubstituted or substituted with an aryl group; or a phosphine oxide group which is unsubstituted or substituted with an aryl group.

According to an exemplary embodiment of the present specification, A and B of Chemical Formula 1 are the same as or different from each other, and are each independently an alkyl group having 1 to 10 carbon atoms, which is unsubstituted or substituted with an aryl group having 6 to 30 carbon atoms; an amine group which is substituted with an aryl group having 6 to 30 carbon atoms, which is unsubstituted or substituted with a methyl group, or a heteroaryl group having 6 to 30 carbon atoms and including one or more of N, O and S, which is unsubstituted or substituted with an aryl group; a heteroaryl group including O or S, which is substituted with an aryl group having 6 to 30 carbon atoms; or a heteroaryl group having 6 to 30 carbon atoms and including one or more of N, O and S, which is unsubstituted or substituted with an aryl group having 6 to 30 carbon atoms or a heteroaryl group including any one of N, O and S; a silyl group which is unsubstituted or substituted with an aryl group having 6 to 30 carbon atoms; or a phosphine oxide group which is unsubstituted or substituted with an aryl group having 6 to 30 carbon atoms.

According to an exemplary embodiment of the present specification, A and B of Chemical Formula 1 are the same as or different from each other, and are each independently a methyl group substituted with a phenyl group; an amine group which is substituted with a phenyl group, a biphenyl group, a terphenyl group, a phenanthrene group, a naphthyl group, a dimethylfluorene group, a dibenzofuran group, a dibenzothiophene group, or a carbazole group substituted with a phenyl group; a dibenzofuran group which is unsubstituted or substituted with a phenyl group; a dibenzothiophene group which is unsubstituted or substituted with a phenyl group; a benzonaphthofuran group; a benzonaphthothiophene group; a thiophene group which is substituted with a phenyl group; a carbazole group which is unsubstituted or substituted with a phenyl group; a benzocarbazole group which is unsubstituted or substituted with a phenyl group; a pyridine group which is unsubstituted or substituted with a phenyl group; a pyrimidine group which is unsubstituted or substituted with a phenyl group; a triazine group which is unsubstituted or substituted with a phenyl group, a biphenyl group, a naphthyl group, a dimethylfluorene group, a pyridine group, a dibenzofuran group, or a dibenzothiophene group; a benzimidazole group which is unsubstituted or substituted with a phenyl group or a biphenyl group; a quinoline group which is unsubstituted or substituted with a phenyl group or a biphenyl group; a quinazoline group which is unsubstituted or substituted with a phenyl group, a biphenyl group, a dibenzofuran group, or a dibenzothiophene group;

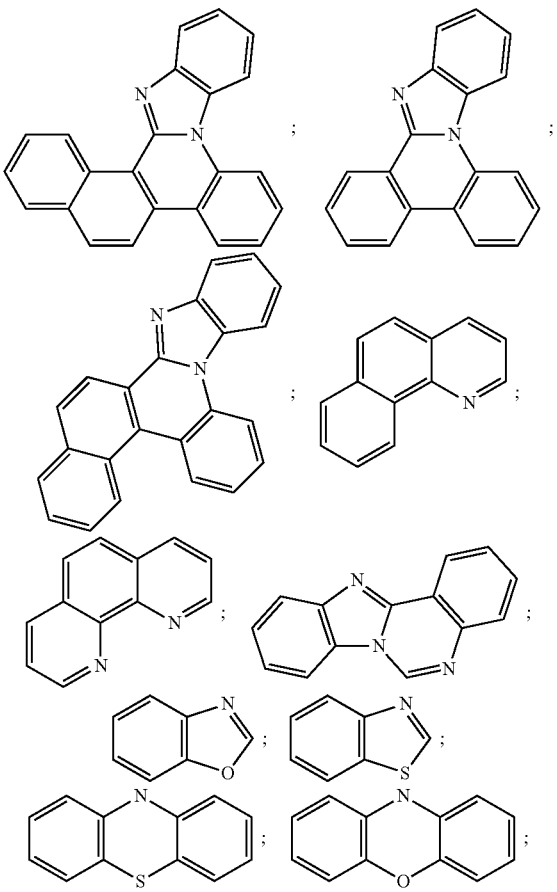

a silyl group which is substituted with a phenyl group; or a phosphine oxide group which is substituted with a phenyl group or a naphthyl group.

According to an exemplary embodiment of the present specification, A and B of Chemical Formula 1 are the same as or different from each other, and are each independently a phenyl group which is unsubstituted or substituted with a nitrile group; a dimethylfluorene group; a dibenzofuran group; a dibenzothiophene group; a carbazole group which is unsubstituted or substituted with a phenyl group; a triazine group which is unsubstituted or substituted with a phenyl group or a biphenyl group; a pyrimidine group which is unsubstituted or substituted with a phenyl group; a pyridine group which is unsubstituted or substituted with a phenyl group; or an amine group which is substituted with a phenyl group, a biphenyl group, a terphenyl group, a dimethylfluorene group, a dibenzothiophene group, a dibenzofuran group, or a carbazole group substituted with a phenyl group.

According to an exemplary embodiment of the present specification, A and B of Chemical Formula 1 may be any one of the following compounds.

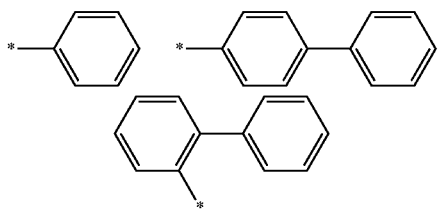

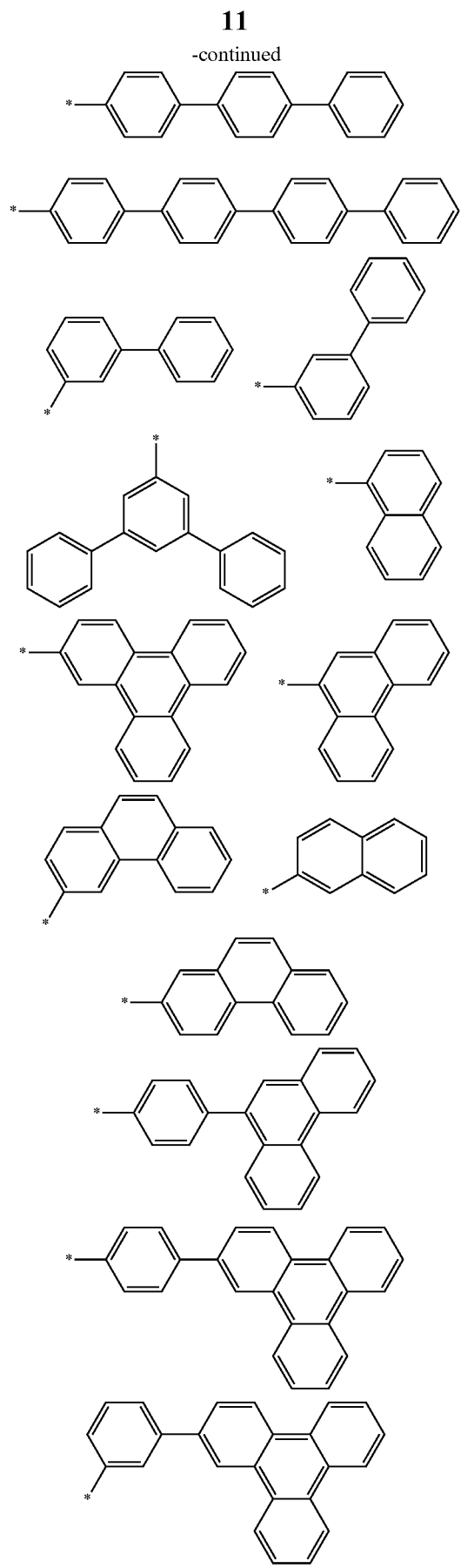
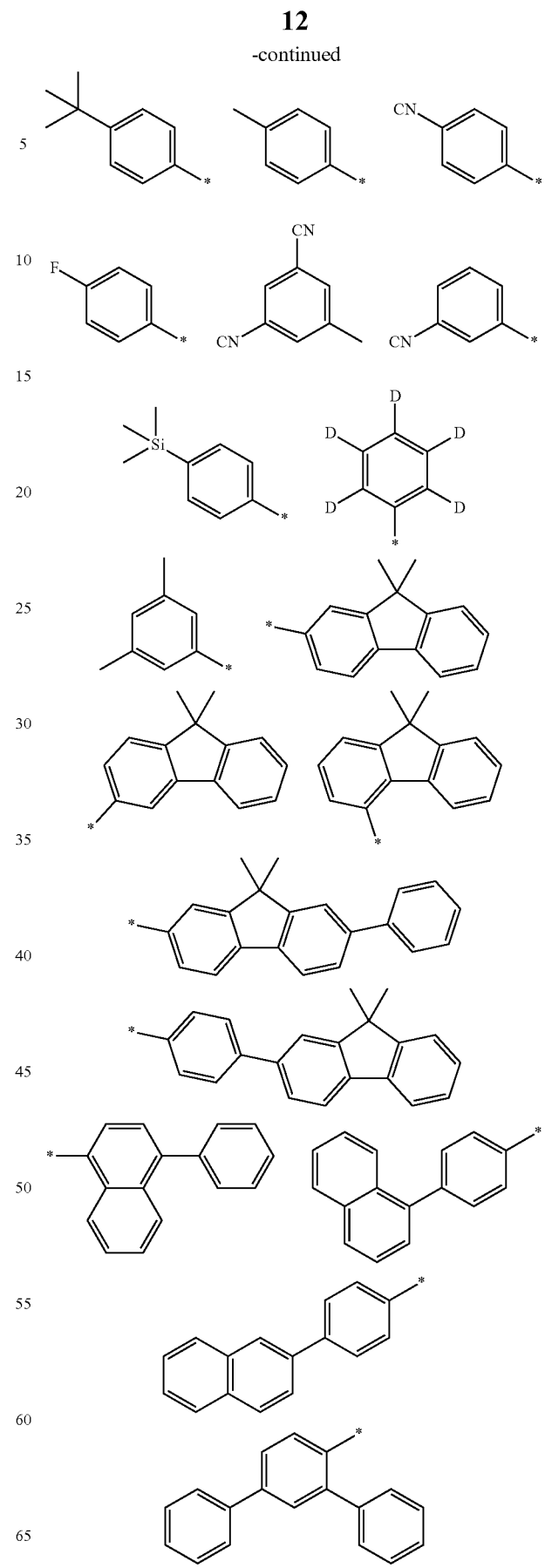

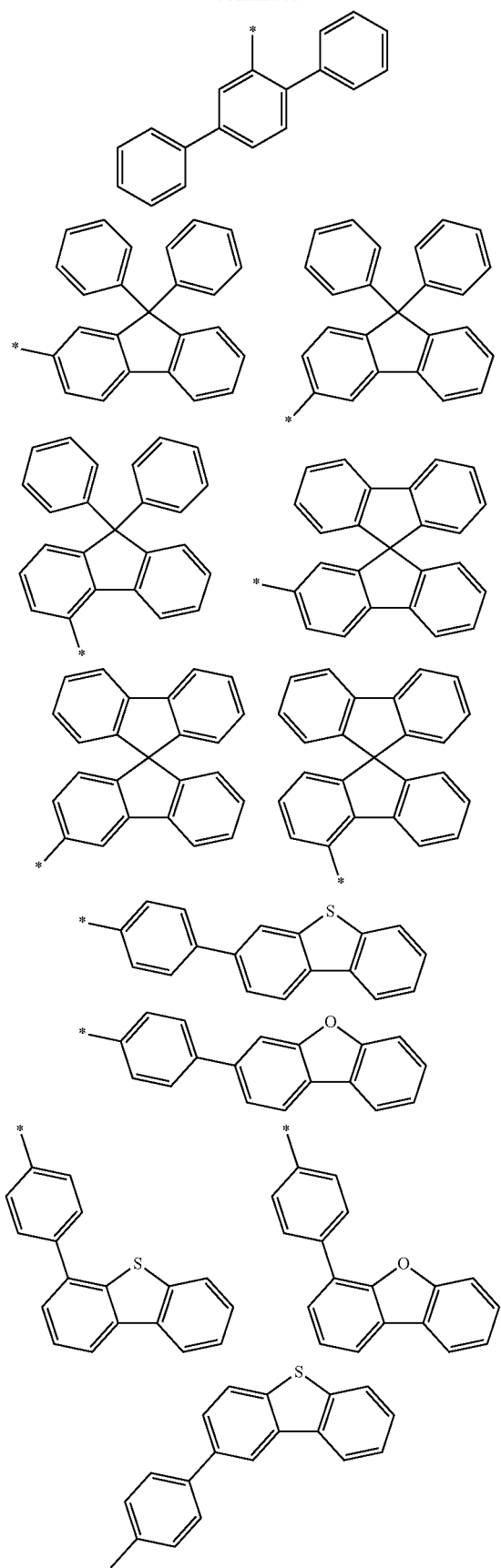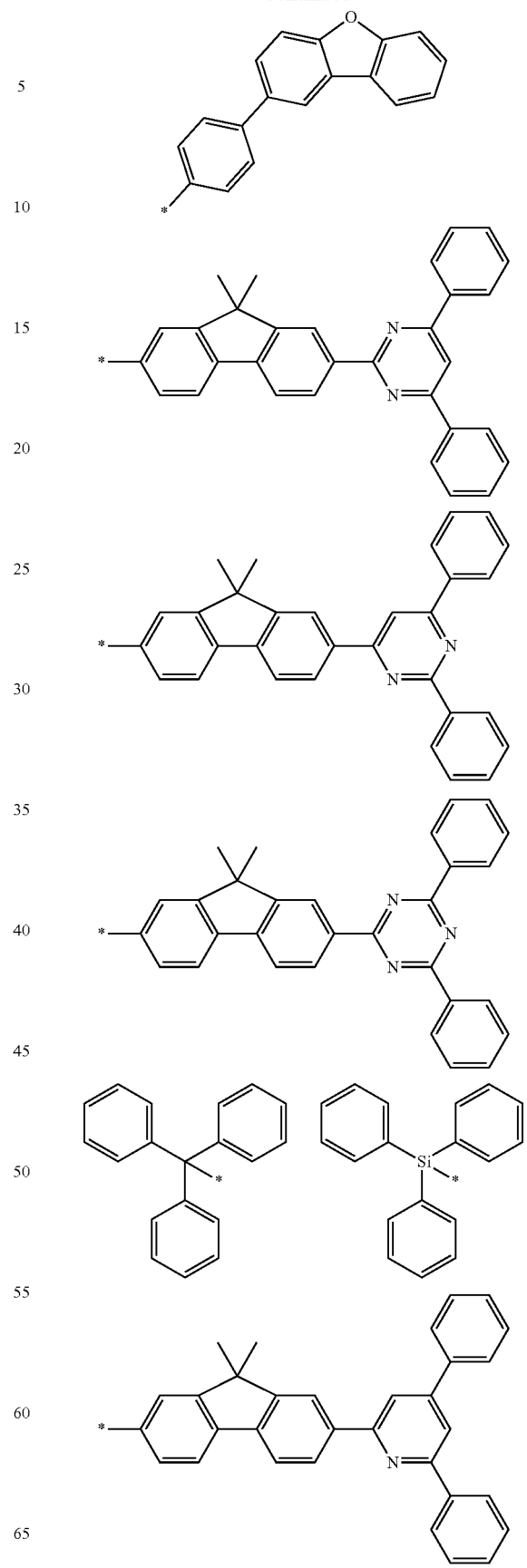

-continued
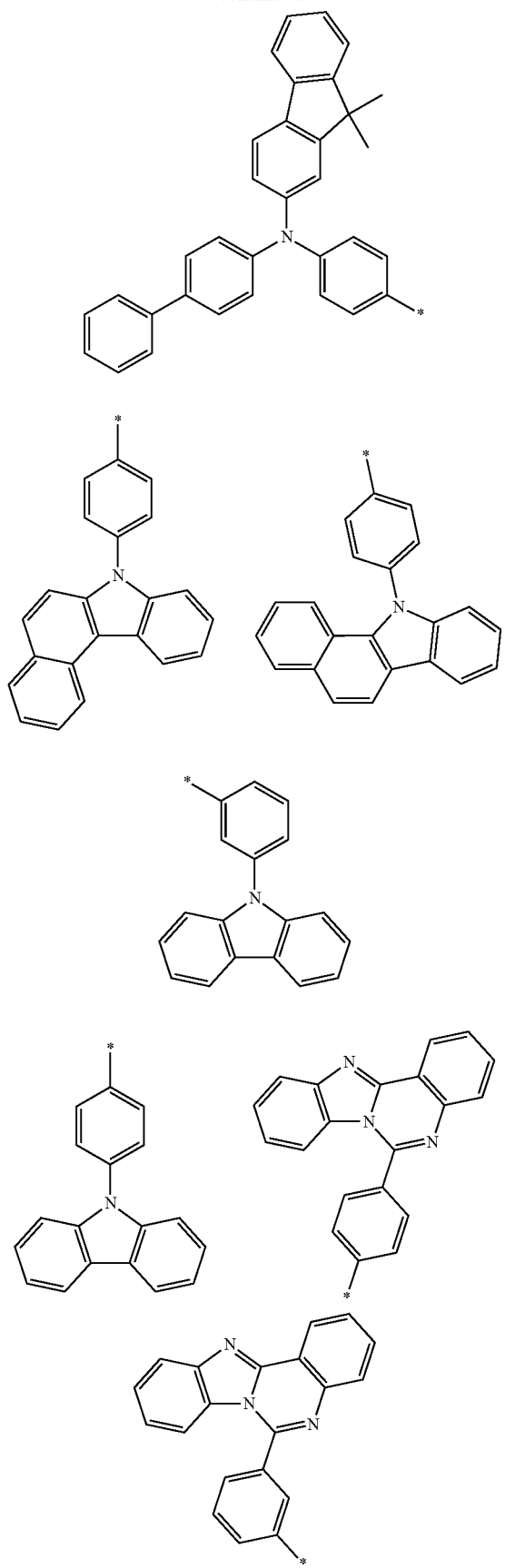
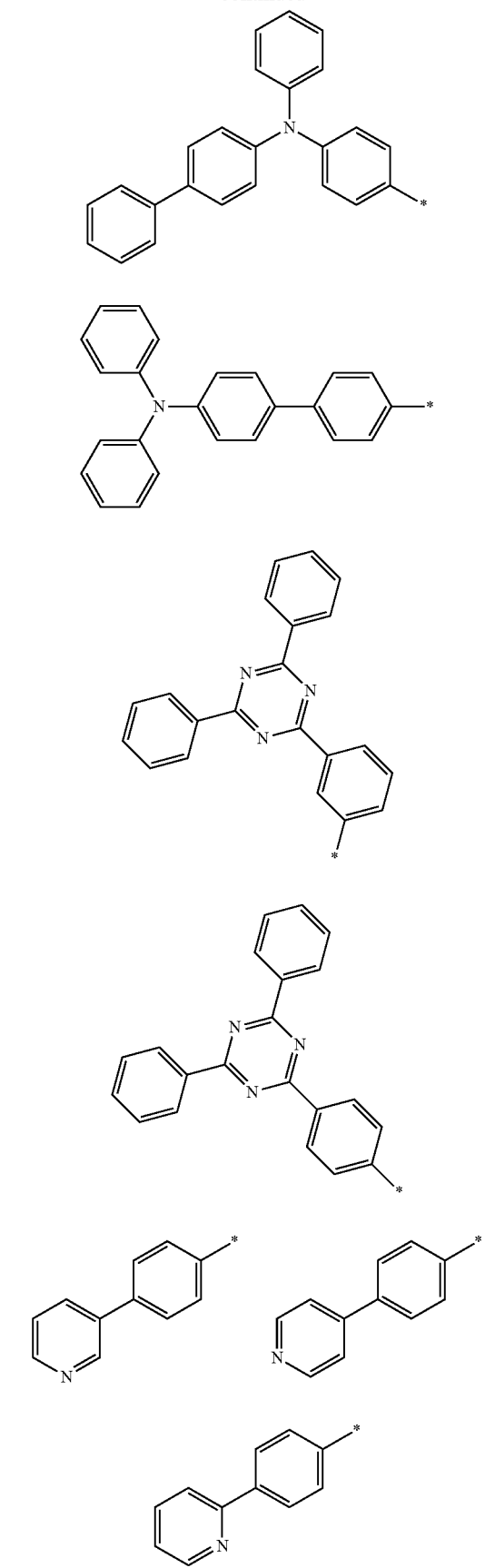

-continued
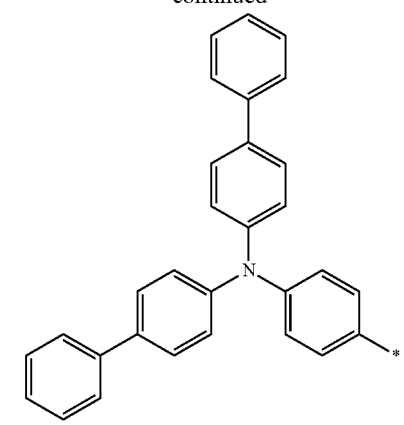
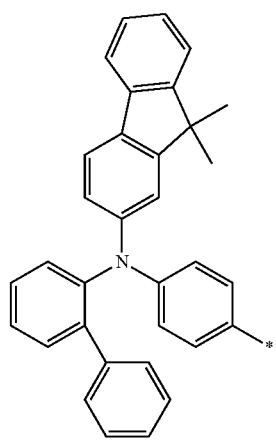
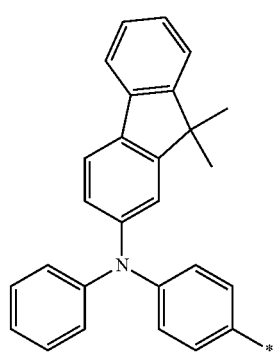
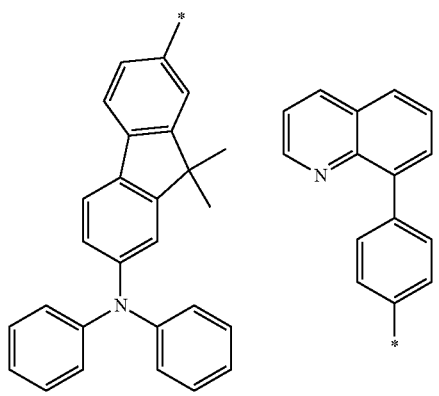
-continued
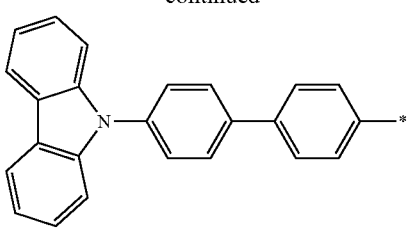
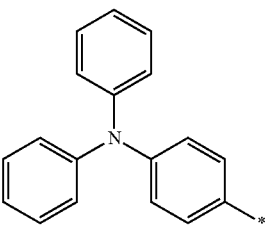
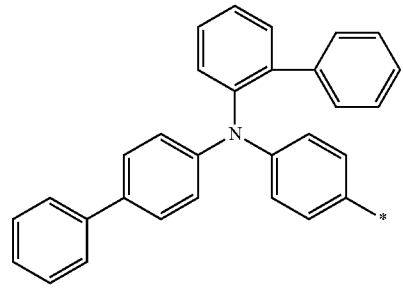
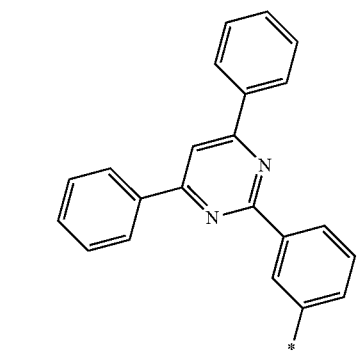
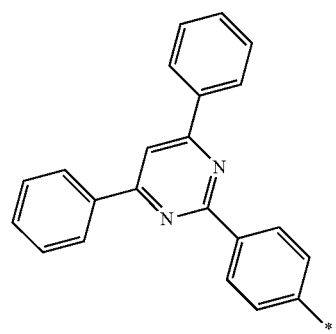

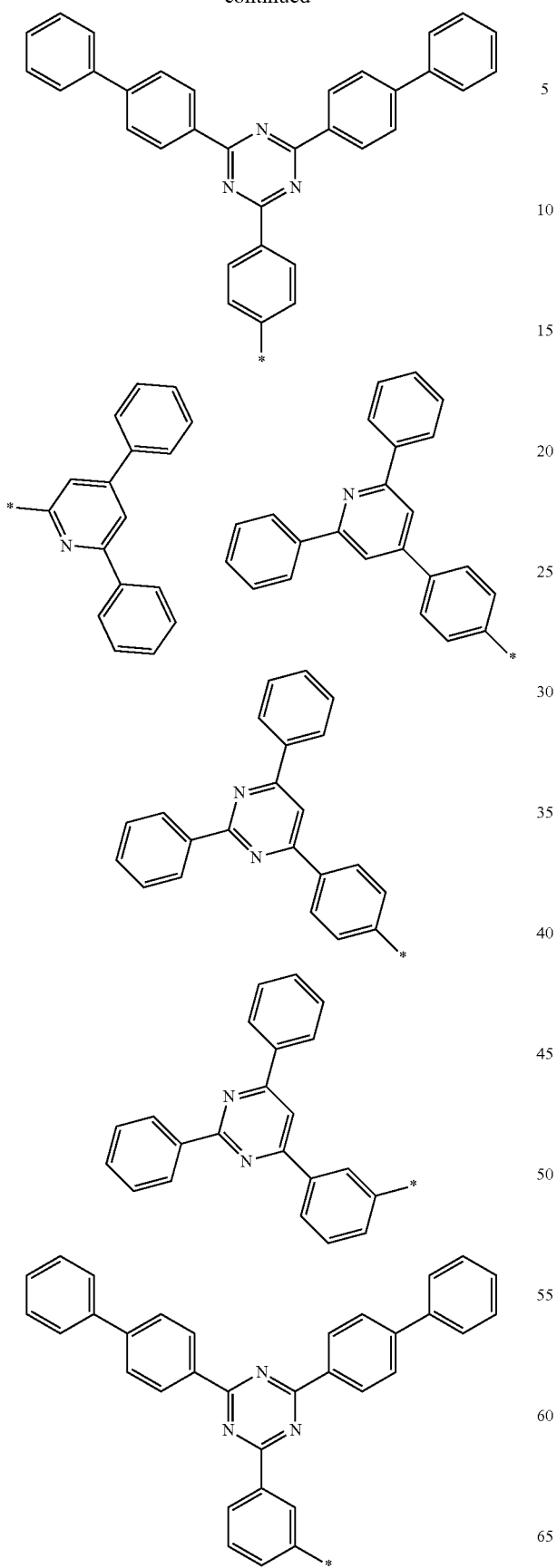
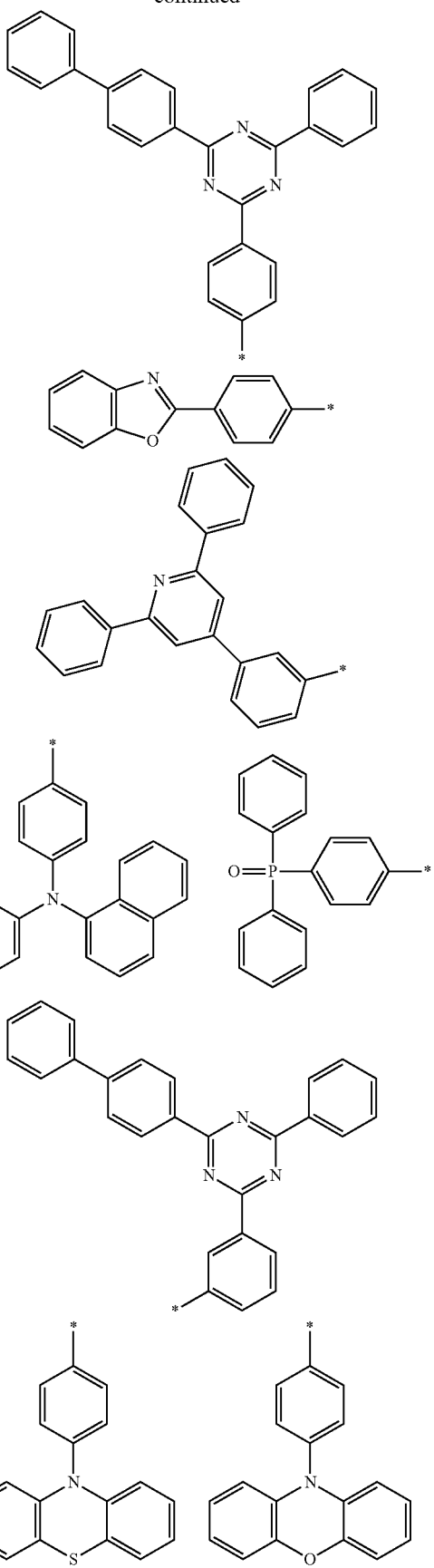

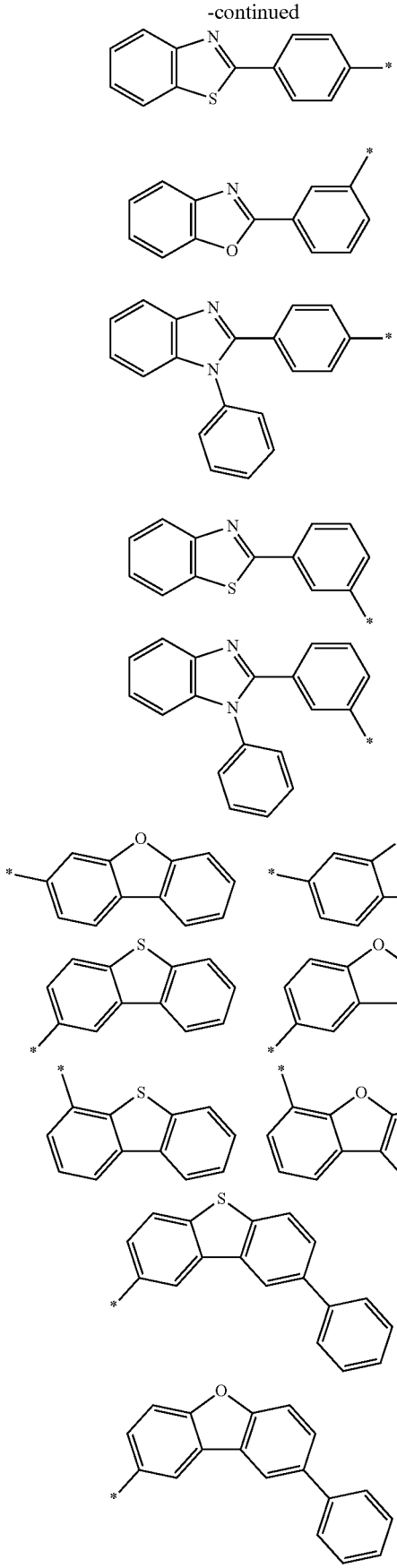
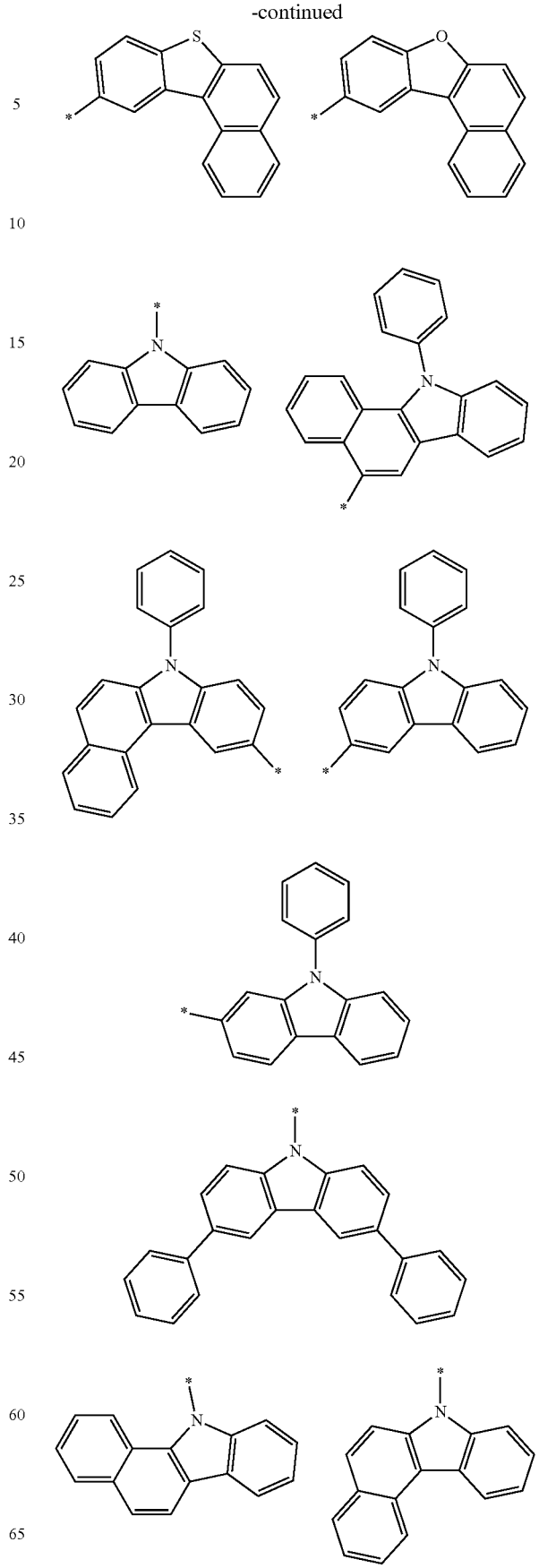

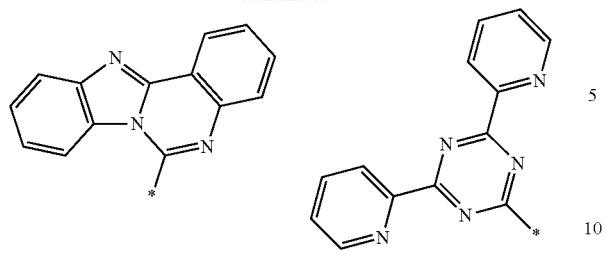
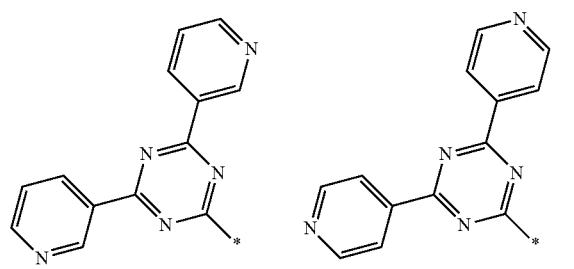
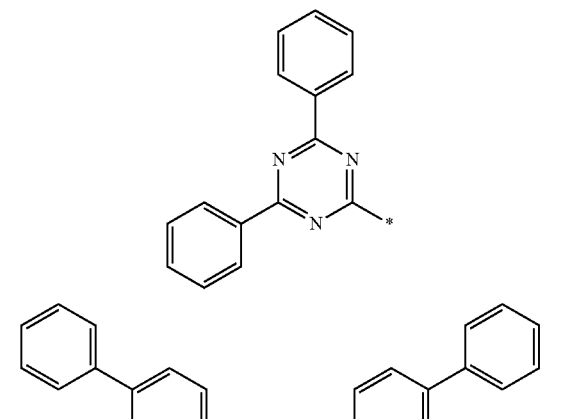
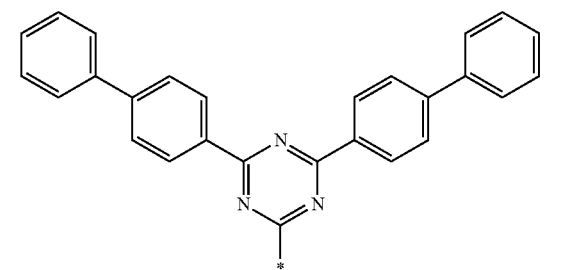
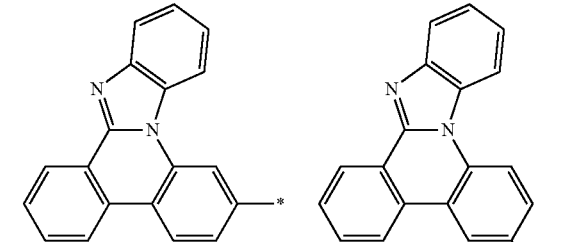
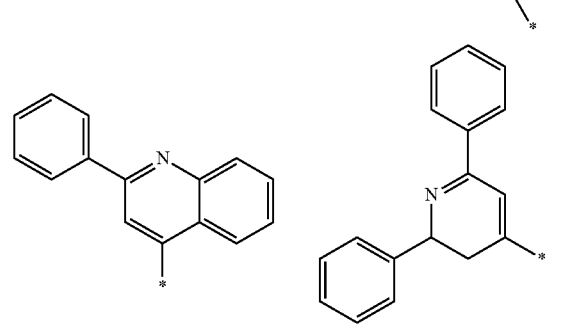
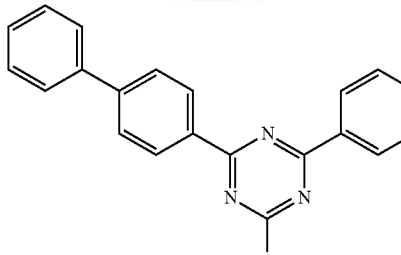
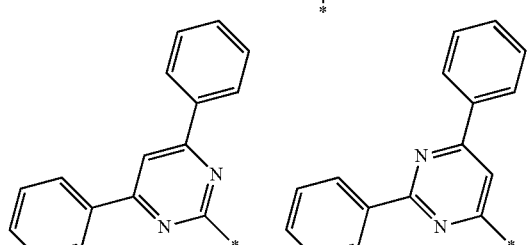
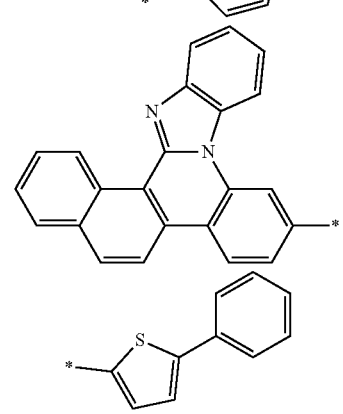
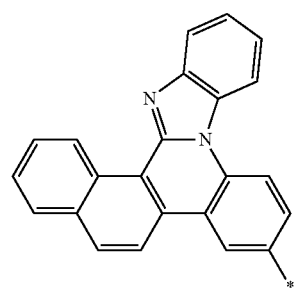
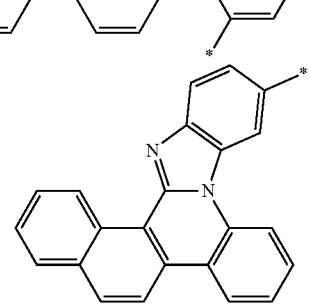

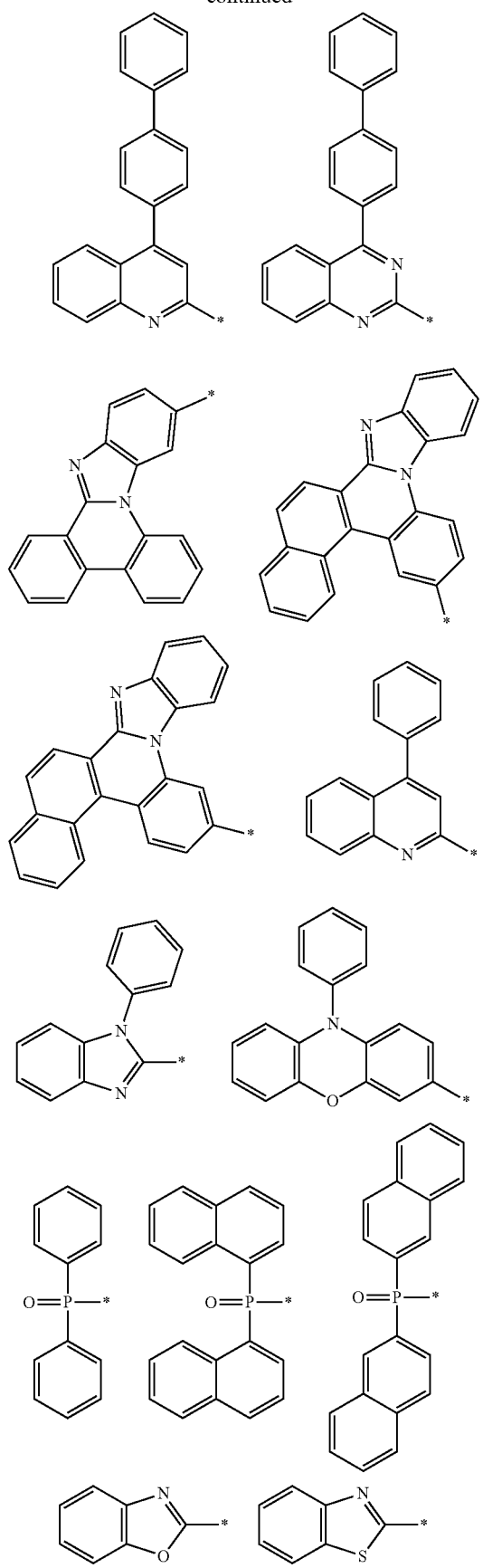
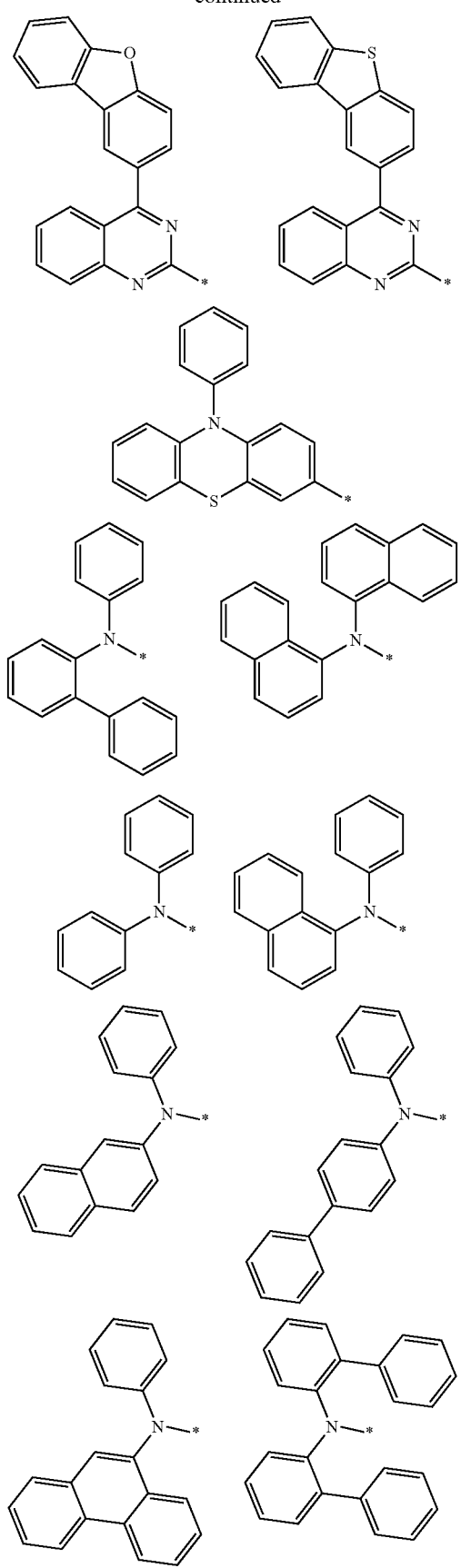

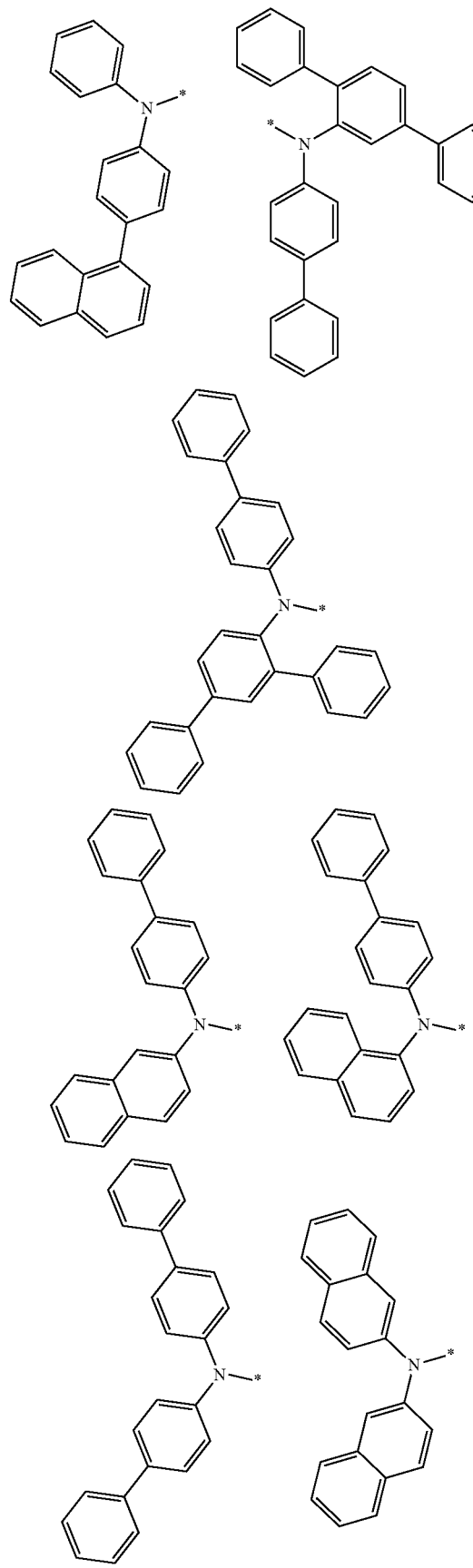
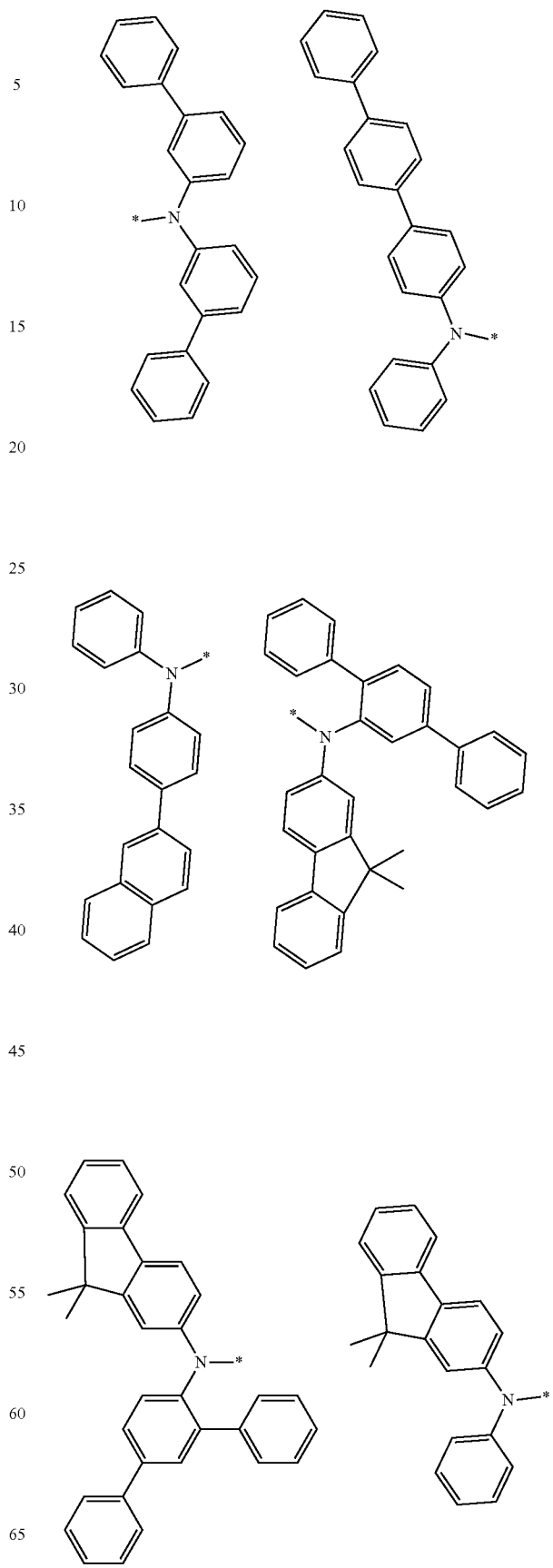

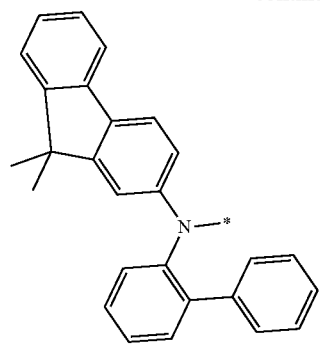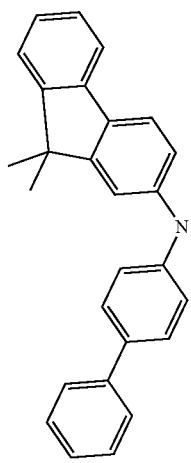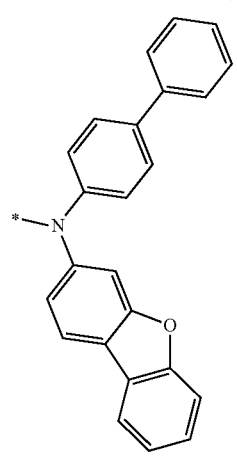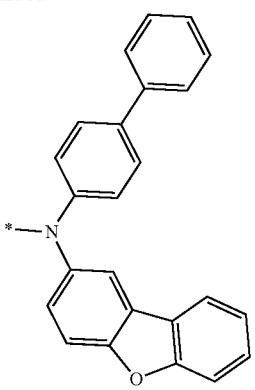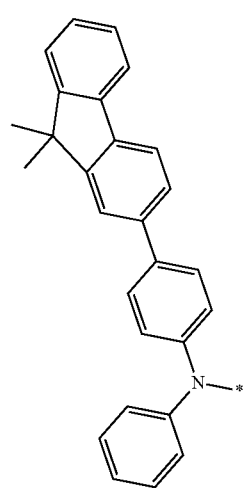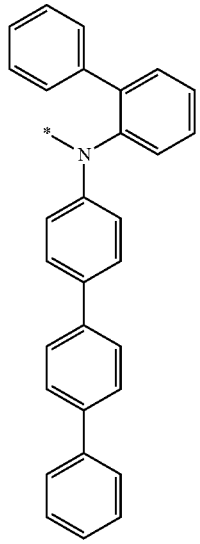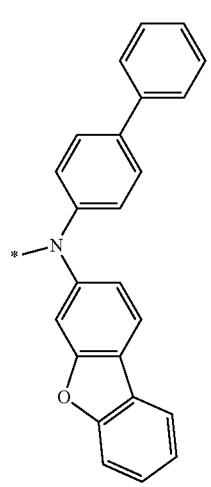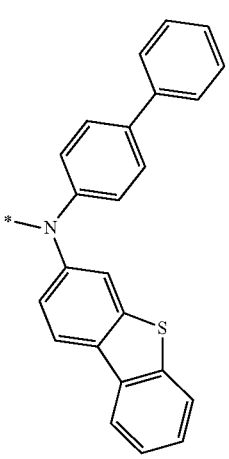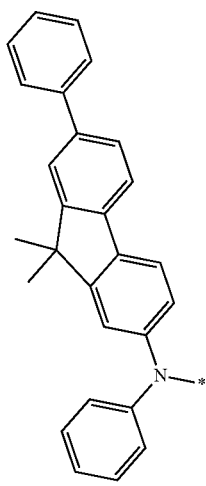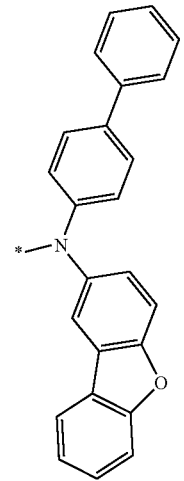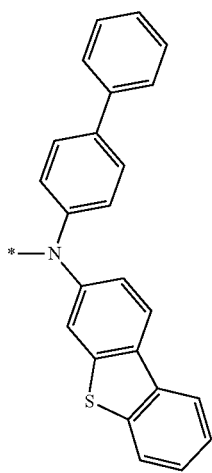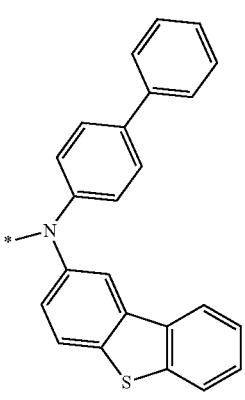

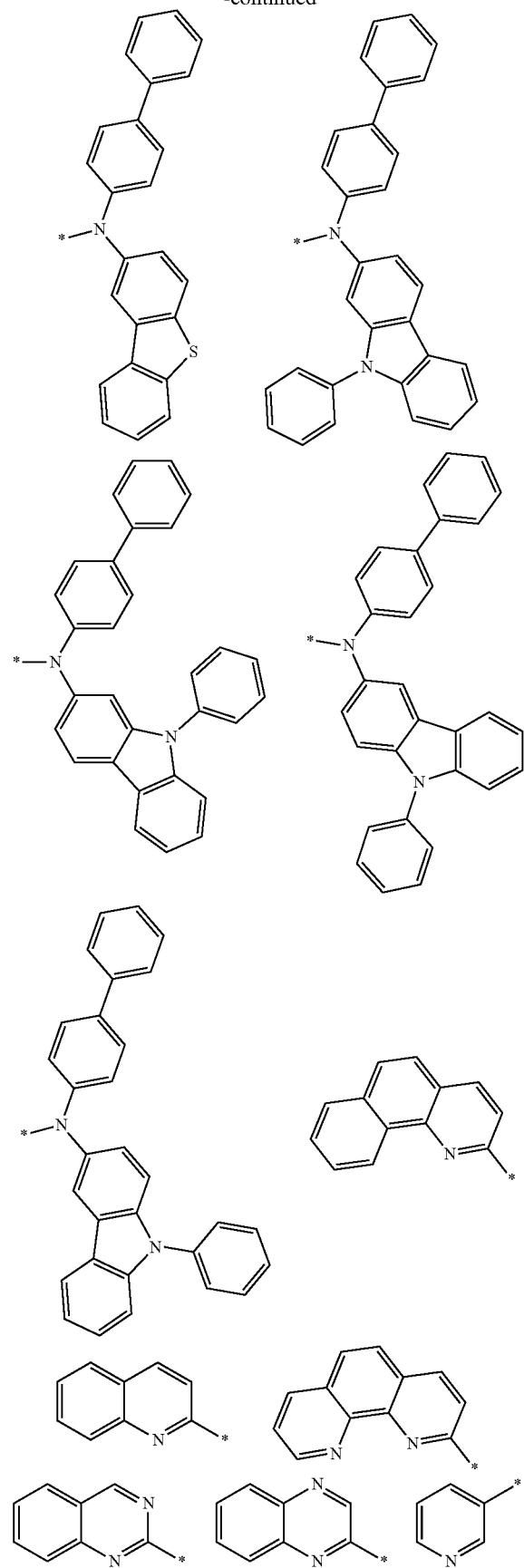
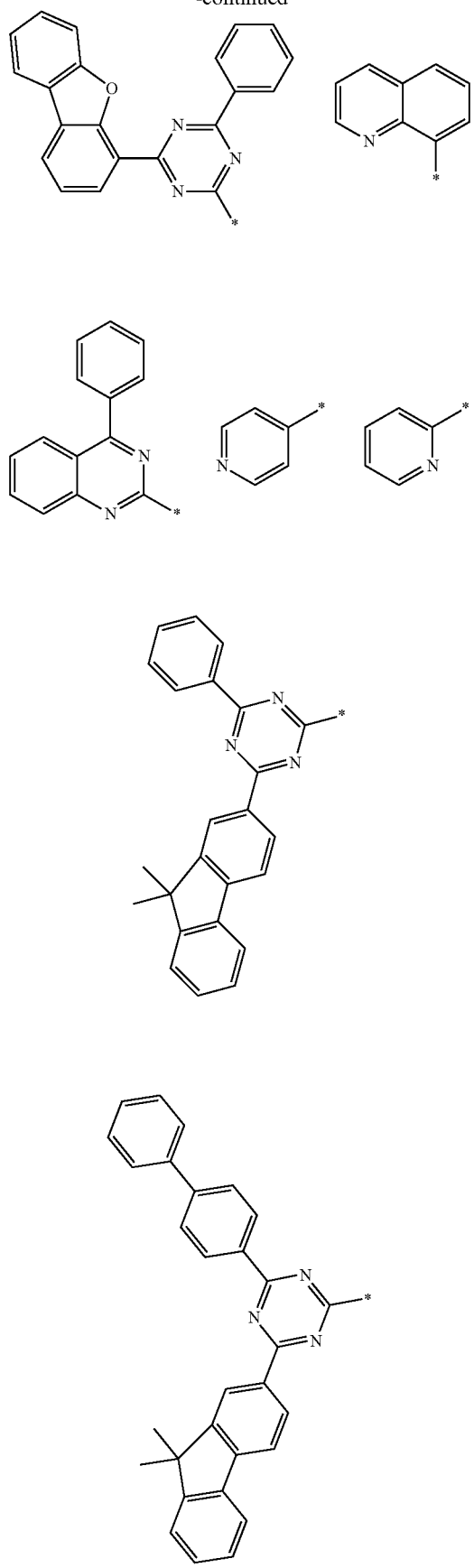

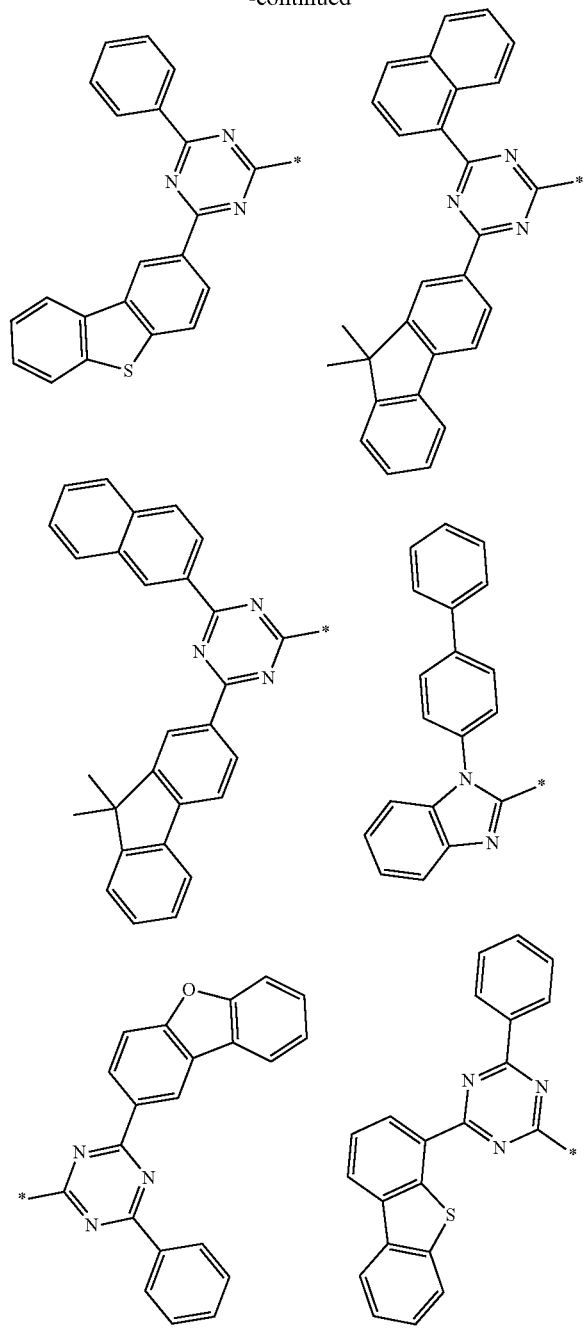

According to an exemplary embodiment of the present specification, ✶ is a moiety linked to L1 or L2.

According to an exemplary embodiment of the present specification, R1 and R2 are a monocyclic or polycyclic aryl group having 6 to 30 carbon atoms.

According to an exemplary embodiment of the present specification, R1 and R2 are a phenyl group.

According to an exemplary embodiment of the present specification, R3 to R8 are hydrogen.

According to an exemplary embodiment of the present specification, L1 and L2 of Chemical Formula 1 are the same as or different from each other, and are each independently a direct bond; an arylene group having 6 to 30; or an N-containing heteroarylene group having 3 to 30 carbon atoms.

According to an exemplary embodiment of the present specification, L1 and L2 of Chemical Formula 1 are a direct bond, a phenylene group, a biphenylene group, or a carbazolene group.

In the present specification, Chemical Formula 1 may be any one selected from the following compounds.

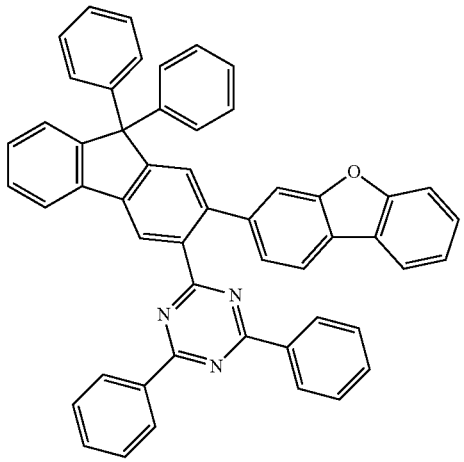

1-1

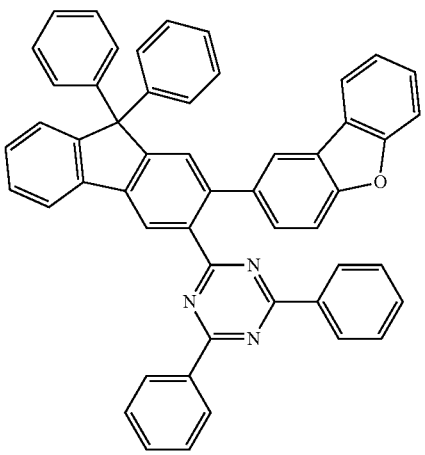

1-2

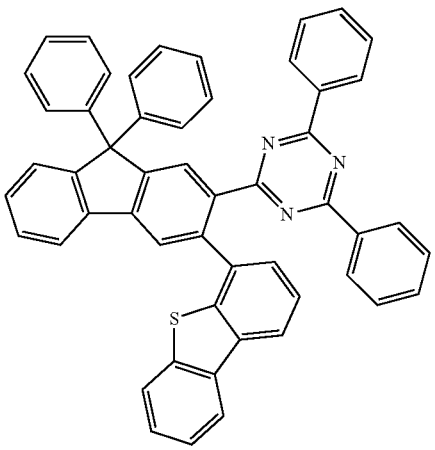

1-3

1-4
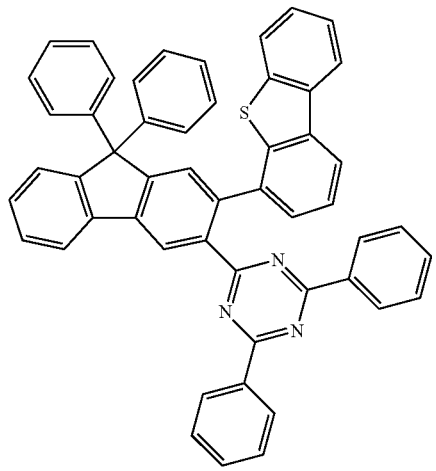
1-5
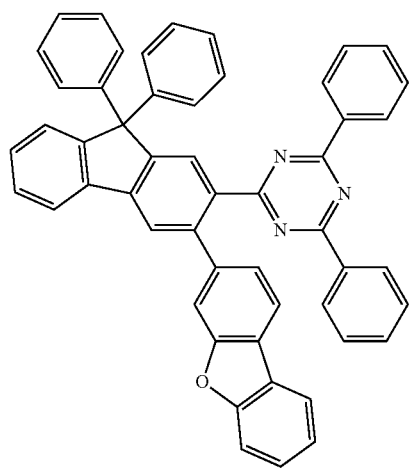
1-6
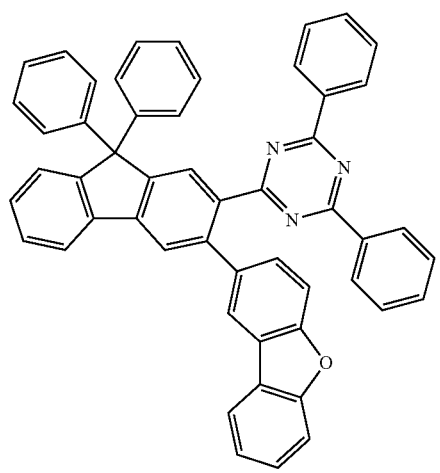
1-7
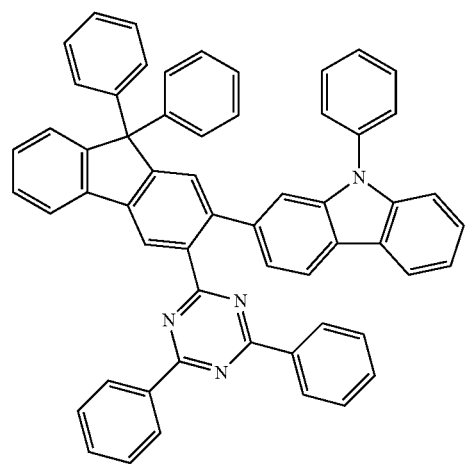
1-8
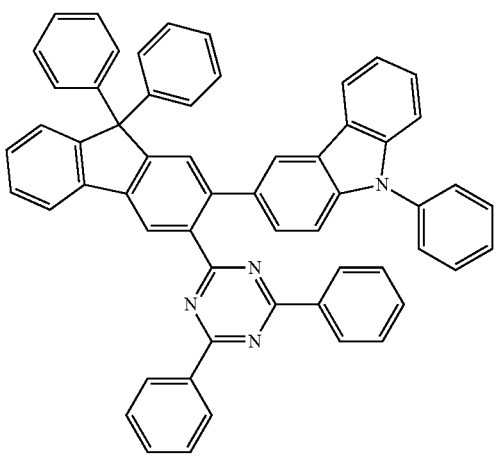
1-9
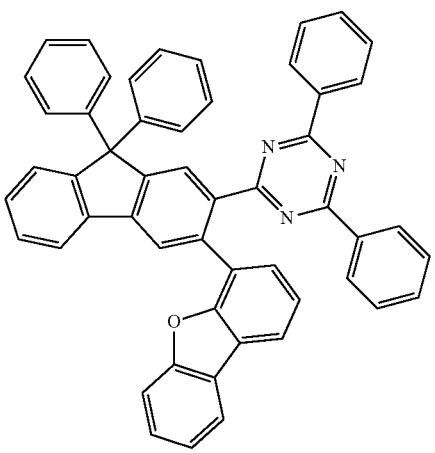

-continued
1-10
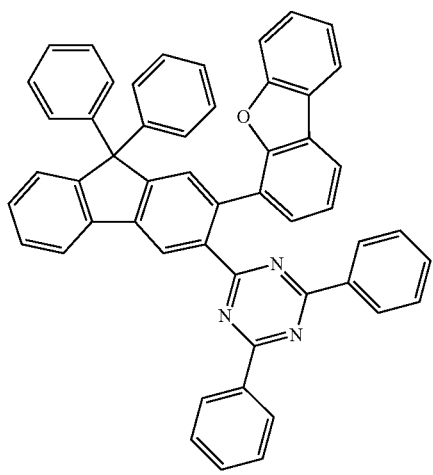
1-11
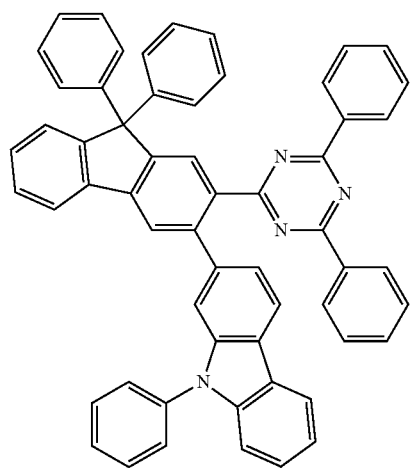
1-12
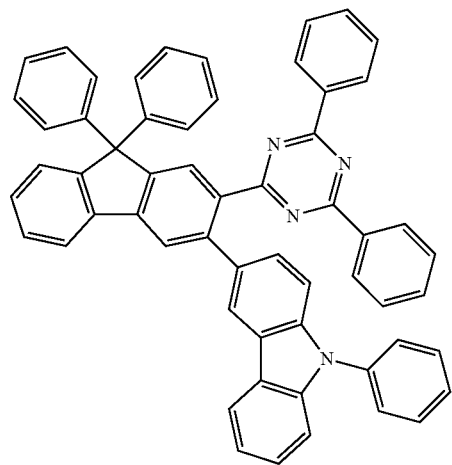
-continued
1-13
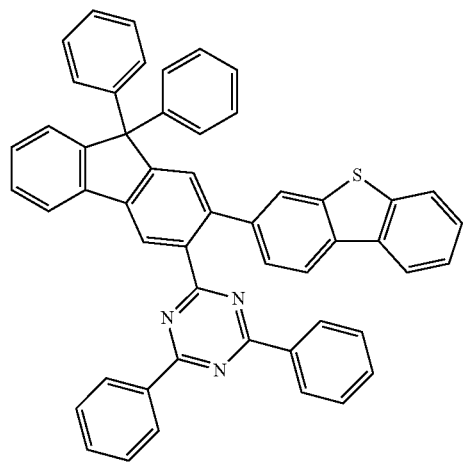
1-14
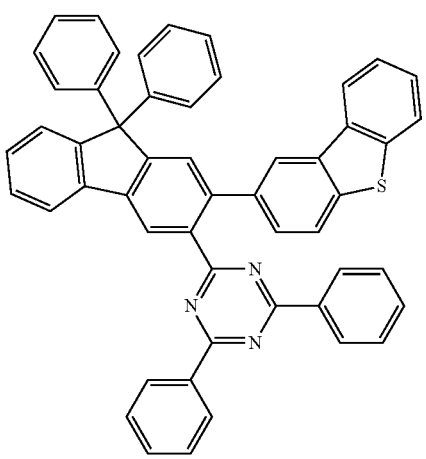
1-15

1-16
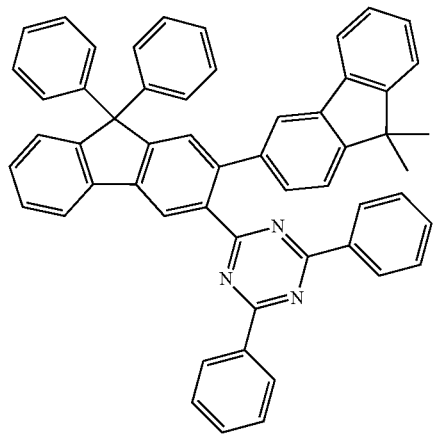
1-17
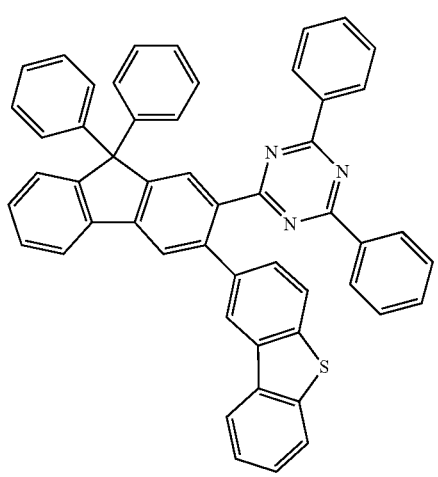
1-18
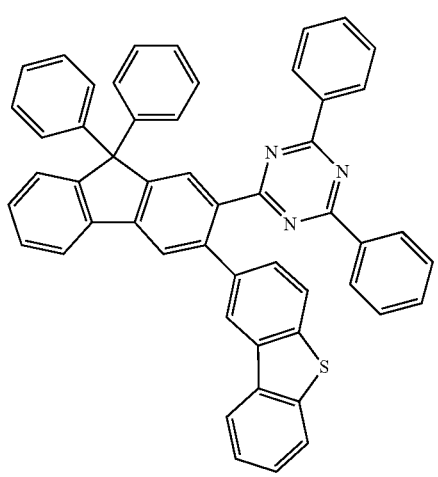
1-19
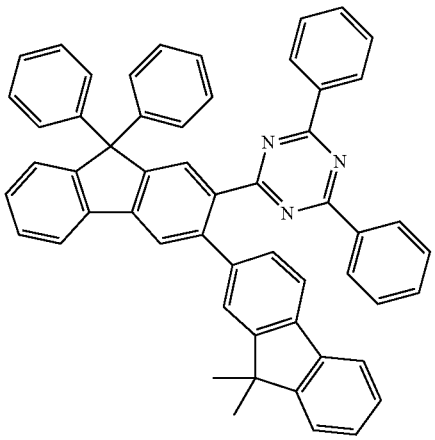
1-20
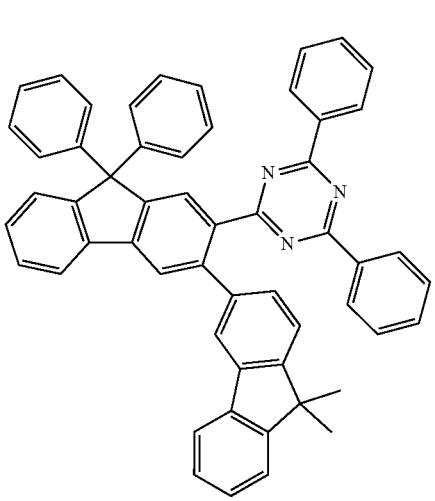
1-21
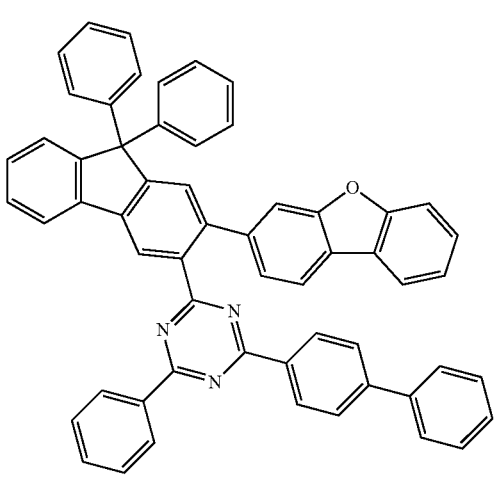

1-22
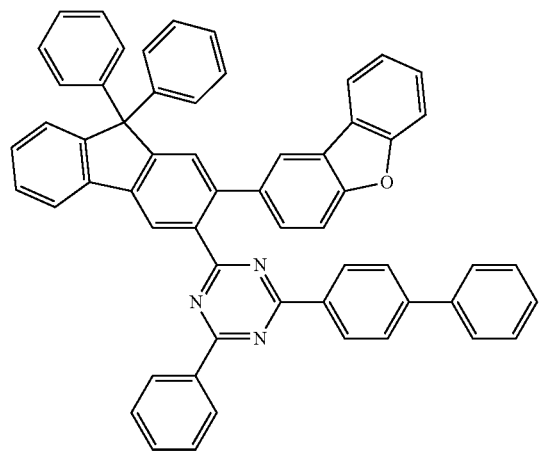
1-25
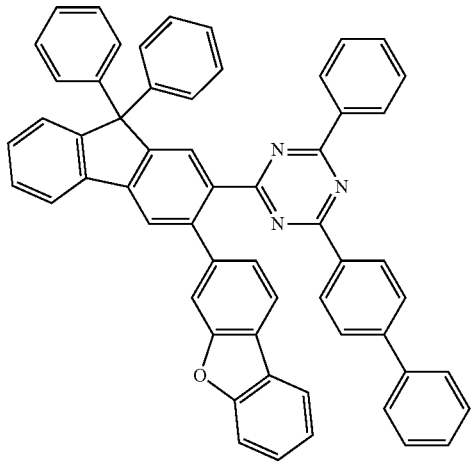
1-23
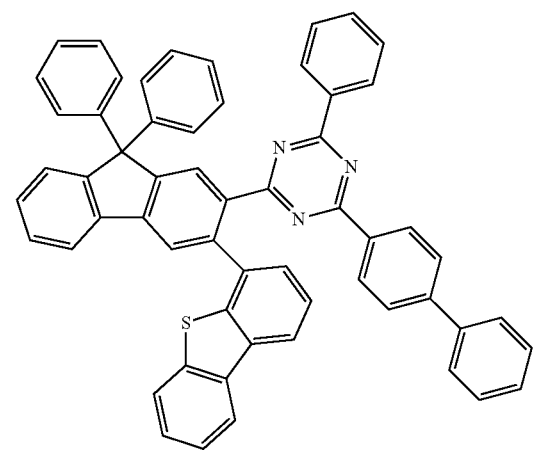
1-26
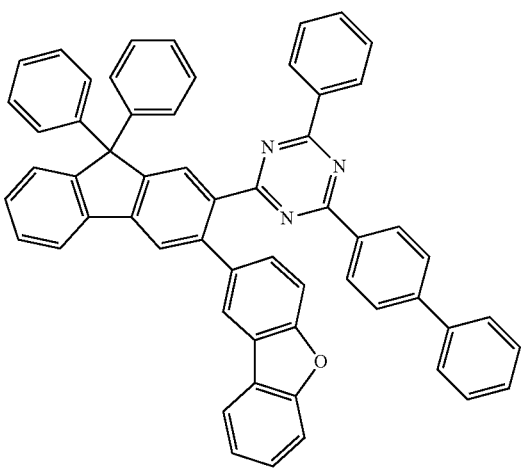
1-24
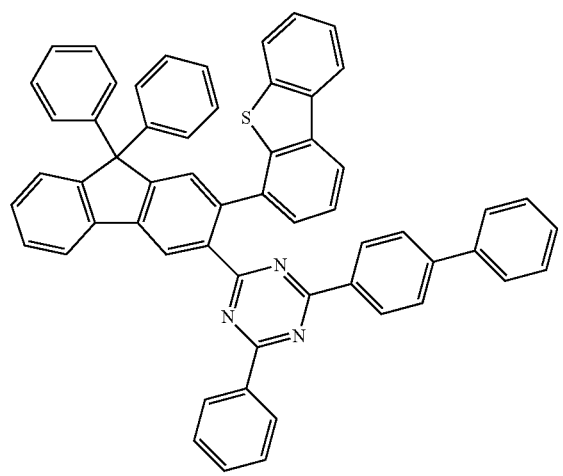
1-27
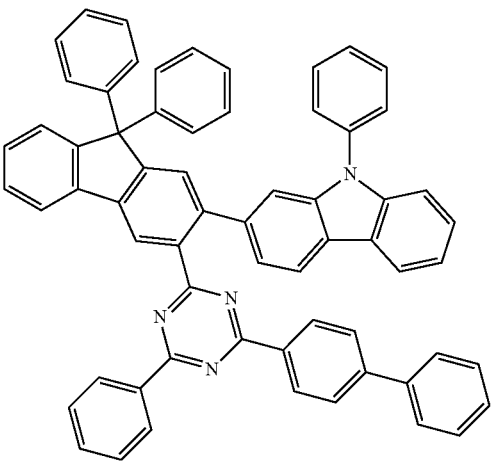

1-28
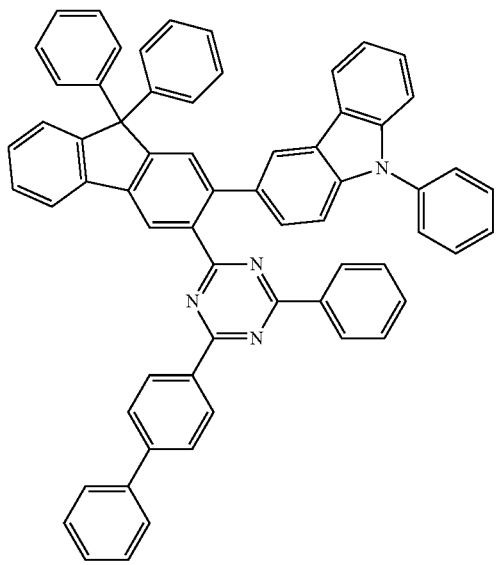
1-29
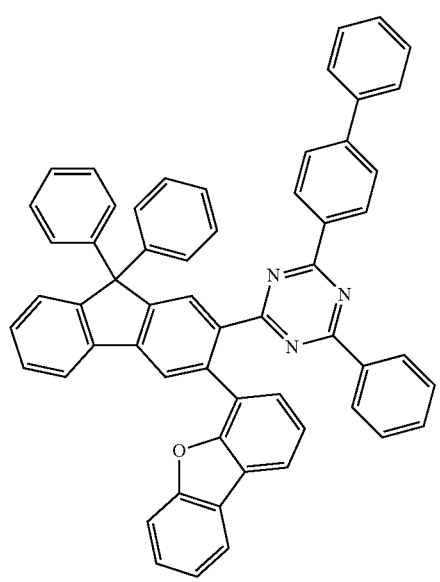
1-30
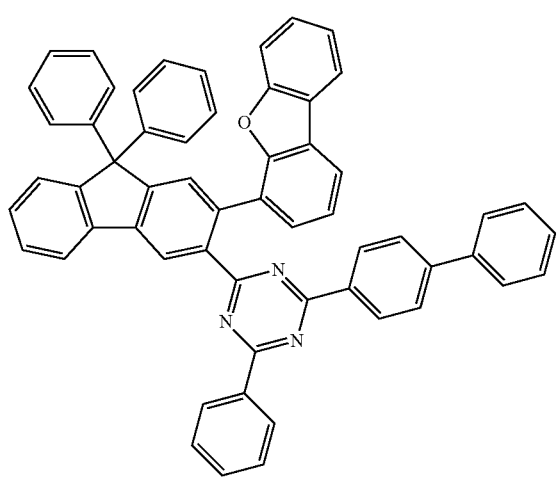
1-31
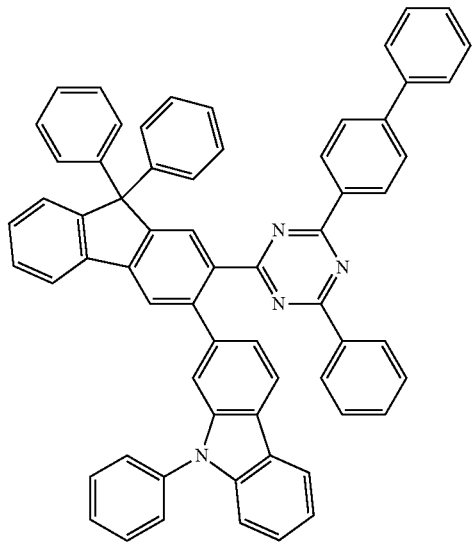
1-32
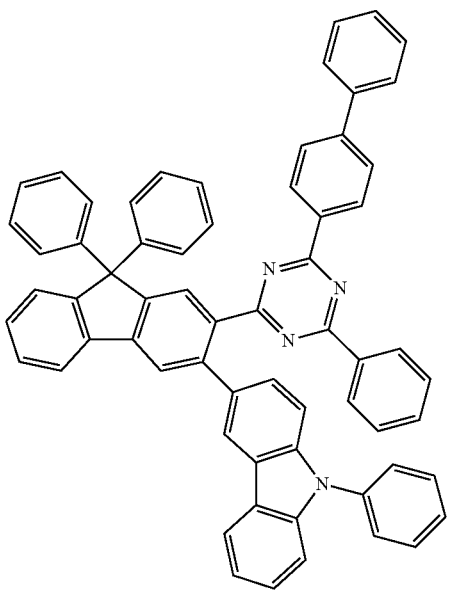
1-33
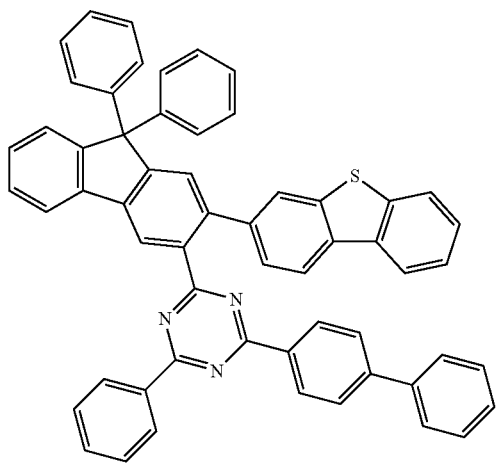

1-34
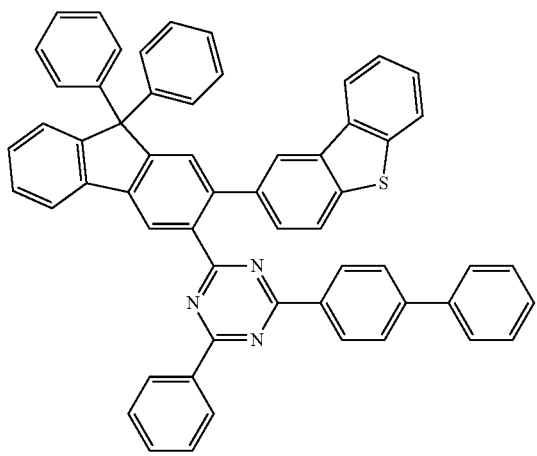
1-35
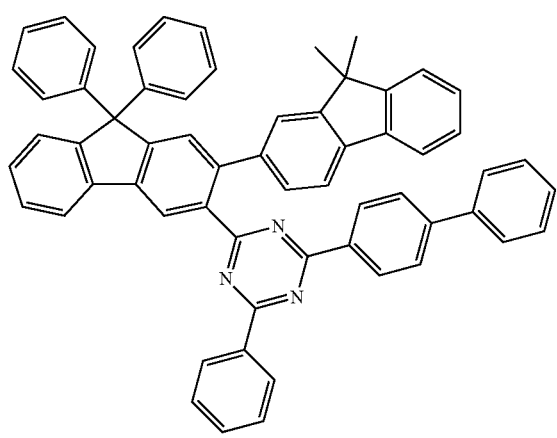
1-36
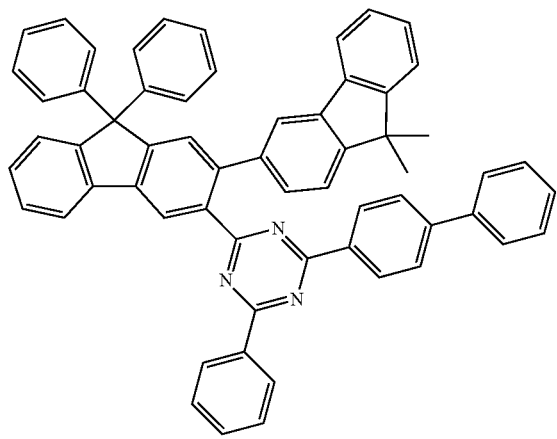
1-37
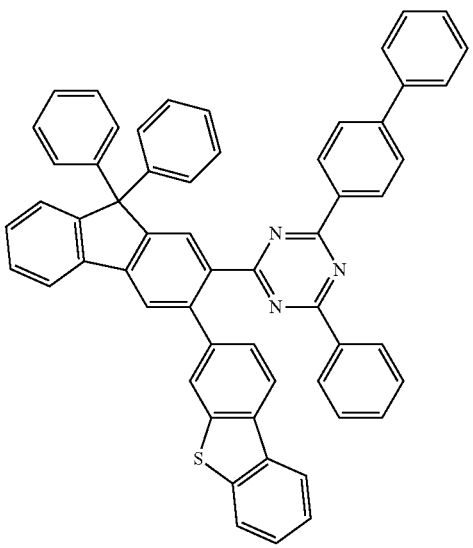
1-38
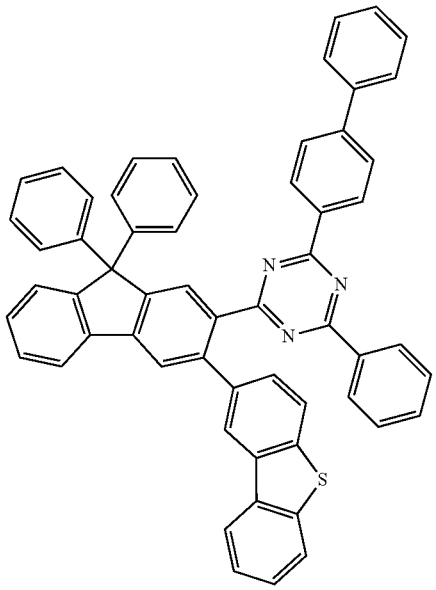

1-39
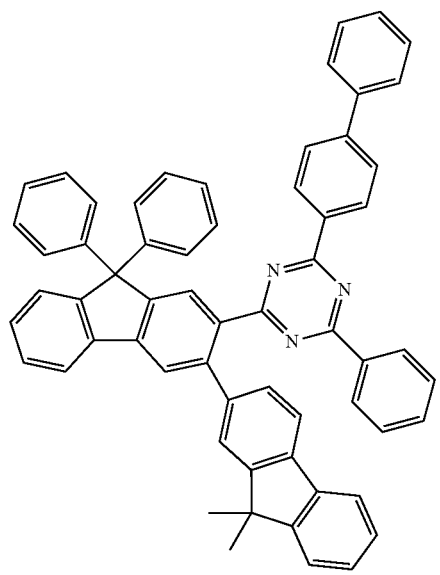
1-40
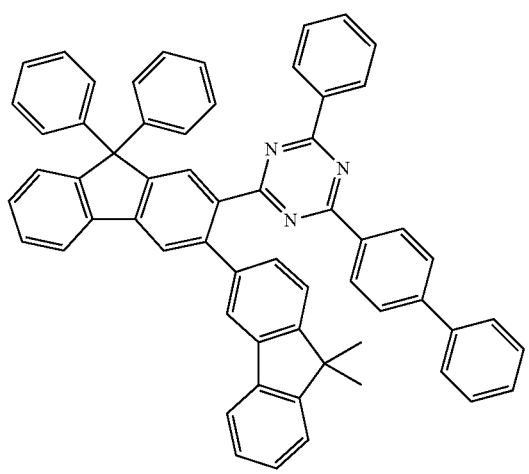
1-41
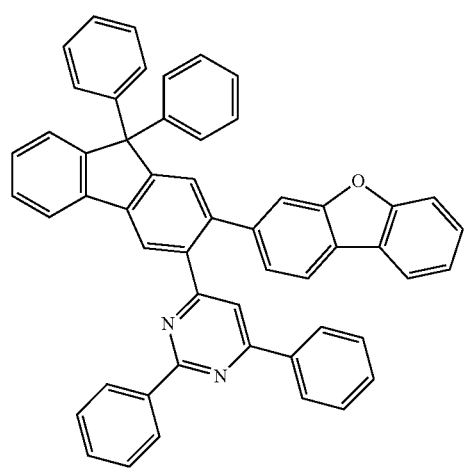
1-42
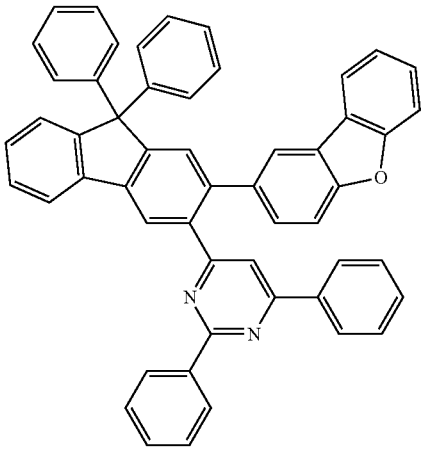
1-43
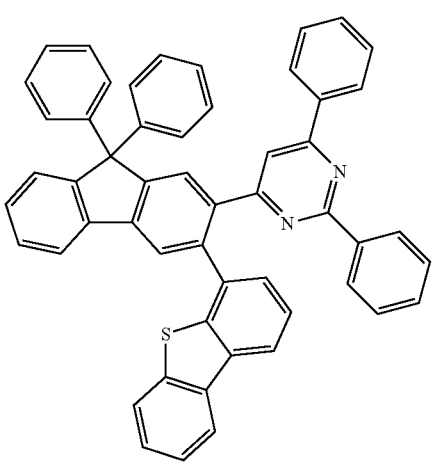
1-44
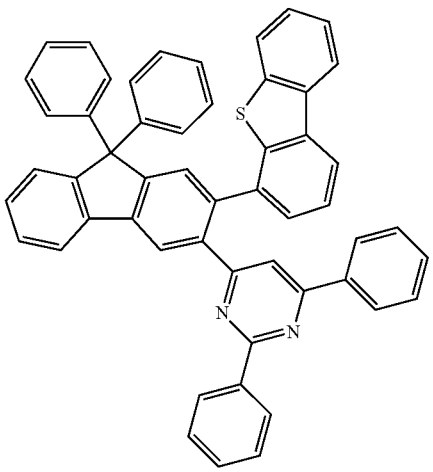

1-45
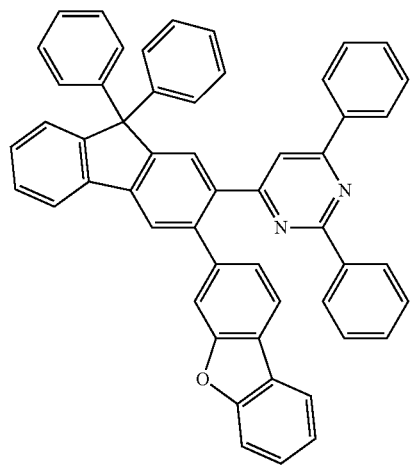
1-48
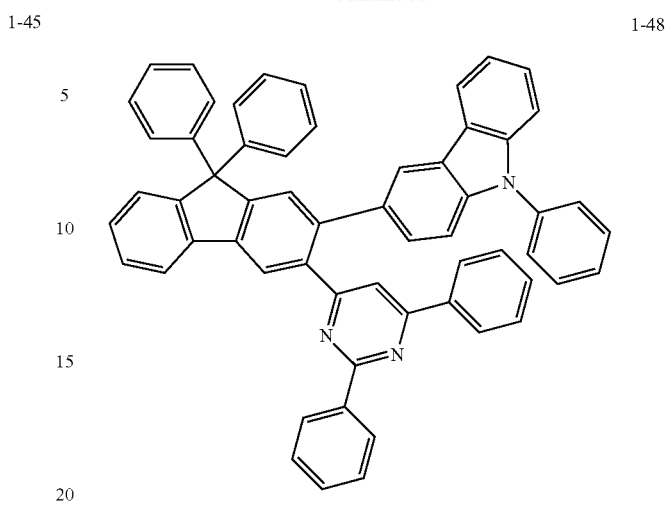
1-46
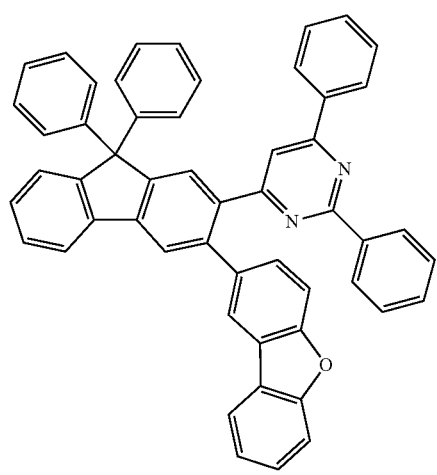
1-49
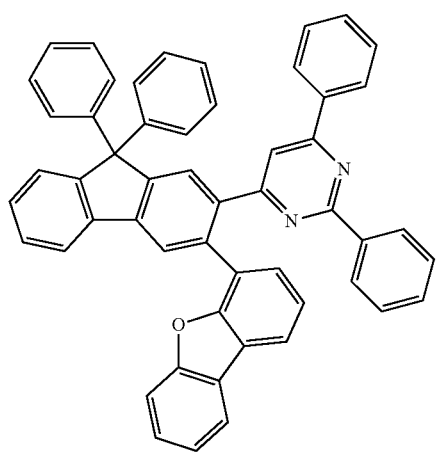
1-47
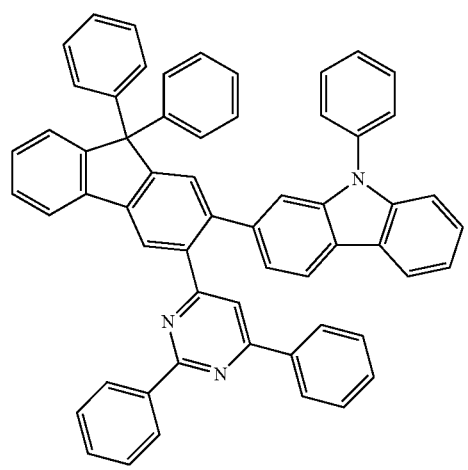
1-50
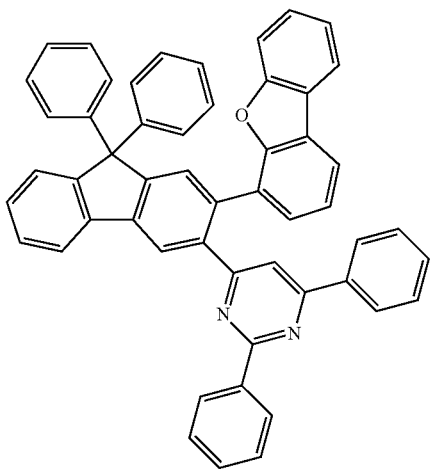

1-51
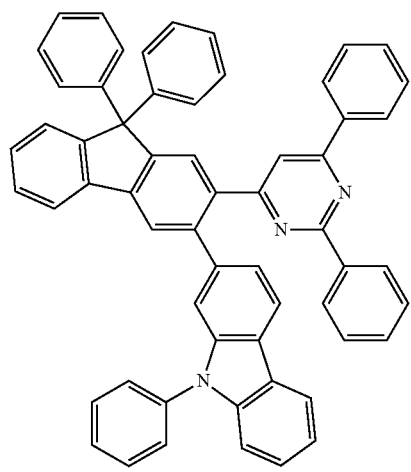
1-52
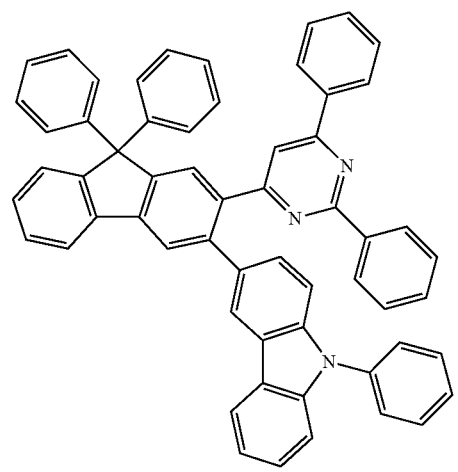
1-53
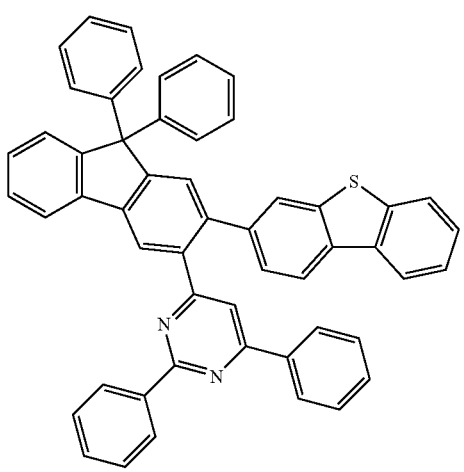
1-54
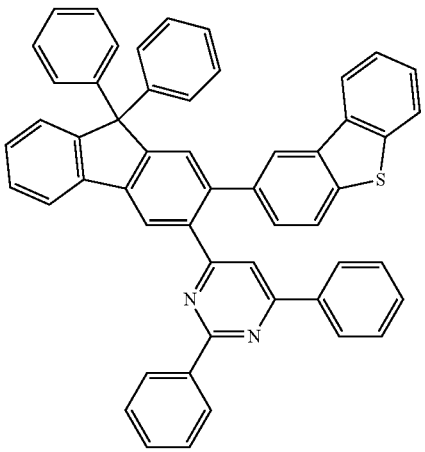
1-55
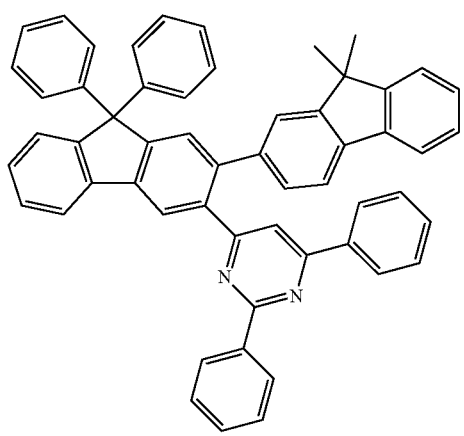
1-56
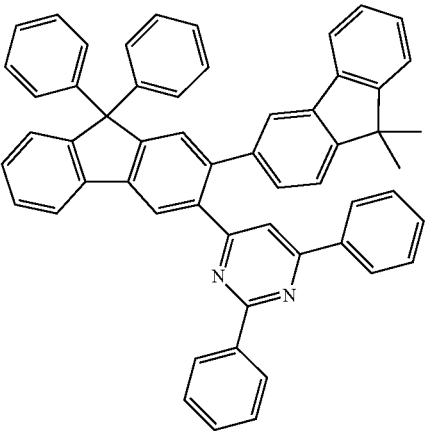

1-57
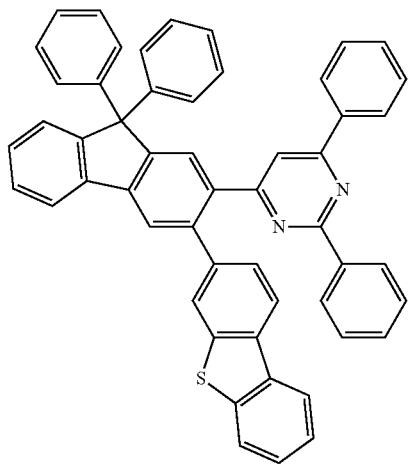
1-60
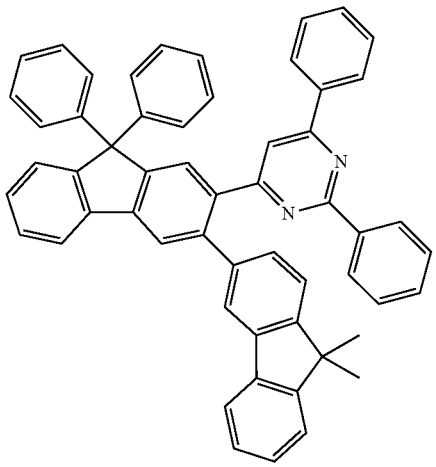
1-58
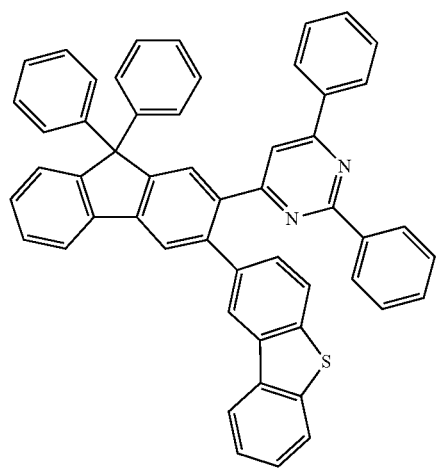
1-61
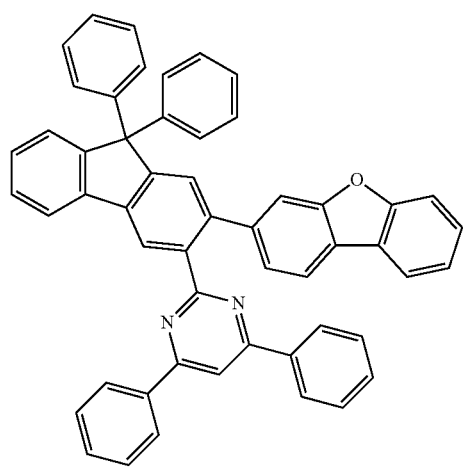
1-59
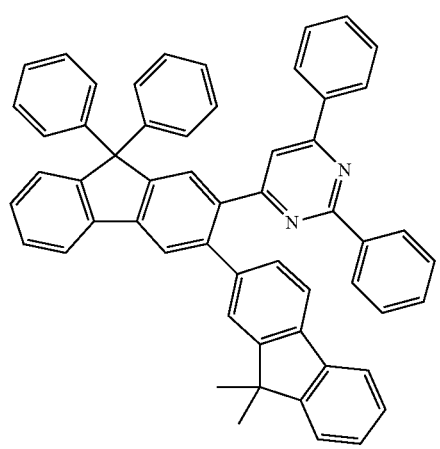
1-62
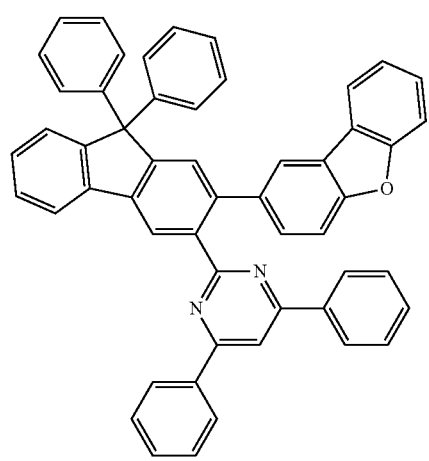

1-63
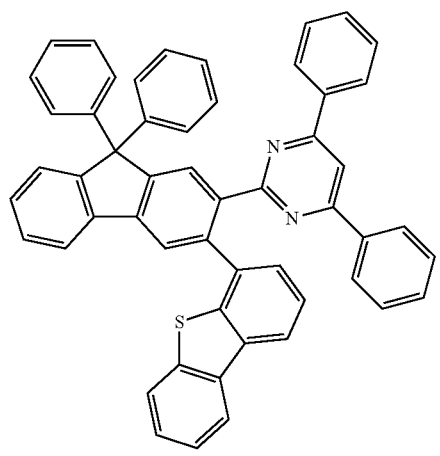
1-64
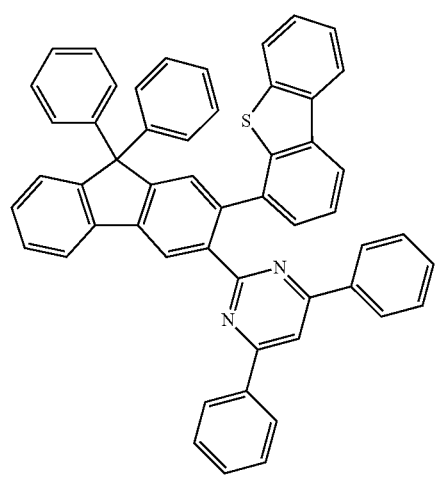
1-65
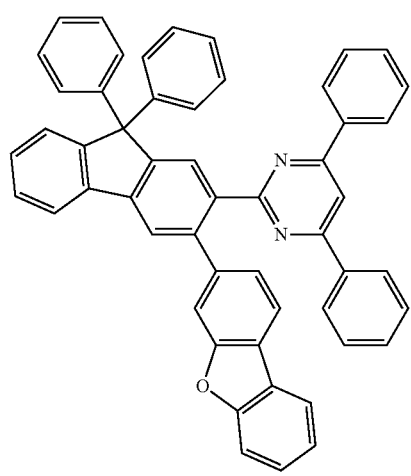
1-66
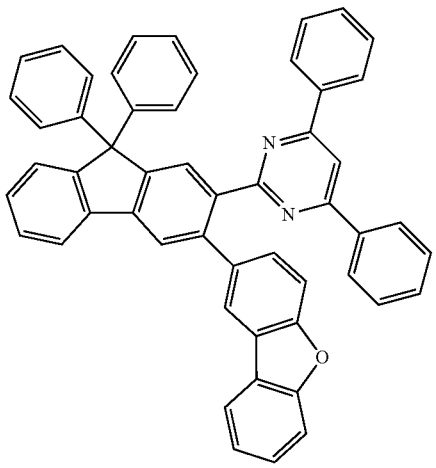
1-67
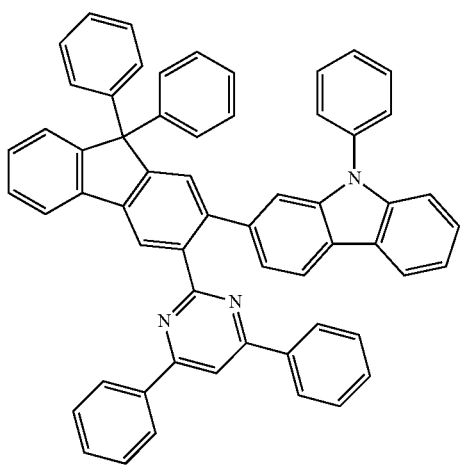
1-68
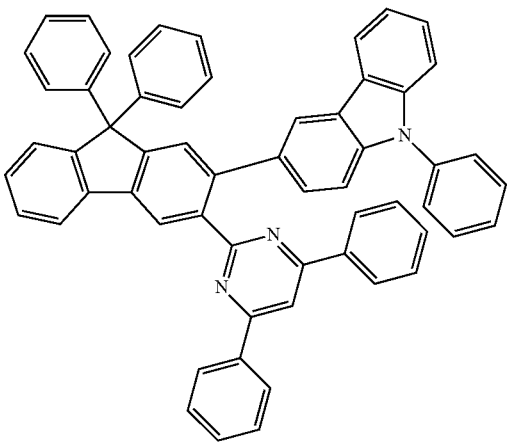

-continued
1-69
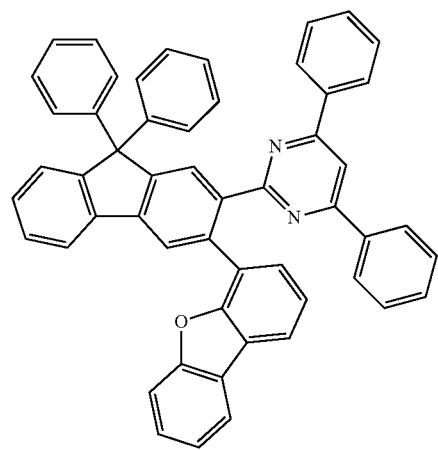
1-70
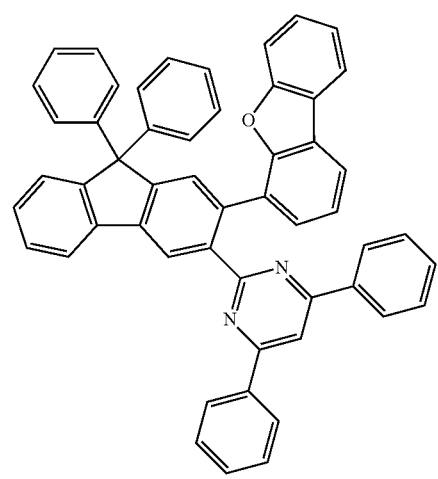
1-71
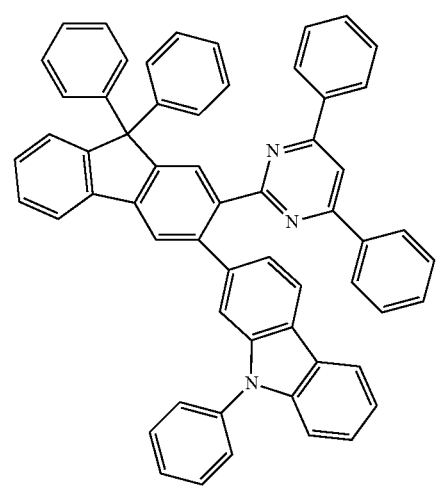
-continued
1-72
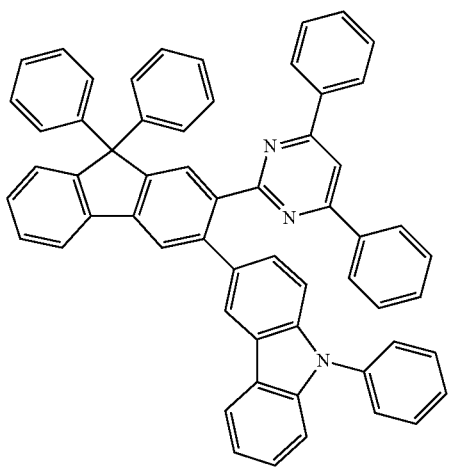
1-73
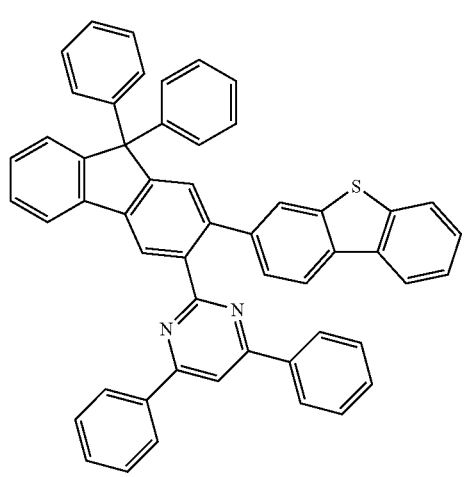
1-74
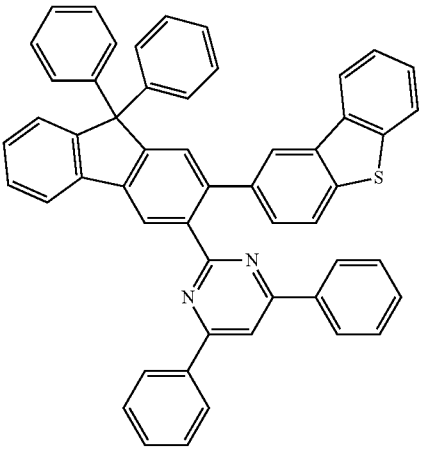

-continued
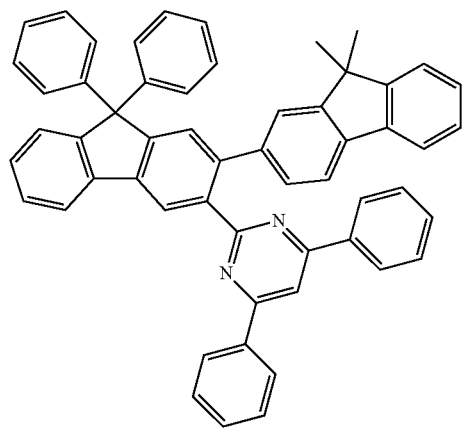
1-75
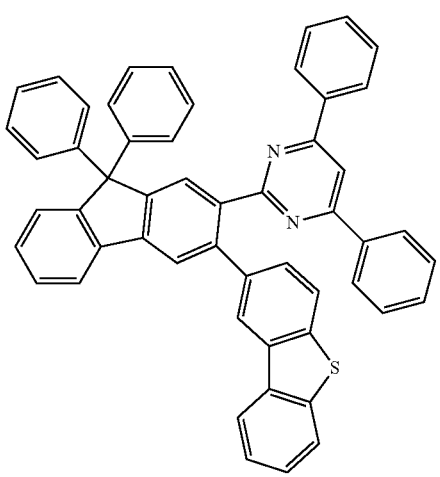
1-78
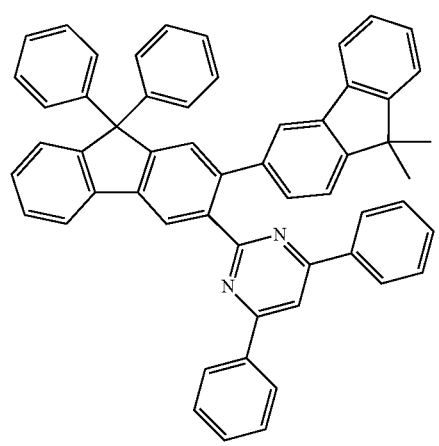
1-76
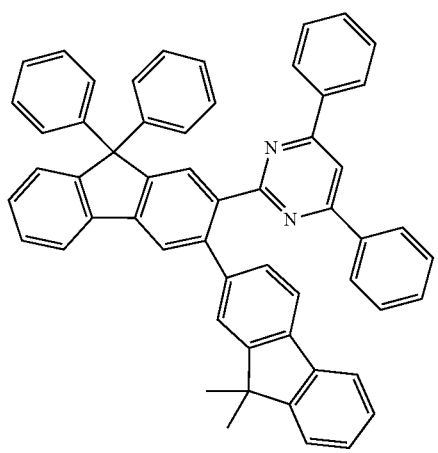
1-79
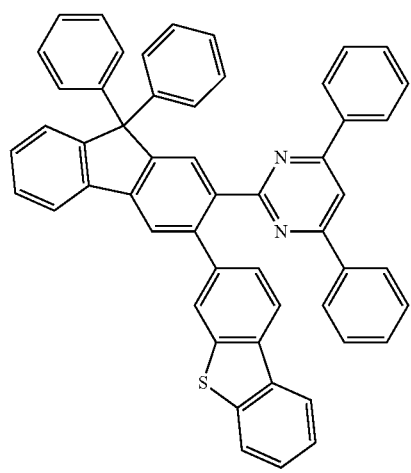
1-77
1-80

1-81
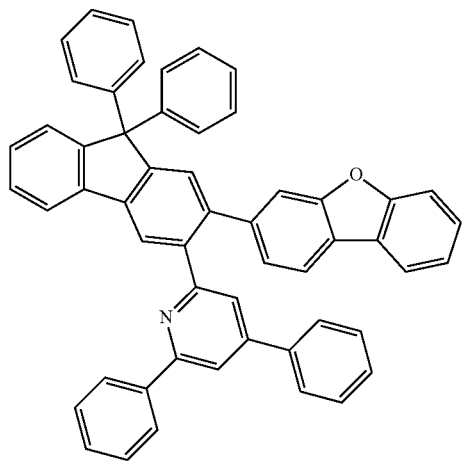
1-84
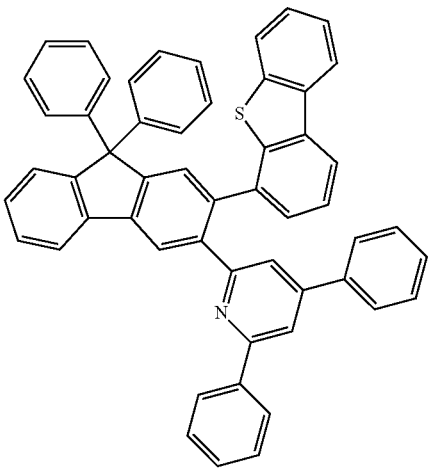
1-82
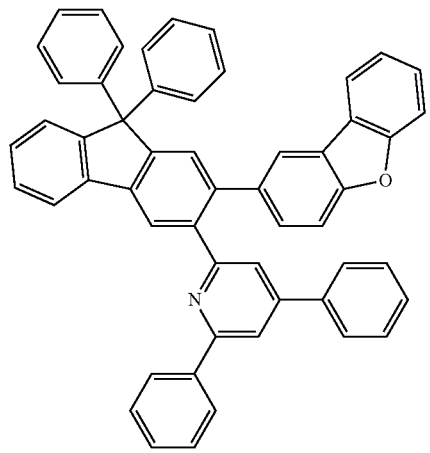
1-85
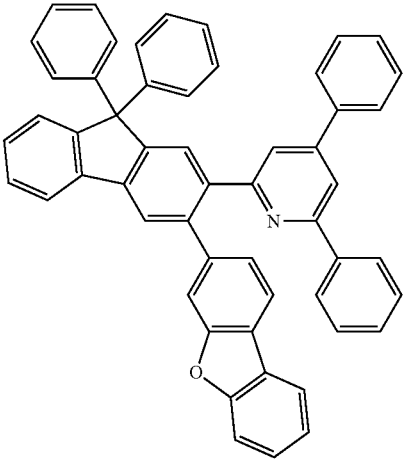
1-83
1-86
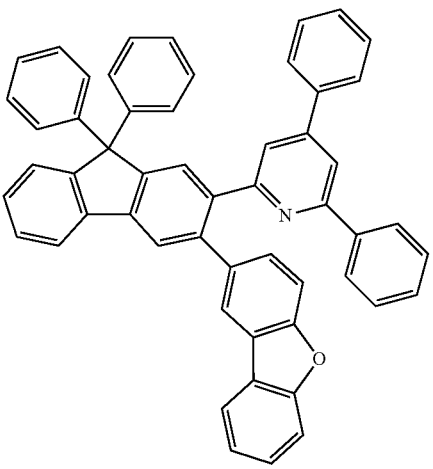

1-87
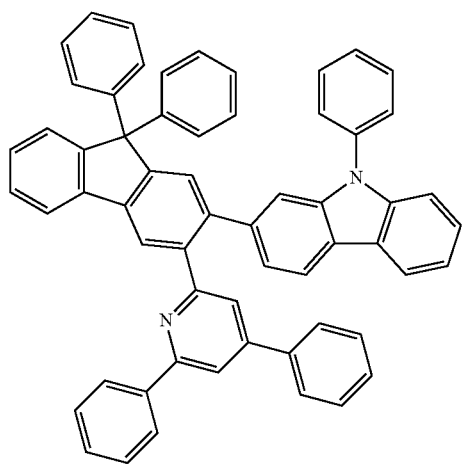
1-88
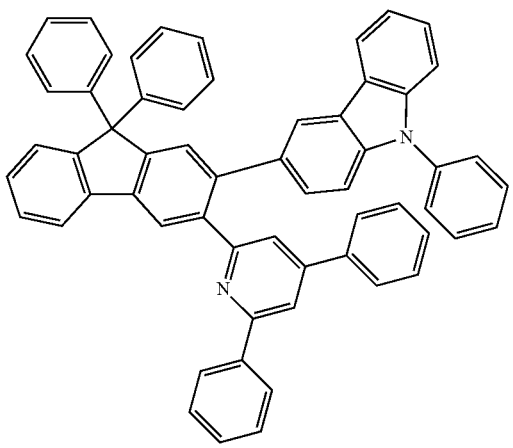
1-89
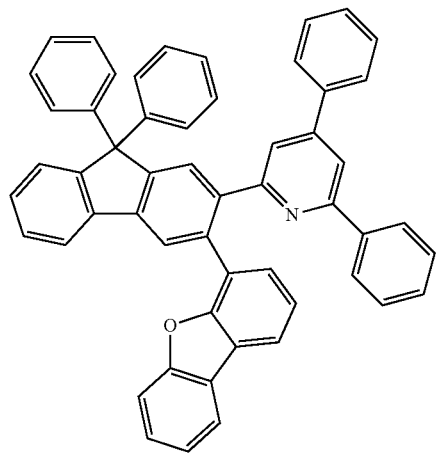
1-90
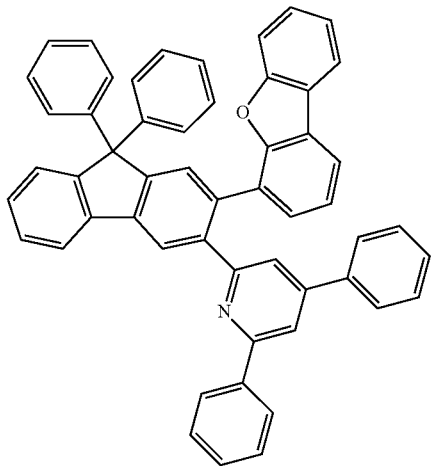
1-91
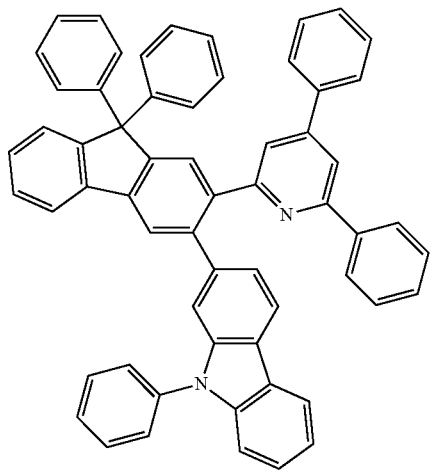
1-92
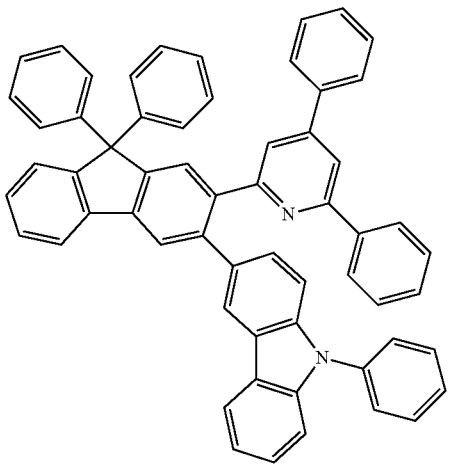

1-93
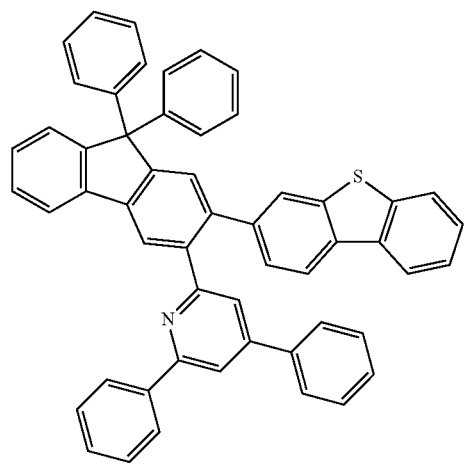
1-94
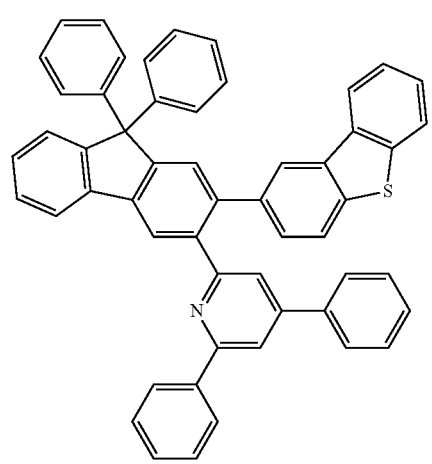
1-95
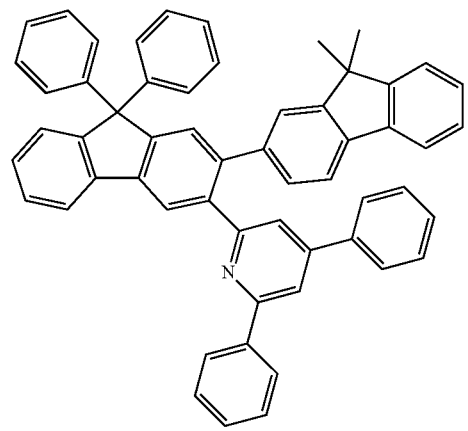
1-96
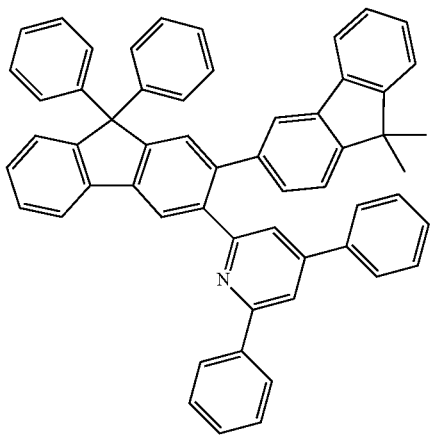
1-97
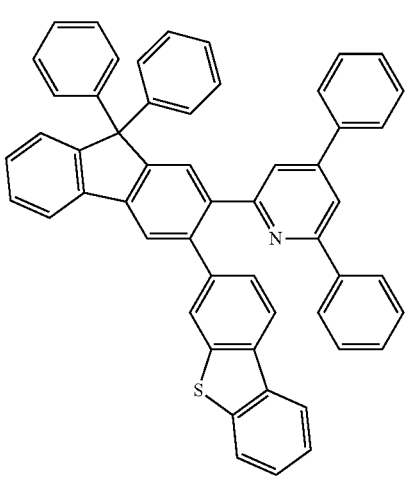
1-98
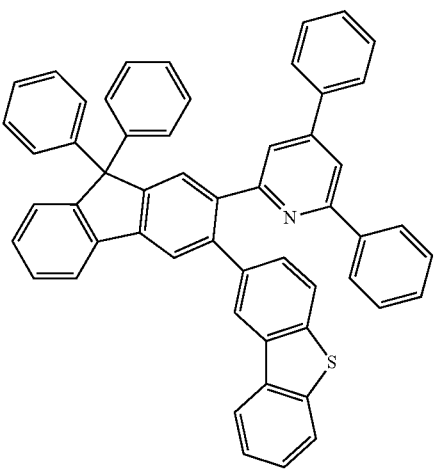

-continued
1-99
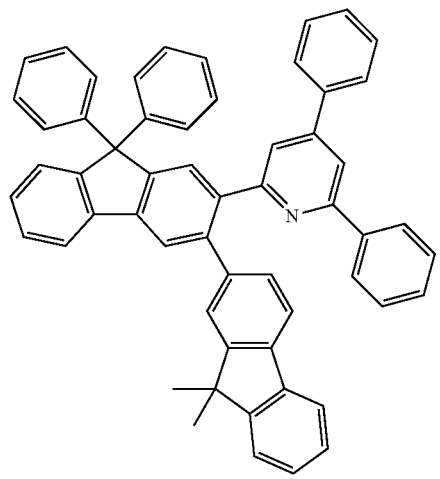
1-102
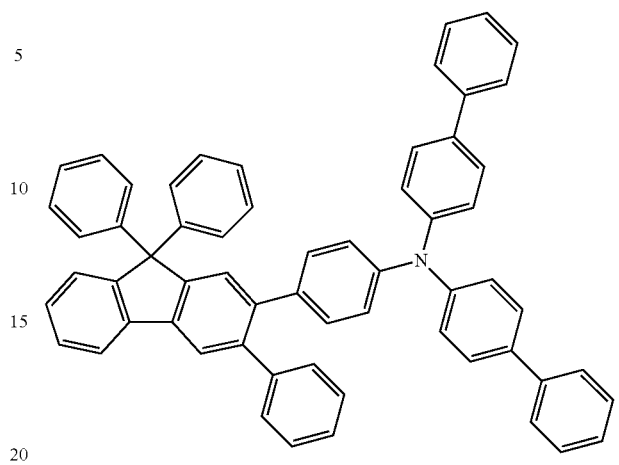
1-100
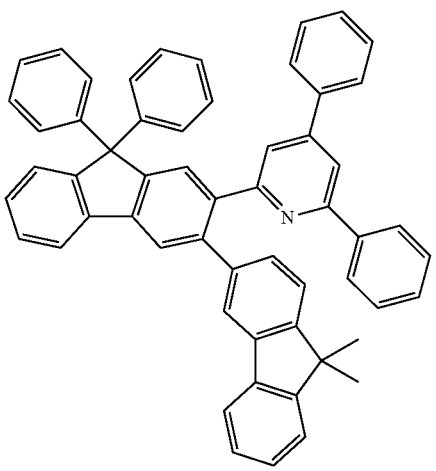
1-103
1-101
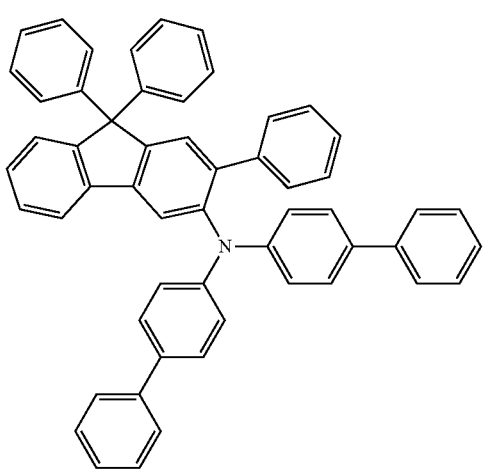
1-104
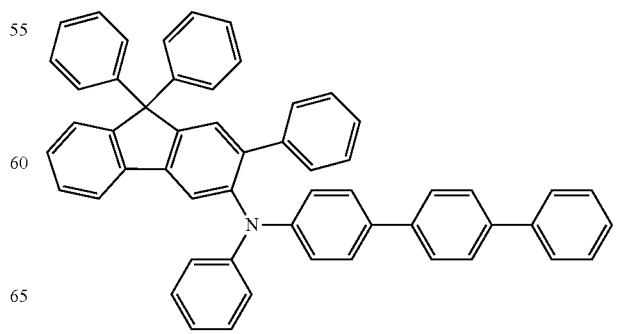

1-105
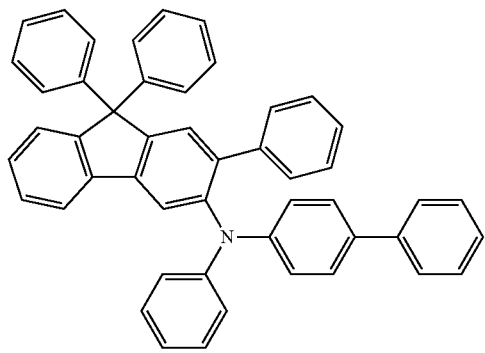
1-106
1-107
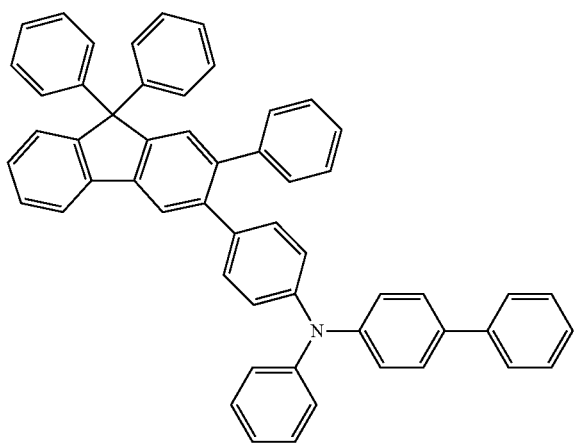
1-108
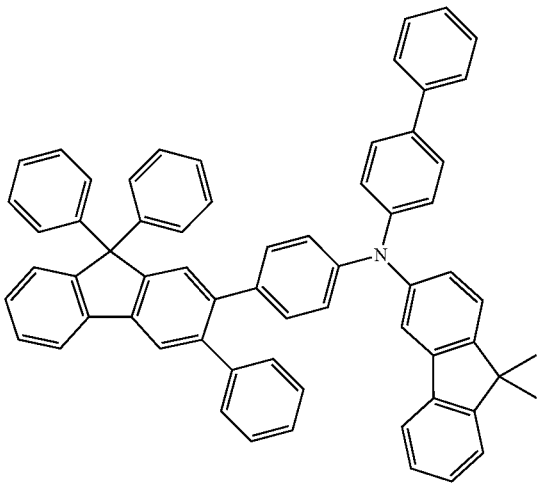
1-109
1-110
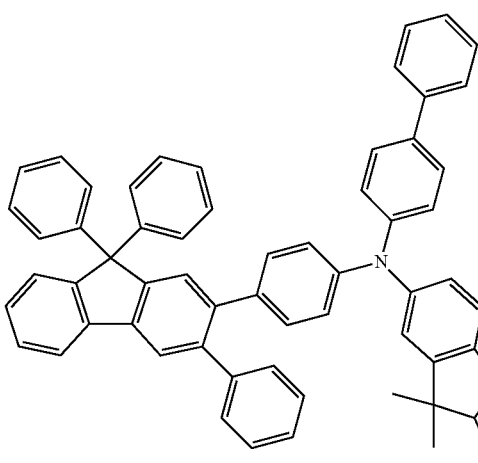

-continued
1-111
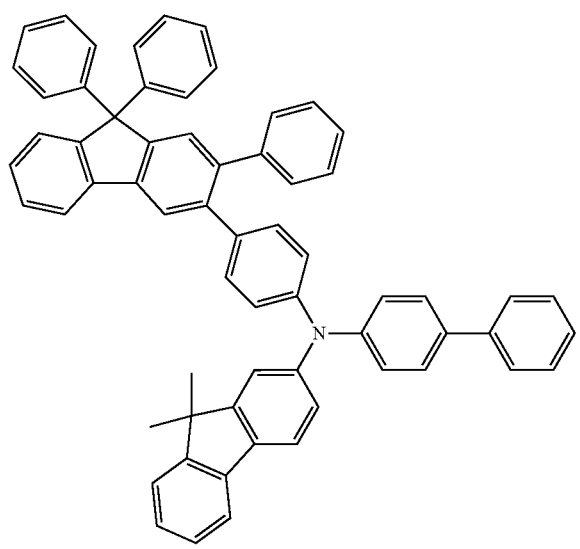
1-112
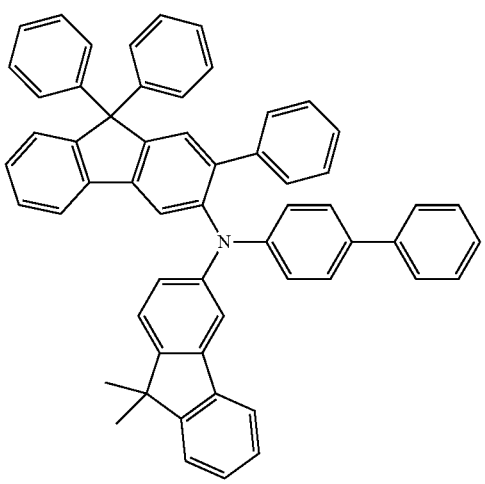
1-113
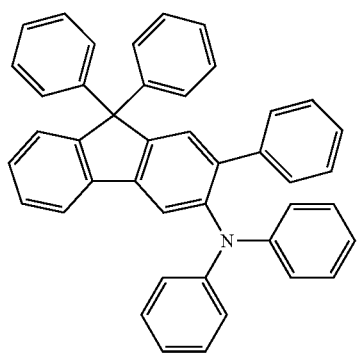
-continued
1-114
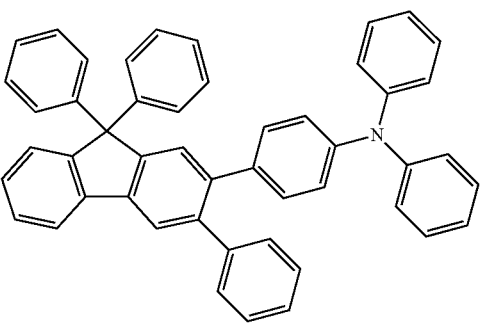
1-115
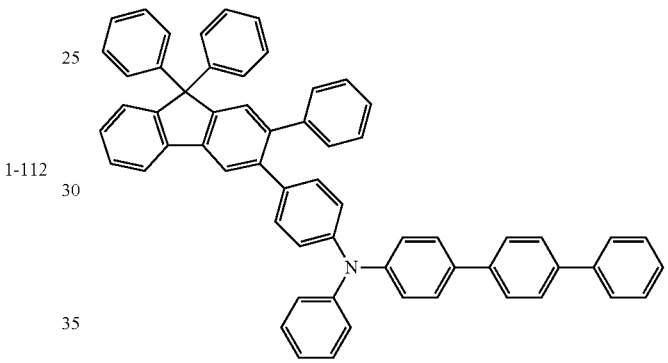
1-116
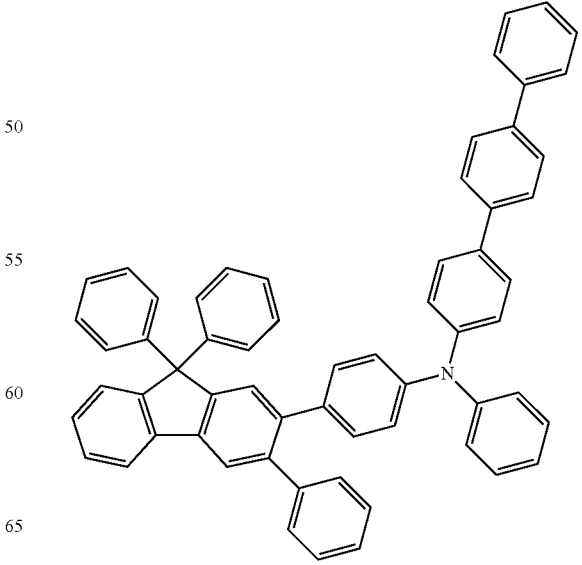

1-117
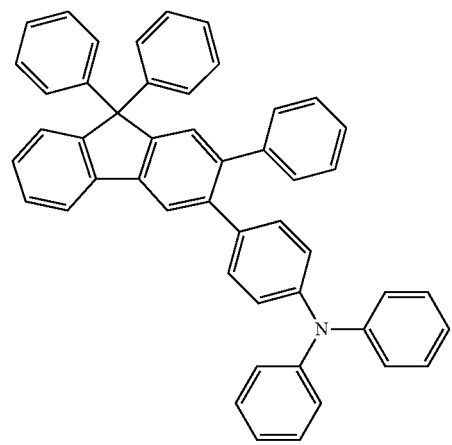
1-120
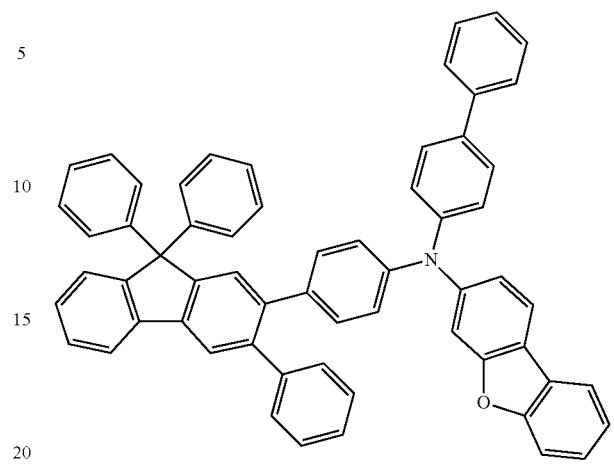
1-118
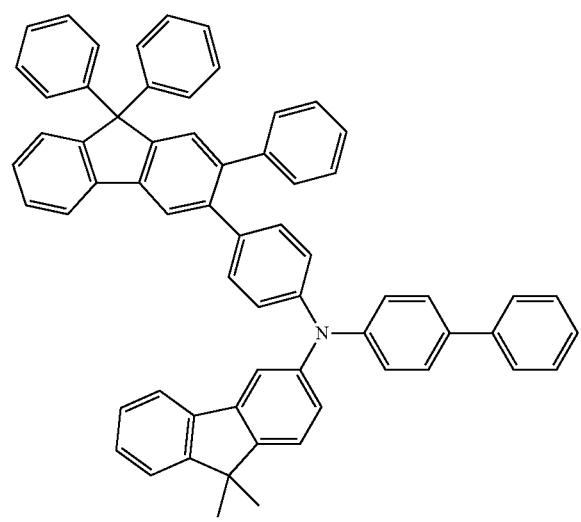
1-121
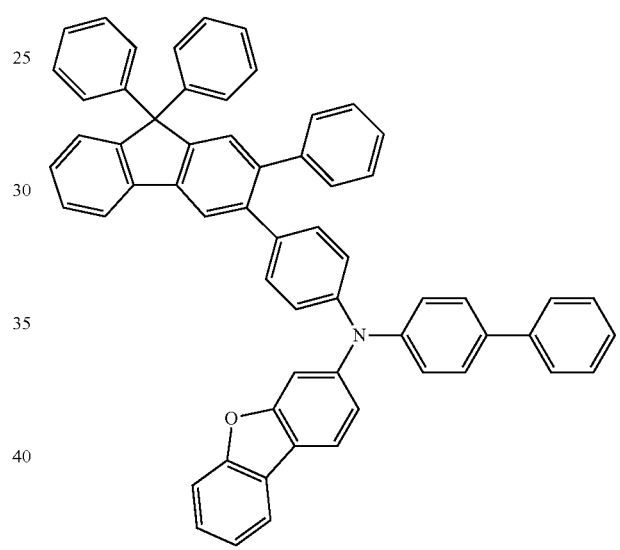
1-119
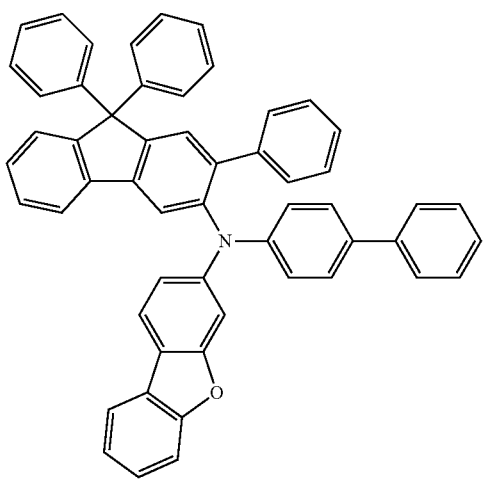
1-122
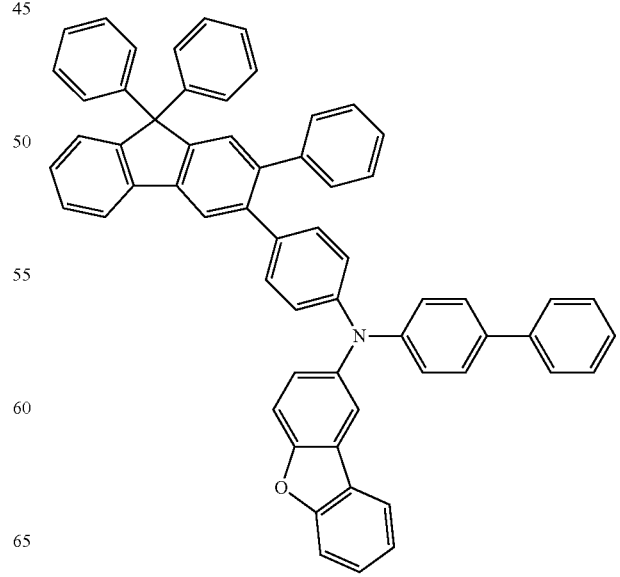

1-123
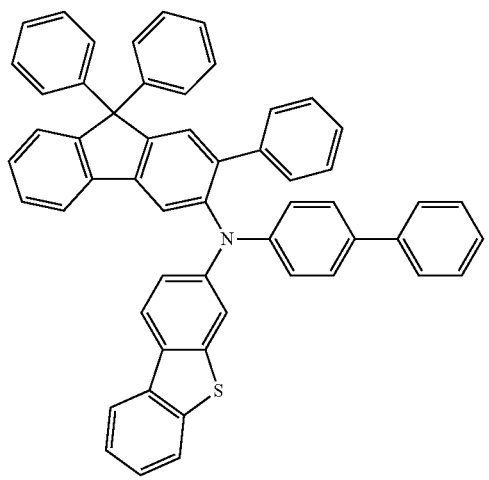
1-124
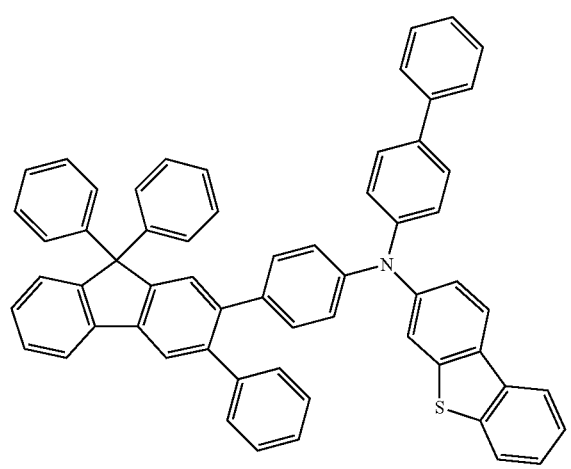
1-125
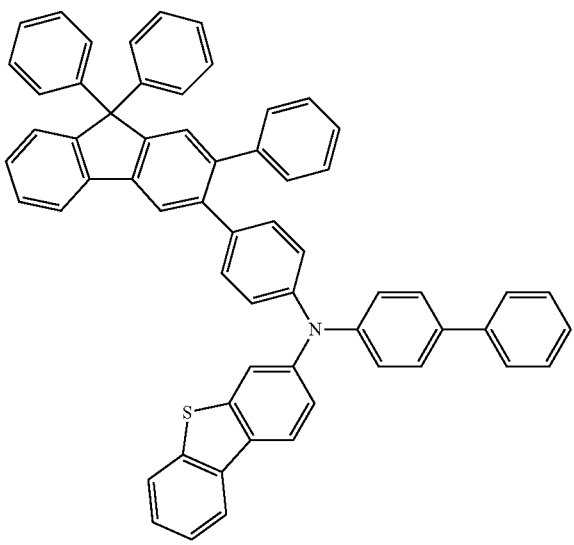
1-126
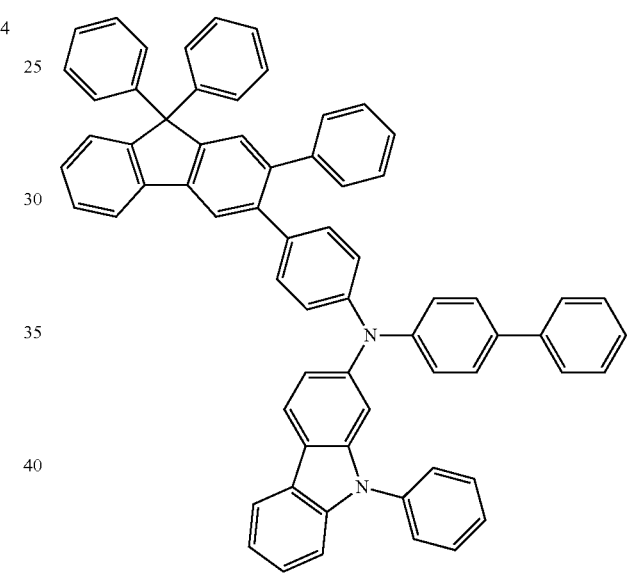
1-127
1-128
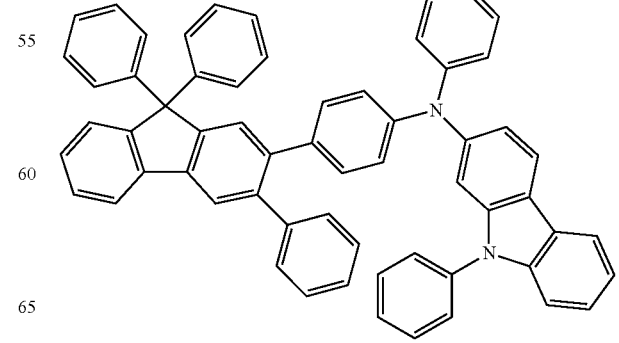

1-129
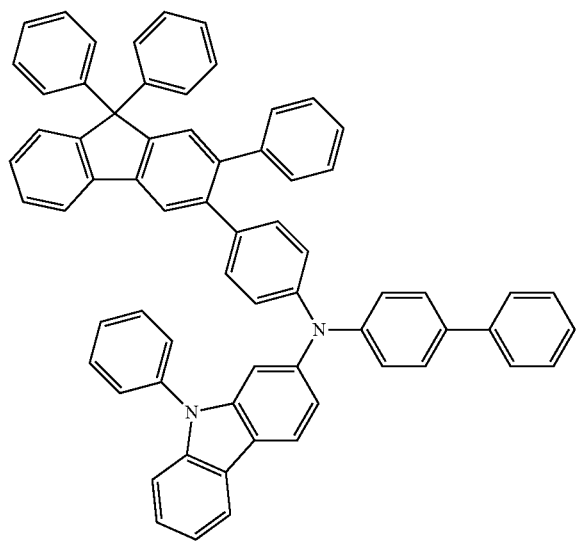
1-130
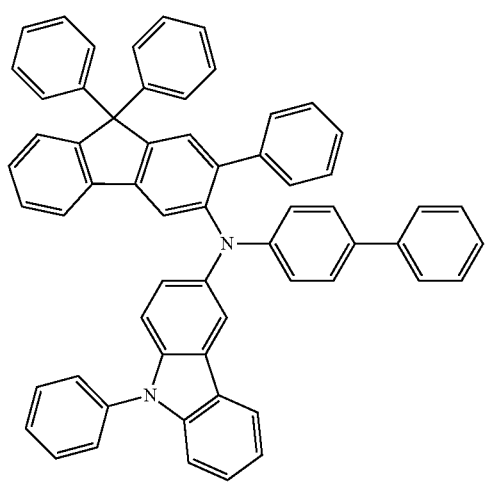
1-131
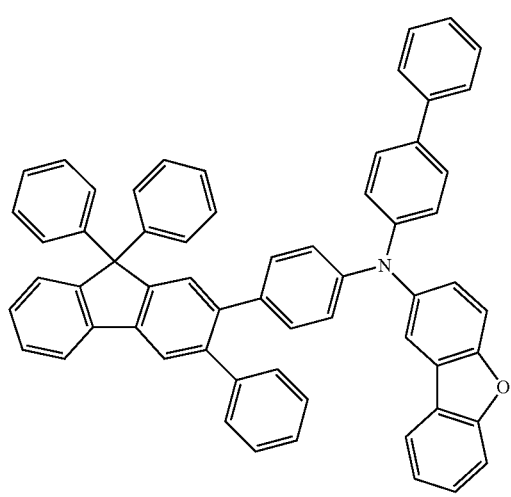
1-132
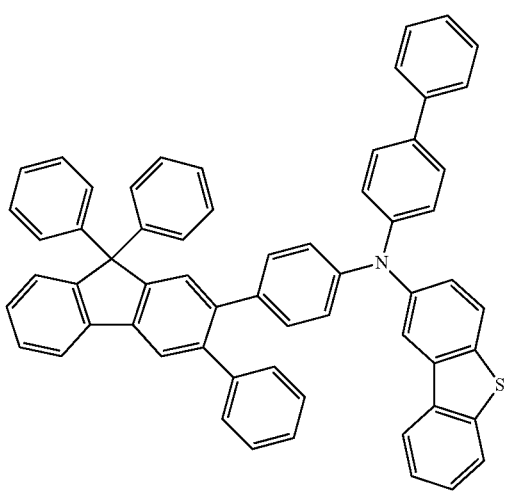
1-133
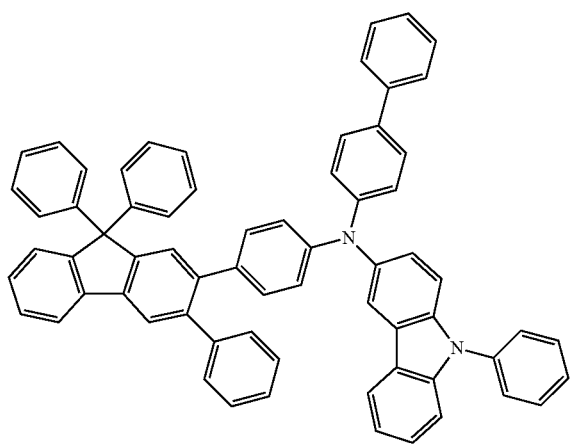
1-134
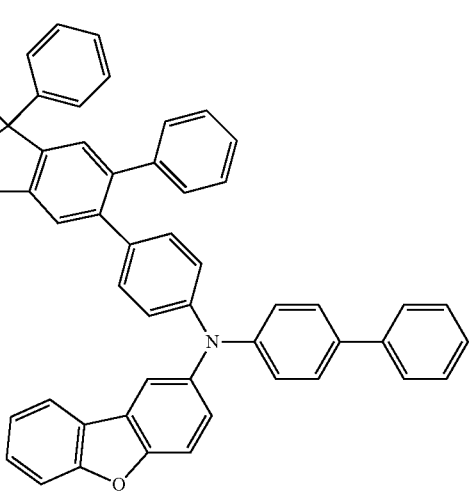

1-135
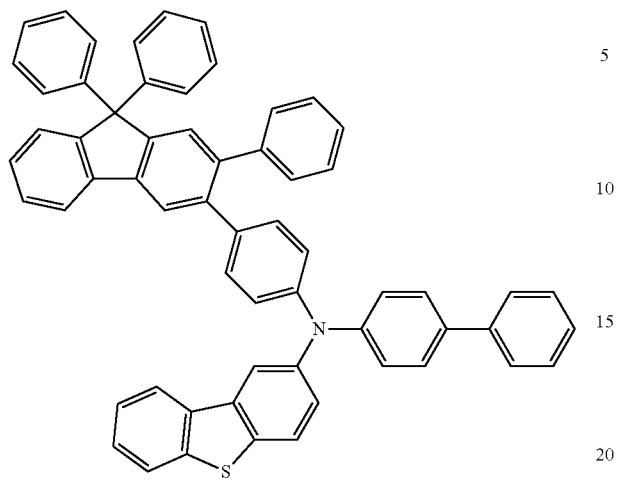
1-136
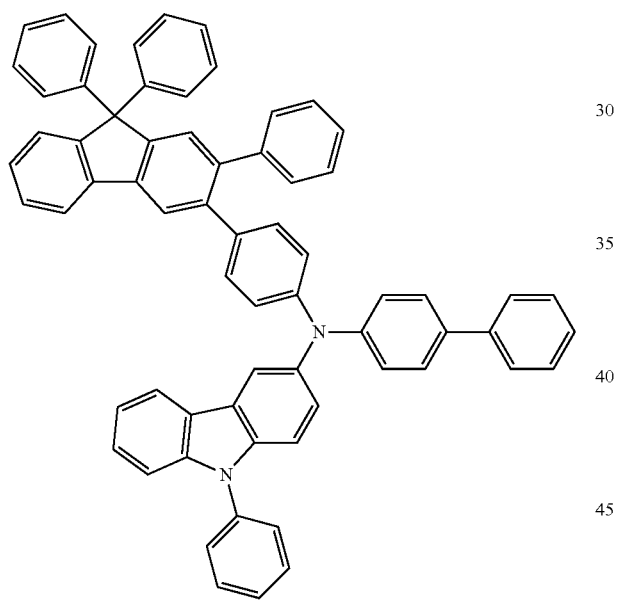
1-137
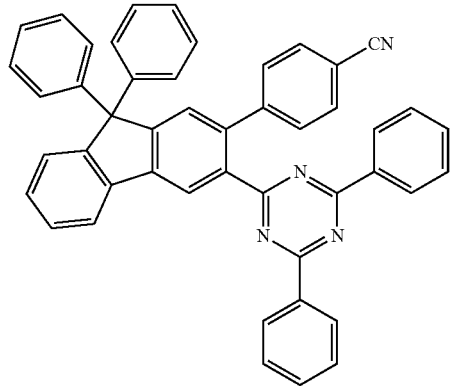
1-138
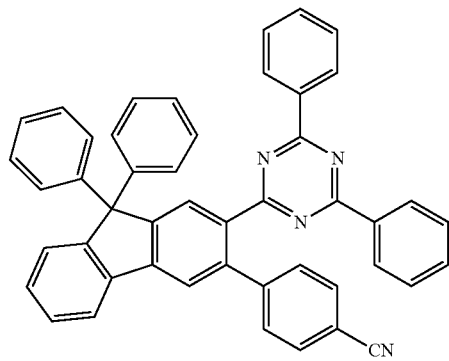
1-139
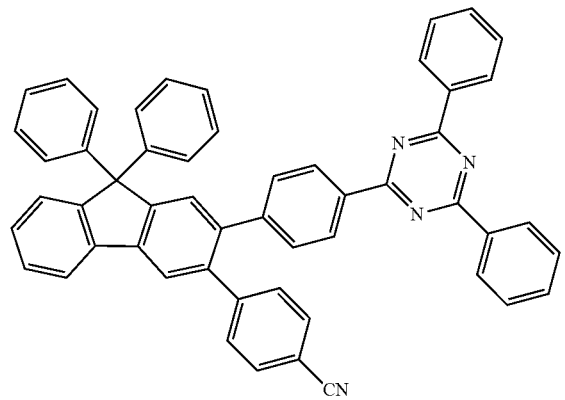
1-140
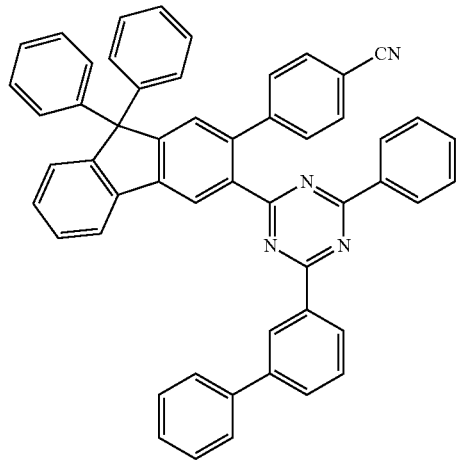

-continued
1-141
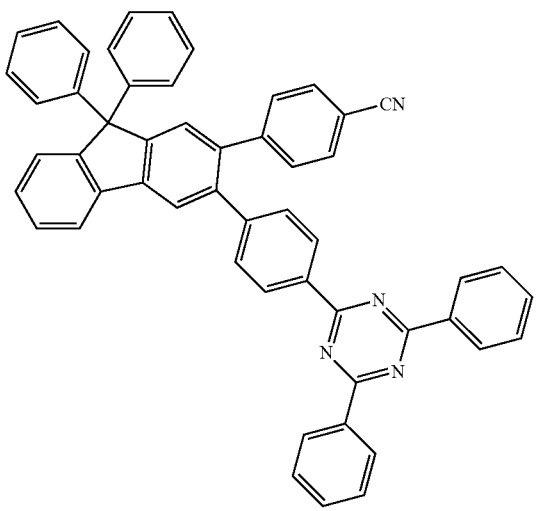
1-142
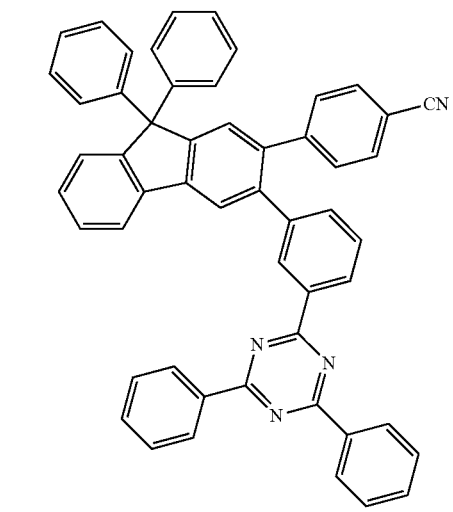
1-143
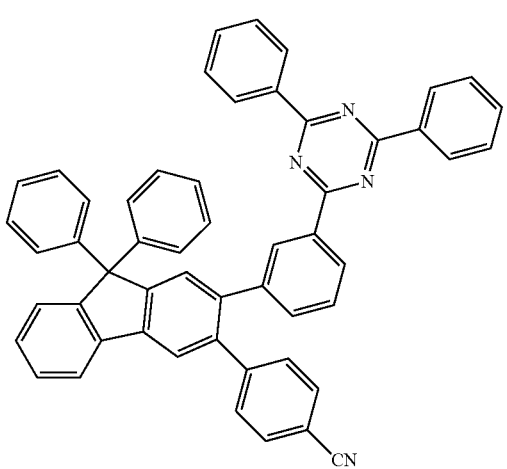
1-144
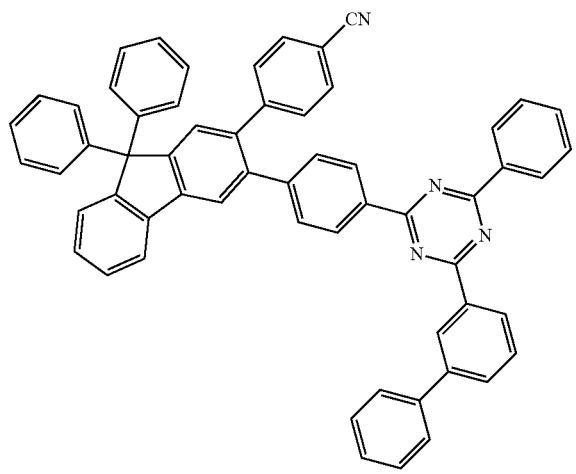
1-145
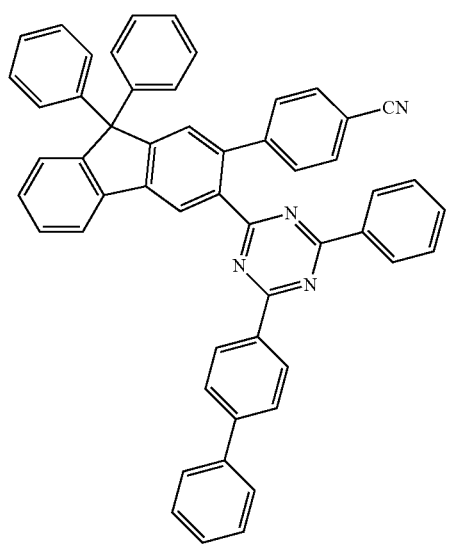
1-146
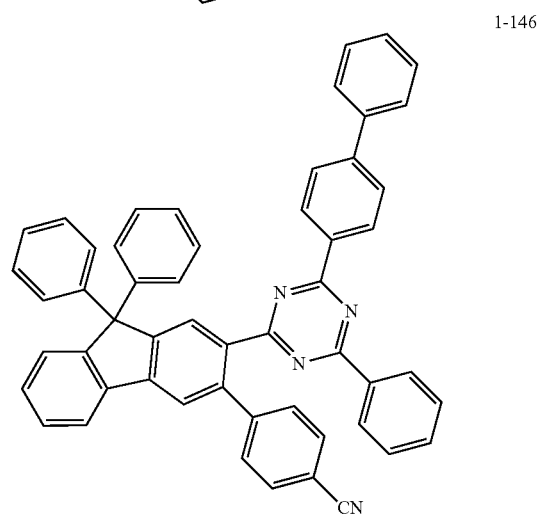

-continued
1-147
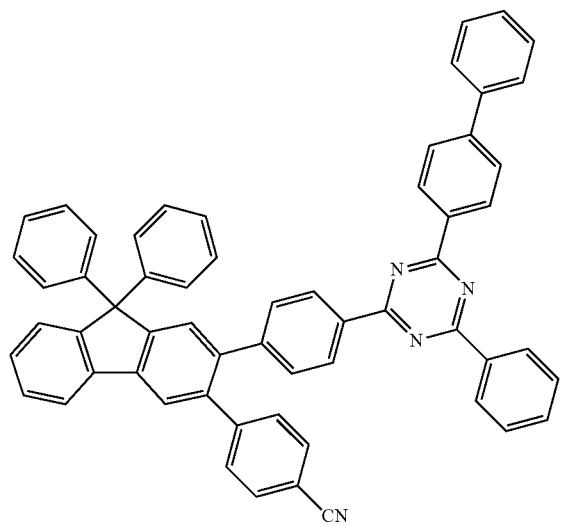
1-148
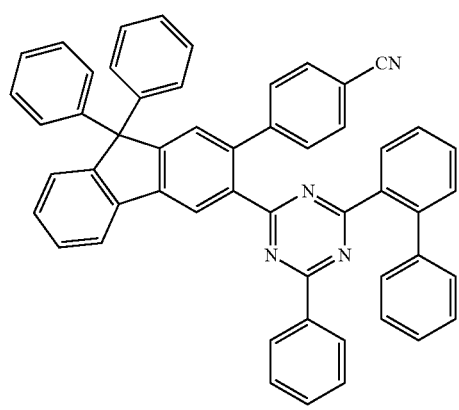
1-149
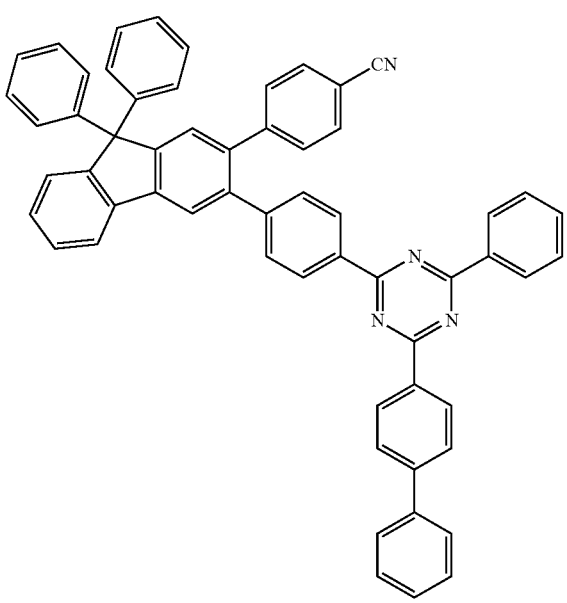
-continued
1-150
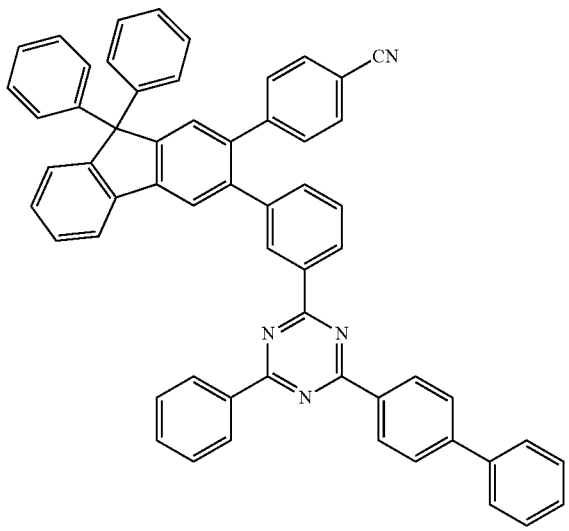
1-151
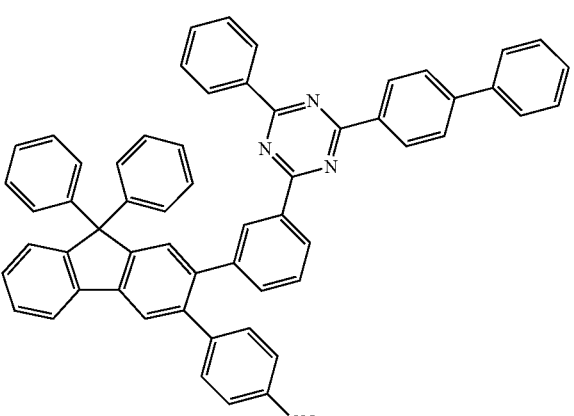
1-152
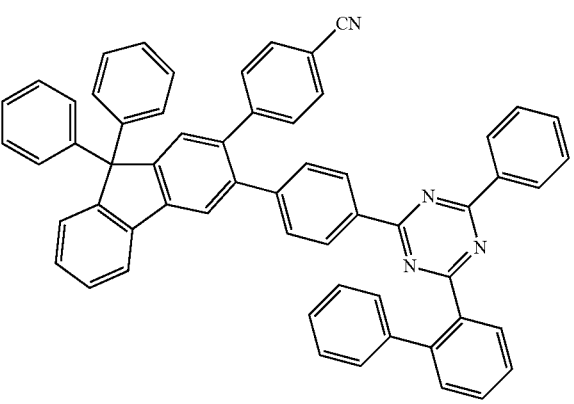

1-153
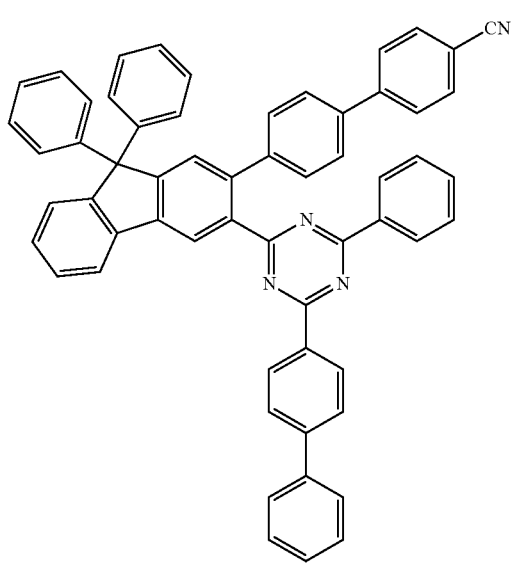
1-154
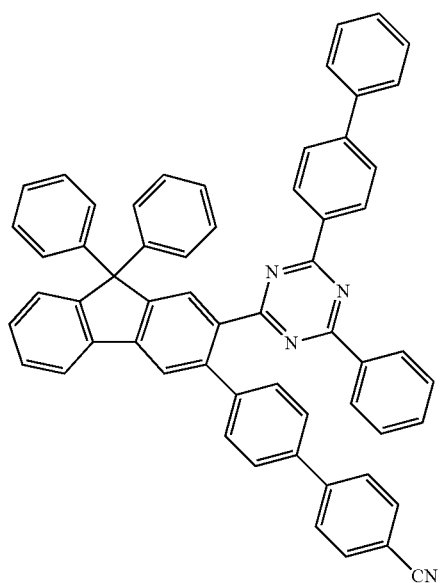
1-155
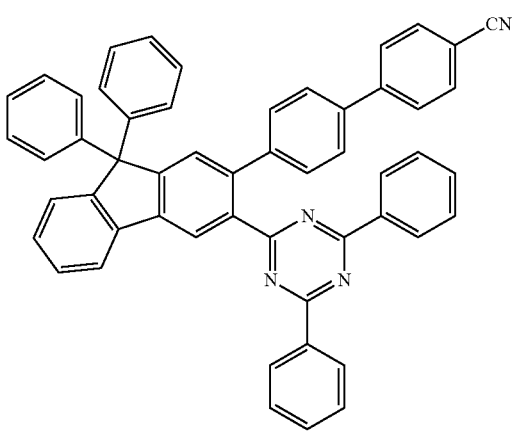
1-156
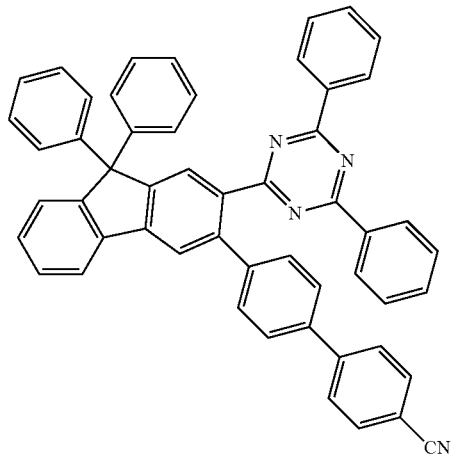
1-157
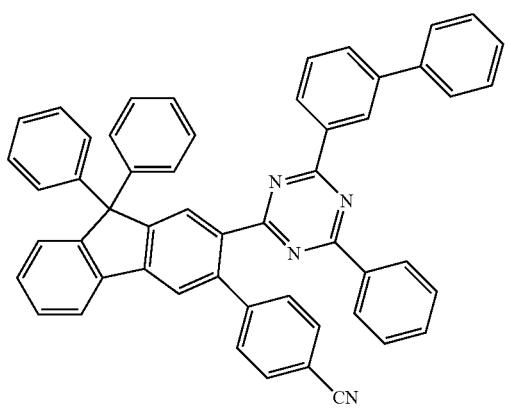
1-158
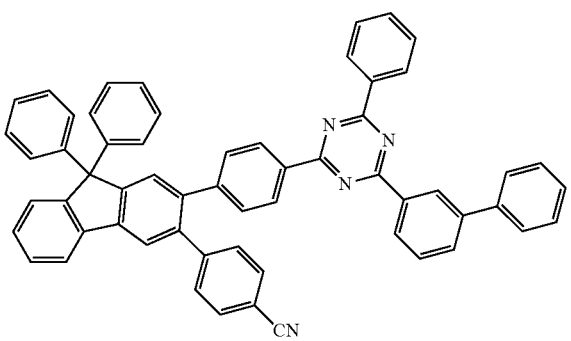

1-159
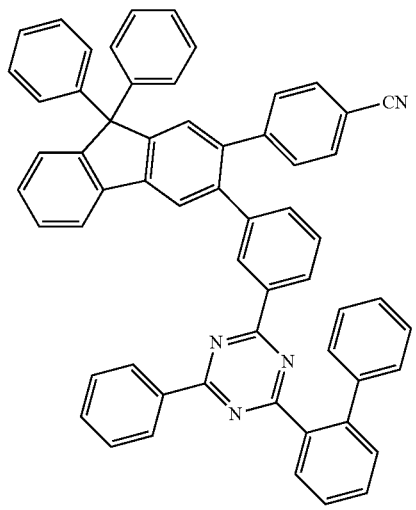
1-160
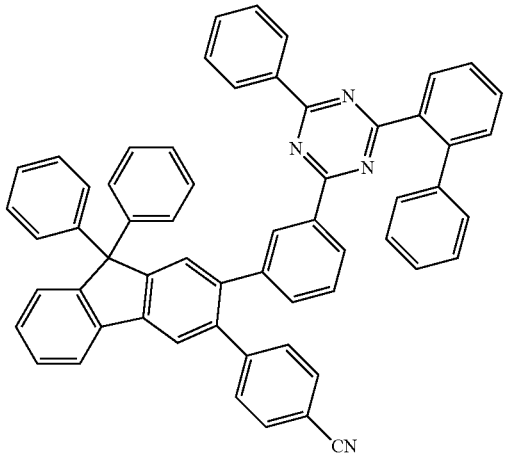
1-161
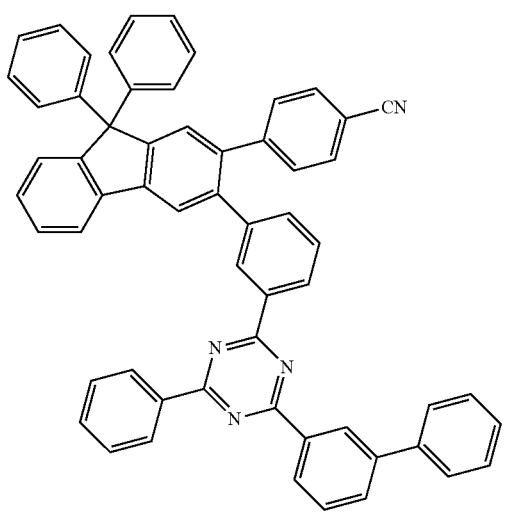
1-162
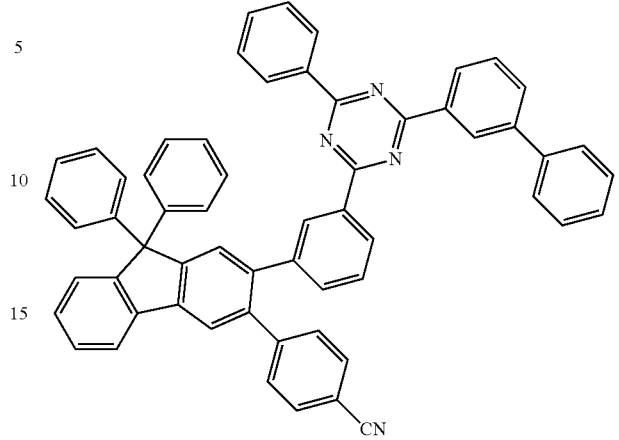
1-163
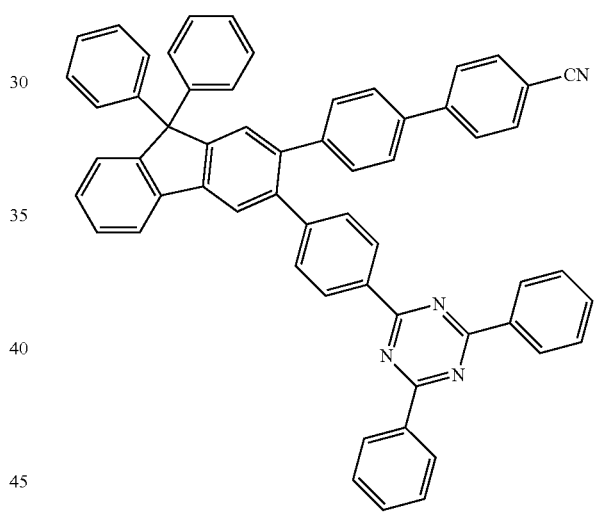
1-164
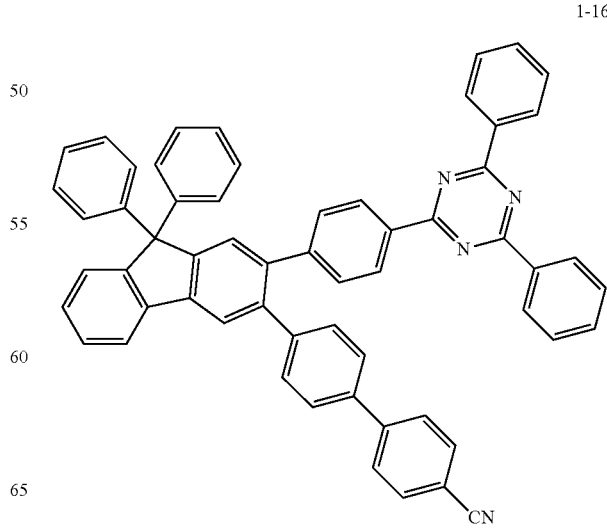

1-165
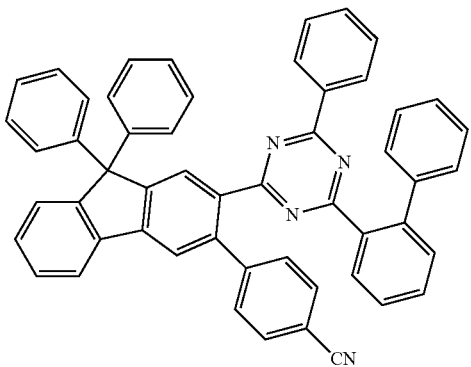
1-166
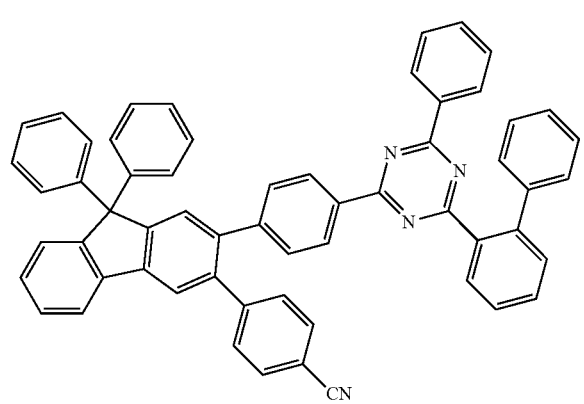
1-167
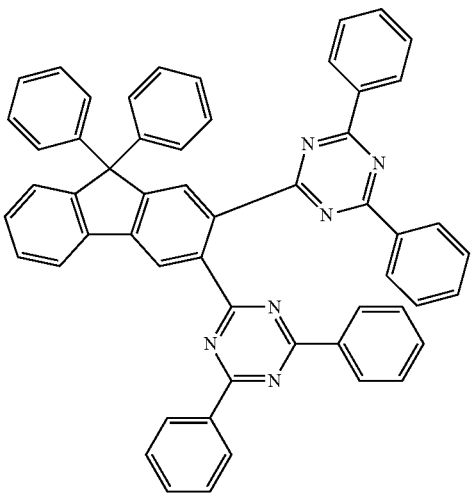
1-168
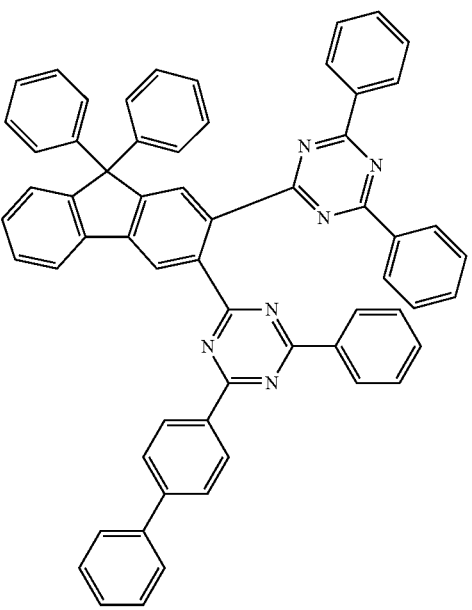
1-169
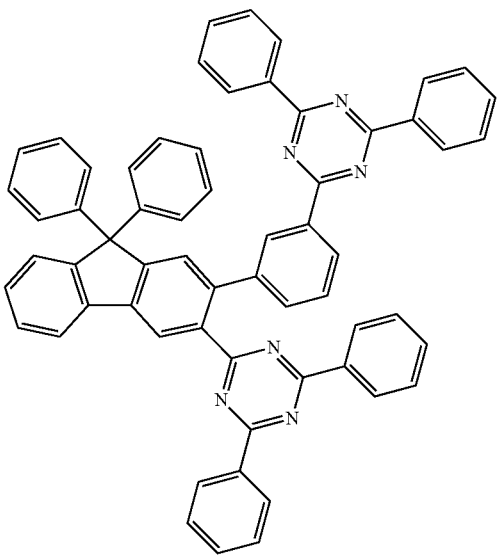
1-170
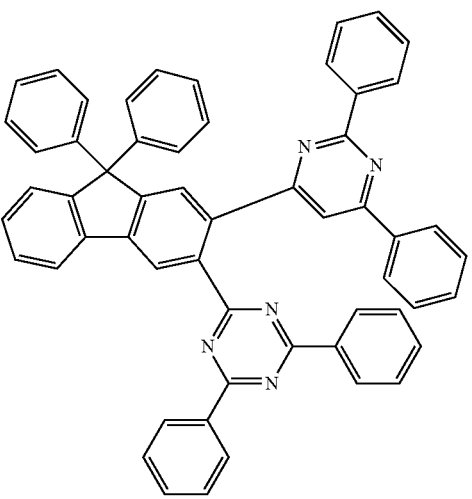

-continued
1-171
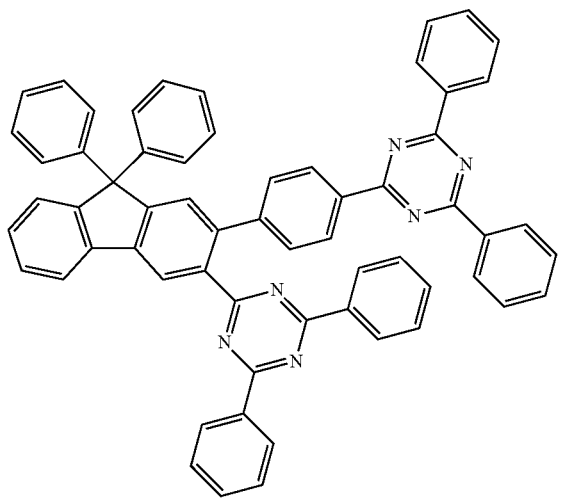
1-172
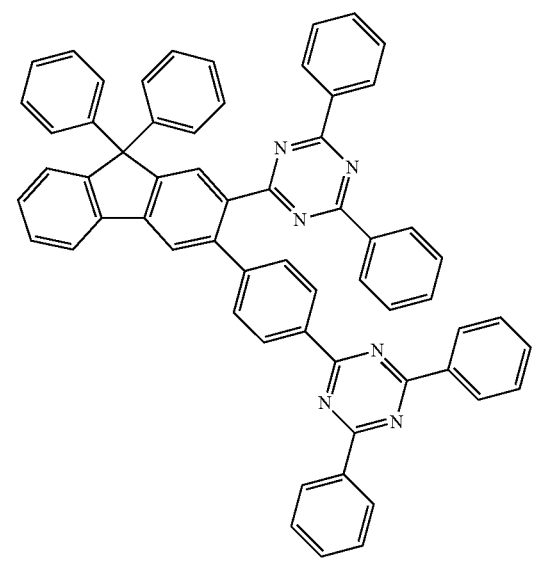
1-173
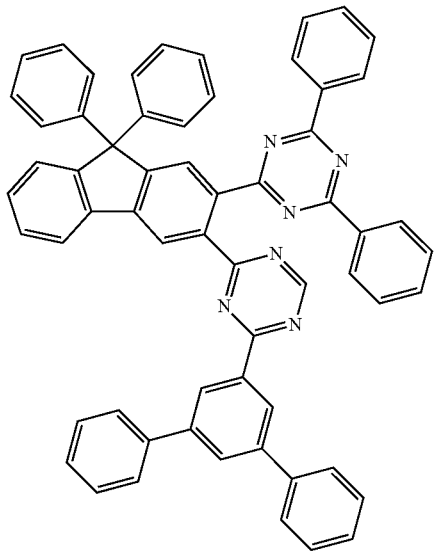
1-174
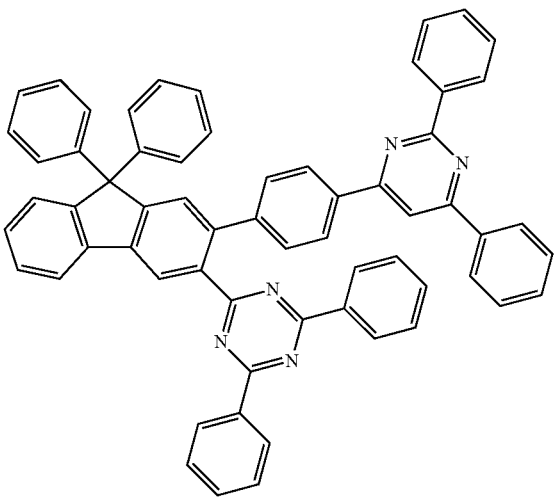
1-175
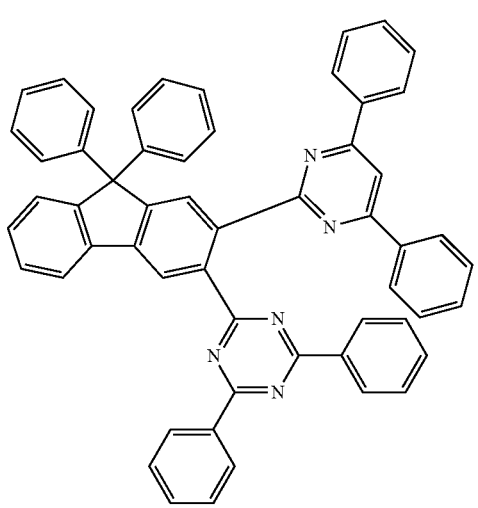
1-176
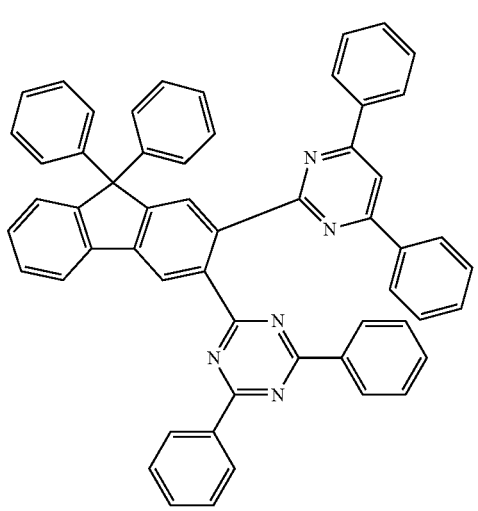

1-177
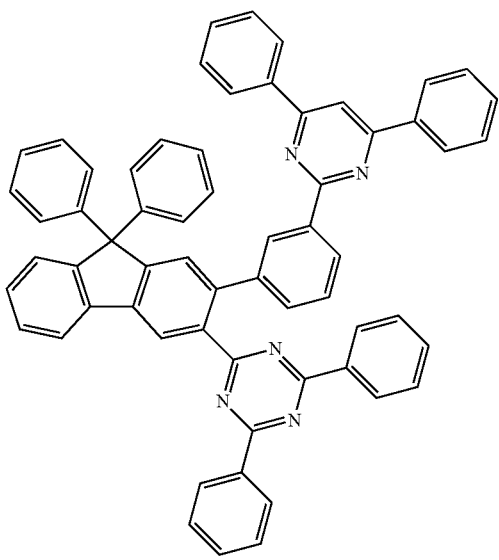
1-178
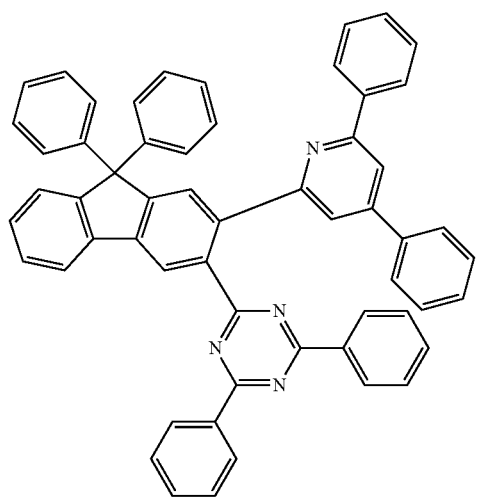
1-179
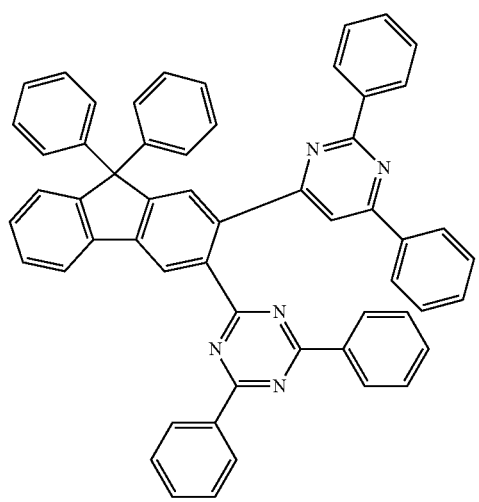
1-180
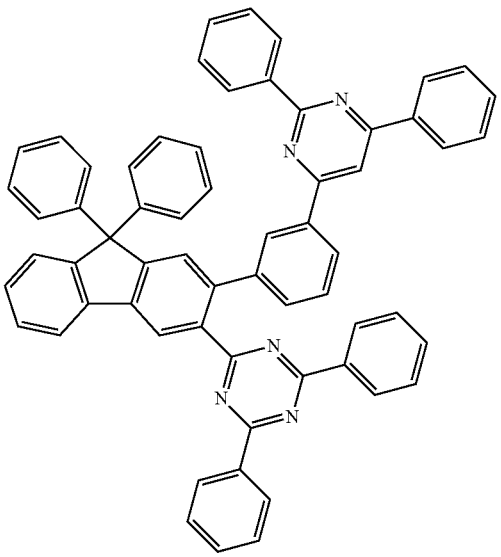
1-181
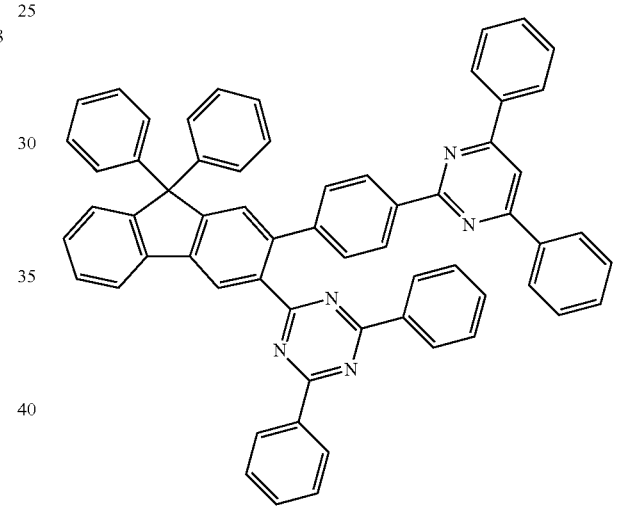
1-182
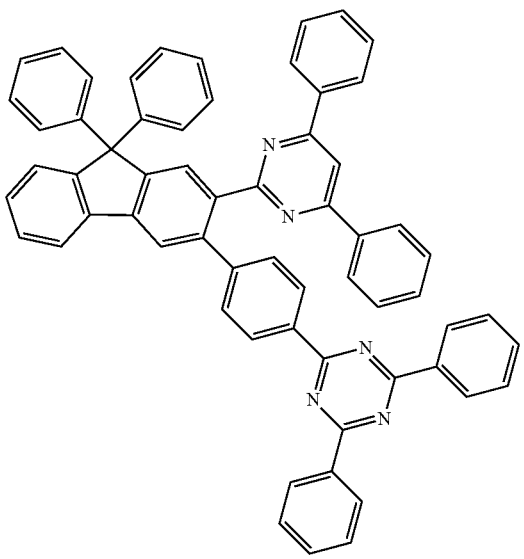

1-183
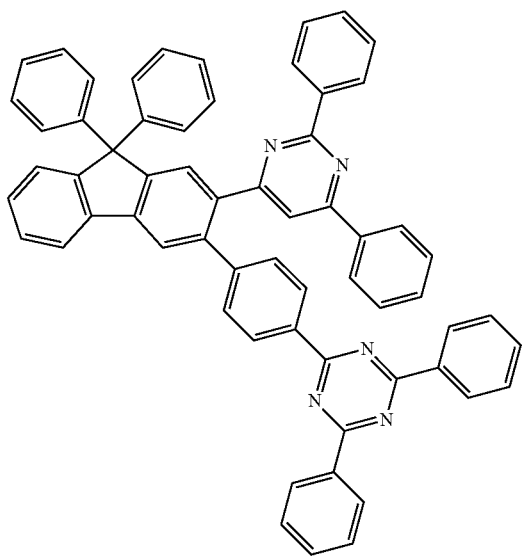
1-184
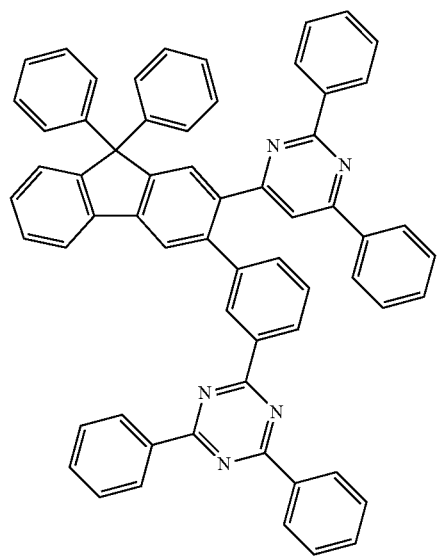
1-185
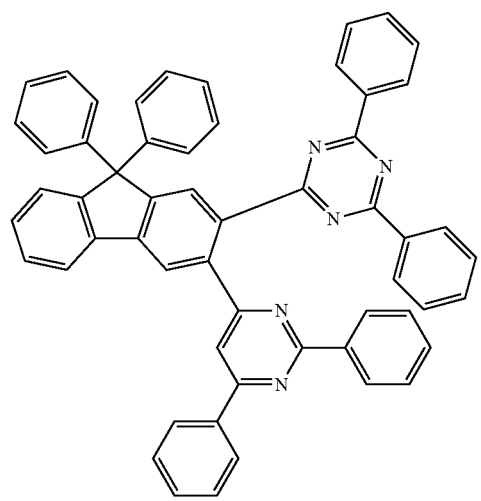
1-186
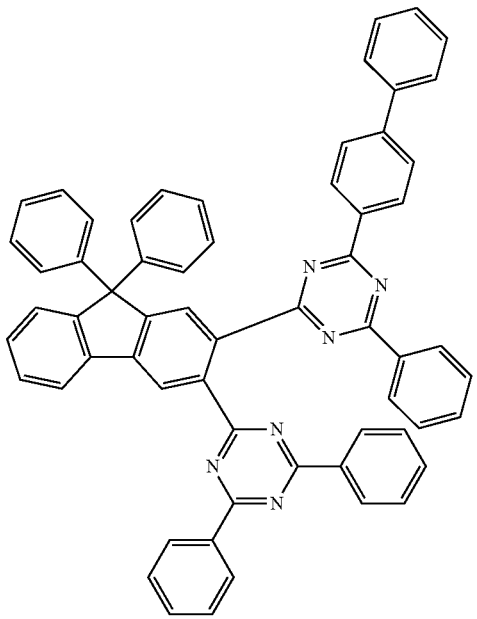
1-187
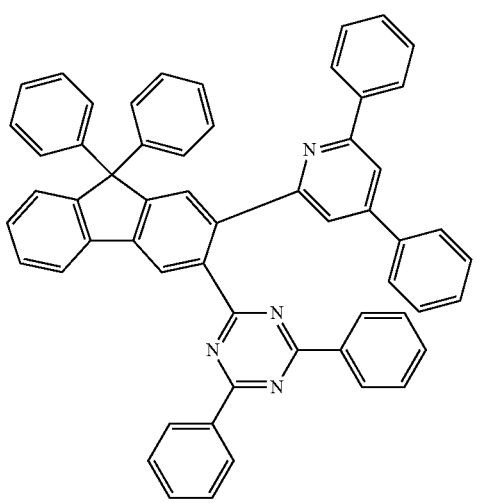
1-188
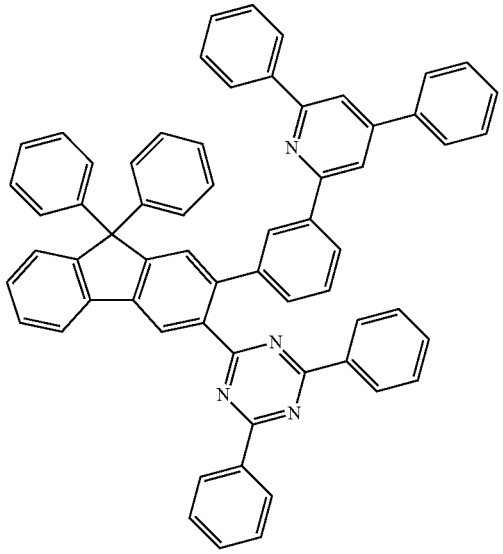

1-189
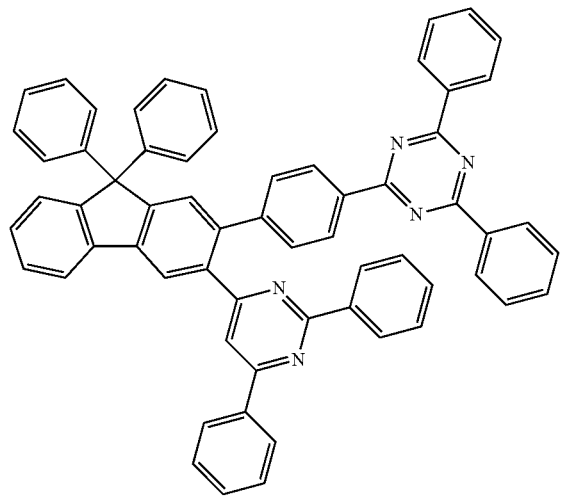
1-190
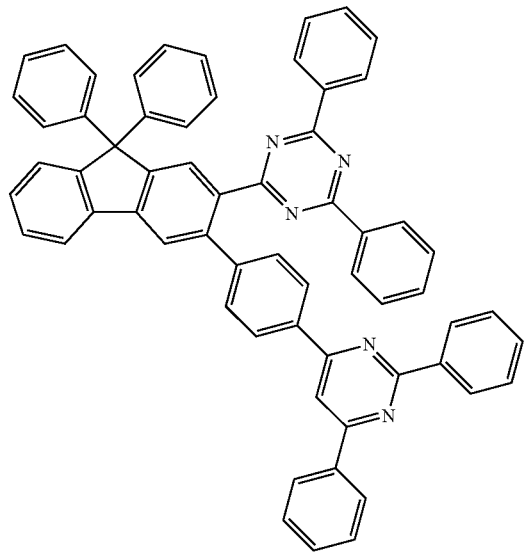
1-191
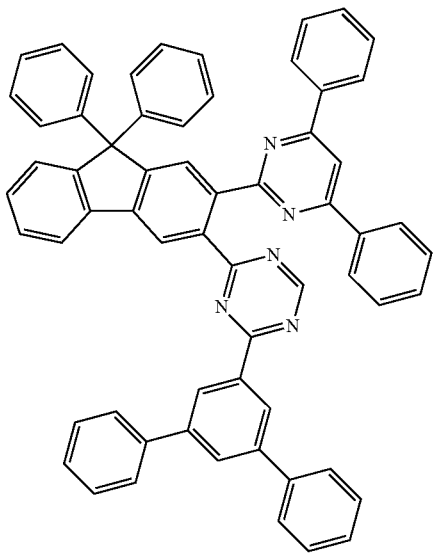
1-192
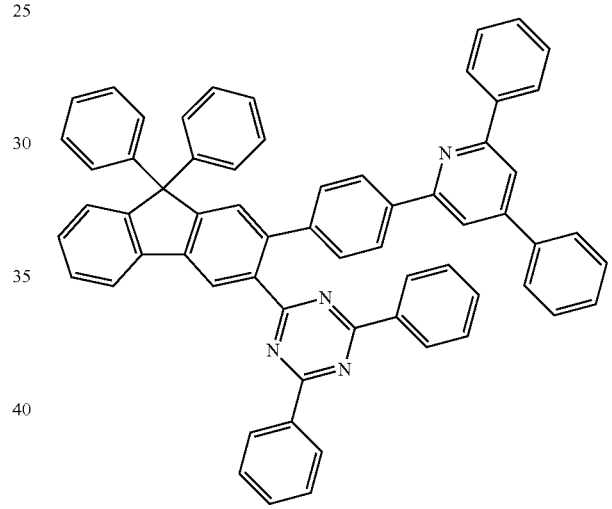
1-193
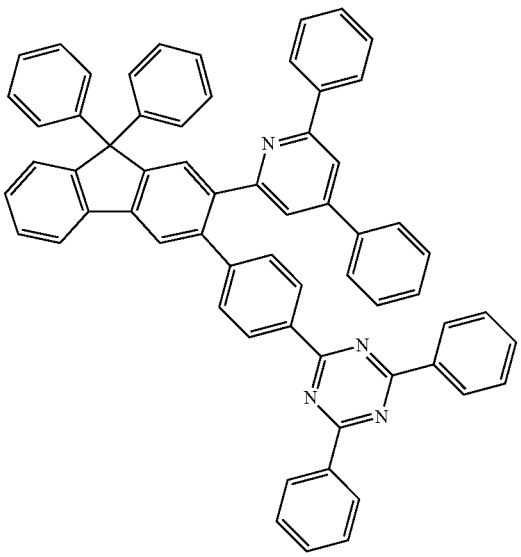

1-194
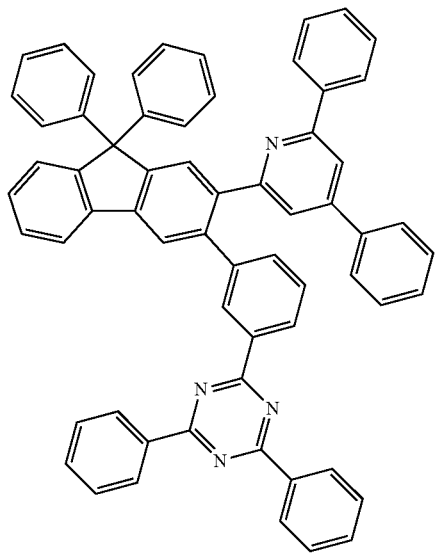
1-195
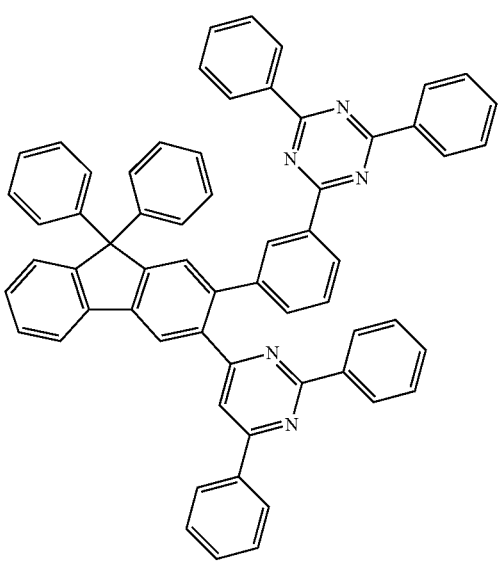
1-196
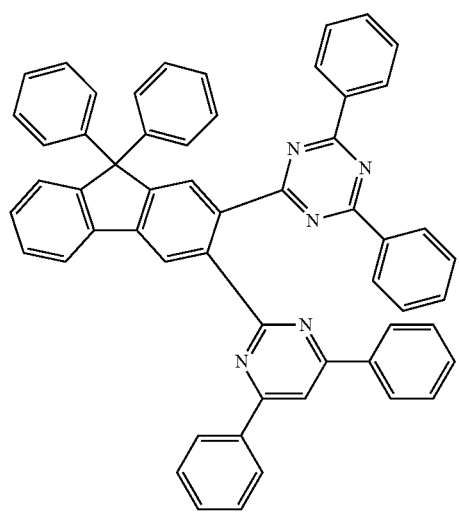
1-197
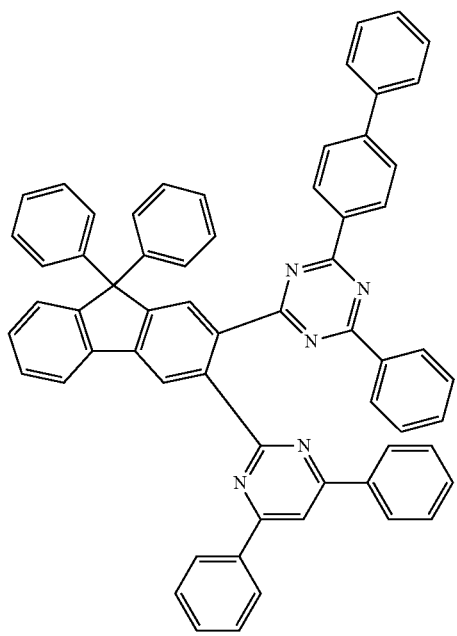
1-198
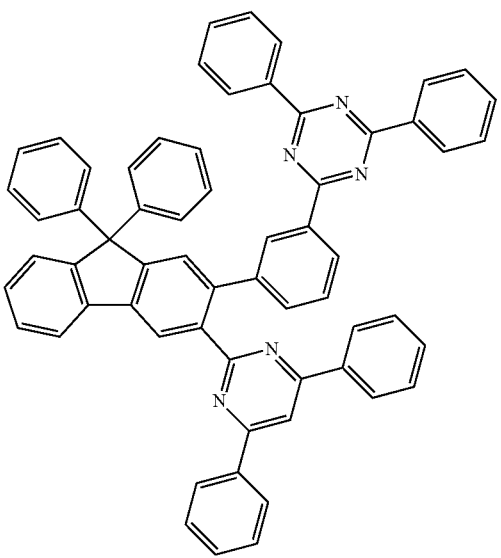

1-199
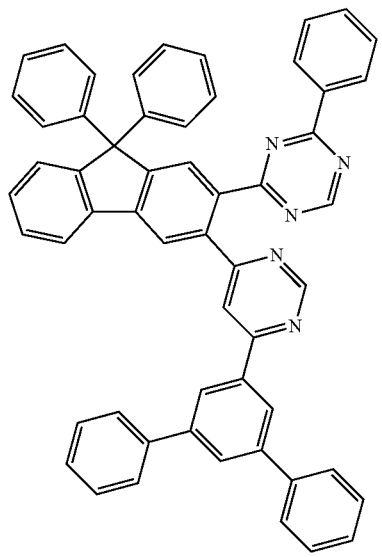
1-202
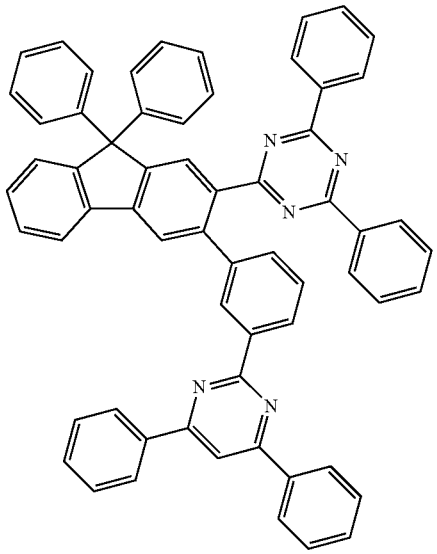
1-200
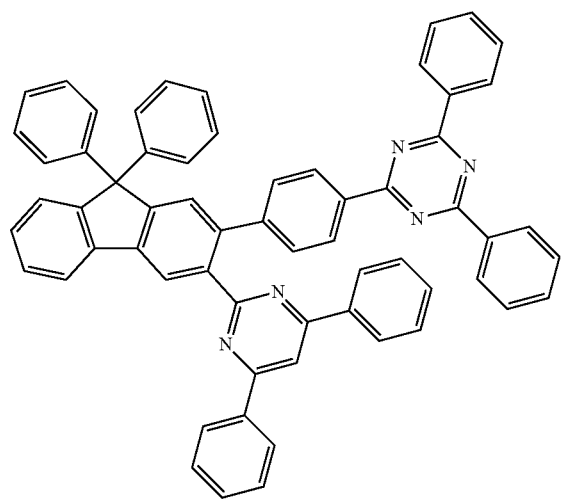
1-203
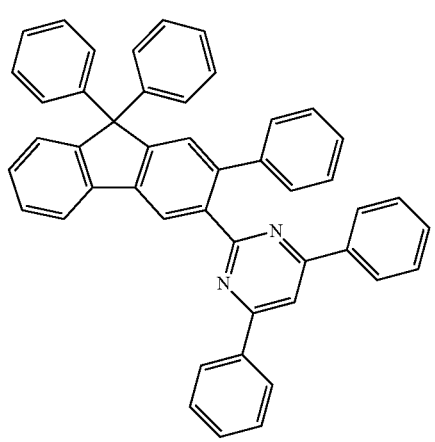
1-201
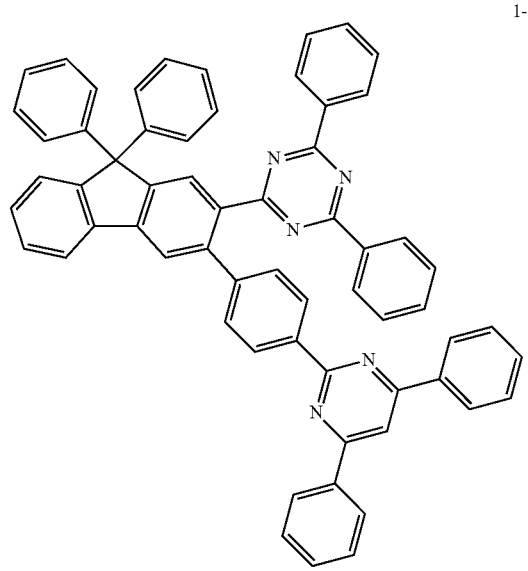
1-204
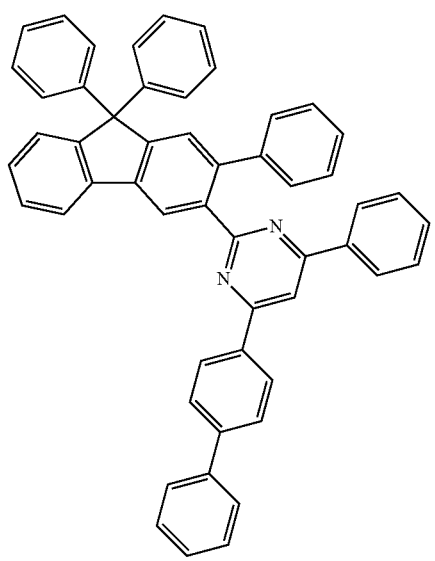

-continued
1-205
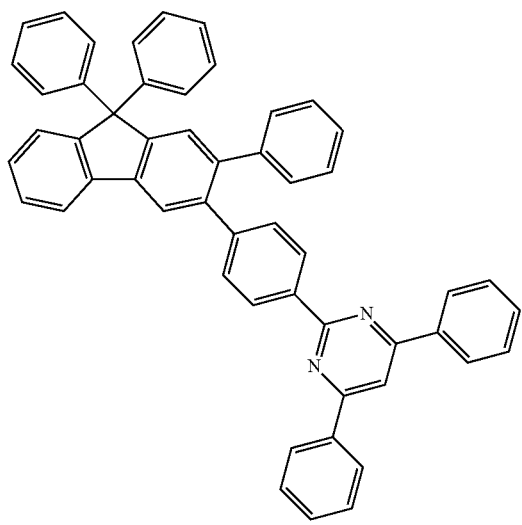
1-208
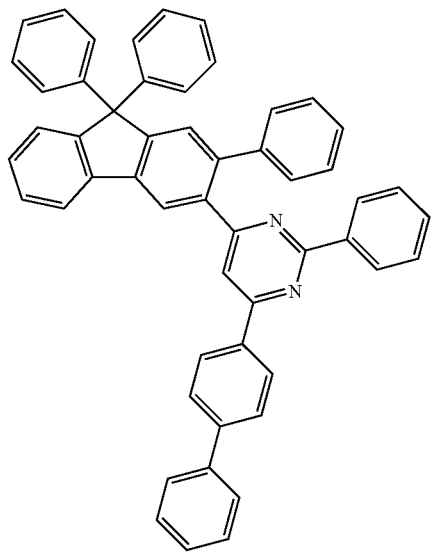
1-206
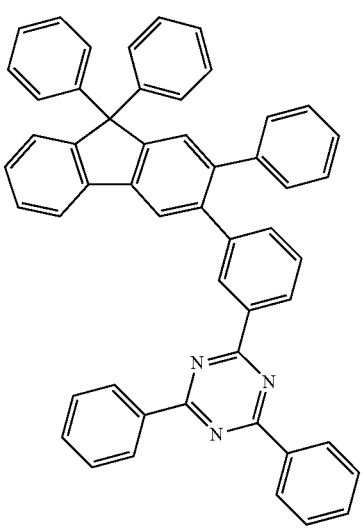
1-209
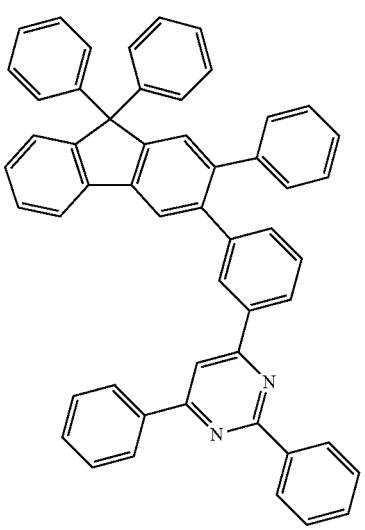
1-207
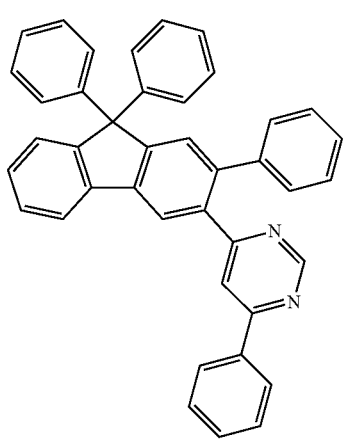
1-210

1-211
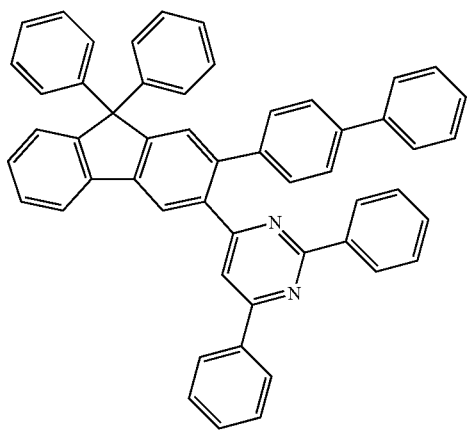
1-212
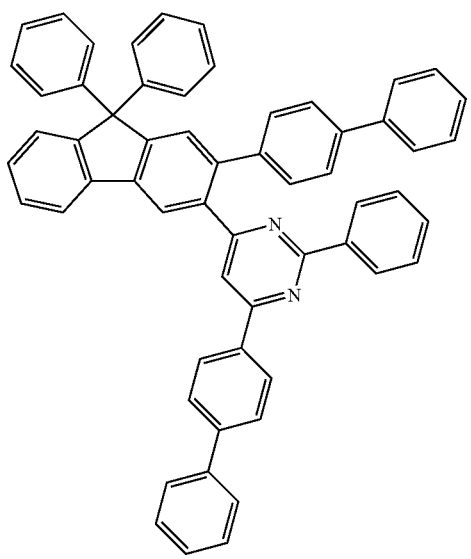
1-213
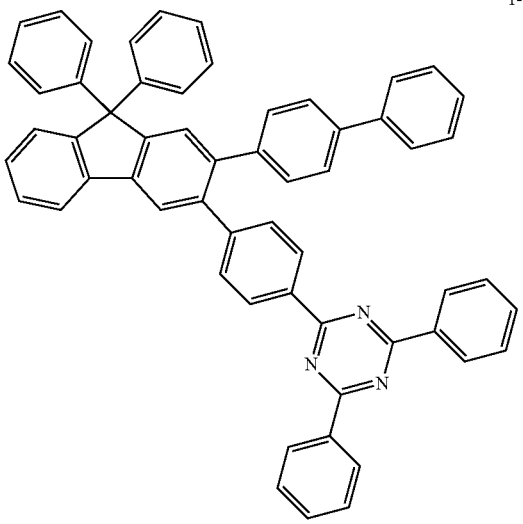
1-214
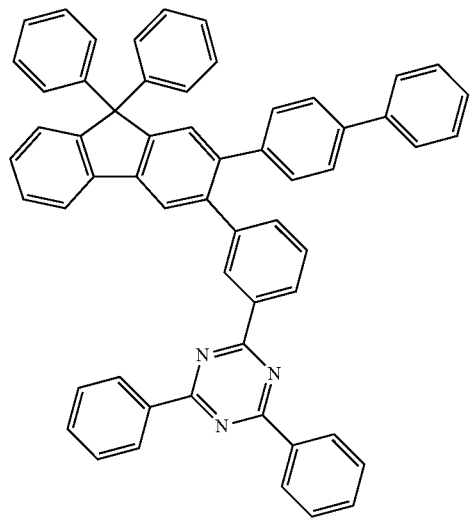
1-215
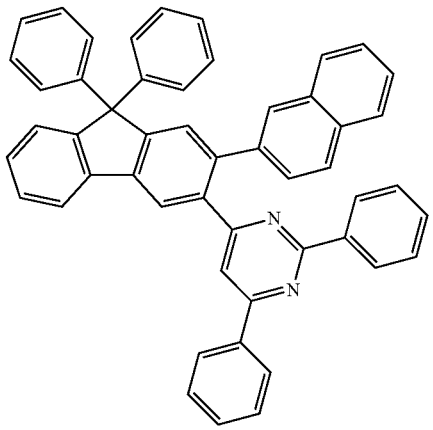
1-216
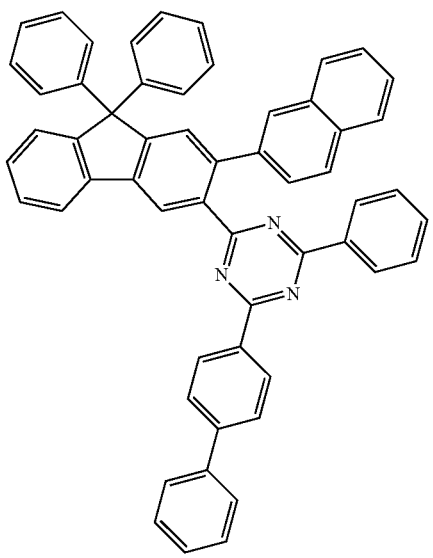

1-217
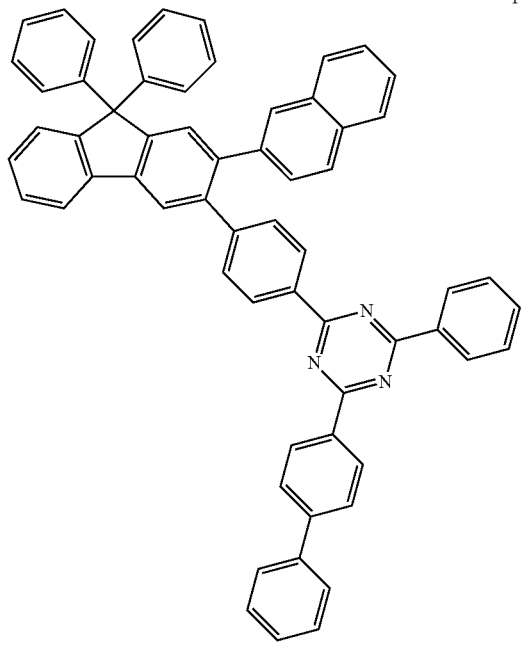
1-218
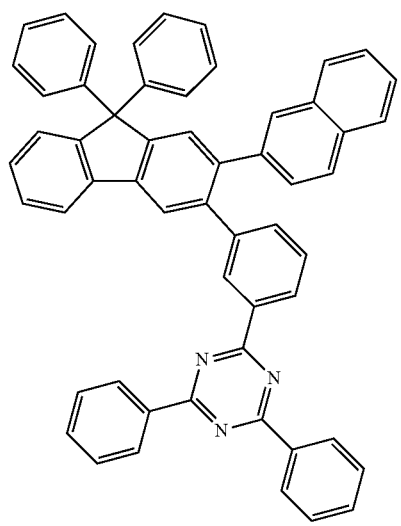
1-219
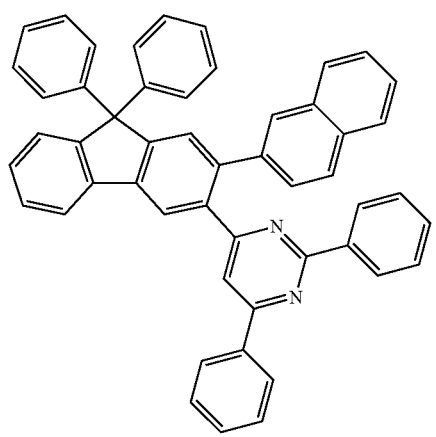
1-220
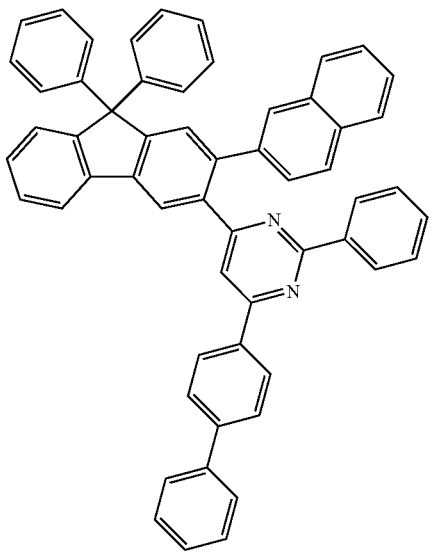
1-221
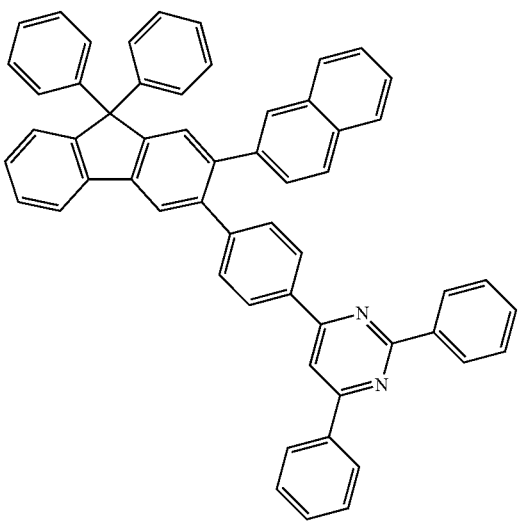
1-222
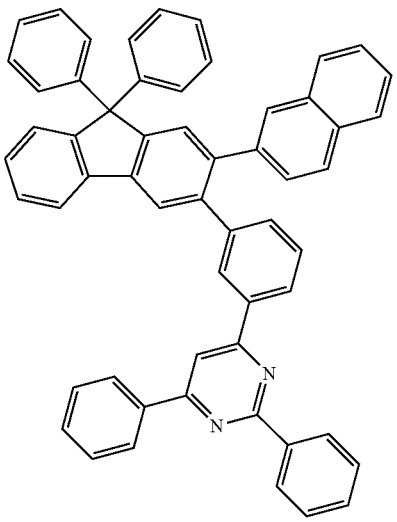

1-223
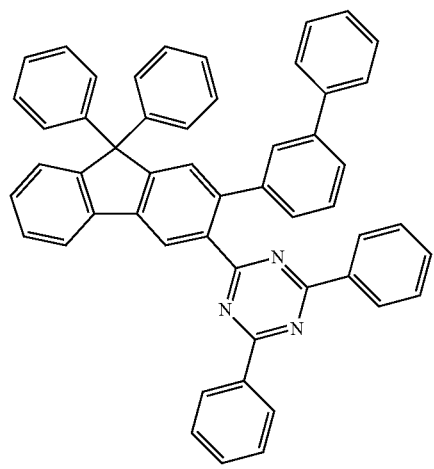
1-224
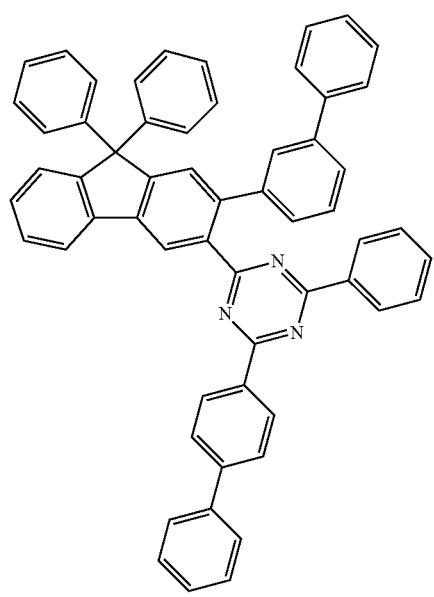
1-225
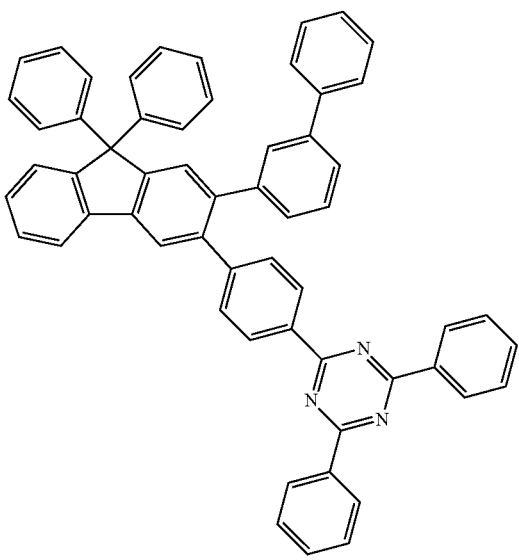
1-226
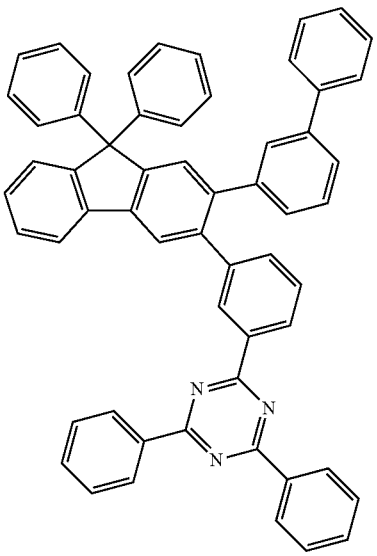
1-227
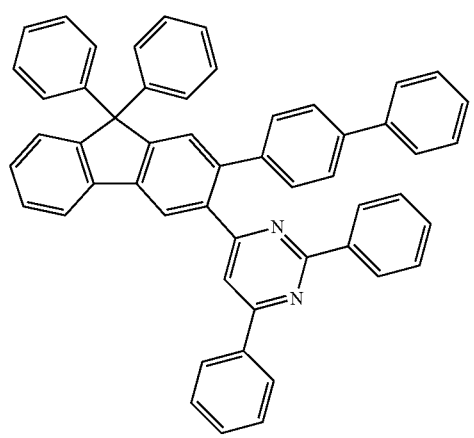
1-228
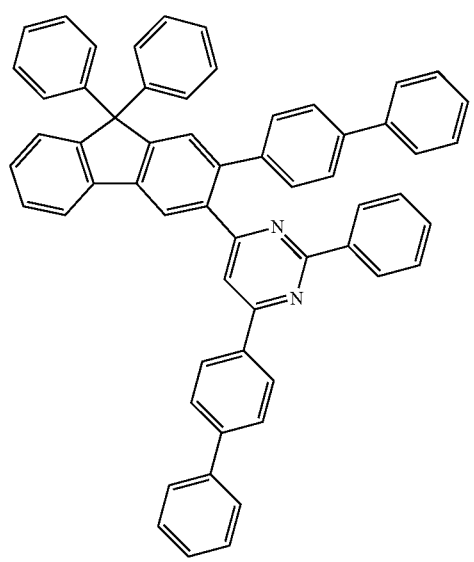

1-229
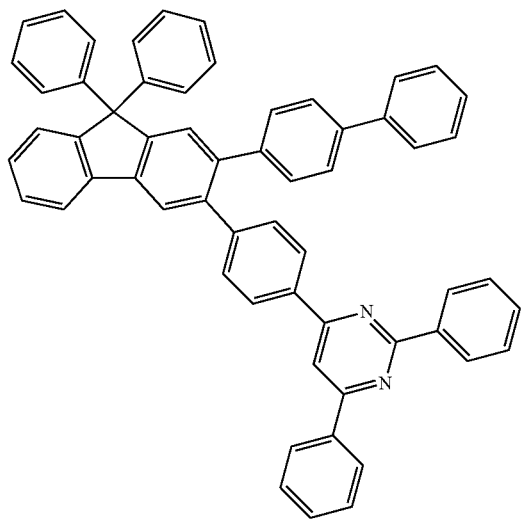
1-230
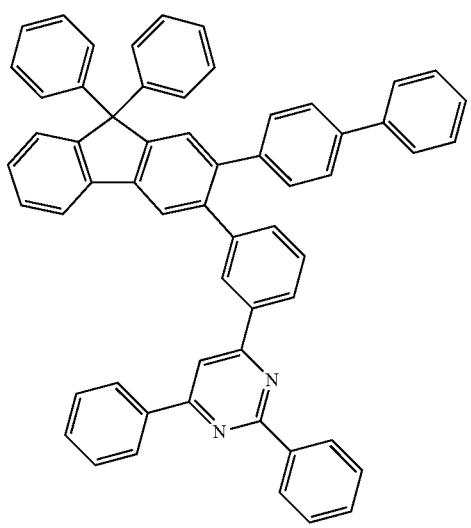
1-231
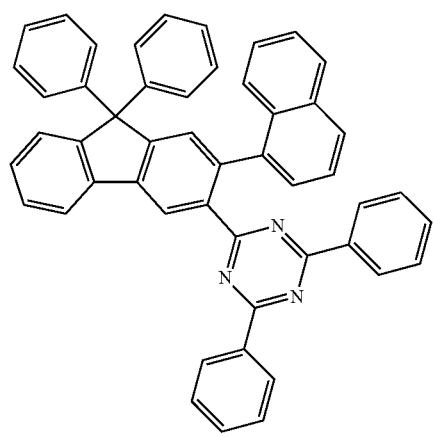
1-232
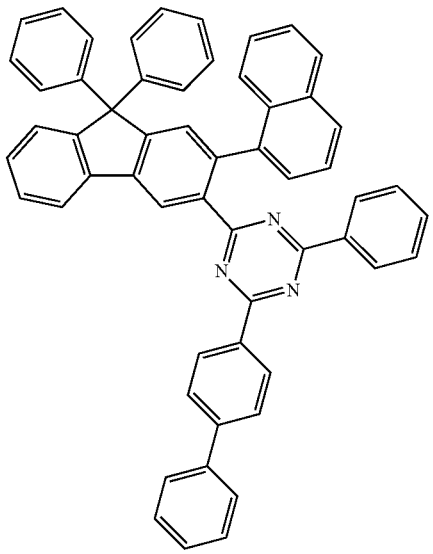
1-233
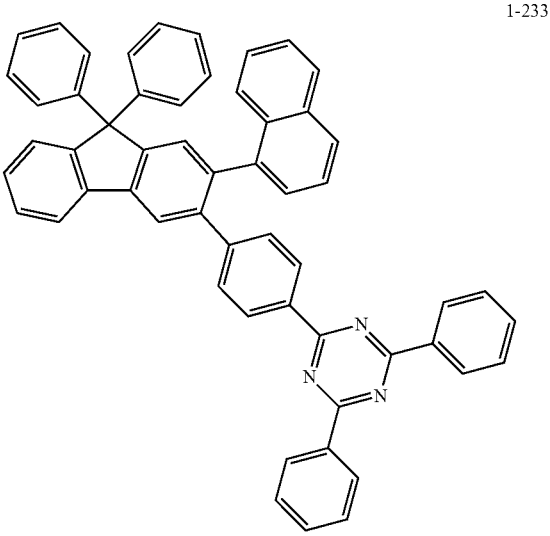
1-234
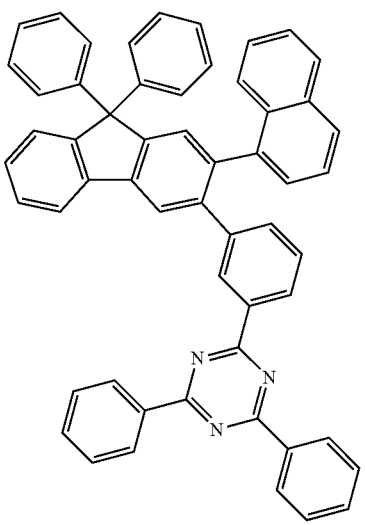

-continued
1-235
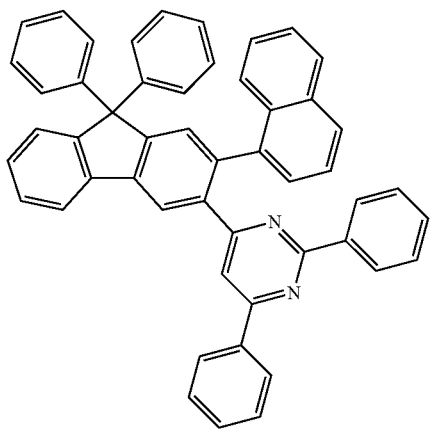
1-236
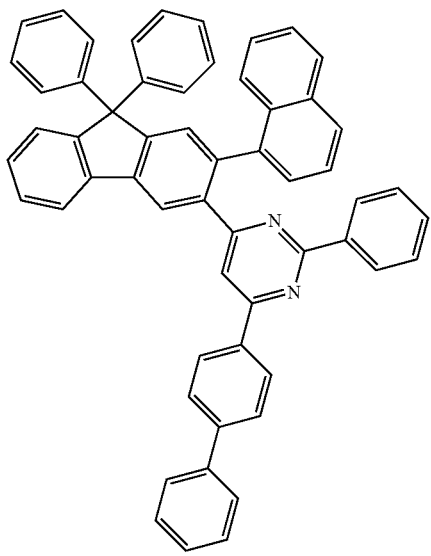
1-237
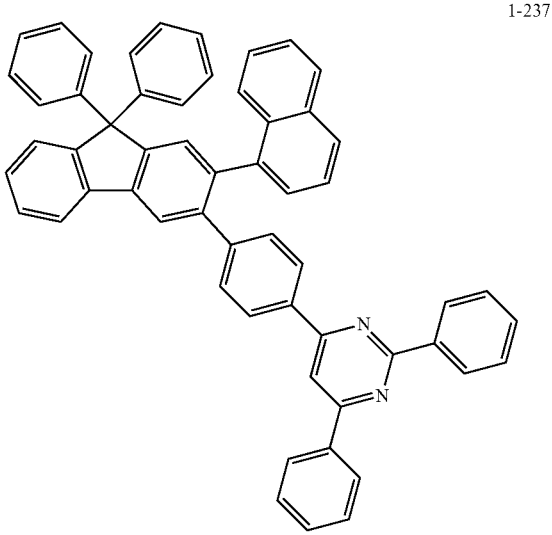
-continued
1-238
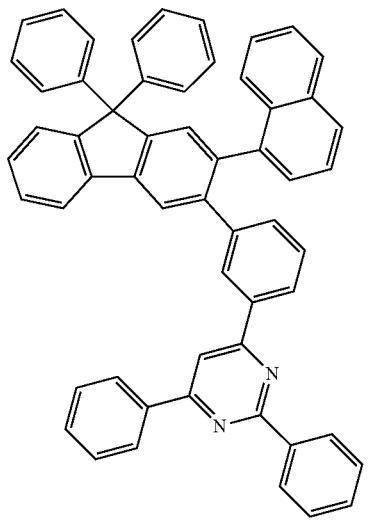
1-239
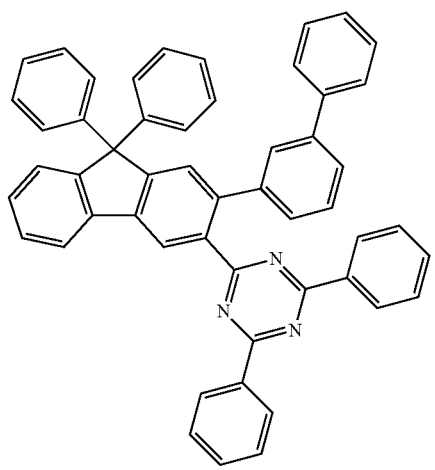
1-240
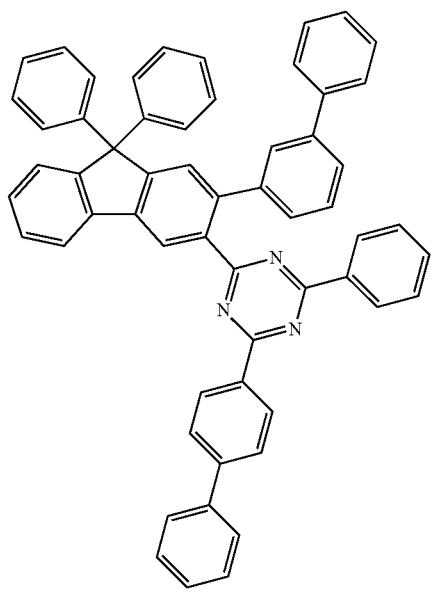

1-241
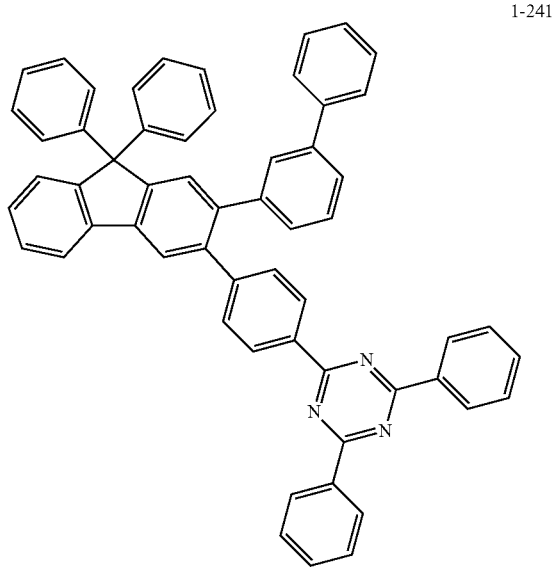
1-244
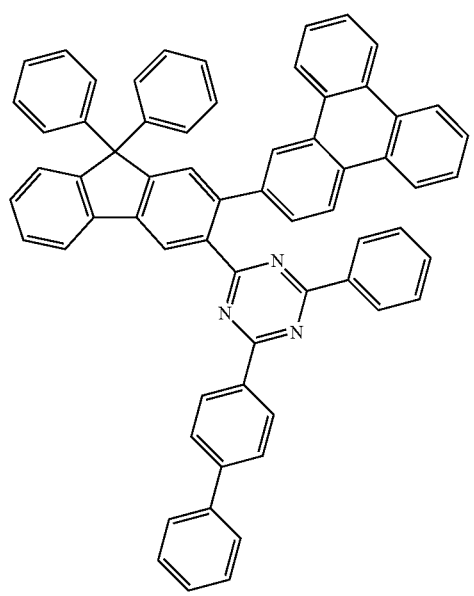
1-242
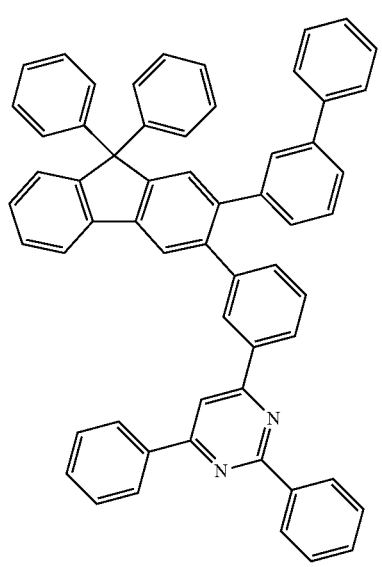
1-243
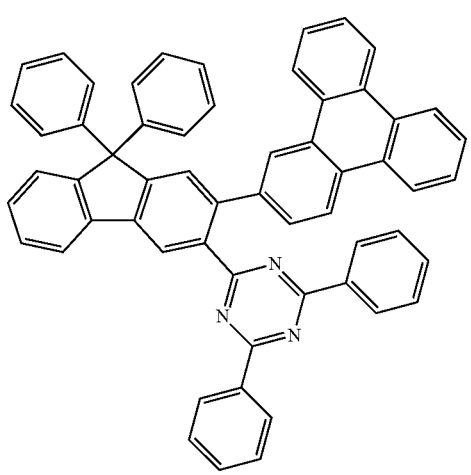
1-245
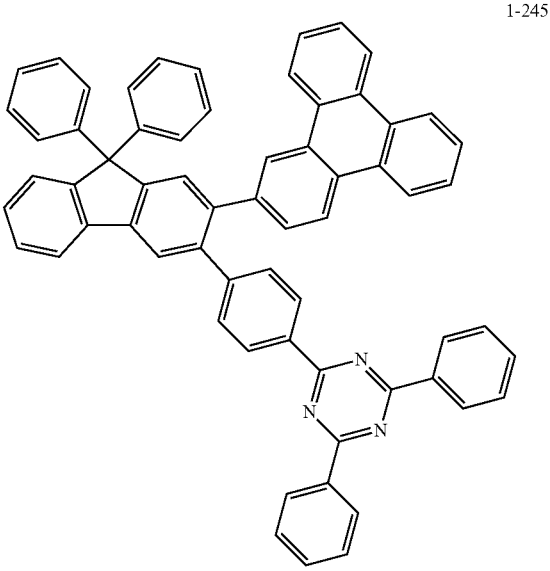

1-246
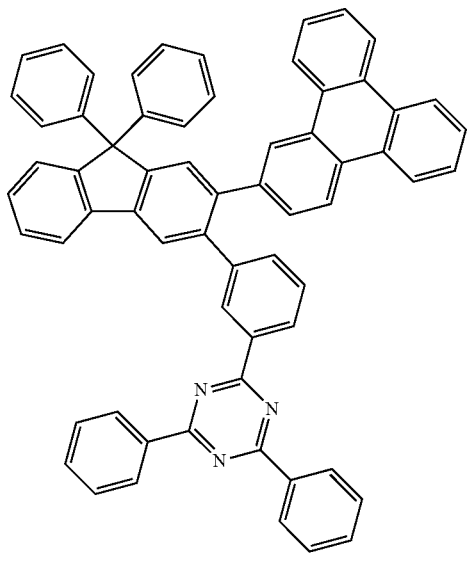
1-249
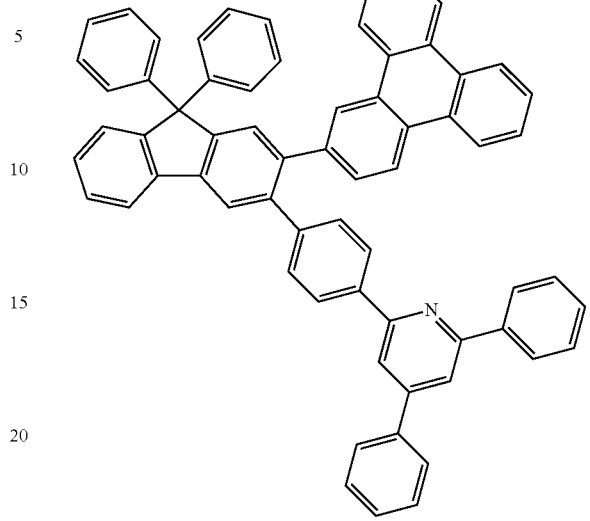
1-247
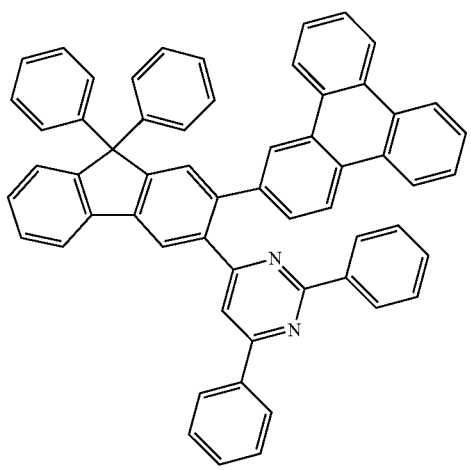
1-250
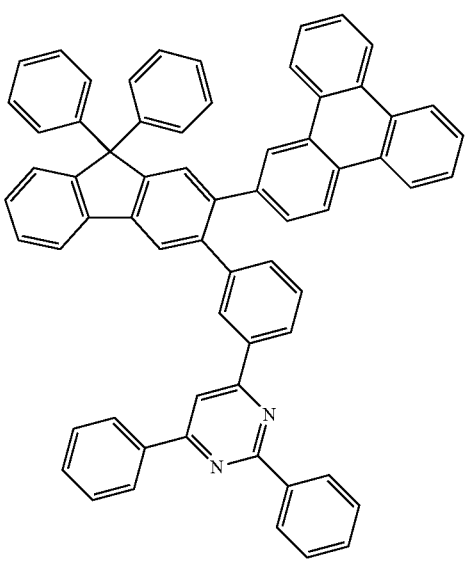
1-248
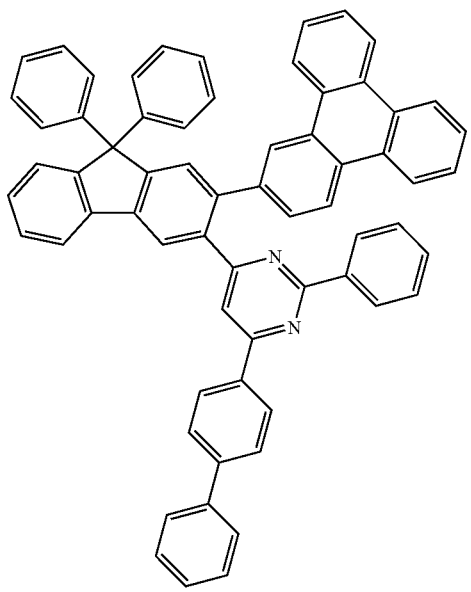
1-251
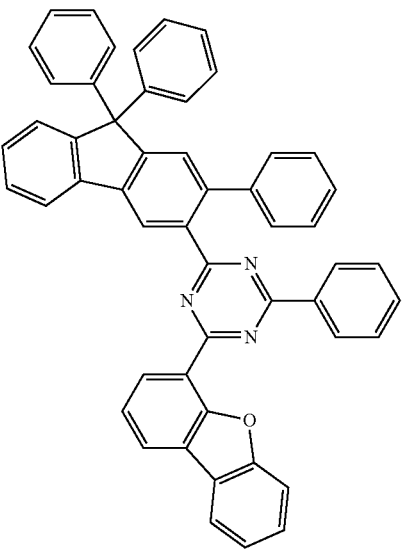

1-252
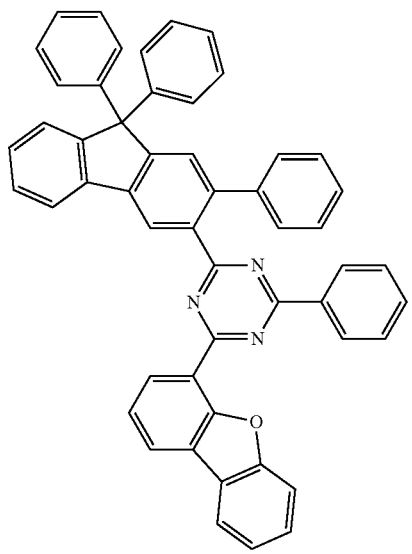
1-253
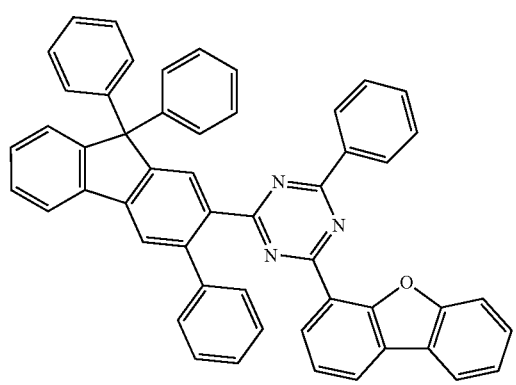
1-254
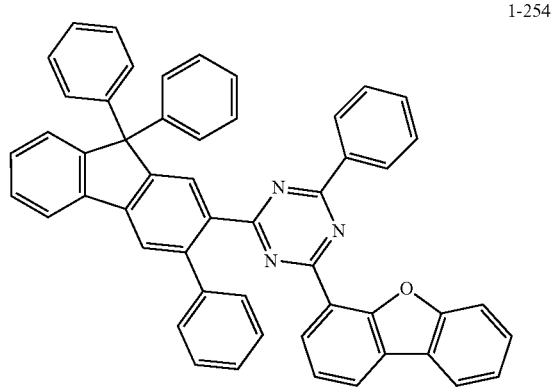
1-255
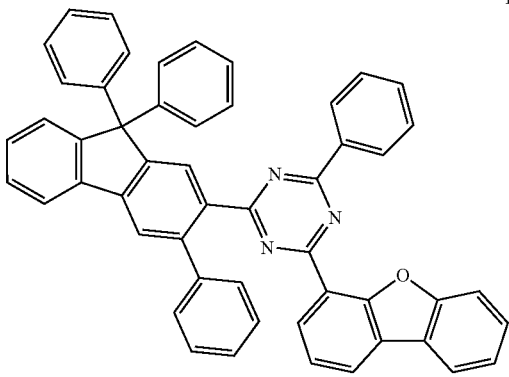
1-256
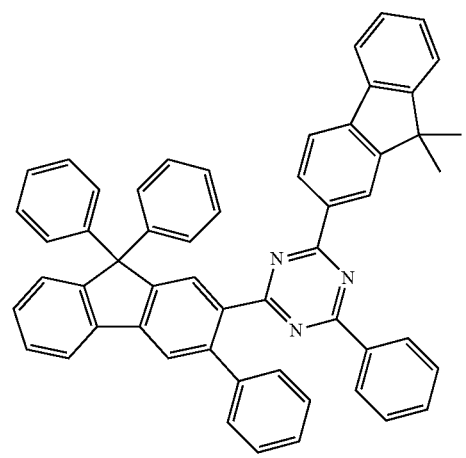
1-257
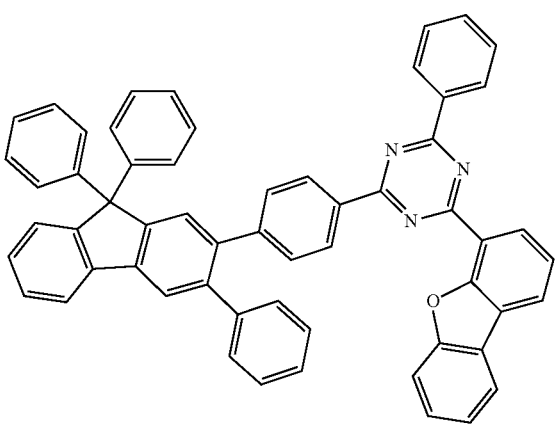
1-258

-continued
1-259
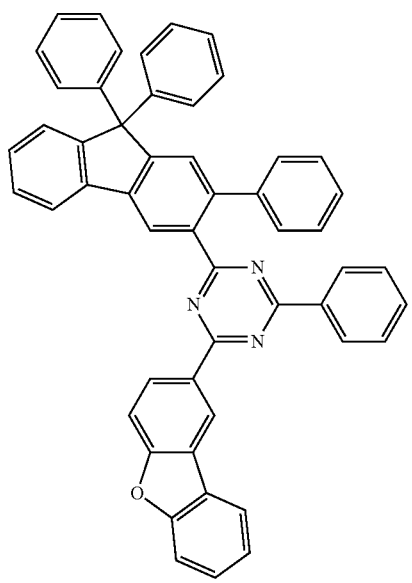
1-260
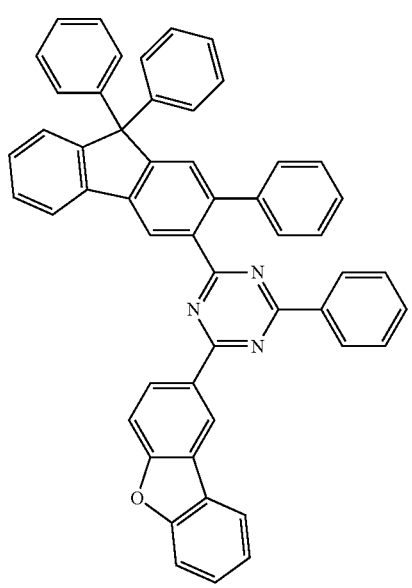
1-261
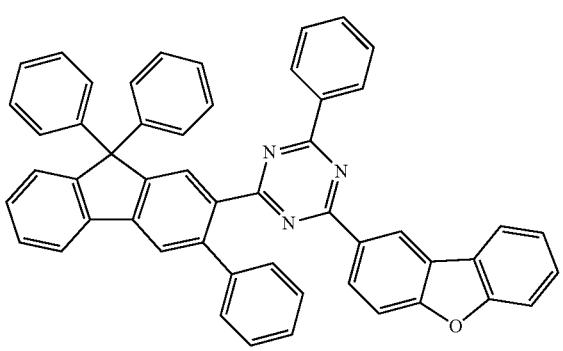
-continued
1-262
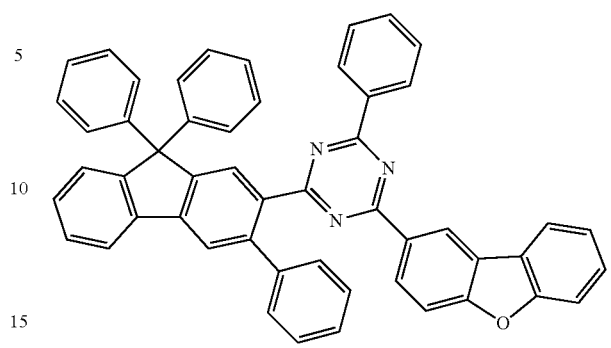
1-263
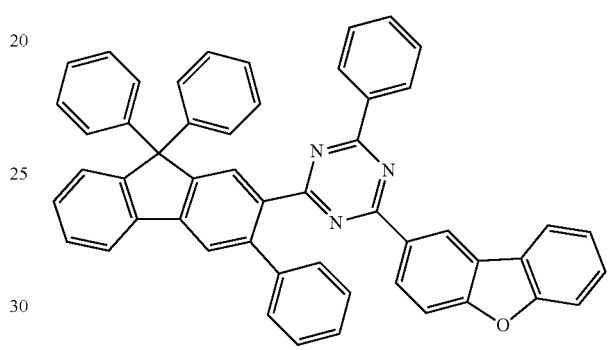
1-264
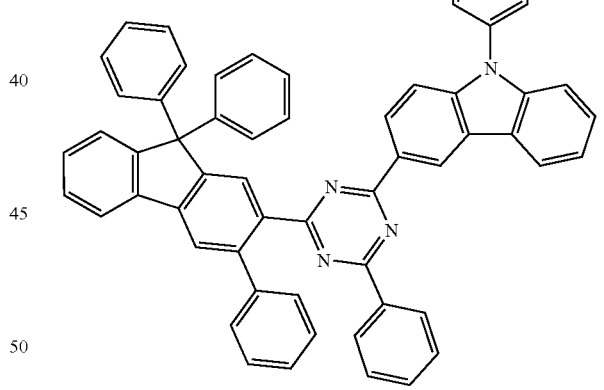
1-265
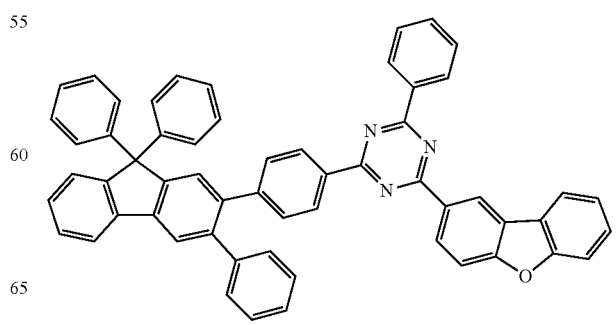

-continued
1-266
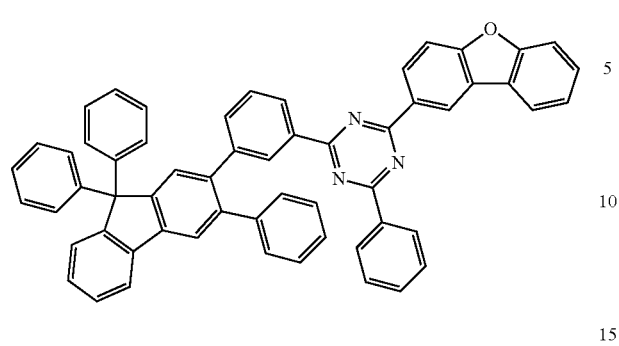
1-267
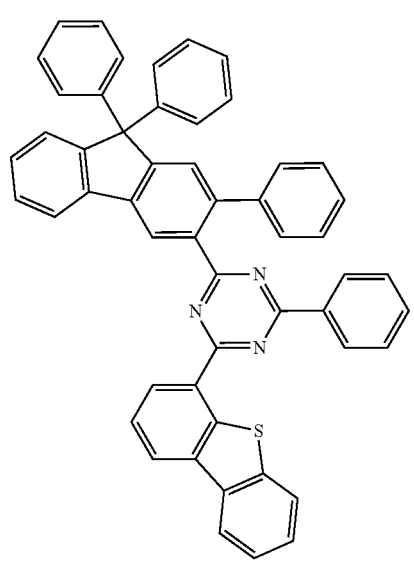
1-268
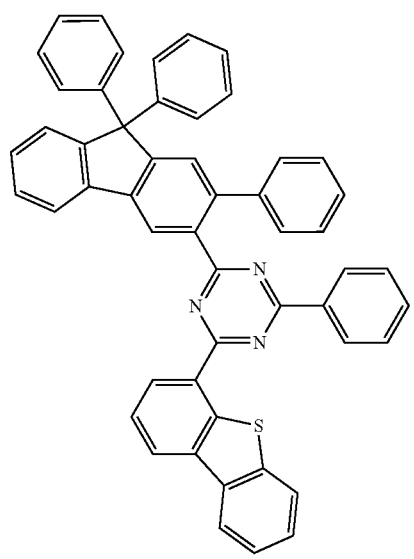
-continued
1-269
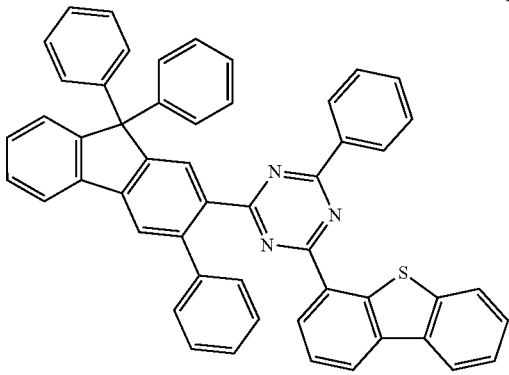
1-270
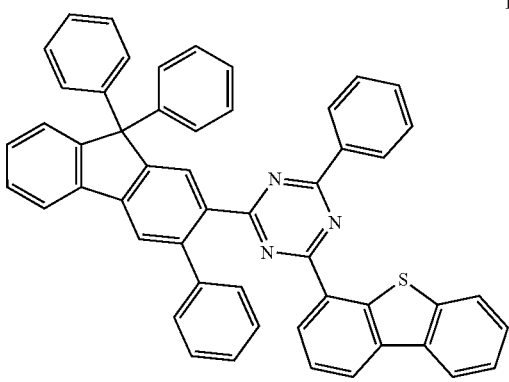
1-271
1-272
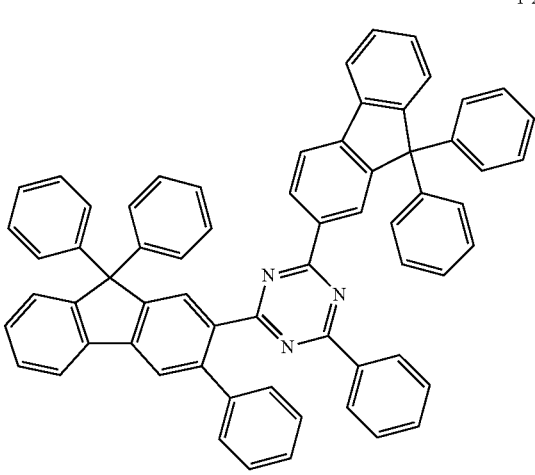

1-273
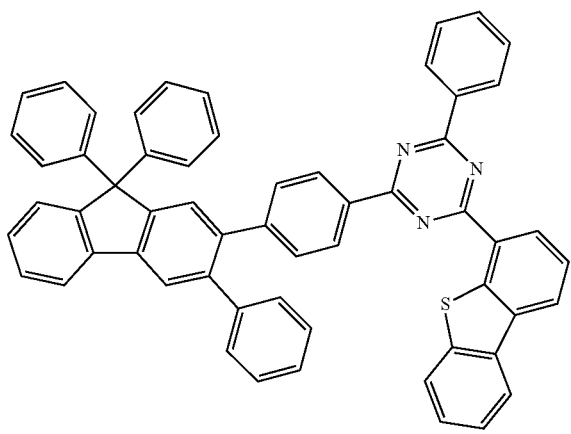
1-274
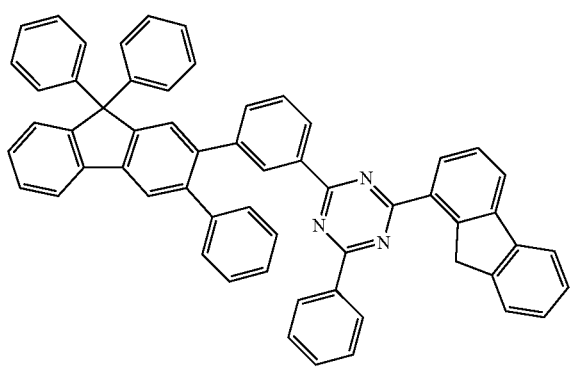
1-275
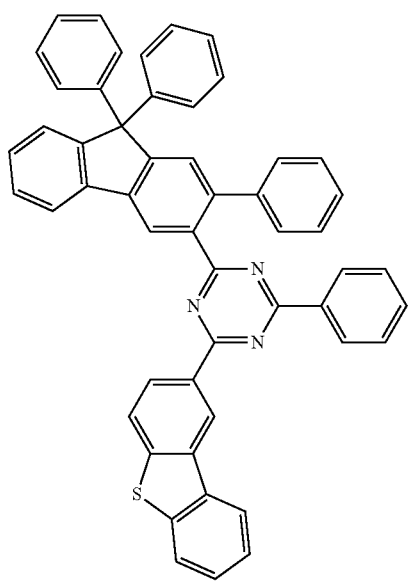
1-276
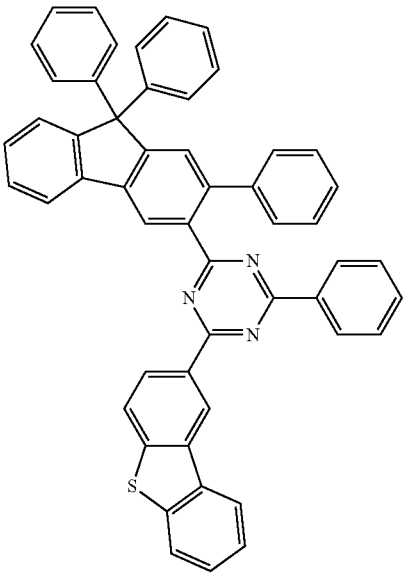
1-277
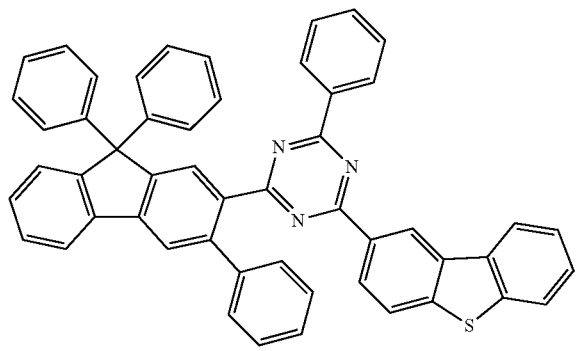
1-278
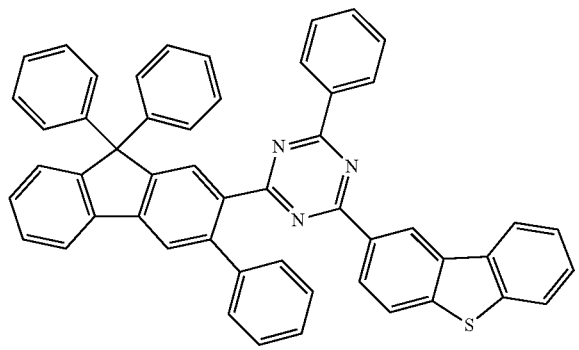

1-279
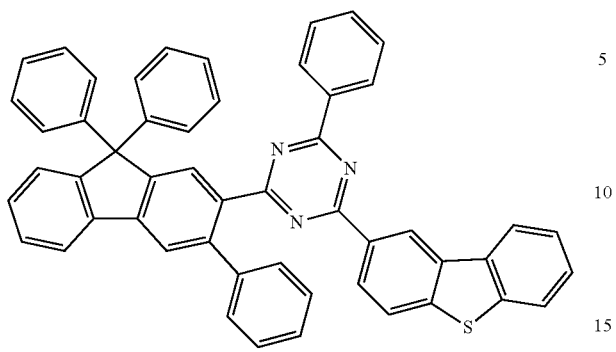
1-280
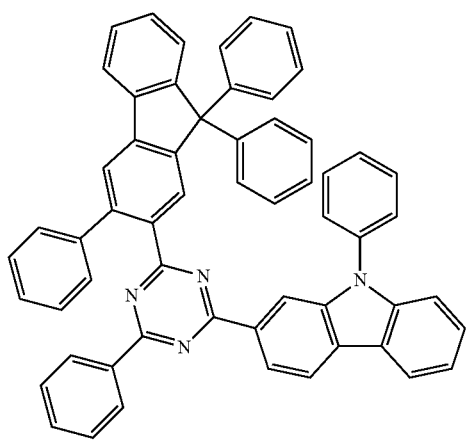
1-281
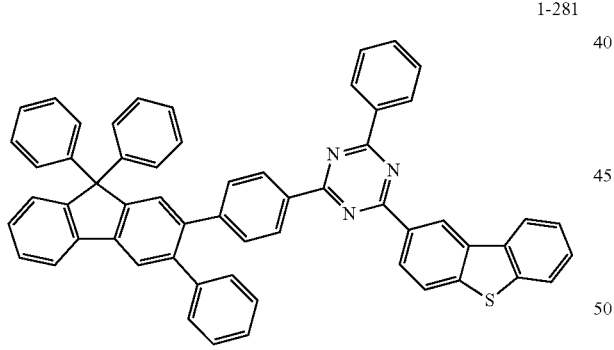
1-282
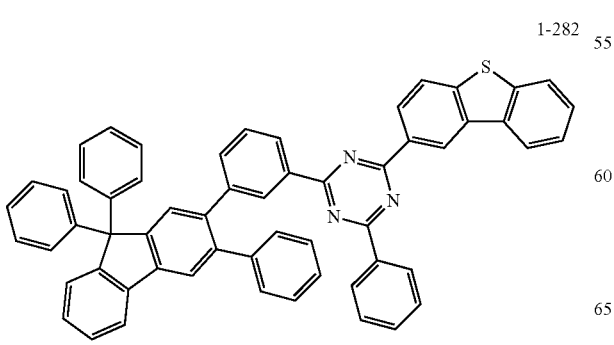
1-283
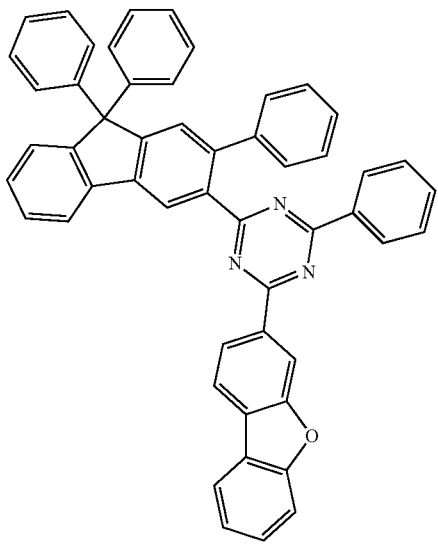
1-284
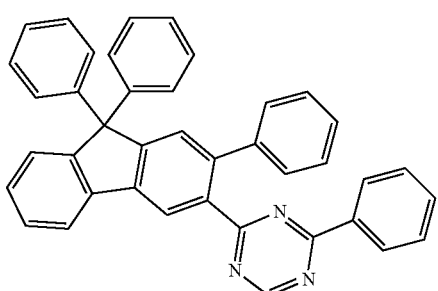
1-285
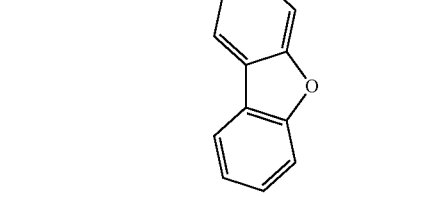
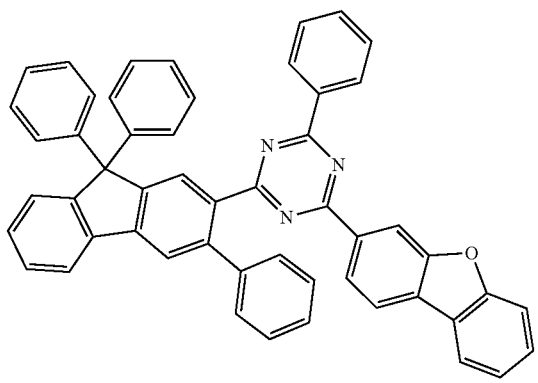

-continued
1-286
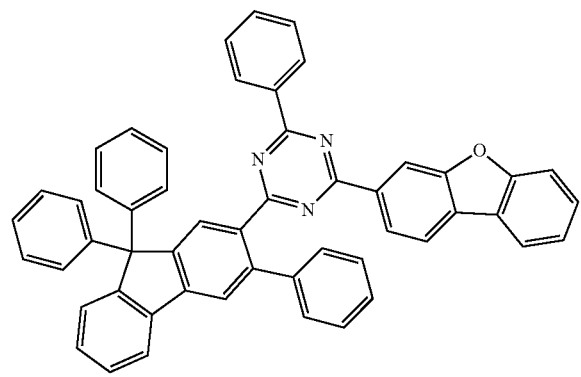
1-289
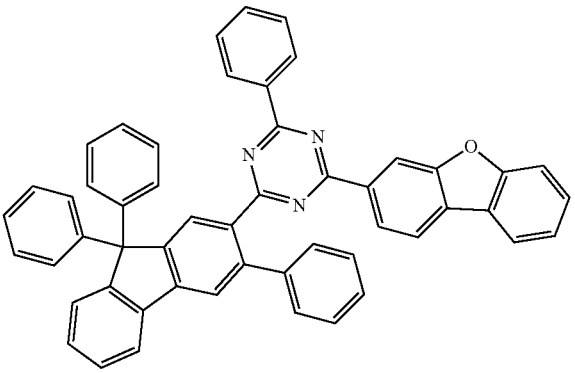
1-287
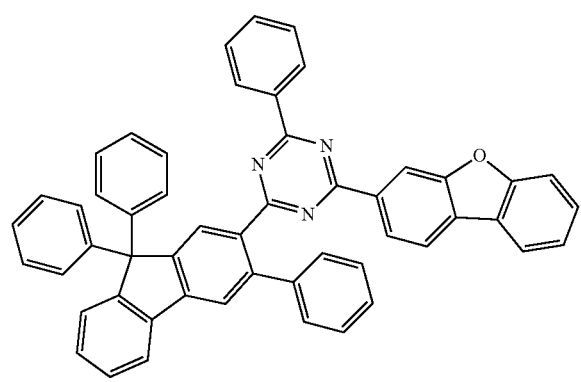
1-290
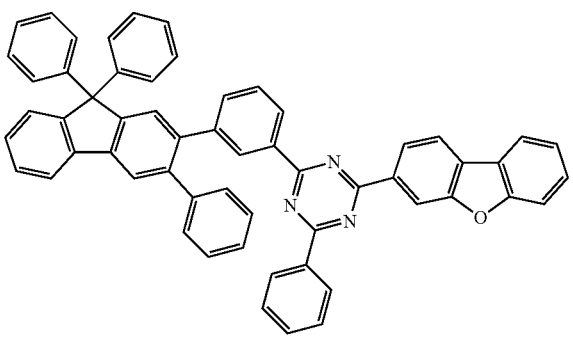
1-288
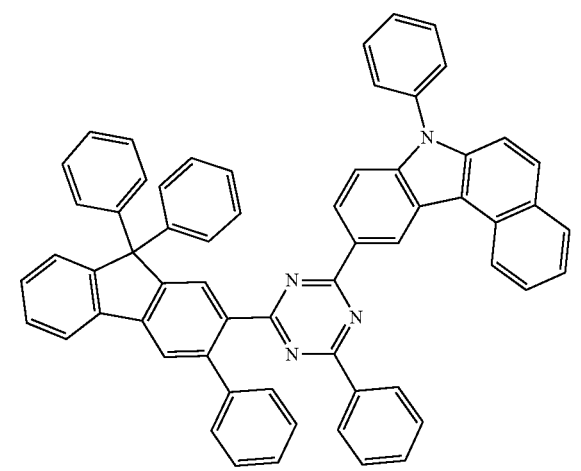
1-291
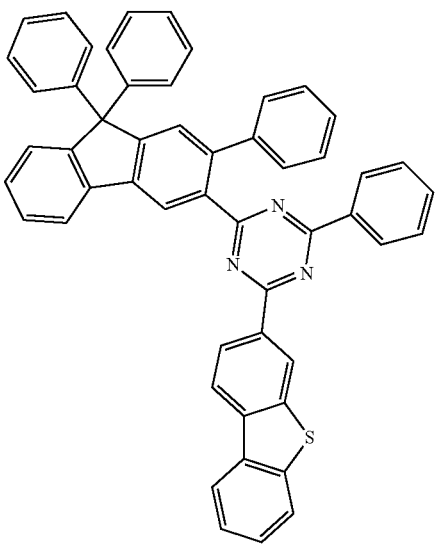

1-292
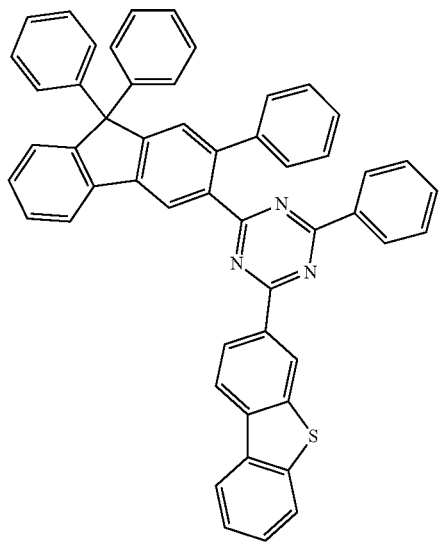
1-293
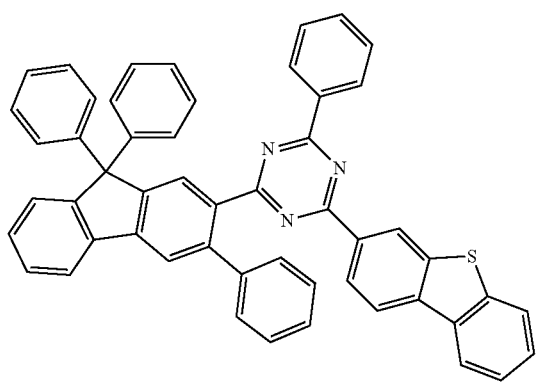
1-294
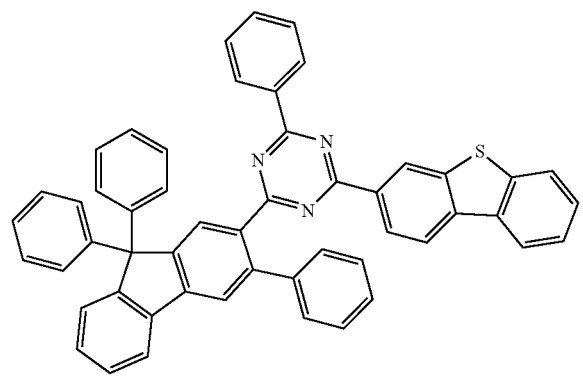
1-295
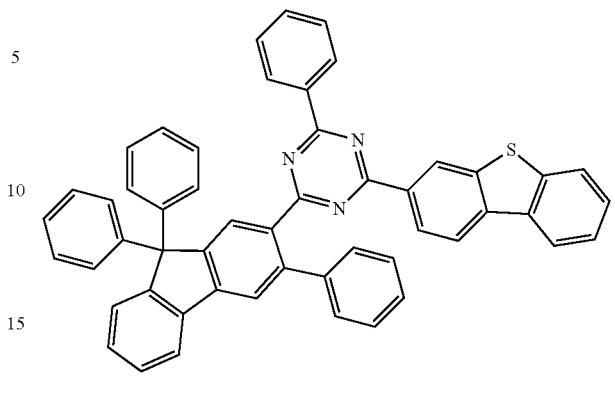
1-296
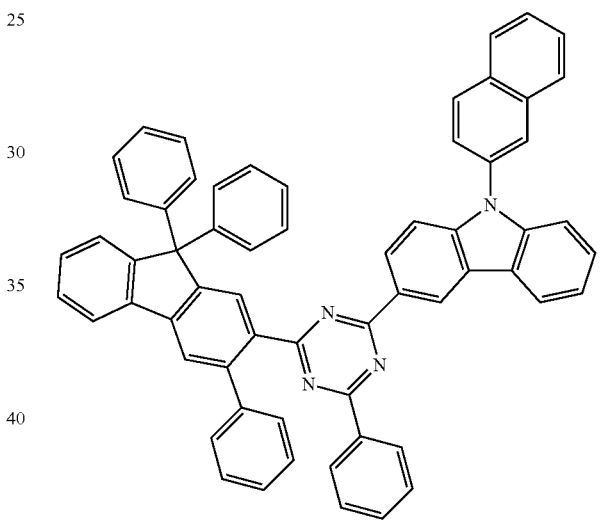
1-297
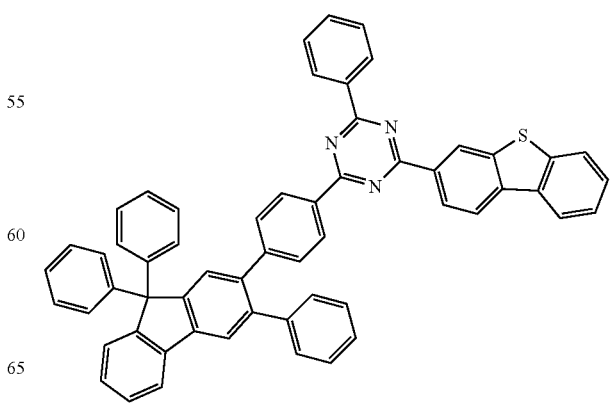

-continued
1-298
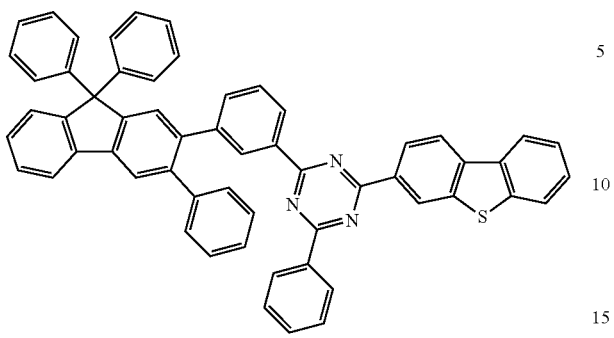
1-299
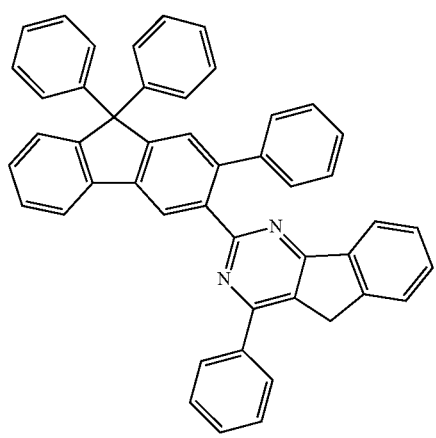
1-300
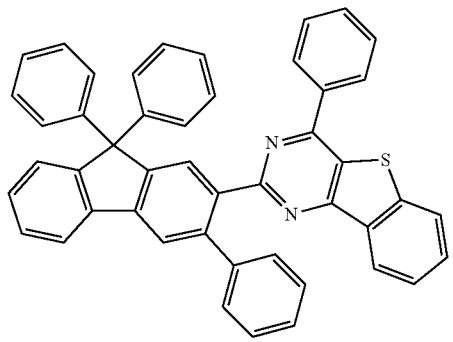
1-301
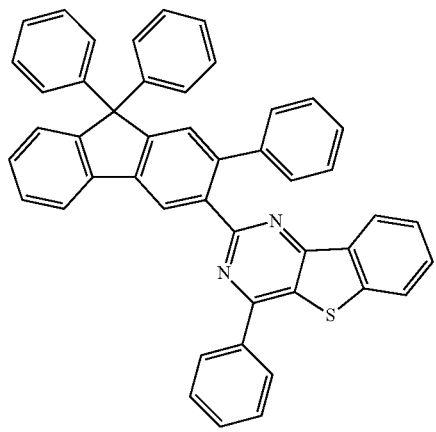
-continued
1-302
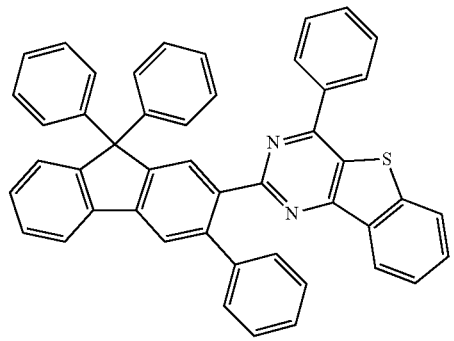
1-303
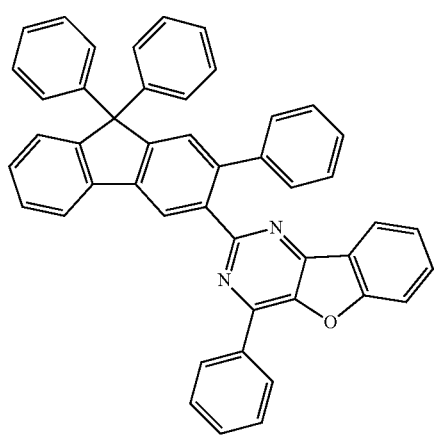
1-304
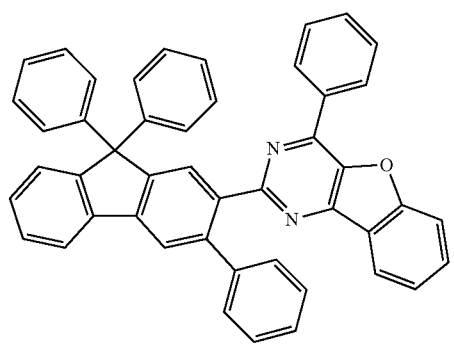
1-305
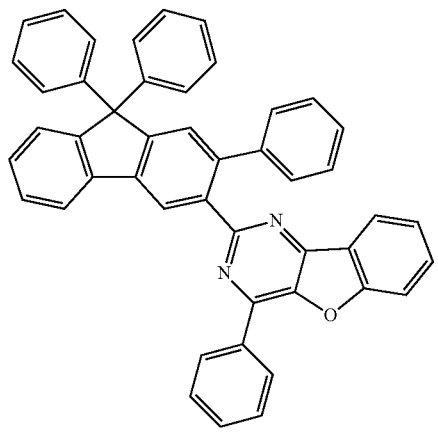

1-306
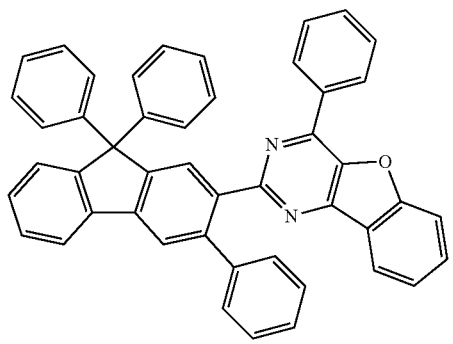
1-310
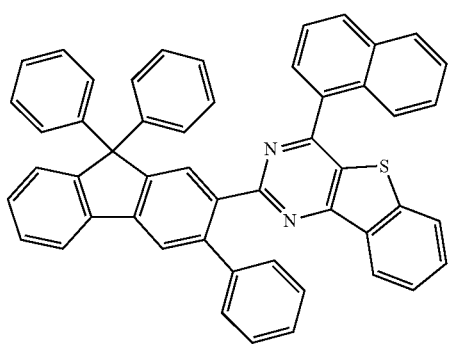
1-307
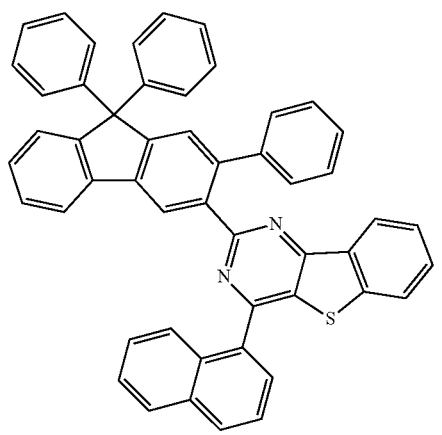
1-311
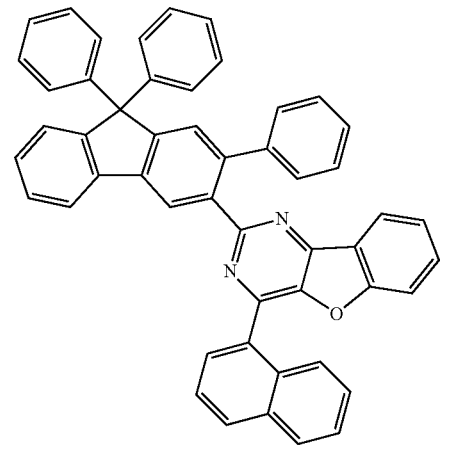
1-308
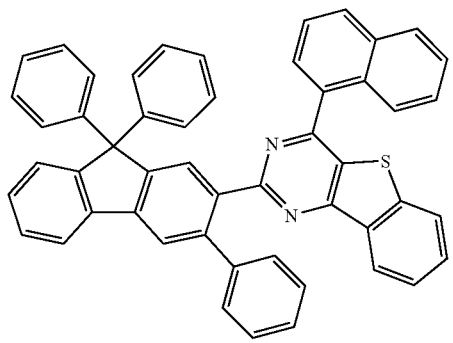
1-312
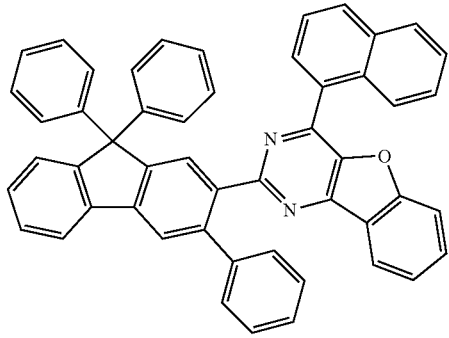
1-309
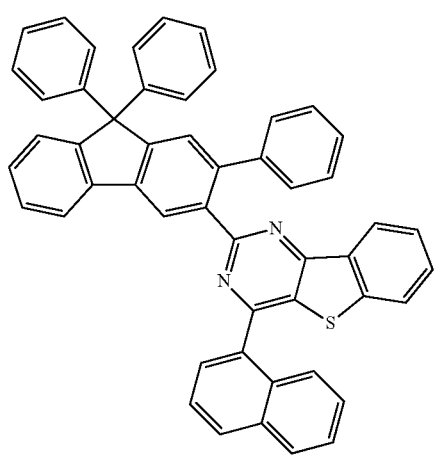
1-313
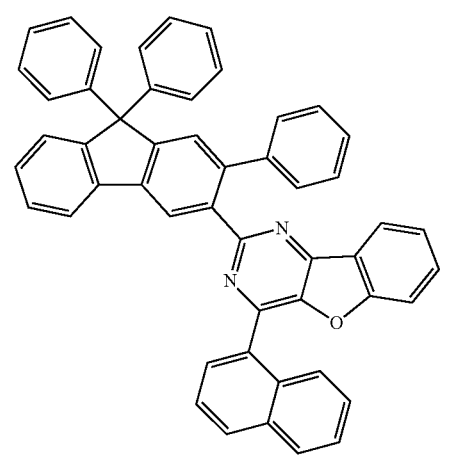

1-314
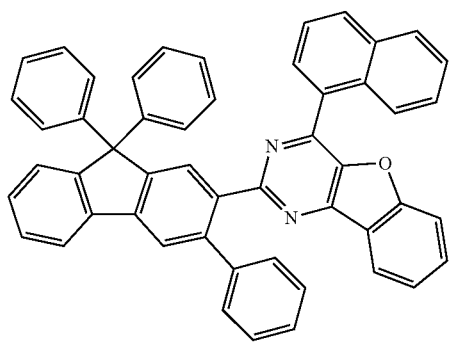
1-315
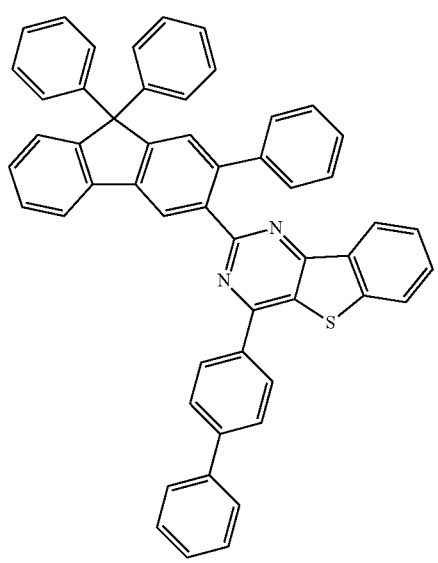
1-316
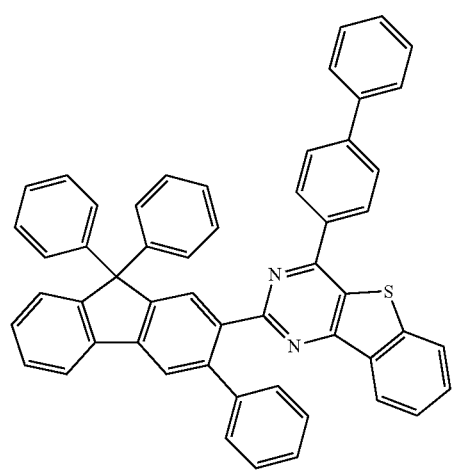
1-317
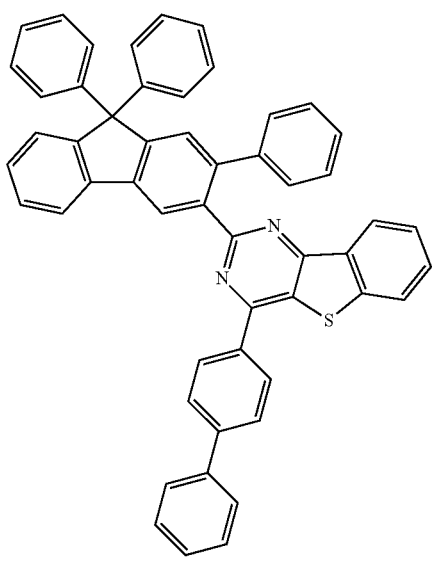
1-318
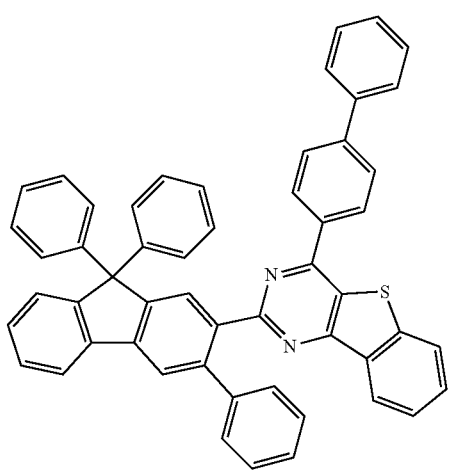
1-319
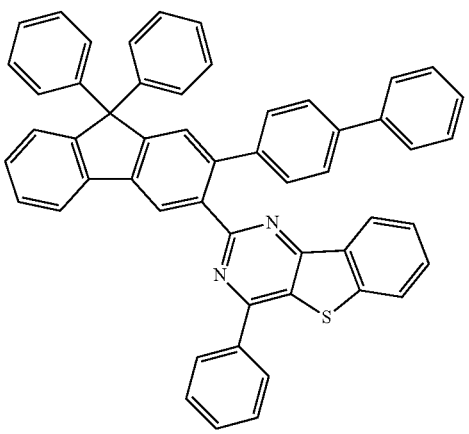

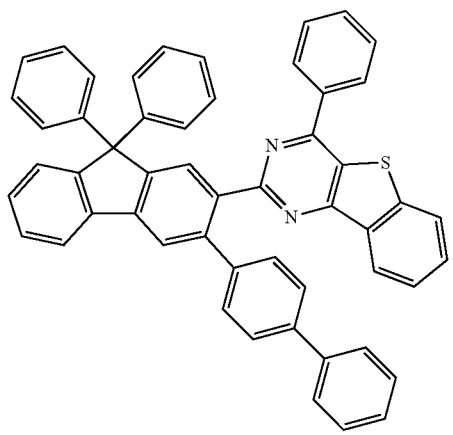
1-320
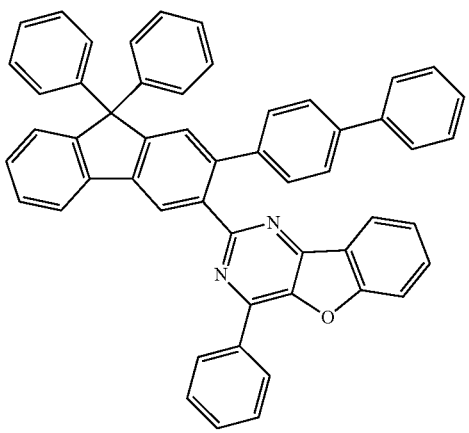
1-323
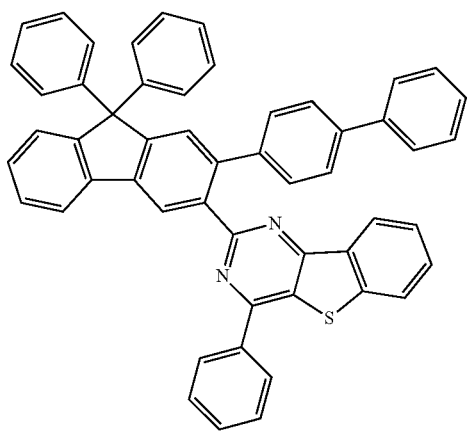
1-321
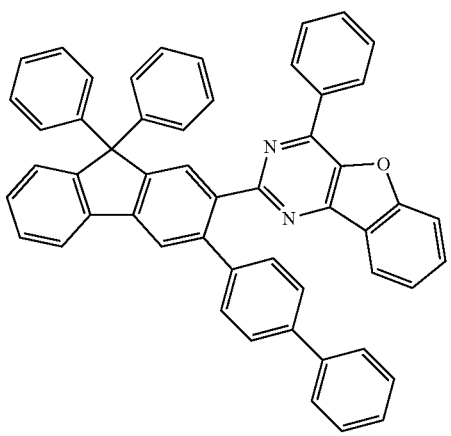
1-324
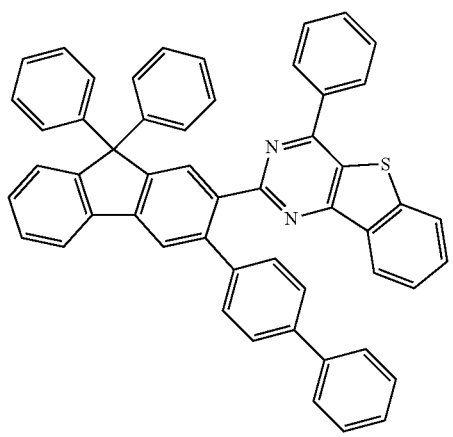
1-322
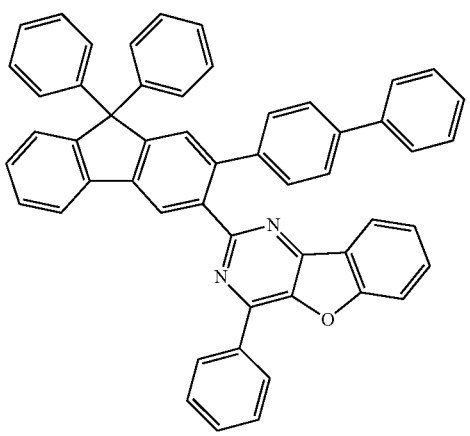
1-325

-continued
1-326
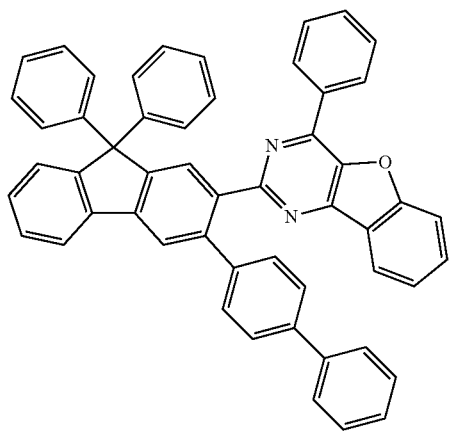
1-327
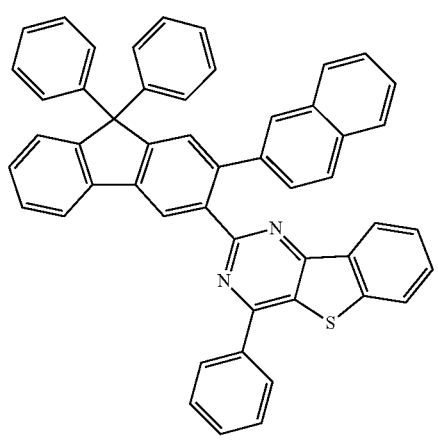
1-328
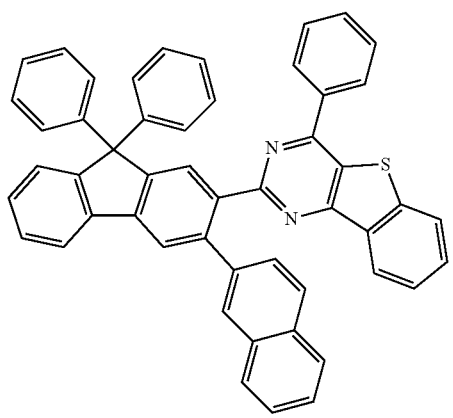
1-329
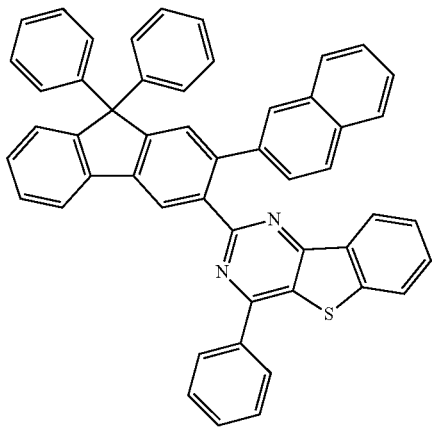
1-330
1-331
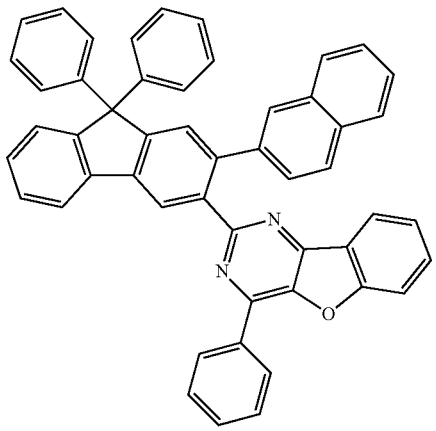

1-332
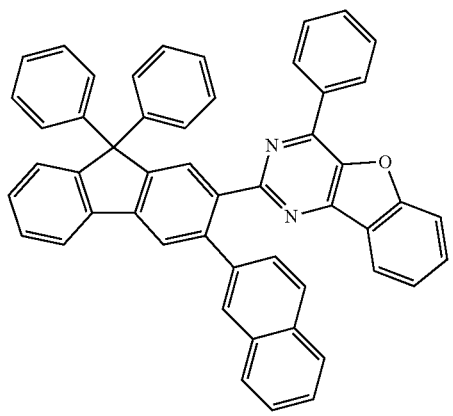
1-333
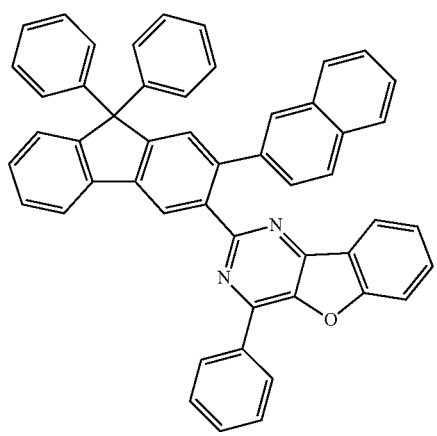
1-334
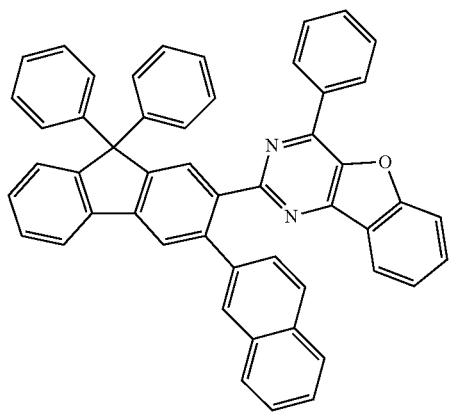
1-335
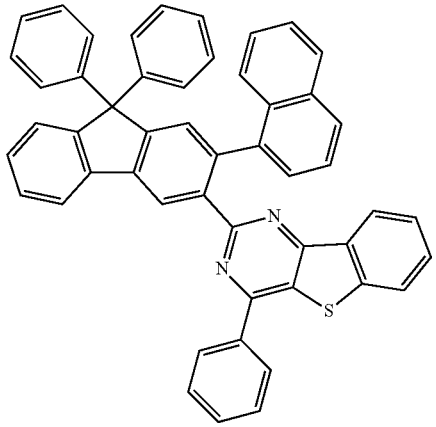
1-336
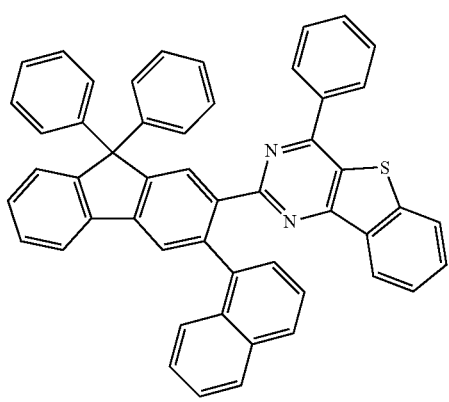
1-337
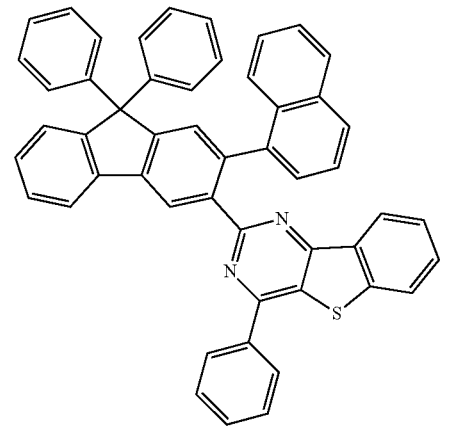
1-338
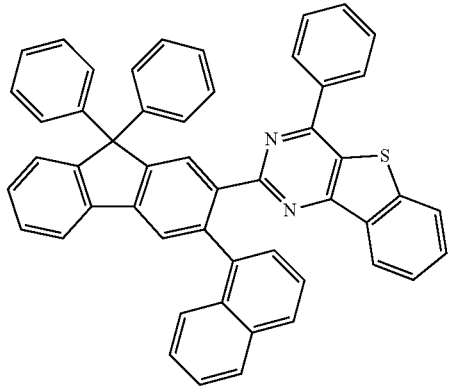

1-339
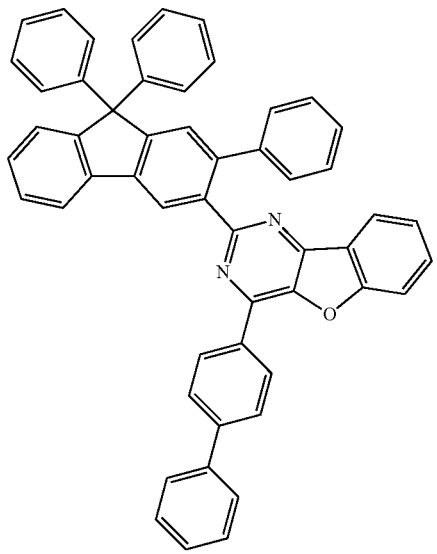
1-340
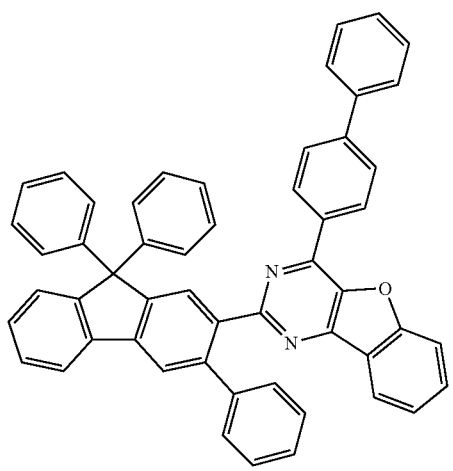
1-341
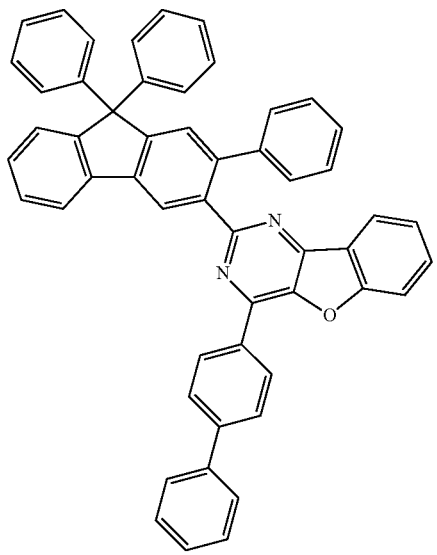
1-342
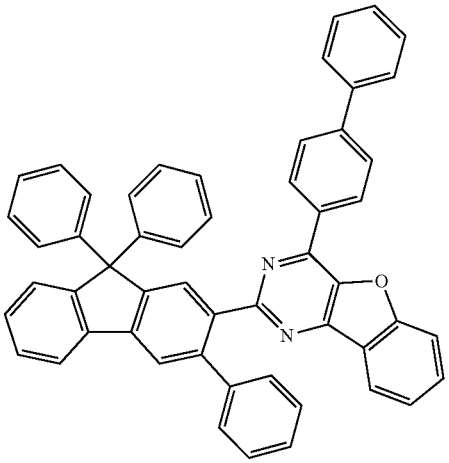
1-343
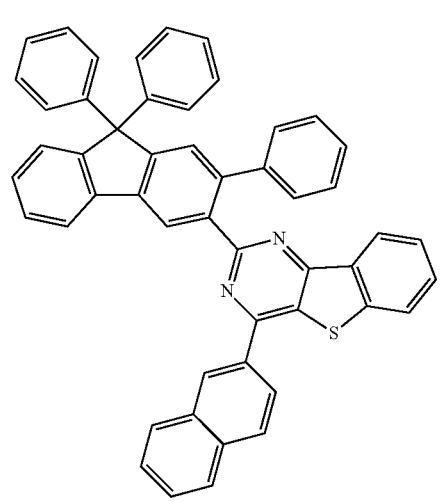
1-344
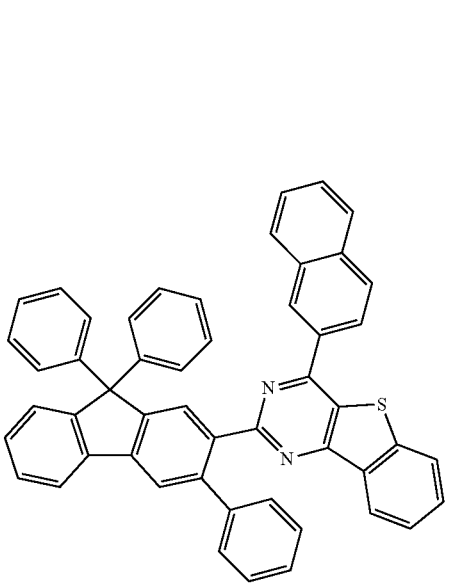

1-345
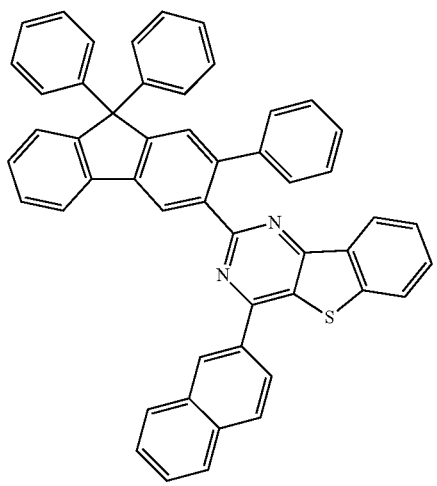
1-346
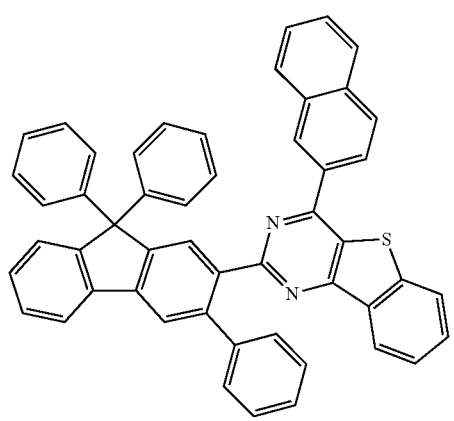
1-347
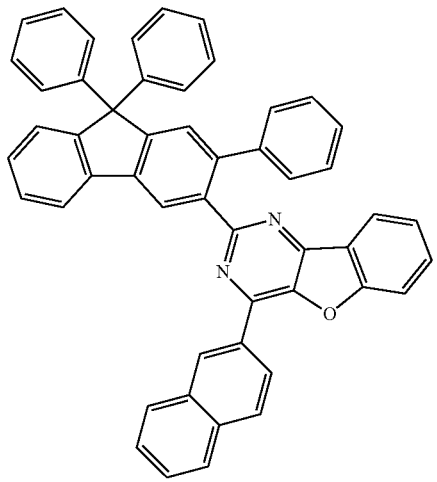
1-348
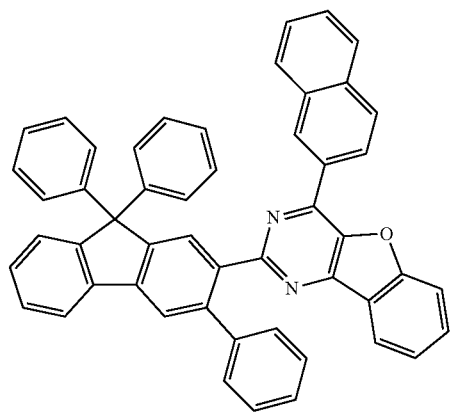
1-349
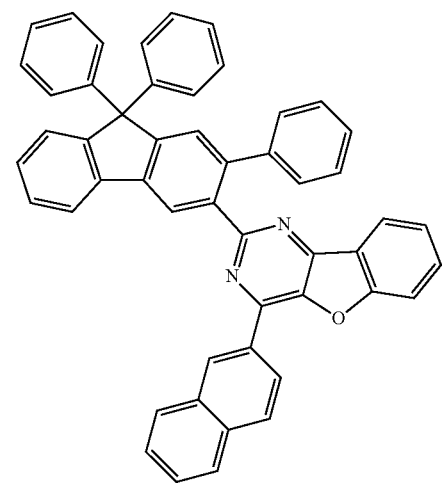
1-350
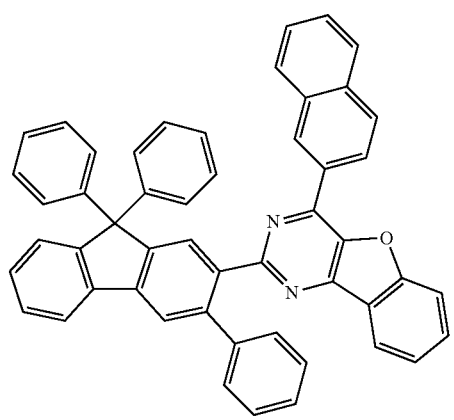

-continued
1-351
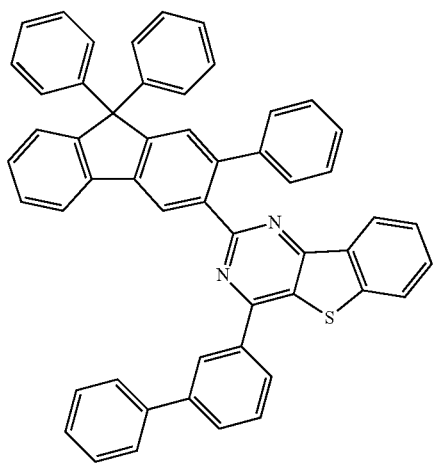
1-352
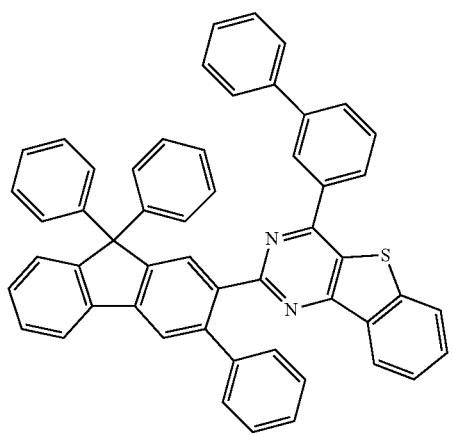
1-353
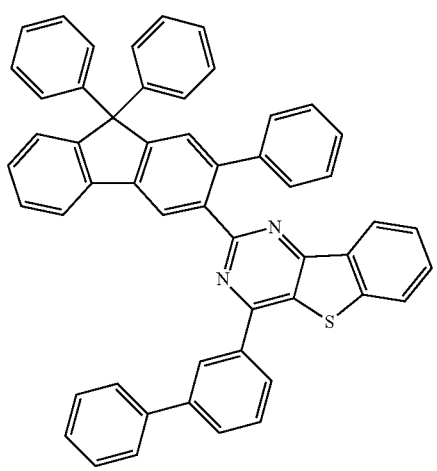
1-354
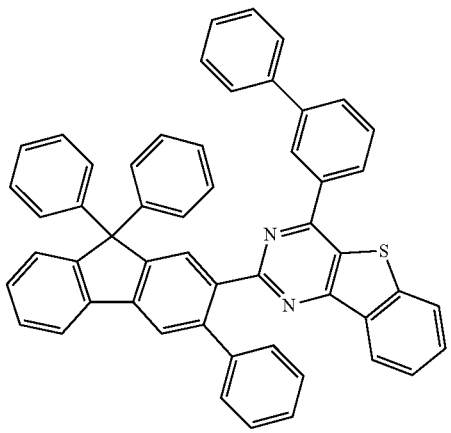
1-355
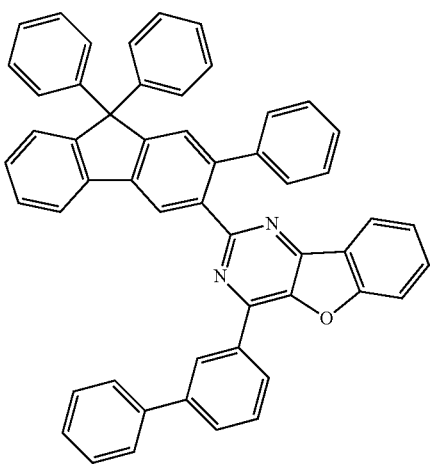
1-356
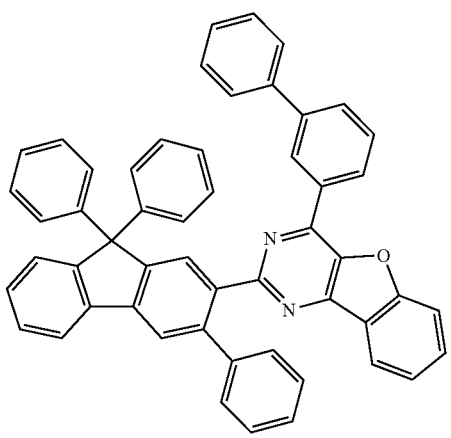

1-357
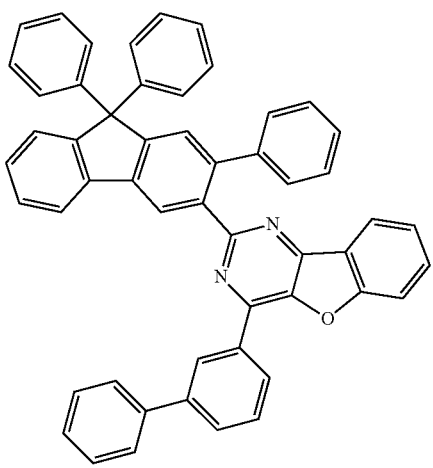
1-358
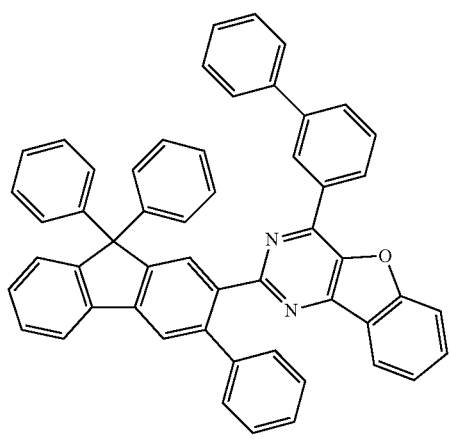
1-359
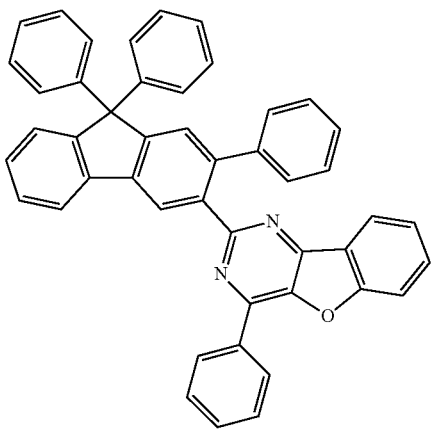
1-360
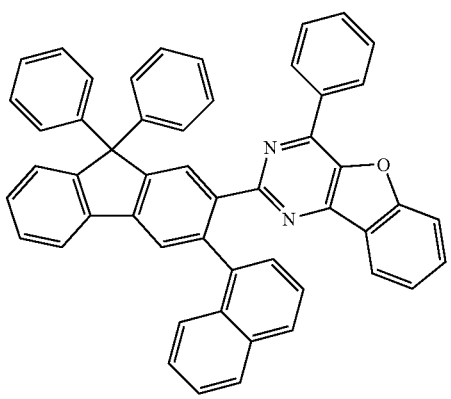
1-361
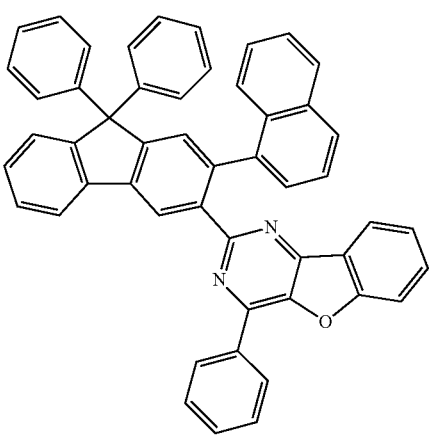
1-362
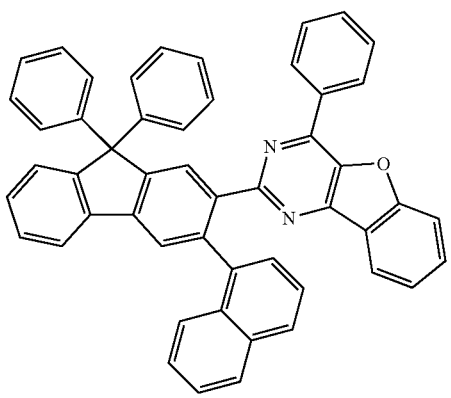

1-363
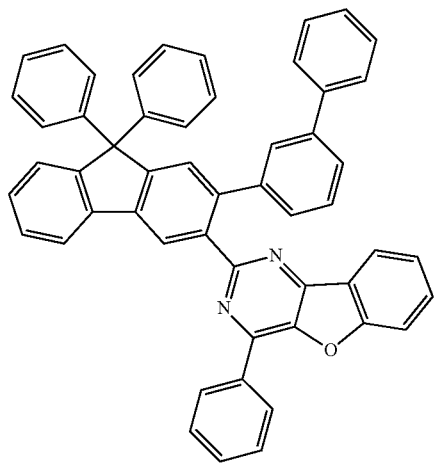
1-366
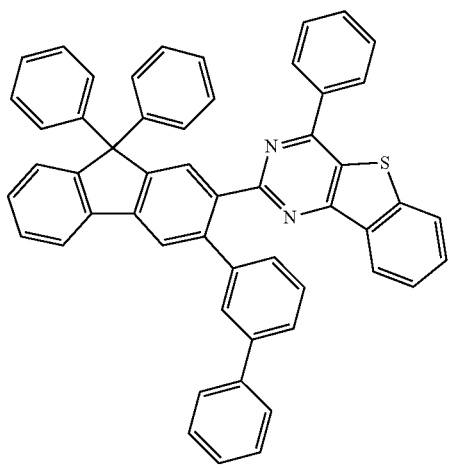
1-364
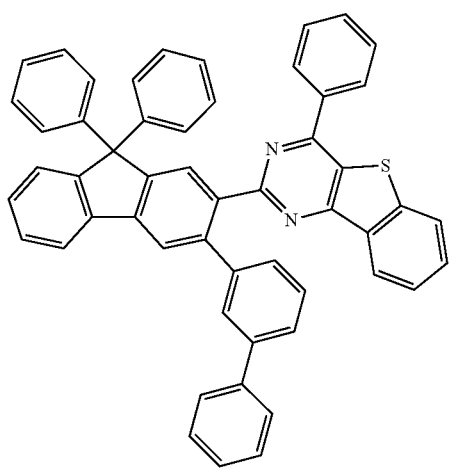
1-367
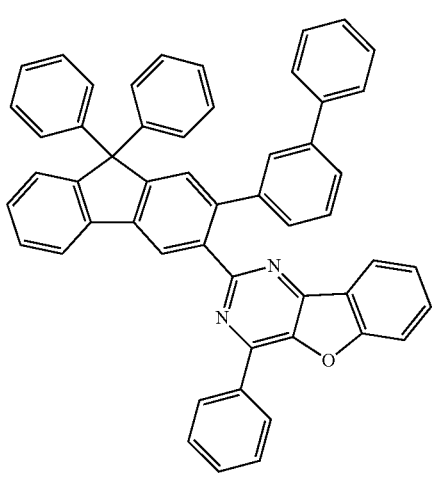
1-365
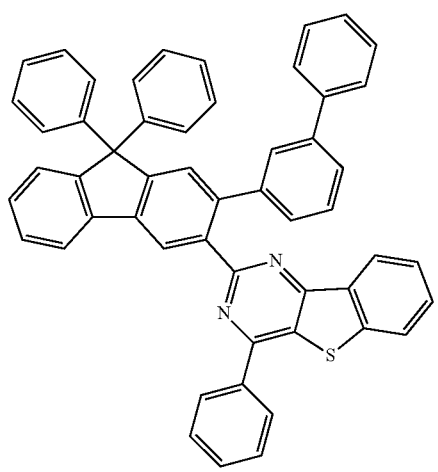
1-368
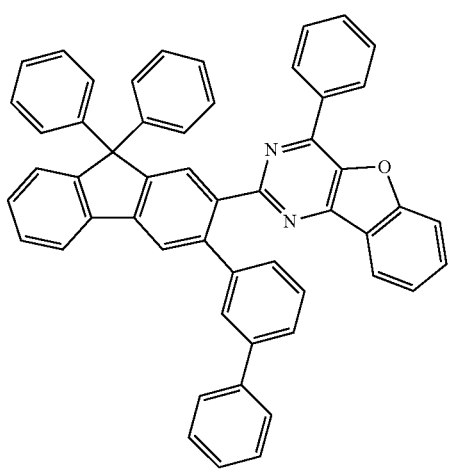

1-369
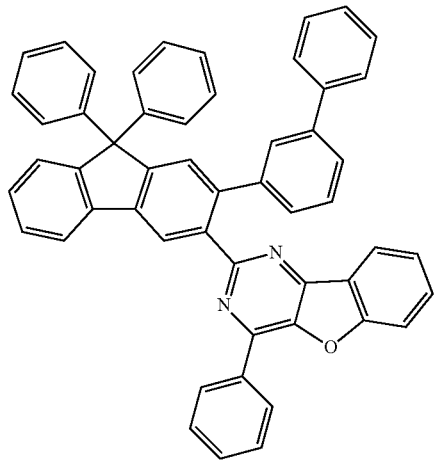
1-370
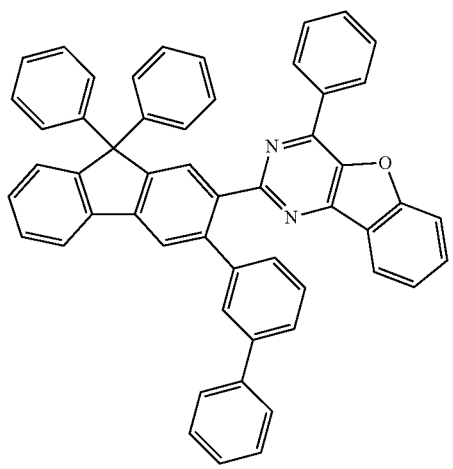
1-371
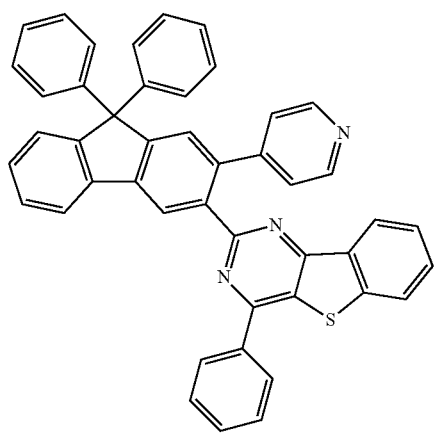
1-372
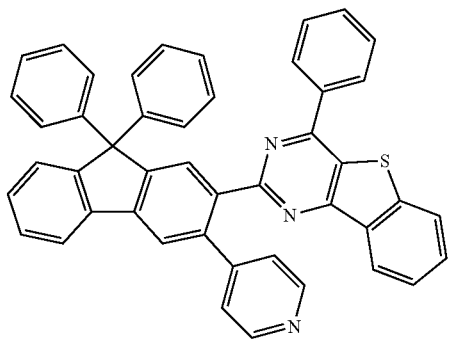
1-373
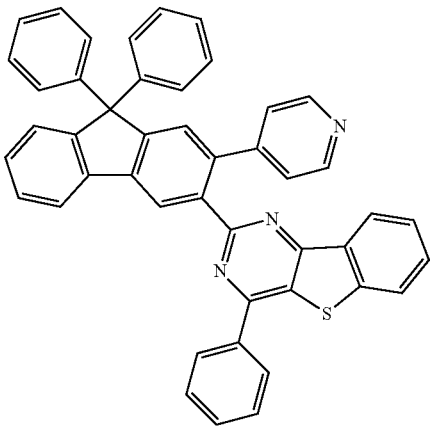
1-374
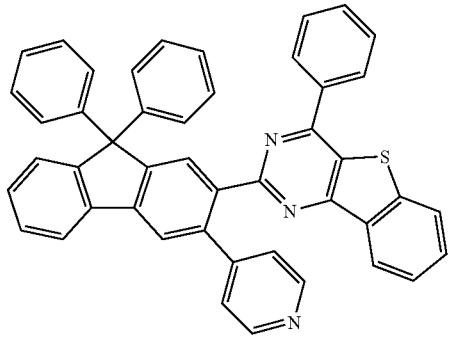
1-375
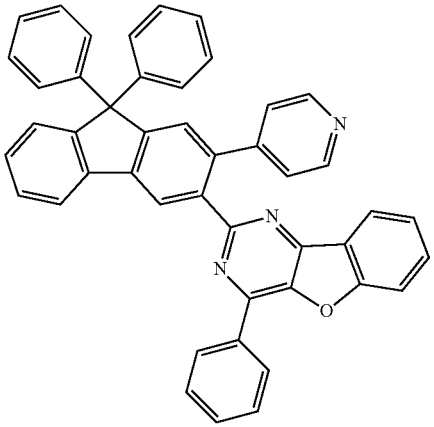

1-376
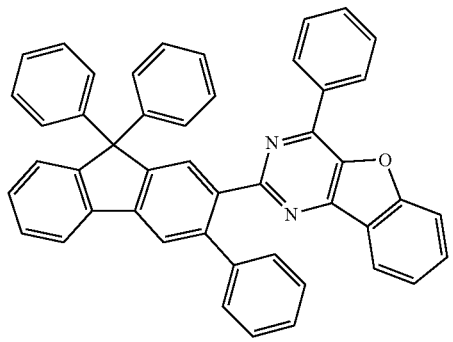
1-377
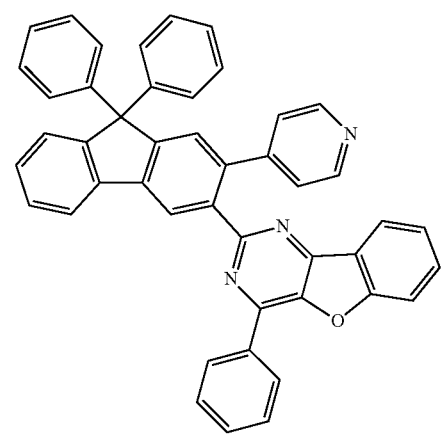
1-378
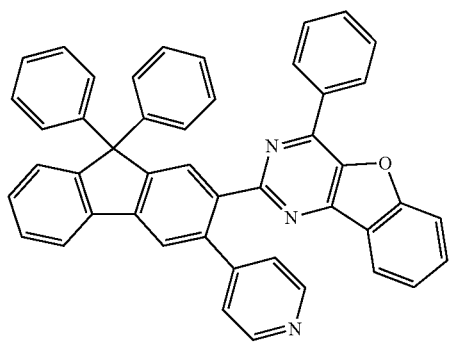
1-379
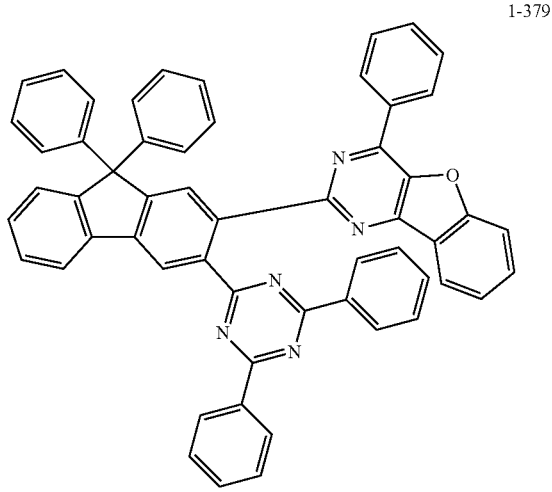
1-380
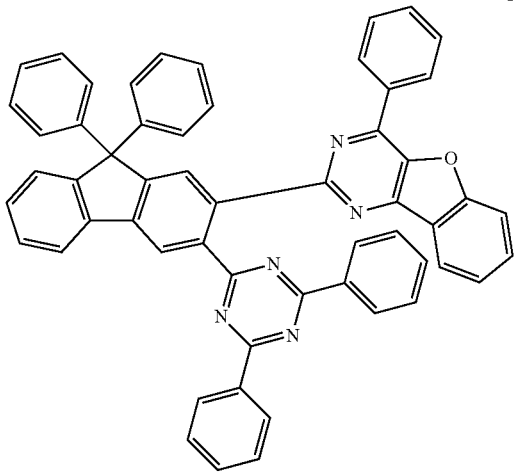
1-381
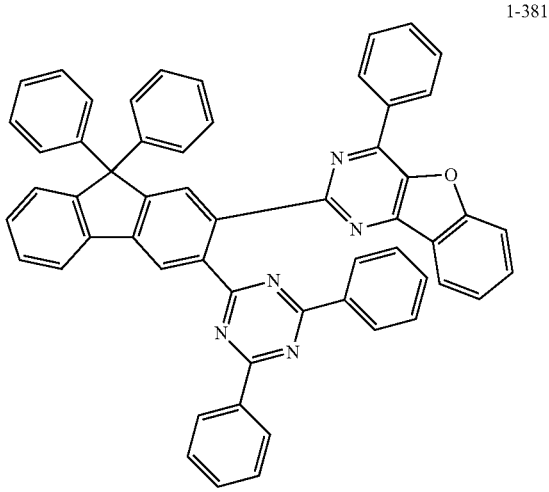
1-382
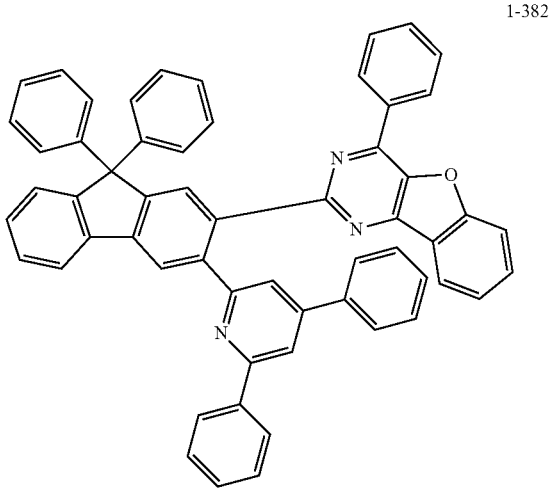

1-383
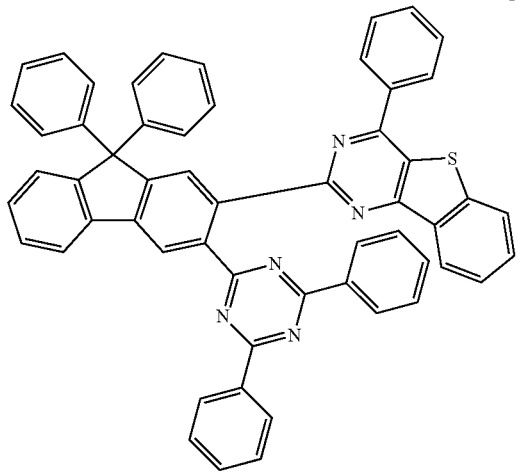
1-384
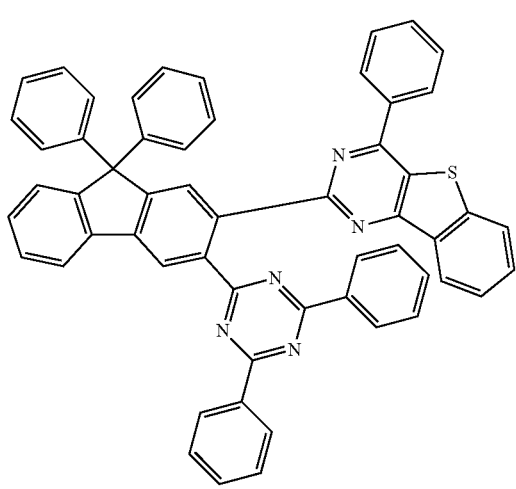
1-385
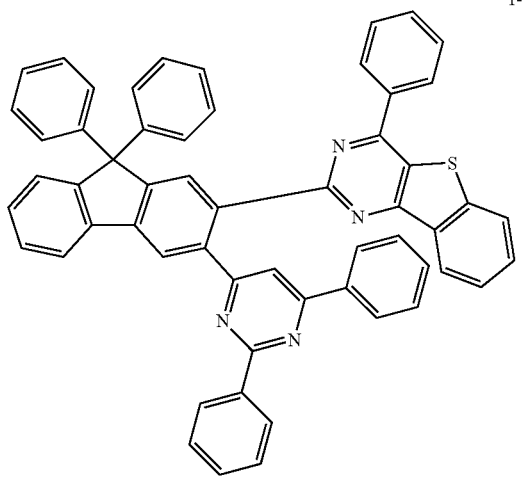
1-386
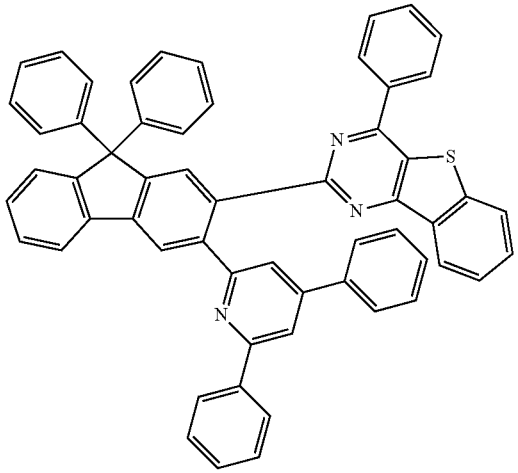
1-387
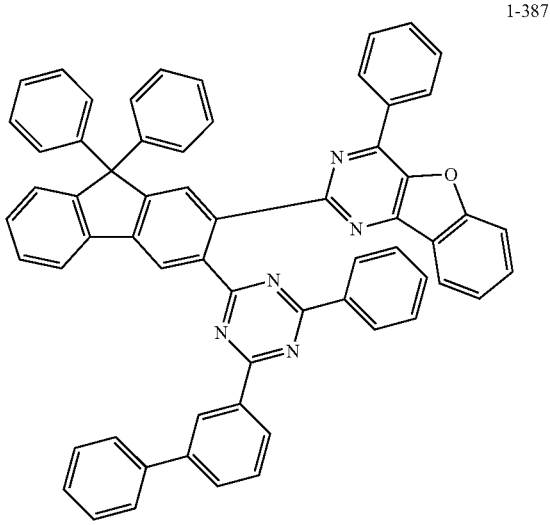
1-388
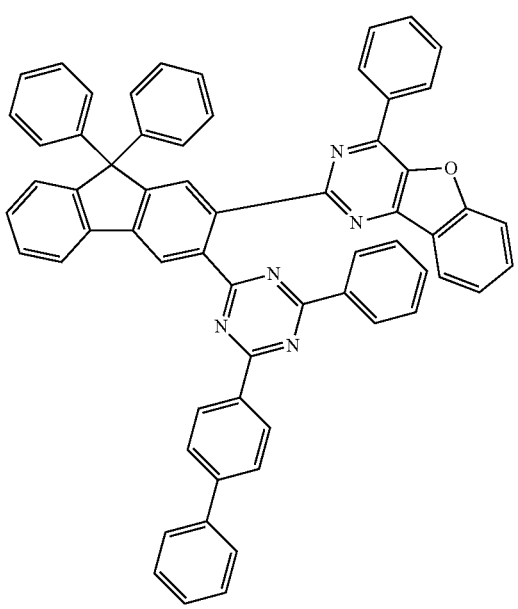

1-389
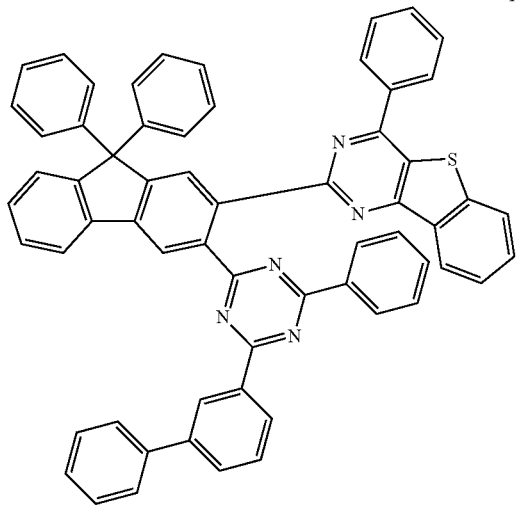
1-390
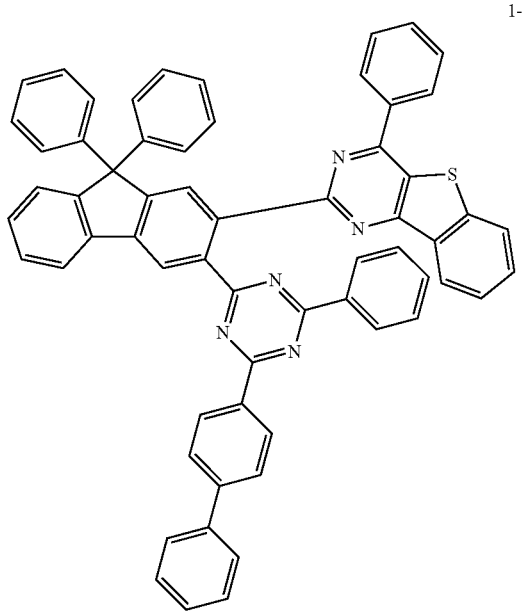
1-391
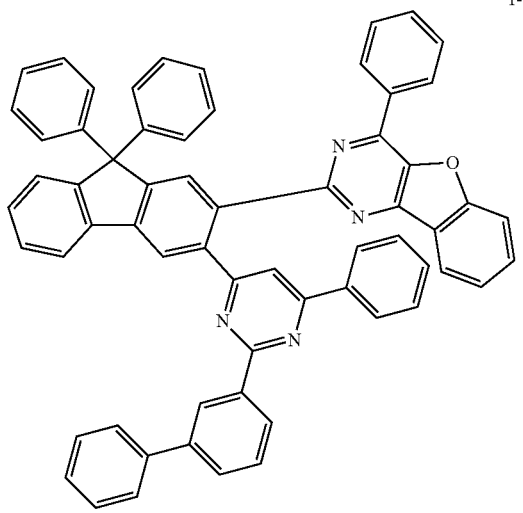
1-392
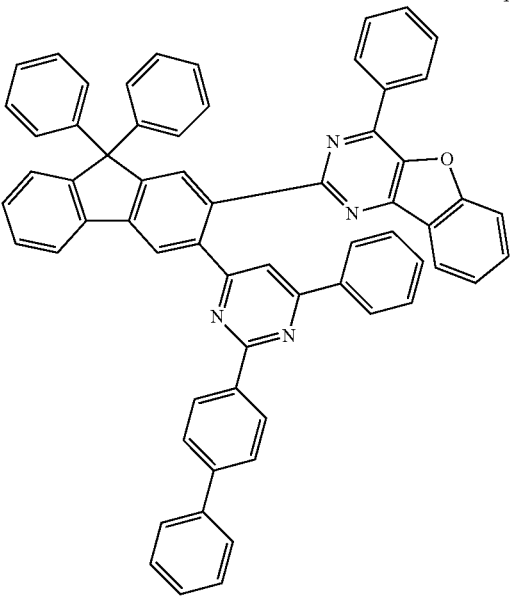
1-393
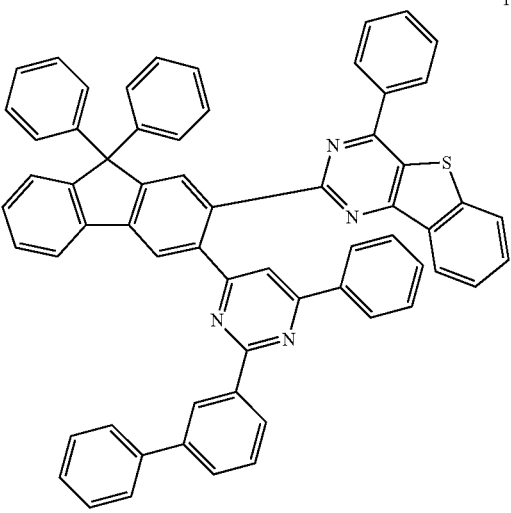

1-394
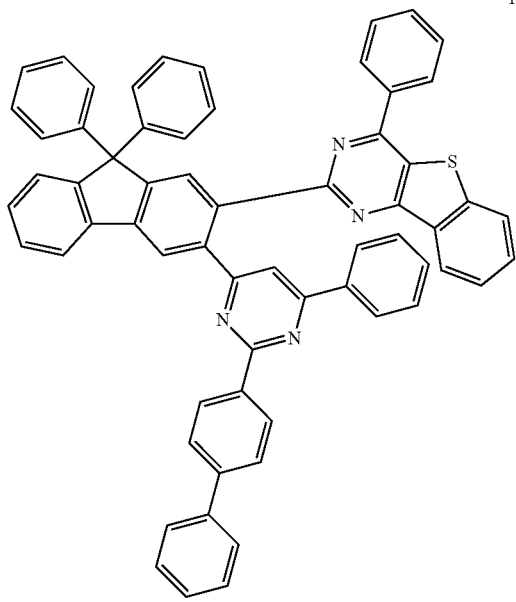
1-395
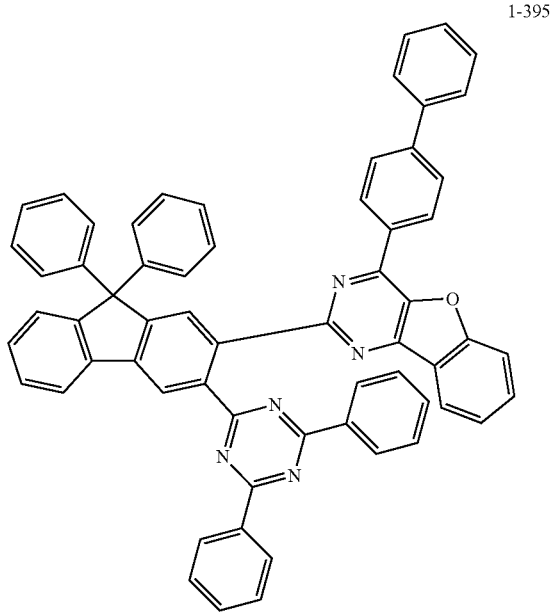
1-396
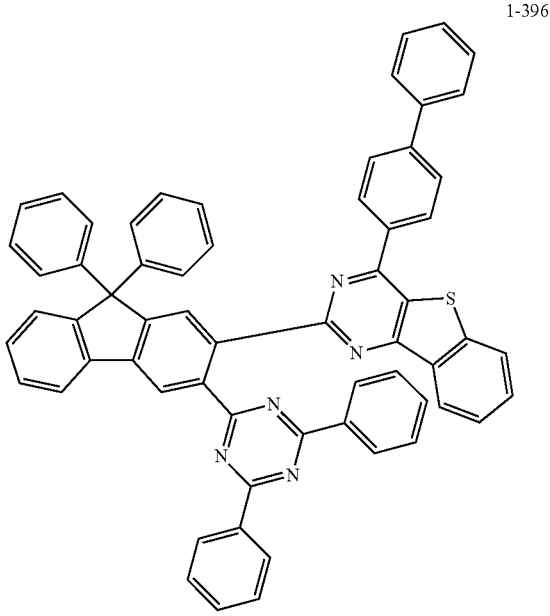
1-397
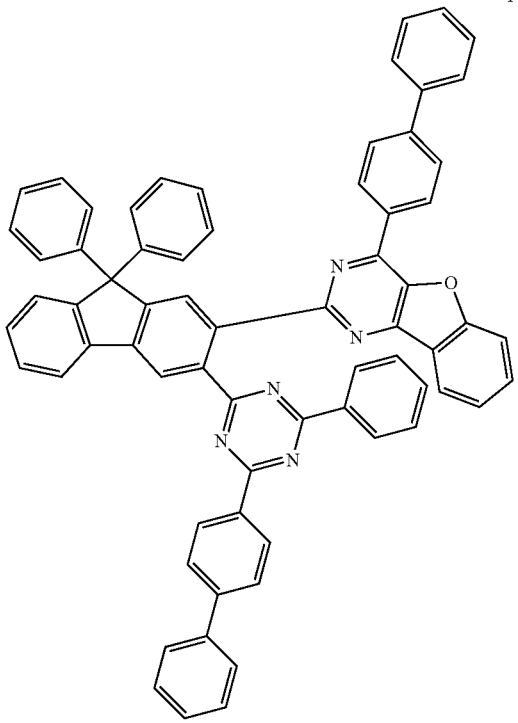

1-398
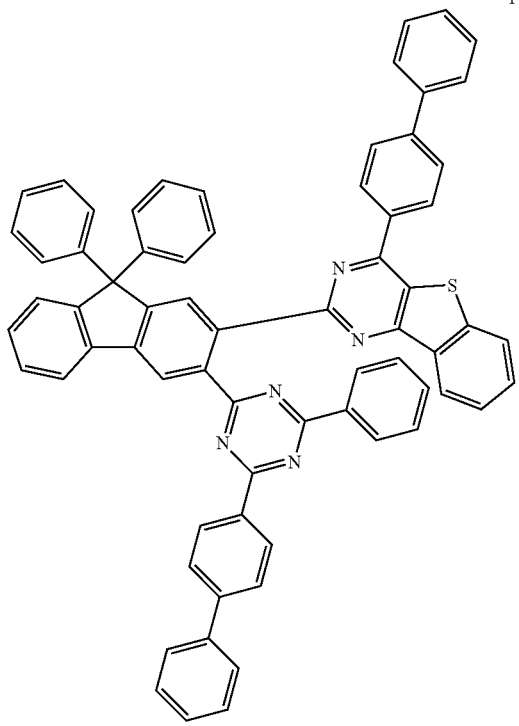
1-399
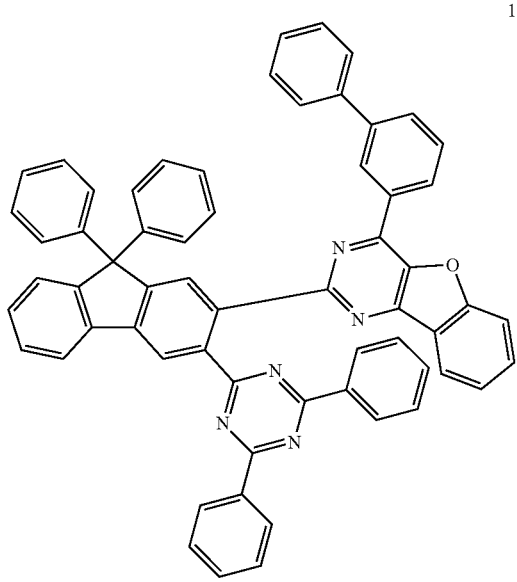
1-400
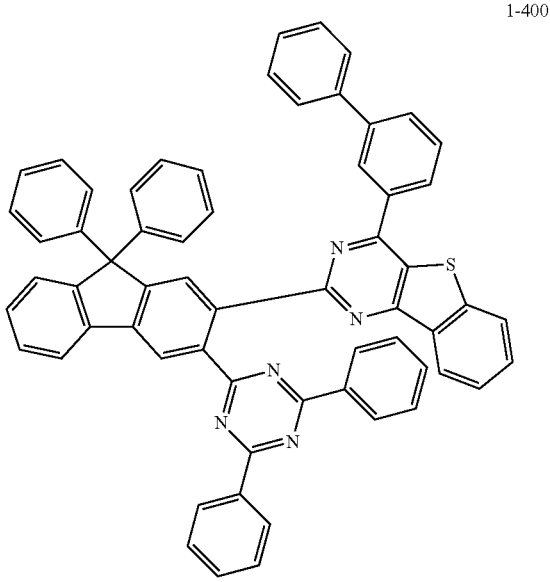
1-401
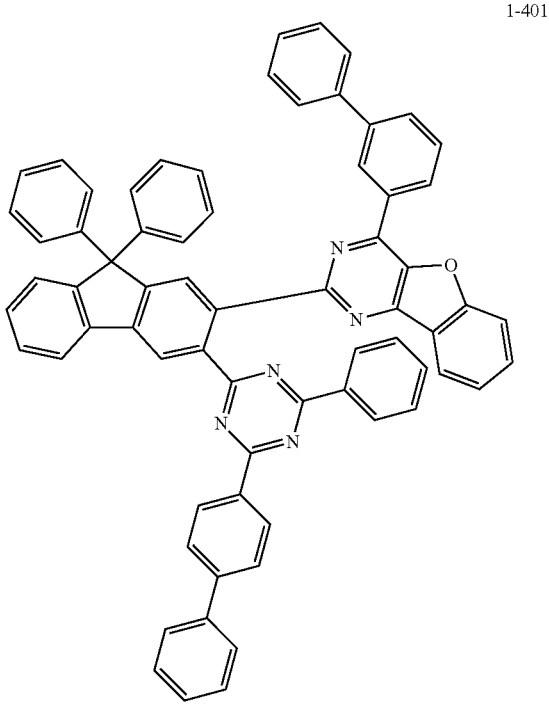

1-402

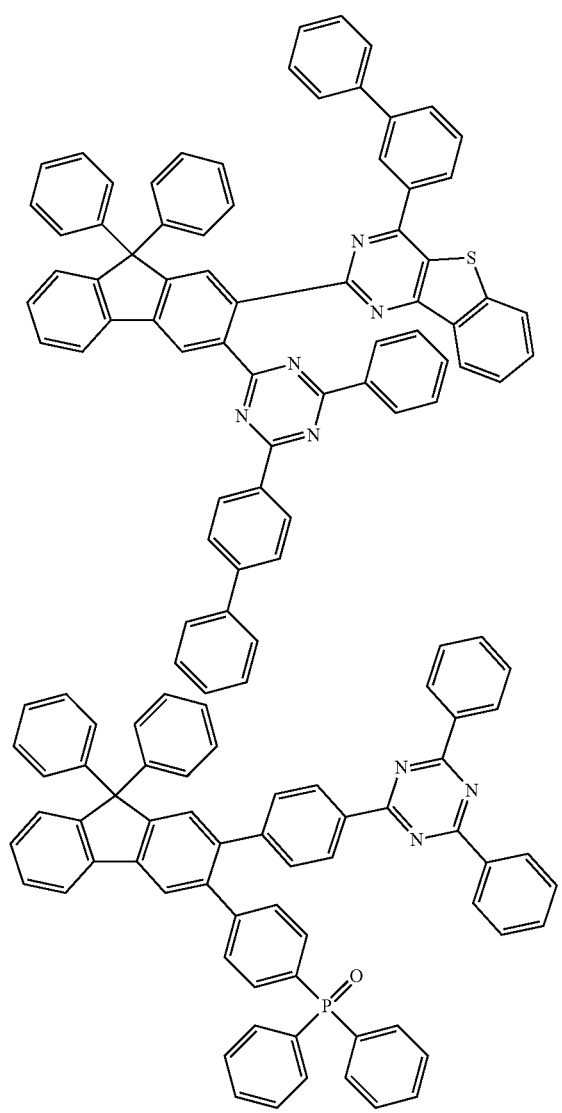

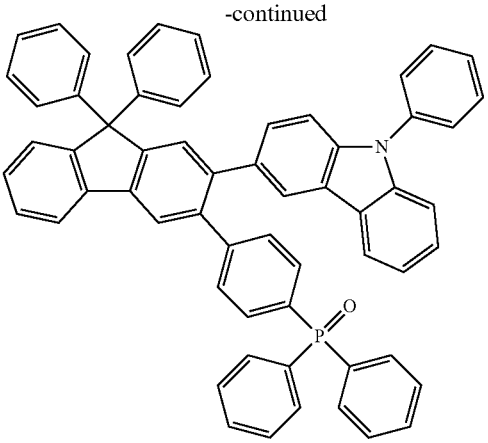

According to an exemplary embodiment of the present specification, the compound of Chemical Formula 1 may be prepared by the following reaction formulae, but the reaction formulae are not limited thereto. In the following reaction formulae, the type and number of substituents may be determined as a person skilled in the art appropriately selects a publicly-known starting material. As the type of reaction and the reaction condition, those known in the art may be used.

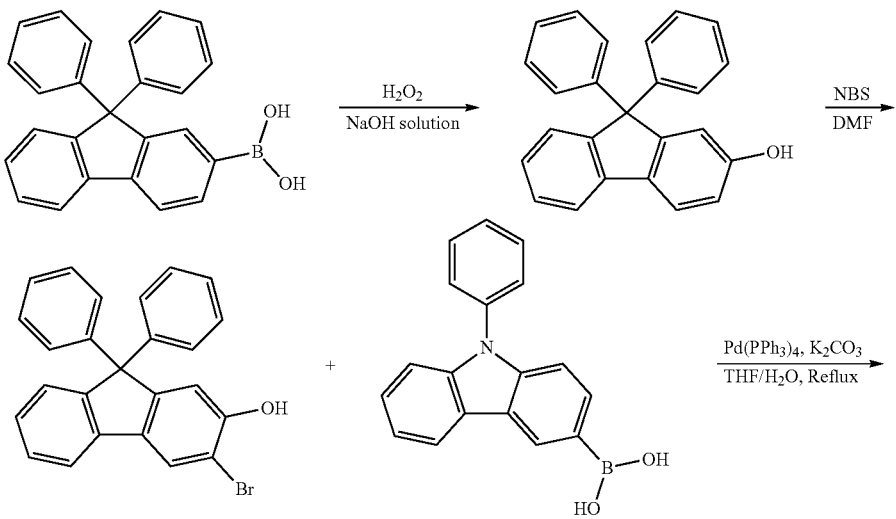

-continued
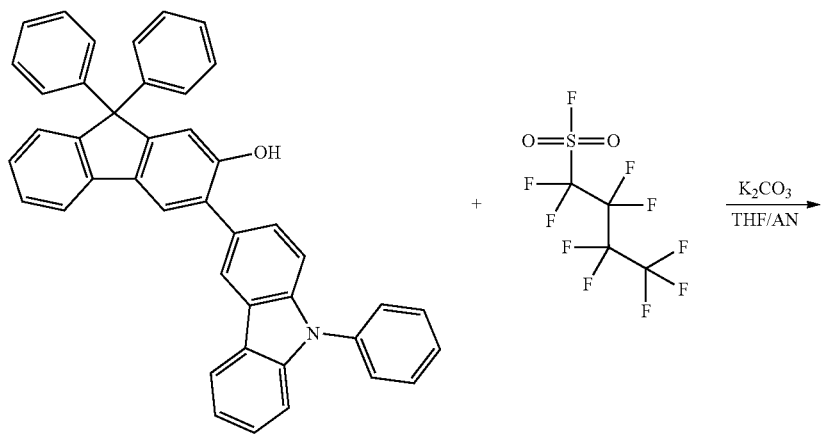
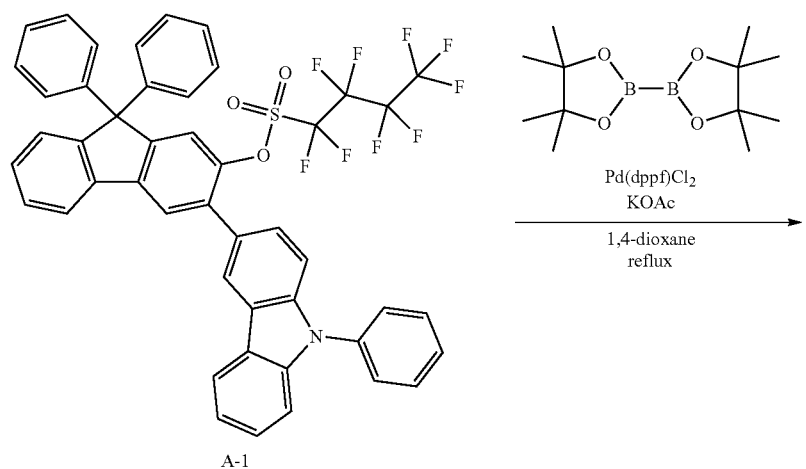
A-1
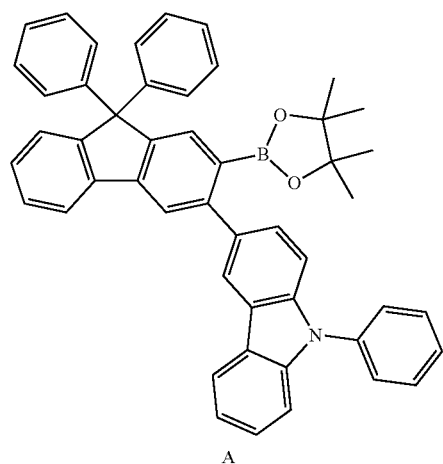
A
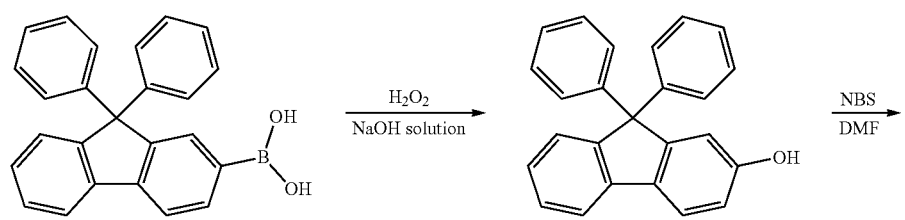

-continued
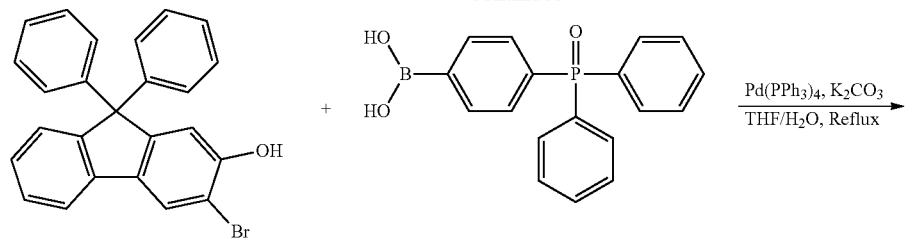
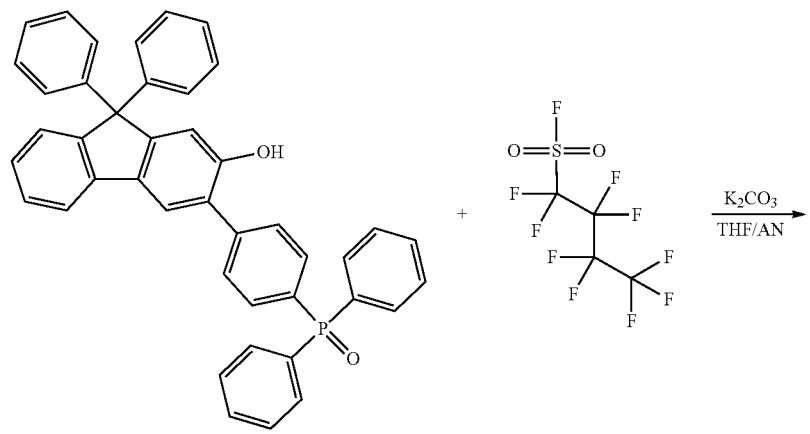
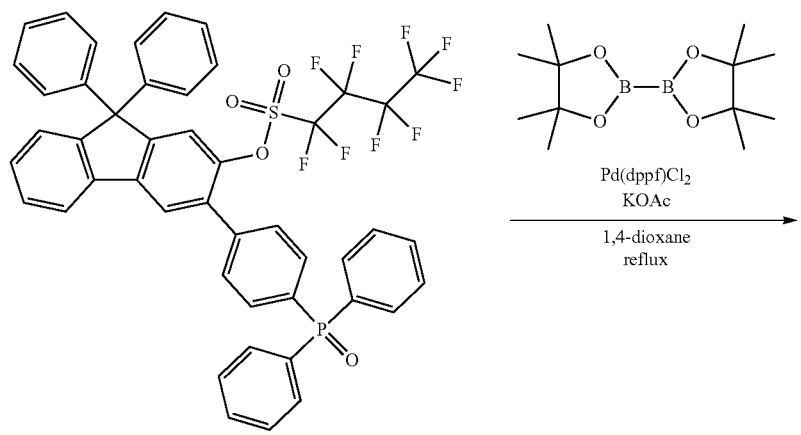
B-1
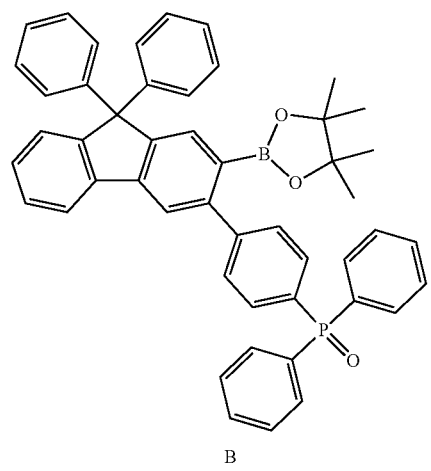
B

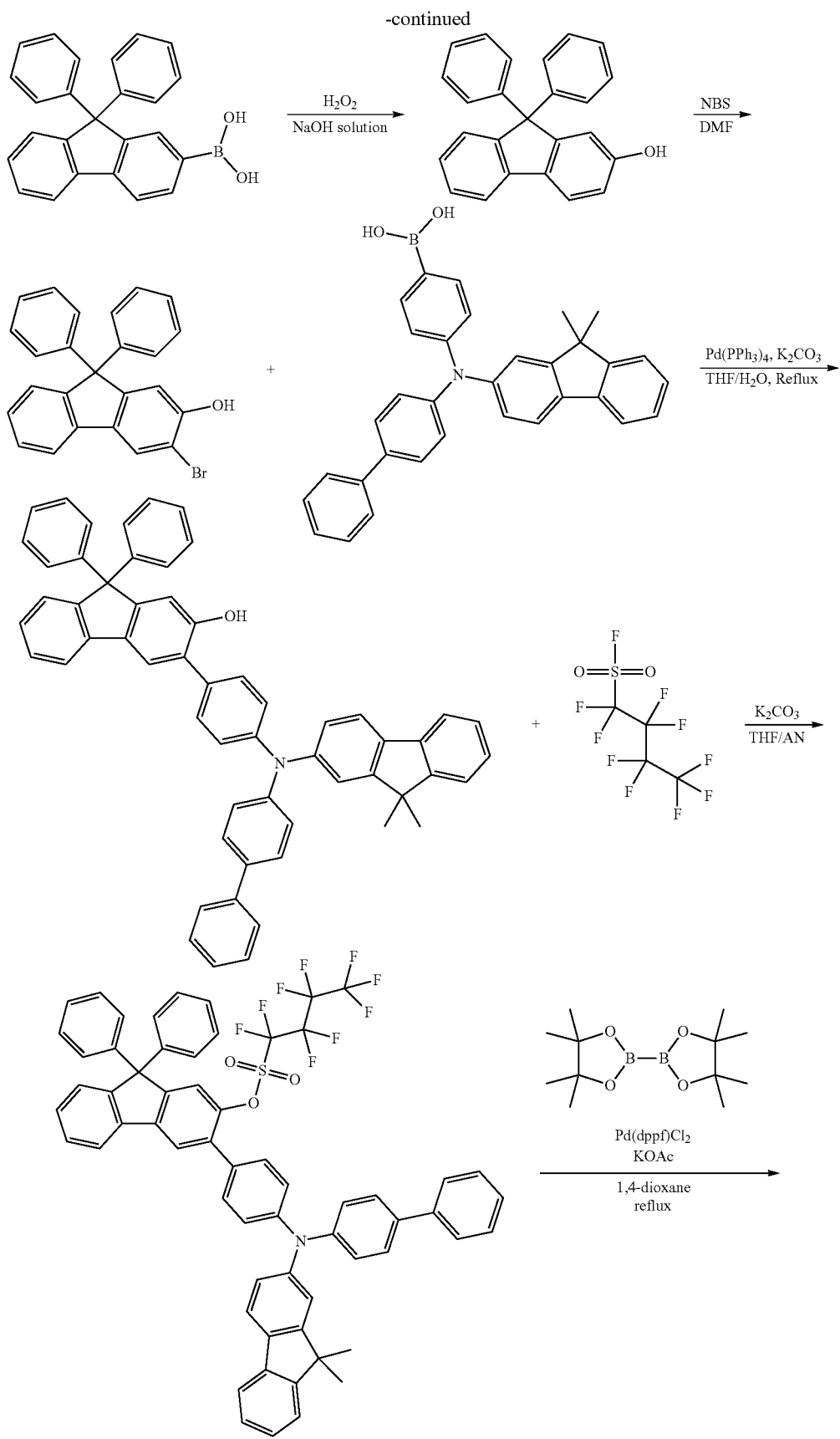

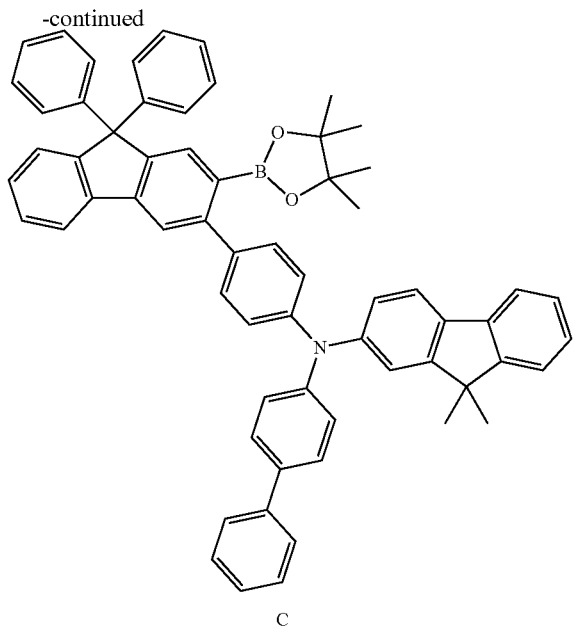

C

An exemplary embodiment of the present specification provides an organic light emitting device including: a first electrode; a second electrode disposed to face the first electrode; and an organic material layer having one or more layers disposed between the first electrode and the second electrode, in which one or more layers of the organic material layer include the above-described compound.

According to an exemplary embodiment of the present specification, the organic material layer of the organic light emitting device of the present specification may be composed of a mono layer structure, but may be composed of a multi-layer structure in which organic material layers having two or more layers are stacked. For example, the organic light emitting device of the present invention may have a structure including a hole injection layer, a hole transporting layer, an electron blocking layer, a light emitting layer, a hole blocking layer, an electron transporting layer, an electron injection layer, and the like as organic material layers. However, the structure of the organic light emitting device is not limited thereto, and may include fewer or more organic layers.

For example, the structure of the organic light emitting device of the present specification may have a structure as illustrated in FIGS. 1 and 2, but is not limited thereto.

FIG. 1 exemplifies a structure of an organic light emitting device in which a first electrode 2, a light emitting layer 3, and a second electrode 4 are sequentially stacked on a substrate 1. FIG. 1 is an exemplified structure of the organic light emitting device according to an exemplary embodiment of the present specification, and may further include other organic material layers.

FIG. 2 exemplifies a structure of an organic light emitting device in which a first electrode 2, a hole injection layer 5, a hole transporting layer 6, a light emitting layer 3, an electron transporting layer 7, an electron injection layer 8, and a second electrode 4 are sequentially stacked on a substrate 1. FIG. 2 exemplifies a structure according to another exemplary embodiment of the present specification, and may further include other organic material layers.

According to an exemplary embodiment of the present specification, the organic material layer includes a hole injection layer, a hole transporting layer, or an electron blocking layer, and the hole injection layer, the hole transporting layer, or the electron blocking layer includes the compound represented by Chemical Formula 1.

According to an exemplary embodiment of the present specification, the organic material layer includes a light emitting layer, and the light emitting layer includes the compound represented by Chemical Formula 1.

According to an exemplary embodiment of the present specification, the organic material layer includes a light emitting layer, and the light emitting layer includes the compound represented by Chemical Formula 1 as a host of the light emitting layer.

According to an exemplary embodiment of the present specification, the organic material layer includes a hole blocking layer, an electron transporting layer, or an electron injection layer, and the hole blocking layer, the electron transporting layer, or the electron injection layer includes the compound represented by Chemical Formula 1.

According to an exemplary embodiment of the present specification, the organic material layer includes a light emitting layer, and the light emitting layer includes a compound represented by the following Chemical Formula A2.

[Chemical Formula 2]

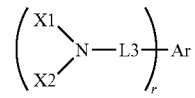

In Chemical Formula 2,

Ar is a benzofluorene skeleton, a fluoranthene skeleton, a pyrene skeleton, or a chrysene skeleton, L3 is a single bond, a $C_6$ to $C_{30}$ aryl group, or a $C_5$ to $C_{30}$ heterocyclic group, X1 and X2 are the same as or different from each other, and are each independently selected from the group consisting of a substituted or unsubstituted $C_6$ to $C_{30}$ aryl group, a substituted or unsubstituted $C_5$ to $C_{30}$ heterocyclic group, a substituted or unsubstituted $C_1$ to $C_{30}$ alkyl group, and a substituted or unsubstituted $C_7$ to $C_{30}$ arylalkyl group, and X1 and X2 may be bonded to each other to form a saturated or unsaturated ring, r is an integer of 1 or more, and when r is 2 or more, X1s are the same as or different from each other, and X2s are the same as or different from each other.

According to an exemplary embodiment of the present specification, the organic material layer includes a light emitting layer, and the light emitting layer includes the compound represented by Chemical Formula 2 as a dopant of the light emitting layer.

According to an exemplary embodiment of the present specification, L3 is a direct bond.

According to an exemplary embodiment of the present specification, r is 2.

In an exemplary embodiment of the present specification, Ar is a divalent pyrene group which is unsubstituted or substituted with deuterium, a methyl group, an ethyl group, an isopropyl group, or a tert-butyl group; or a divalent chrysene group which is unsubstituted or substituted with deuterium, a methyl group, an ethyl group, or a tert-butyl group.

According to an exemplary embodiment of the present specification, X1 and X2 are the same as or different from each other, and are each independently a substituted or unsubstituted aryl group having 6 to 30 carbon atoms.

According to an exemplary embodiment of the present specification, X1 and X2 are the same as or different from each other, and are each independently an aryl group having 6 to 30 carbon atoms, which is unsubstituted or substituted with a methyl group, an ethyl group, an isopropyl group, a tert-butyl group, a nitrile group or a silyl group substituted with an alkyl group.

According to an exemplary embodiment of the present specification, X1 and X2 are the same as or different from each other, and are each independently an aryl group having 6 to 30 carbon atoms, which is unsubstituted or substituted with a methyl group.

According to an exemplary embodiment of the present specification, X1 and X2 are the same as or different from each other, and are each independently a substituted or unsubstituted phenyl group; a substituted or unsubstituted biphenyl group; or a substituted or unsubstituted terphenyl group.

According to an exemplary embodiment of the present specification, X1 and X2 are the same as or different from each other, and are each independently a phenyl group which is unsubstituted or substituted with a methyl group, an ethyl group, an isopropyl group, a tert-butyl group, a nitrile group or a silyl group substituted with an alkyl group.

According to an exemplary embodiment of the present specification, X1 and X2 are the same as or different from each other, and are each independently a biphenyl group which is unsubstituted or substituted with a methyl group, an ethyl group, an isopropyl group, a tert-butyl group, a nitrile group or a silyl group substituted with an alkyl group.

According to an exemplary embodiment of the present specification, X1 and X2 are the same as or different from each other, and are each independently a terphenyl group which is unsubstituted or substituted with a methyl group, an ethyl group, an isopropyl group, a tert-butyl group, a nitrile group or a silyl group substituted with an alkyl group.

According to an exemplary embodiment of the present specification, X1 and X2 are the same as or different from each other, and are each independently a substituted or unsubstituted heteroaryl group having 6 to 30 carbon atoms.

According to an exemplary embodiment of the present specification, X1 and X2 are the same as or different from each other, and are each independently a heteroaryl group having 6 to 30 carbon atoms, which is unsubstituted or substituted with a methyl group, an ethyl group, an isopropyl group, a tert-butyl group, a nitrile group, a silyl group substituted with an alkyl group, or a phenyl group.

According to an exemplary embodiment of the present specification, X1 and X2 are the same as or different from each other, and are each independently a dibenzofuran group which is unsubstituted or substituted with a methyl group, an ethyl group, an isopropyl group, a tert-butyl group, a nitrile group, a silyl group substituted with an alkyl group, or a phenyl group.

According to an exemplary embodiment of the present specification, X1 and X2 are the same as or different from each other, and are each independently selected from a substituted or unsubstituted aryl group having 6 to 30 carbon atoms; and a substituted or unsubstituted heteroaryl group having 6 to 30 carbon atoms.

According to an exemplary embodiment of the present specification, X1 and X2 are the same as or different from each other, and are each independently selected from an aryl group having 6 to 30 carbon atoms, which is unsubstituted or substituted with a methyl group; and a heteroaryl group having 6 to 30 carbon atoms, which is unsubstituted or substituted with a methyl group, an ethyl group, an isopropyl group, a tert-butyl group, a nitrile group, a silyl group substituted with an alkyl group, or a phenyl group.

According to an exemplary embodiment of the present specification, X1 and X2 are the same as or different from each other, and are each independently selected from a phenyl group substituted with a methyl group; and a dibenzofuran group.

According to an exemplary embodiment of the present specification, Chemical Formula 2 is selected from the following compound.

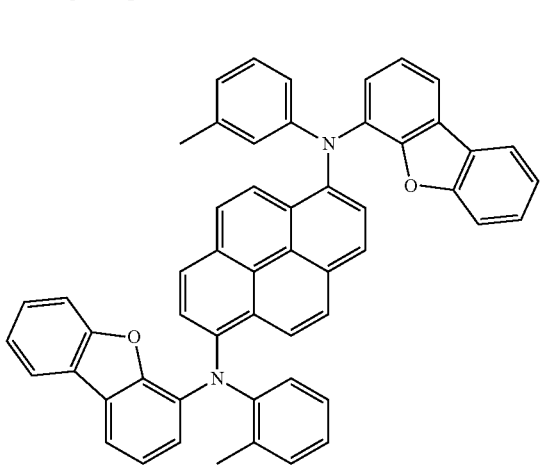 [SMILES: Cc1cccc(N(c2ccc3ccc4c(N(c5ccccc5C)c5cccc6c5oc5ccccc56)ccc5ccc2c3c54)c2cccc3c2oc2ccccc23)c1]

According to an exemplary embodiment of the present specification, the organic material layer includes a light emitting layer, and the light emitting layer includes a compound represented by the following Chemical Formula 3.

[Chemical Formula 3]

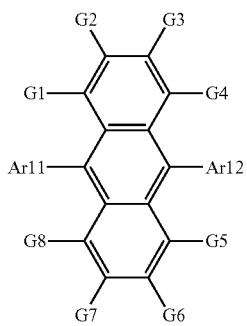

Ar11 and Ar12 are the same as or different from each other, and are each independently a substituted or unsubstituted monocyclic aryl group; or a substituted or unsubstituted polycyclic aryl group, and G1 to G8 are the same as or different from each other, and are each independently hydrogen; a substituted or unsubstituted monocyclic aryl group; or a substituted or unsubstituted polycyclic aryl group.

According to an exemplary embodiment of the present specification, the organic material layer includes a light emitting layer, and the light emitting layer includes the compound represented by Chemical Formula 3 as a host of the light emitting layer.

According to an exemplary embodiment of the present specification, Ar11 and Ar12 are the same as or different from each other, and are each independently a substituted or unsubstituted polycyclic aryl group.

According to an exemplary embodiment of the present specification, Ar11 and Ar12 are the same as or different from each other, and are each independently a substituted or unsubstituted polycyclic aryl group having 10 to 30 carbon atoms.

According to an exemplary embodiment of the present specification, Ar11 and Ar12 are the same as or different from each other, and are each independently a substituted or unsubstituted naphthyl group.

According to an exemplary embodiment of the present specification, Ar11 and Ar12 are the same as or different from each other, and are each independently a substituted or unsubstituted 1-naphthyl group, or a substituted or unsubstituted 2-naphthyl group.

According to an exemplary embodiment of the present specification, Ar11 is a 1-naphthyl group, and Ar12 is a 2-naphthyl group.

According to an exemplary embodiment of the present specification, G1 to G8 are hydrogen.

According to an exemplary embodiment of the present specification, Chemical Formula 3 is selected from the following compound.

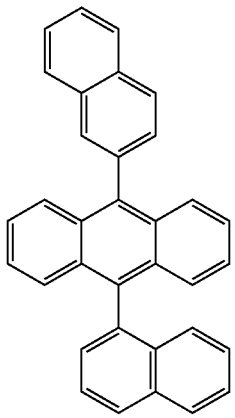 [SMILES: c1ccc2cc(-c3c4ccccc4c(-c4cccc5ccccc45)c4ccccc34)ccc2c1]

According to an exemplary embodiment of the present specification, the light emitting layer includes a host.

According to an exemplary embodiment of the present specification, the light emitting layer includes a dopant.

According to an exemplary embodiment of the present specification, the light emitting layer includes a phosphorescent dopant.

In an exemplary embodiment of the present specification, the light emitting layer includes both a host and a dopant.

According to an exemplary embodiment of the present specification, the organic material layer includes a light emitting layer, and the light emitting layer includes the compound represented by Chemical Formula 2 as a dopant of the light emitting layer, and includes the compound represented by Chemical Formula 3 as a host of the light emitting layer.

According to an exemplary embodiment of the present specification, the electron blocking layer includes the compound of Chemical Formula 1.

According to an exemplary embodiment of the present specification, the electron transporting layer includes the compound of Chemical Formula 1.

According to an exemplary embodiment of the present specification, the organic material layer may further include one or more layers selected from the group consisting of a hole injection layer, a hole transporting layer, a light emitting layer, an electron transporting layer, and an electron injection layer.

The organic light emitting device of the present specification may be manufactured by the materials and methods known in the art, except that one or more layers of the organic material layer include the compound of the present specification, that is, the compound represented by Chemical Formula 1.

When the organic light emitting device includes a plurality of organic material layers, the organic material layers may be formed of the same material or different materials.

For example, the organic light emitting device of the present specification may be manufactured by sequentially stacking a first electrode, an organic material layer, and a second electrode on a substrate. At this time, the organic light emitting device may be manufactured by depositing a metal or a metal oxide having conductivity, or an alloy thereof on a substrate to form a first electrode, forming an organic material layer including a hole injection layer, a hole transporting layer, a light emitting layer, and an electron transporting layer thereon, and then depositing a material, which may be used as a second electrode, thereon, by using a physical vapor deposition (PVD) method such as sputtering or e-beam evaporation. In addition to the method described above, an organic light emitting device may be made by sequentially depositing a second electrode material, an organic material layer, and a first electrode material on a substrate. Further, the compound represented by Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

According to an exemplary embodiment of the present specification, the first electrode is a positive electrode, and the second electrode is a negative electrode.

According to another exemplary embodiment of the present specification, the first electrode is a negative electrode, and the second electrode is a positive electrode.

As the positive electrode material, materials having a high work function are usually preferred so as to facilitate the injection of holes into an organic material layer. Specific examples of the positive electrode material which may be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or $SnO_2$:Sb; a conductive polymer such as poly(3-methylthiophene), poly[3,4-(ethylene-1,2-dioxy)thiophene] (PEDOT), polypyrrole, and polyaniline; and the like, but are not limited thereto.

As the negative electrode material, materials having a low work function are usually preferred so as to facilitate the injection of electrons into an organic material layer. Specific examples of the negative electrode material include: a metal such as magnesium, calcium, sodium, potassium, titanium, indium, yttrium, lithium, gadolinium, aluminum, silver, tin, and lead, or an alloy thereof; a multi-layer structured material such as LiF/Al or $LiO_2$/Al and Mg/Ag; and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. The highest occupied molecular orbital (HOMO) of the hole injection material is preferably a value between the work function of the positive electrode material and the HOMO of the neighboring organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based conductive polymers, and the like, but are not limited thereto.

The hole transporting layer is a layer which accepts holes from a hole injection layer and transports the holes to a light emitting layer, and a hole transporting material is suitably a material having high hole mobility which may accept holes from a positive electrode or a hole injection layer and transfer the holes to a light emitting layer. Specific examples thereof include arylamine-based organic materials, conductive polymers, block copolymers having both conjugated portions and non-conjugated portions, and the like, but are not limited thereto.

A light emitting material for the light emitting layer is a material which may emit light in a visible light region by accepting and combining holes and electrons from a hole transporting layer and an electron transporting layer, respectively, and is preferably a material having good quantum efficiency for fluorescence or phosphorescence. Specific examples thereof include: an 8-hydroxy-quinoline aluminum complex ($Alq_3$); carbazole-based compounds; dimerized styryl compounds; BAlq; 10-hydroxybenzoquinoline-metal compounds; benzoxazole-based, benzothiazole-based and benzoimidazole-based compounds; poly(p-phenylenevinylene) (PPV)-based polymers; spiro compounds; polyfluorene, lubrene, and the like, but are not limited thereto.

The light emitting layer may include a host material and a dopant material. Examples of the host material include a fused aromatic ring derivative, or a hetero ring-containing compound, and the like. Specifically, examples of the fused aromatic ring derivative include an anthracene derivative, a pyrene derivative, a naphthalene derivative, a pentacene derivative, a phenanthrene compound, a fluoranthene compound, and the like, and examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group is or are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transporting layer is a layer which accepts electrons from an electron injection layer and transports the electrons to a light emitting layer, and an electron transporting material is suitably a material having high electron mobility which may proficiently accept electrons from a negative electrode and transfer the electrons to a light emitting layer. Specific examples thereof include: Al complexes of 8-hydroxyquinoline; complexes including $Alq_3$; organic radical compounds; hydroxyflavone-metal complexes; and the like, but are not limited thereto. The electron transporting layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, an effect of injecting electrons from a negative electrode, and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and a derivative thereof, a metal complex compound, a nitrogen-containing 5-membered ring derivative, and the like, but are not limited thereto. Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The organic light emitting device according to the present specification may be a top emission type, a bottom emission type, or a dual emission type according to the materials to be used.

Hereinafter, the present specification will be described in detail with reference to Examples for specifically describing the present specification. However, the Examples according to the present specification may be modified in various forms, and it is not interpreted that the scope of the present specification is limited to the Examples described below in detail. The Examples of the present specification are provided to more completely explain the present specification to a person with ordinary skill in the art.

Preparation Example 1

Compound 1

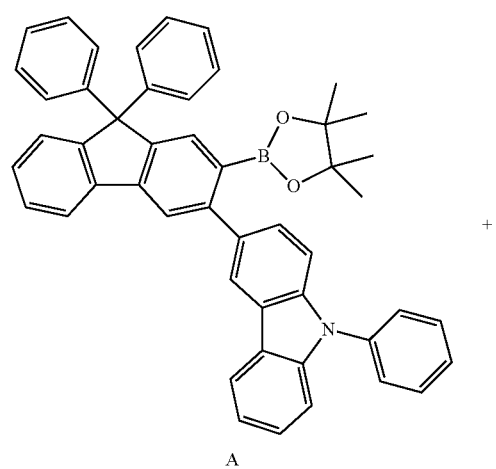

A

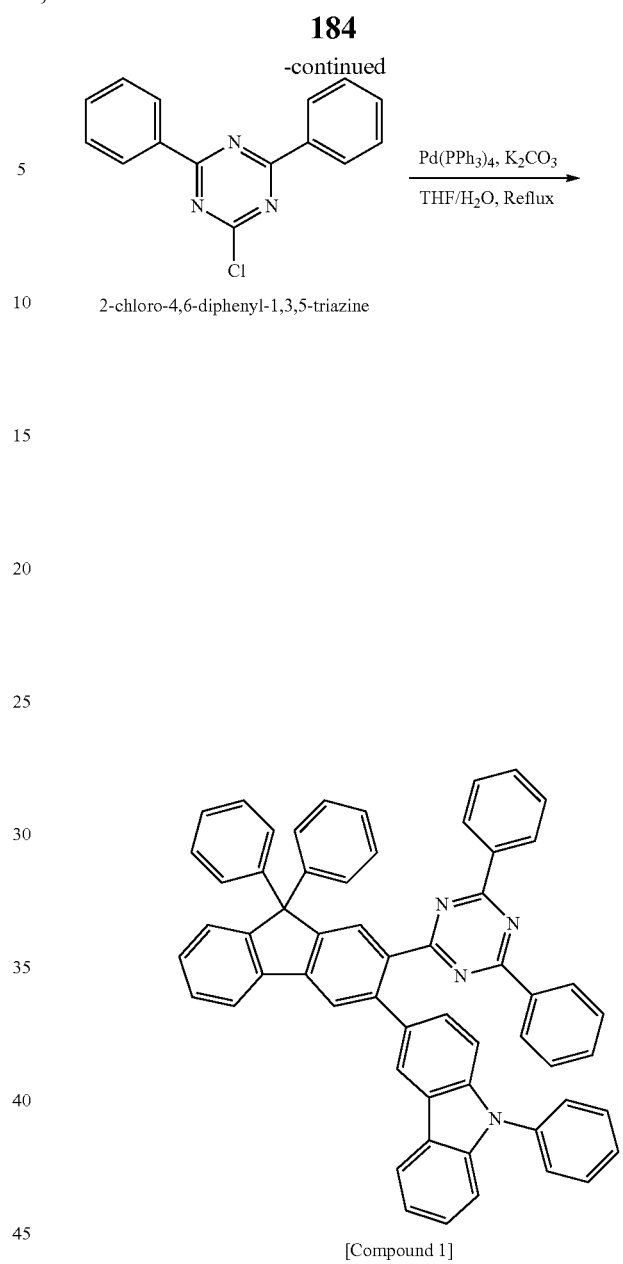

Compound A (14.42 g, 25.71 mmol) and 2-chloro-4,6-diphenyl-1,3,5-triazine (6.18 g, 23.16 mmol) were completely dissolved in 280 ml of tetrahydrofuran in a 500-ml round bottom flask under a nitrogen atmosphere, and then an aqueous 2 M potassium carbonate solution (140 ml) was added thereto, tetrakis-(triphenylphosphine)palladium (0.73 g, 0.63 mmol) was put thereinto, and then the resulting mixture was heated and stirred for 3 hours. The temperature was lowered to room temperature, the aqueous layer was removed, and the residue was dried over anhydrous magnesium sulfate, and then concentrated under reduced pressure, and recrystallized with 180 ml of ethyl acetate to prepare Compound 1 (8.24 g, 49%).

MS[M+H]$^+$=791

Preparation Example 2

Compound 2

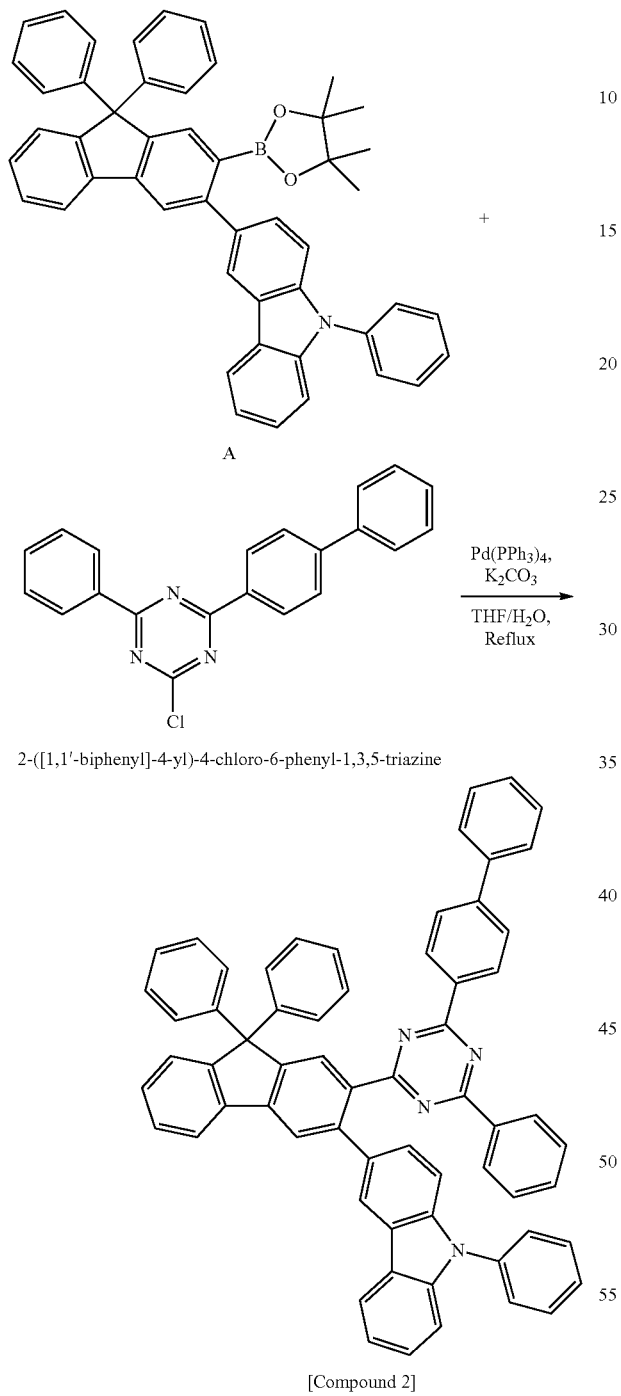

2-([1,1'-biphenyl]-4-yl)-4-chloro-6-phenyl-1,3,5-triazine

[Compound 2]

Compound A (11.76 g, 17.17 mmol) and 2-([1,1'-biphenyl]-4-yl)-4-chloro-6-phenyl-1,3,5-triazine (6.48 g, 18.88 mmol) were completely dissolved in 240 ml of tetrahydrofuran in a 500-ml round bottom flask under a nitrogen atmosphere, and then an aqueous 2 M potassium carbonate solution (120 ml) was added thereto, tetrakis-(triphenylphosphine)palladium (0.60 g, 0.52 mmol) was put thereinto, and then the resulting mixture was heated and stirred for 3 hours. The temperature was lowered to room temperature, the aqueous layer was removed, and the residue was dried over anhydrous magnesium sulfate, and then concentrated under reduced pressure, and recrystallized with 160 ml of ethyl acetate to prepare Compound 2 (7.44 g, 55%). MS[M+H]$^+$=867

Preparation Example 3

Compound 3

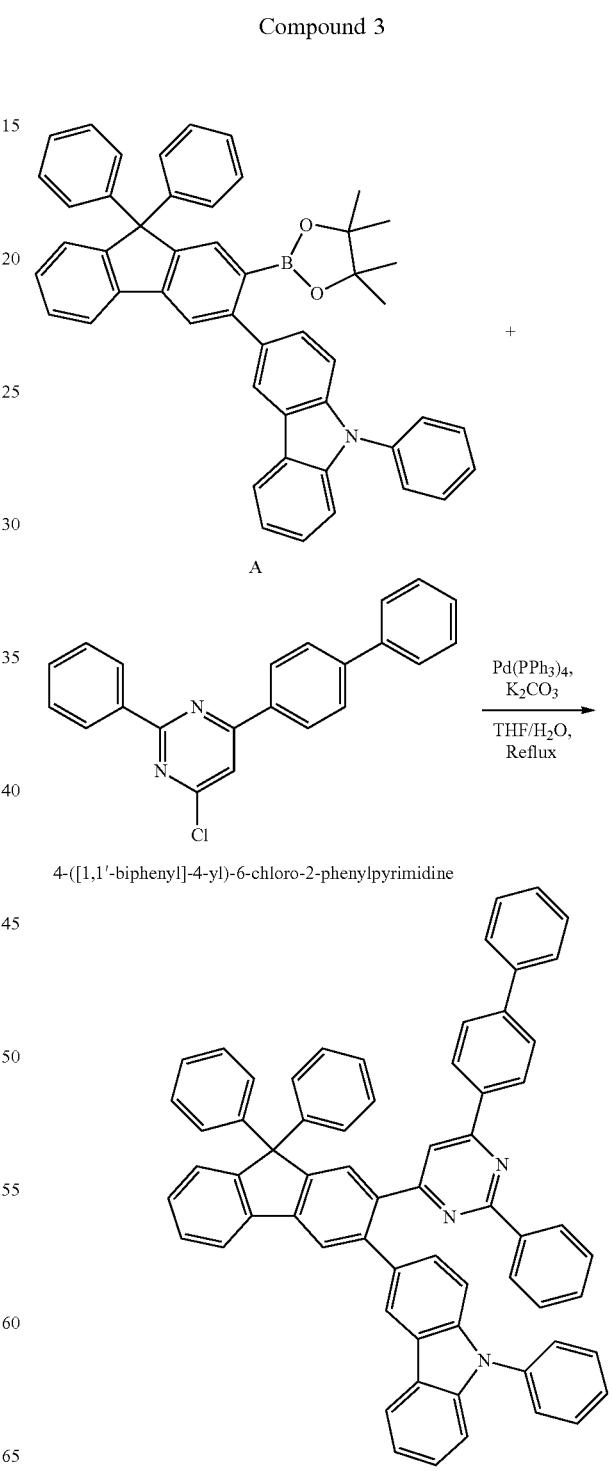

4-([1,1'-biphenyl]-4-yl)-6-chloro-2-phenylpyrimidine

Compound A (8.33 g, 15.70 mmol) and 4-([1,1'-biphenyl]-4-yl)-6-chloro-2-phenylpyrimidine (3.95 g, 11.55 mmol) were completely dissolved in 200 ml of tetrahydrofuran in a 500-ml round bottom flask under a nitrogen atmosphere, and then an aqueous 2 M potassium carbonate solution (100 ml) was added thereto, tetrakis-(triphenylphosphine)palladium (0.42 g, 0.36 mmol) was put thereinto, and then the resulting mixture was heated and stirred for 2 hours. The temperature was lowered to room temperature, the aqueous layer was removed, and the residue was dried over anhydrous magnesium sulfate, and then concentrated under reduced pressure, and recrystallized with 230 ml of ethyl acetate to prepare Compound 3 (5.29 g, 50%).

MS[M+H]$^+$=866

Preparation Example 4

Compound 4

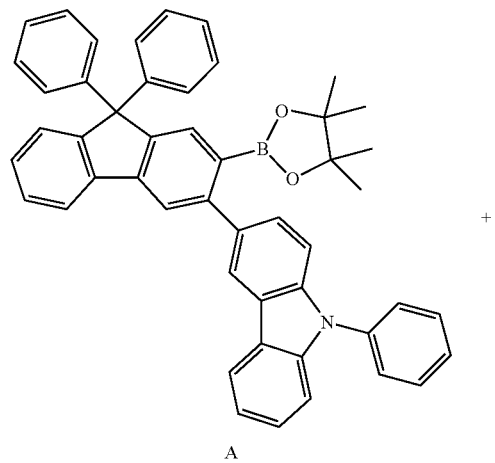

A

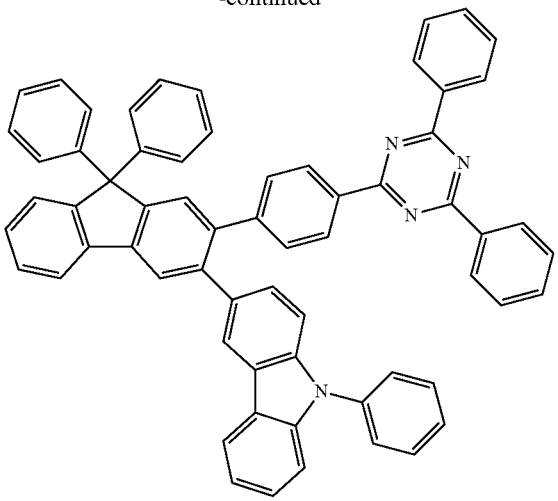

Compound A (6.23 g, 9.09 mmol) and 2-(4-bromophenyl)-4,6-diphenyl-1,3,5-triazine (3.34 g, 8.64 mmol) were completely dissolved in 160 ml of tetrahydrofuran in a 500-ml round bottom flask under a nitrogen atmosphere, and then an aqueous 2 M potassium carbonate solution (80 ml) was added thereto, tetrakis-(triphenylphosphine)palladium (0.32 g, 0.27 mmol) was put thereinto, and then the resulting mixture was heated and stirred for 4 hours. The temperature was lowered to room temperature, the aqueous layer was removed, and the residue was dried over anhydrous magnesium sulfate, and then concentrated under reduced pressure, and recrystallized with 230 ml of tetrahydrofuran to prepare Compound 4 (5.96 g, 76%).

MS[M+H]$^+$=867

Preparation Example 5

Compound 5

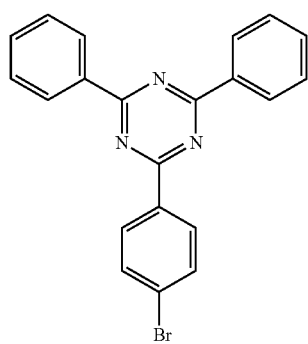

2-(4-bromophenyl)-4,6-diphenyl-1,3,5-triazine

Pd(PPh$_3$)$_4$, K$_2$CO$_3$

THF/H$_2$O, Reflux

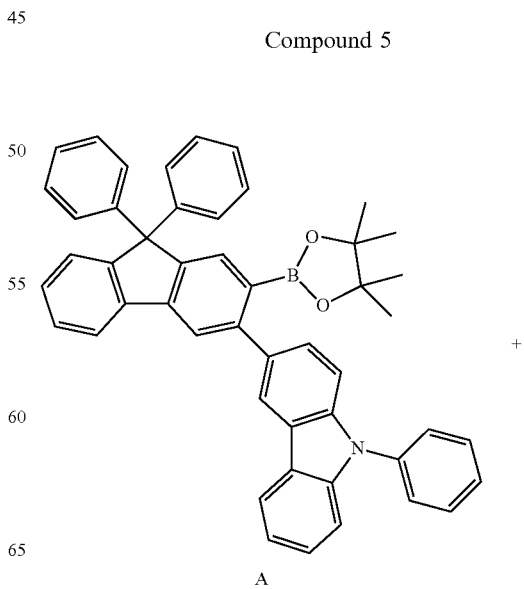

A

-continued

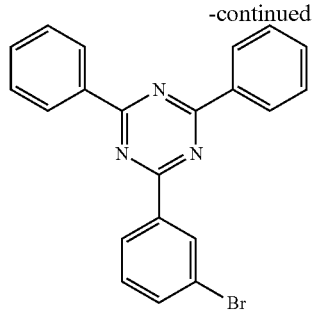

2-(3-bromophenyl)-4,6-diphenyl-1,3,5-triazine

Pd(PPh$_3$)$_4$, K$_2$CO$_3$
THF/H$_2$O, Reflux

Preparation Example 6

Compound 6

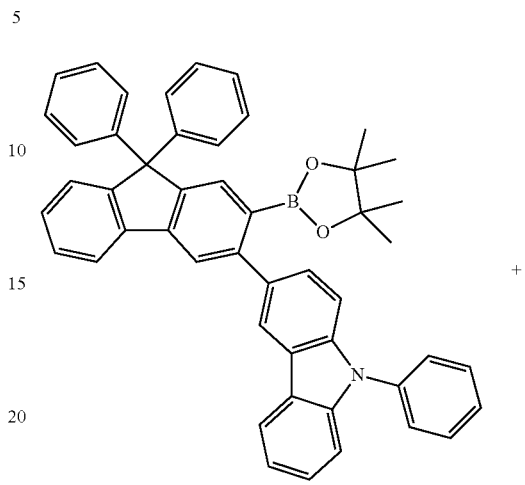

A

+

4-(3-bromophenyl)-2,6-diphenylpyrimidine

Pd(PPh$_3$)$_4$, K$_2$CO$_3$
THF/H$_2$O, Reflux

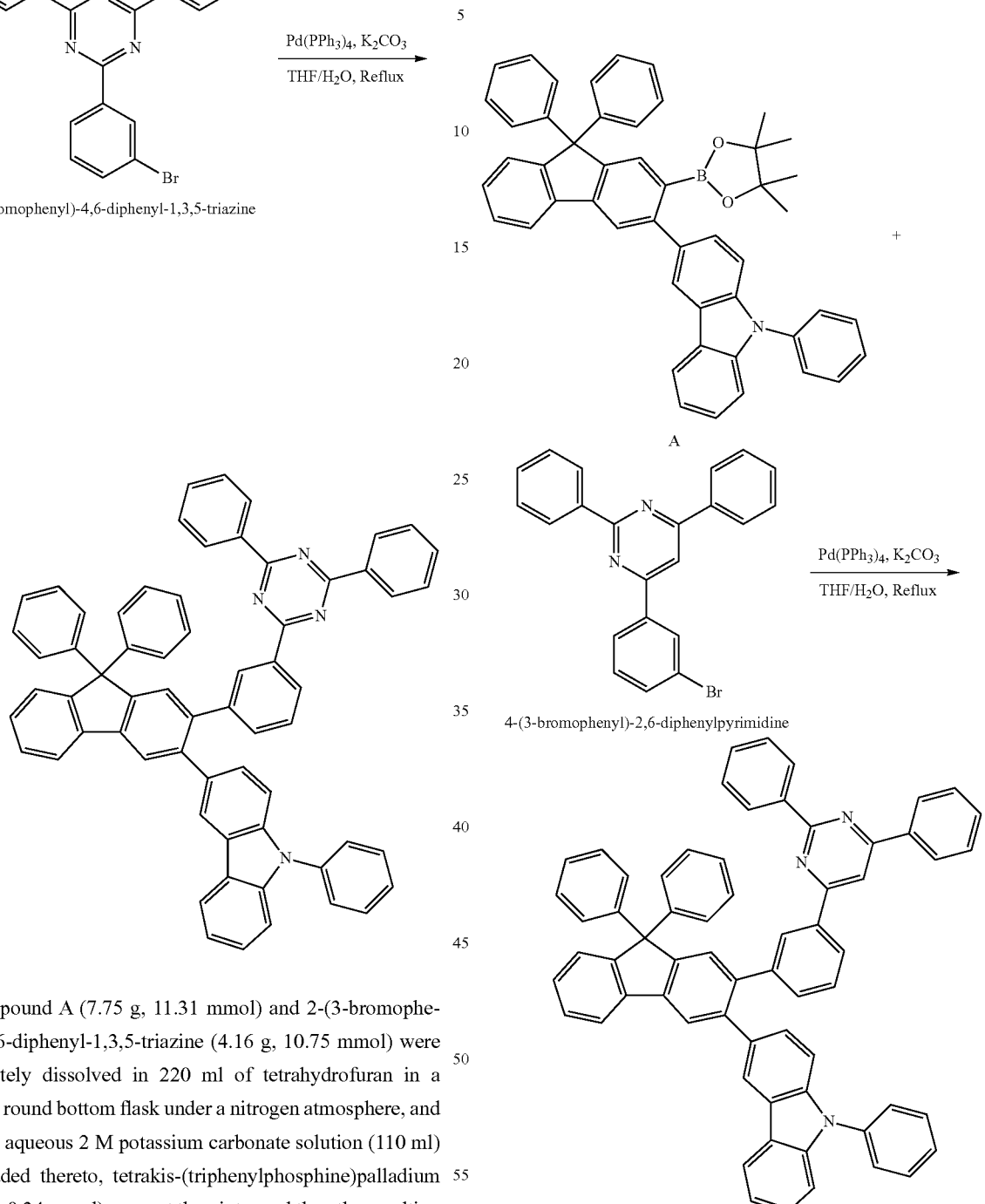

Compound A (7.75 g, 11.31 mmol) and 2-(3-bromophenyl)-4,6-diphenyl-1,3,5-triazine (4.16 g, 10.75 mmol) were completely dissolved in 220 ml of tetrahydrofuran in a 500-ml round bottom flask under a nitrogen atmosphere, and then an aqueous 2 M potassium carbonate solution (110 ml) was added thereto, tetrakis-(triphenylphosphine)palladium (0.39 g, 0.34 mmol) was put thereinto, and then the resulting mixture was heated and stirred for 3 hours. The temperature was lowered to room temperature, the aqueous layer was removed, and the residue was dried over anhydrous magnesium sulfate, and then concentrated under reduced pressure, and recrystallized with 210 ml of ethyl acetate to prepare Compound 5 (6.65 g, 68%).

MS[M+H]$^+$=867

Compound A (6.53 g, 9.53 mmol) and 4-(3-bromophenyl)-2,6-diphenylpyrimidine (3.50 g, 9.06 mmol) were completely dissolved in 200 ml of tetrahydrofuran in a 500-ml round bottom flask under a nitrogen atmosphere, and then an aqueous 2 M potassium carbonate solution (100 ml) was added thereto, tetrakis-(triphenylphosphine)palladium (0.33 g, 0.29 mmol) was put thereinto, and then the resulting mixture was heated and stirred for 6 hours. The temperature was lowered to room temperature, the aqueous layer was removed, and the residue was dried over anhydrous magnesium sulfate, and then concentrated under reduced pressure, and recrystallized with 220 ml of ethyl acetate to prepare Compound 6 (5.72 g, 69%).

MS[M+H]$^+$=866

Preparation Example 7

Compound 7

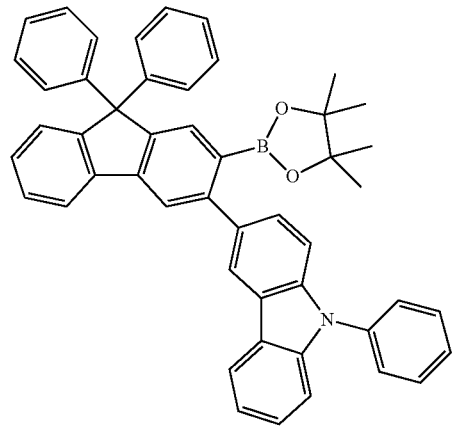

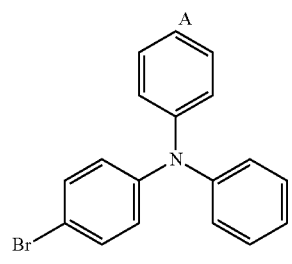

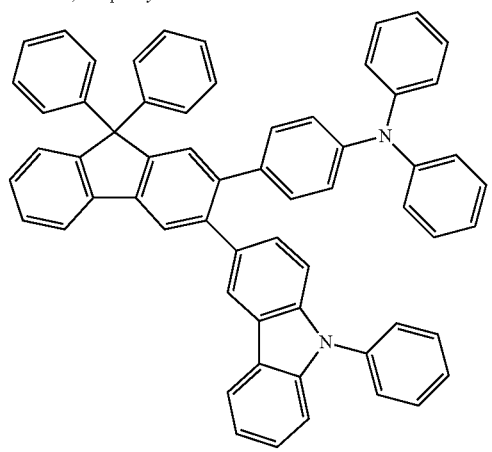

removed, and the residue was dried over anhydrous magnesium sulfate, and then concentrated under reduced pressure, and recrystallized with 180 ml of ethyl acetate to prepare Compound 7 (3.98 g, 71%).

MS[M+H]$^+$=803

Preparation Example 8

Compound 8

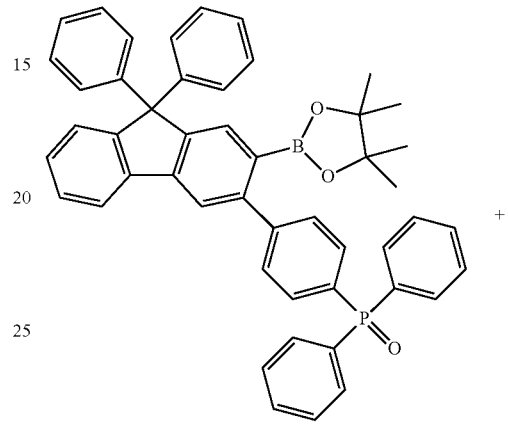

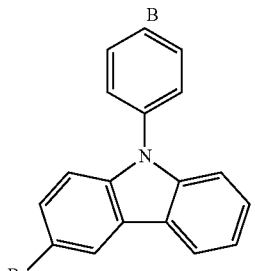

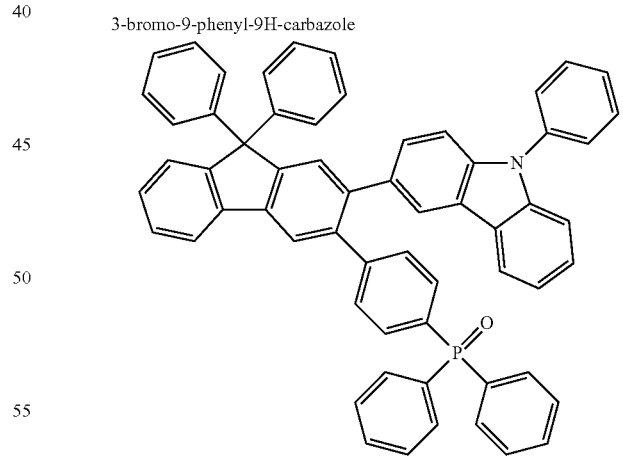

Compound A (4.77 g, 6.96 mmol) and 4-bromo-N,N-diphenylaniline (2.14 g, 6.62 mmol) were completely dissolved in 220 ml of tetrahydrofuran in a 500-ml round bottom flask under a nitrogen atmosphere, and then an aqueous 2 M potassium carbonate solution (110 ml) was added thereto, tetrakis-(triphenylphosphine)palladium (0.24 g, 0.21 mmol) was put thereinto, and then the resulting mixture was heated and stirred for 3 hours. The temperature was lowered to room temperature, the aqueous layer was Compound B (6.26 g, 19.50 mmol) and 3-bromo-9-phenyl-9H-carbazole (13.34 g, 18.53 mmol) were completely dissolved in 280 ml of tetrahydrofuran in a 500-ml round bottom flask under a nitrogen atmosphere, and then an aqueous 2 M potassium carbonate solution (140 ml) was added thereto, tetrakis-(triphenylphosphine)palladium (0.68 g, 0.59 mmol) was put thereinto, and then the resulting mixture was heated and stirred for 8 hours. The temperature was lowered to room temperature, the aqueous layer was removed, and the residue was dried over anhydrous magnesium sulfate, and then concentrated under reduced pressure, and recrystallized with 360 ml of acetone to prepare Compound 8 (9.68 g, 62%).

MS[M+H]$^+$=836

Preparation Example 9

Compound 9

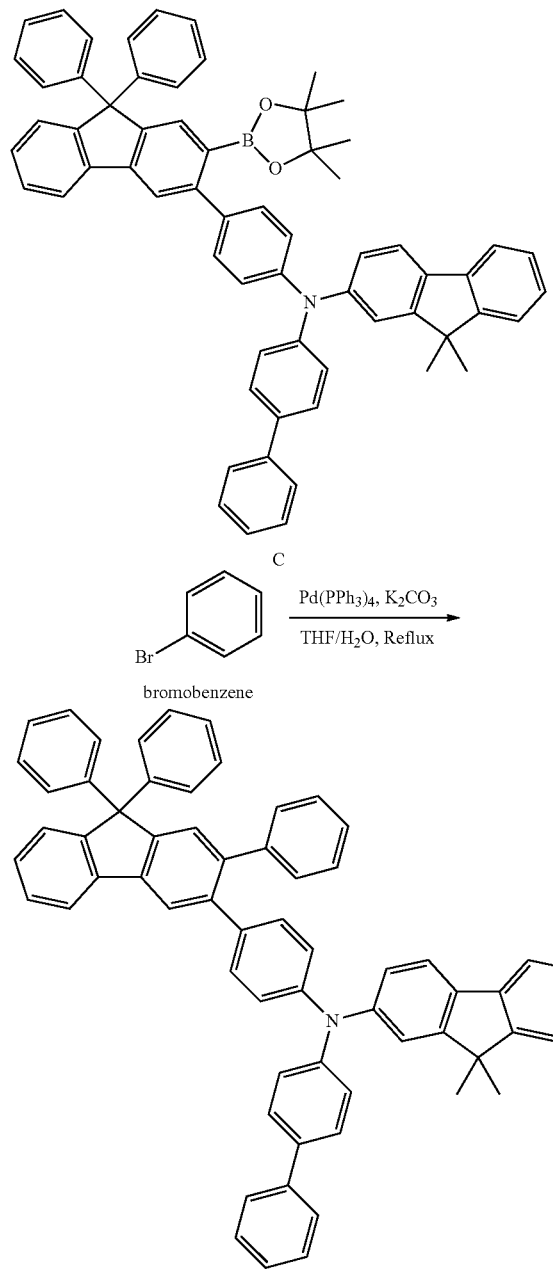

thereinto, and then the resulting mixture was heated and stirred for 3 hours. The temperature was lowered to room temperature, the aqueous layer was removed, and the residue was dried over anhydrous magnesium sulfate, and then concentrated under reduced pressure, and recrystallized with 300 ml of ethanol to prepare Compound 9 (6.59 g, 60%).

MS[M+H]$^+$=830

Preparation Example 10

Compound 10

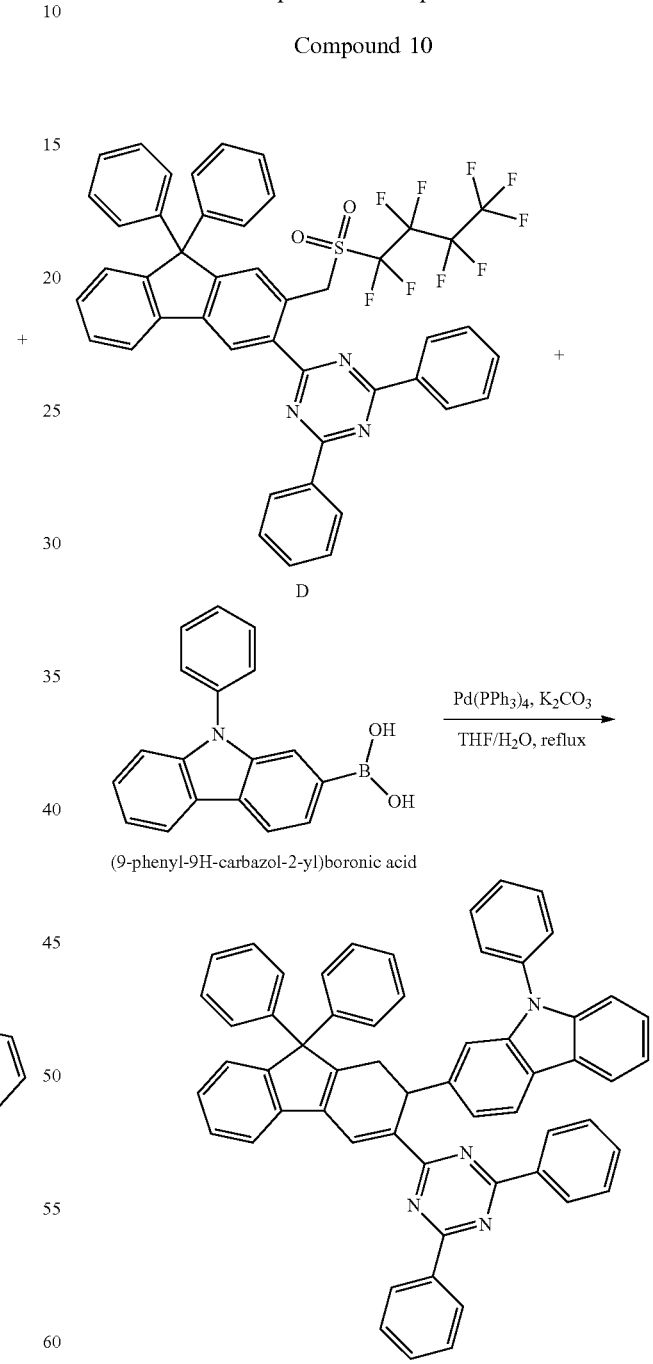

Compound C (13.02 g, 18.22 mmol) and bromobenzene (2.6 g, 16.56 mmol) were completely dissolved in 300 ml of tetrahydrofuran in a 500-ml round bottom flask under a nitrogen atmosphere, and then an aqueous 2 M potassium carbonate solution (150 ml) was added thereto, tetrakis-(triphenylphosphine)palladium (0.57 g, 0.50 mmol) was put Compound D (10.46 g, 12.35 mmol) and (9-phenyl-9H-carbazol-2-yl)boronic acid (3.90 g, 13.58 mmol) were completely dissolved in 240 ml of tetrahydrofuran in a 500-ml round bottom flask under a nitrogen atmosphere, and then an aqueous 2 M potassium carbonate solution (120 ml) was added thereto, tetrakis-(triphenylphosphine)palladium (0.43 g, 0.37 mmol) was put thereinto, and then the resulting mixture was heated and stirred for 4 hours. The temperature was lowered to room temperature, the aqueous layer was removed, and the residue was dried over anhydrous magnesium sulfate, and then concentrated under reduced pressure, and recrystallized with 230 ml of ethyl acetate to prepare Compound 10 (7.09 g, 73%).

MS[M+H]$^+$=791

Preparation Example 11

Compound 11

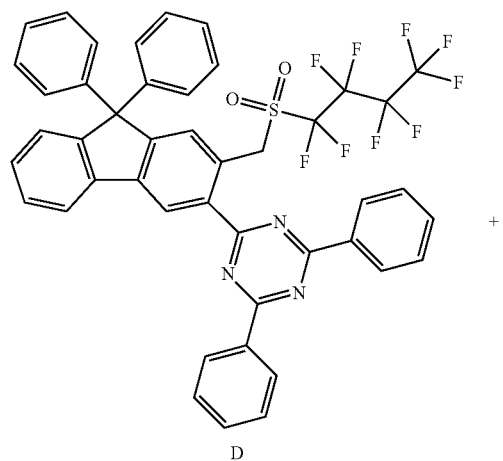

D

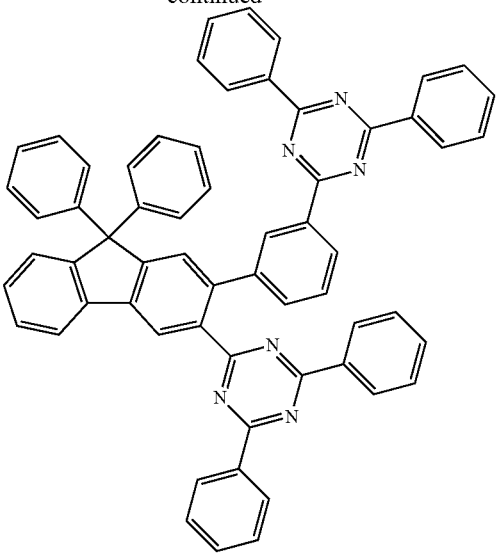

Compound D (9.57 g, 11.30 mmol) and (3-(4,6-diphenyl-1,3,5-triazin-2-yl)phenyl)boronic acid (4.39 g, 12.43 mmol) were completely dissolved in 260 ml of tetrahydrofuran in a 500-ml round bottom flask under a nitrogen atmosphere, and then an aqueous 2 M potassium carbonate solution (130 ml) was added thereto, tetrakis-(triphenylphosphine)palladium (0.39 g, 0.34 mmol) was put thereinto, and then the resulting mixture was heated and stirred for 3 hours. The temperature was lowered to room temperature, the aqueous layer was removed, and the residue was dried over anhydrous magnesium sulfate, and then concentrated under reduced pressure, and recrystallized with 250 ml of tetrahydrofuran to prepare Compound 11 (8.49 g, 88%).

MS[M+H]$^+$=857

Preparation Example 12

Compound 12

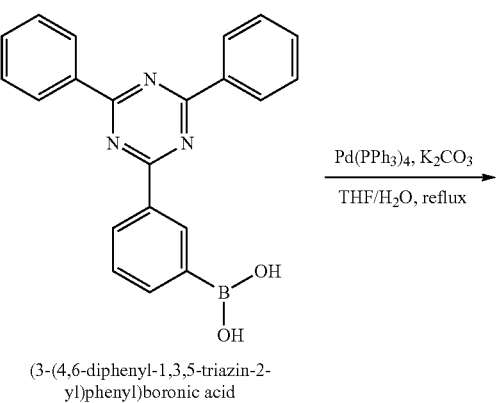

(3-(4,6-diphenyl-1,3,5-triazin-2-yl)phenyl)boronic acid

Pd(PPh$_3$)$_4$, K$_2$CO$_3$
THF/H$_2$O, reflux
→

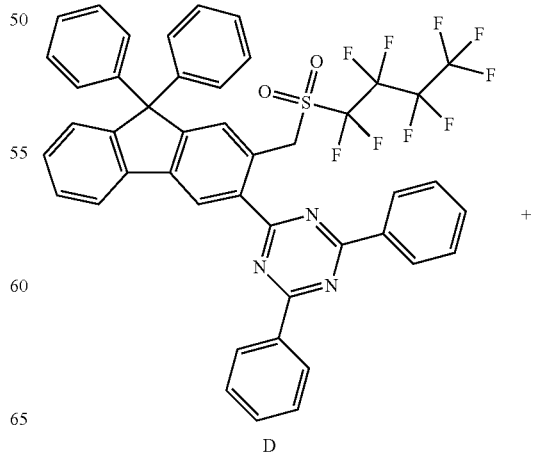

D

-continued

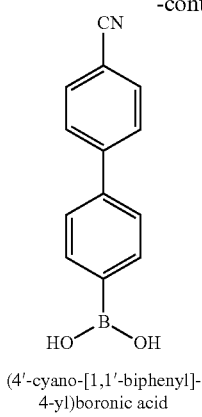

(4'-cyano-[1,1'-biphenyl]-4-yl)boronic acid

Pd(PPh3)4, K2CO3
THF/H2O, reflux →

Preparation Example 13

Compound 13

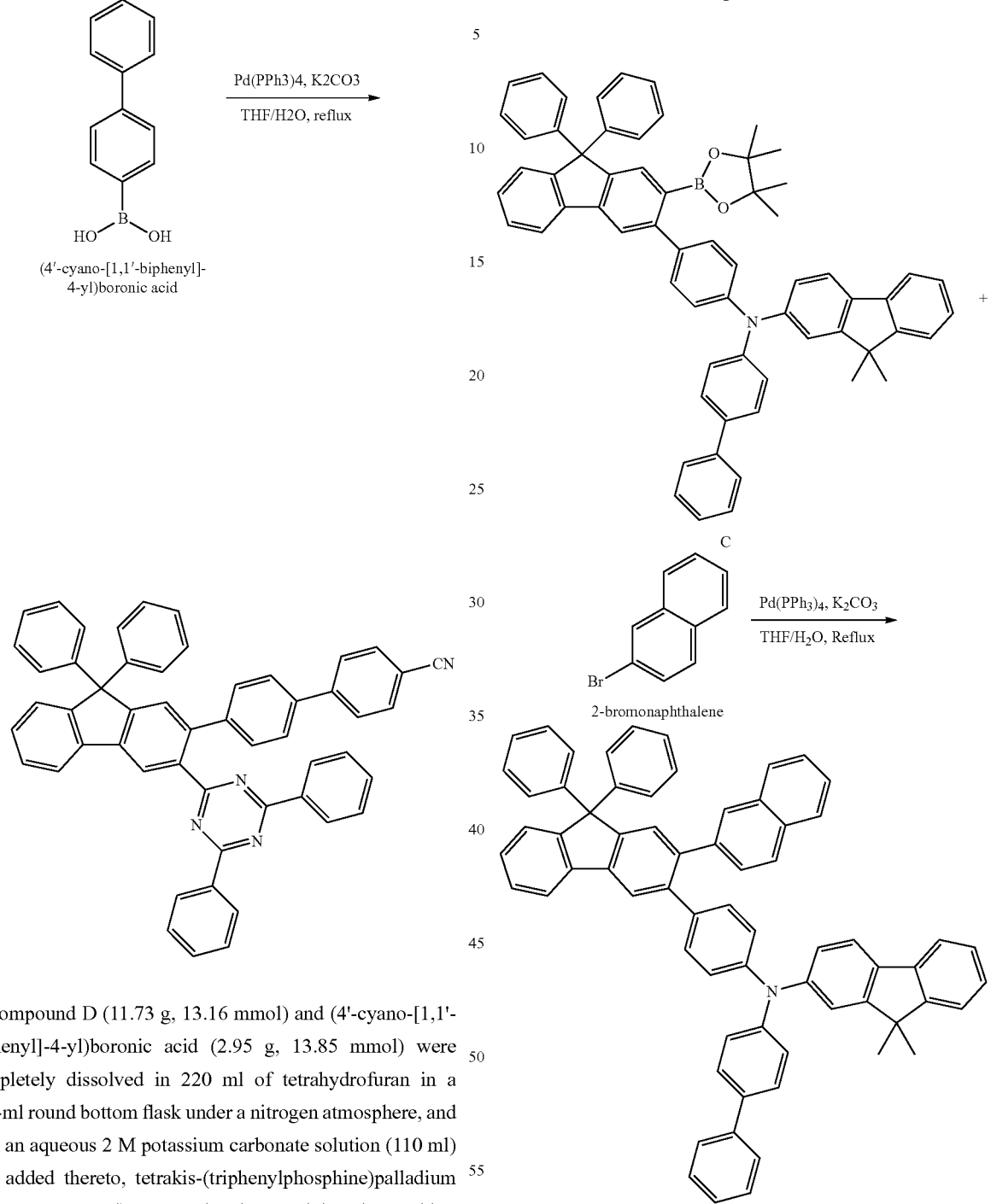

2-bromonaphthalene

Compound D (11.73 g, 13.16 mmol) and (4'-cyano-[1,1'-biphenyl]-4-yl)boronic acid (2.95 g, 13.85 mmol) were completely dissolved in 220 ml of tetrahydrofuran in a 500-ml round bottom flask under a nitrogen atmosphere, and then an aqueous 2 M potassium carbonate solution (110 ml) was added thereto, tetrakis-(triphenylphosphine)palladium (0.48 g, 0.42 mmol) was put thereinto, and then the resulting mixture was heated and stirred for 3 hours. The temperature was lowered to room temperature, the aqueous layer was removed, and the residue was dried over anhydrous magnesium sulfate, and then concentrated under reduced pressure, and recrystallized with 210 ml of tetrahydrofuran to prepare Compound 12 (8.66 g, 77%).

MS[M+H]$^+$=727

Compound C (12.01 g, 13.64 mmol) and 2-bromonaphthalene (2.69 g, 13.0 mmol) were completely dissolved in 240 ml of tetrahydrofuran in a 500-ml round bottom flask under a nitrogen atmosphere, and then an aqueous 2 M potassium carbonate solution (120 ml) was added thereto, tetrakis-(triphenylphosphine)palladium (0.45 g, 0.39 mmol) was put thereinto, and then the resulting mixture was heated and stirred for 4 hours. The temperature was lowered to room temperature, the aqueous layer was removed, and the residue was dried over anhydrous magnesium sulfate, and then concentrated under reduced pressure, and recrystallized with 250 ml of ethyl acetate to prepare Compound 13 (7.25 g, 63%).
MS[M+H]⁺=880

Preparation Example 14

Compound 14

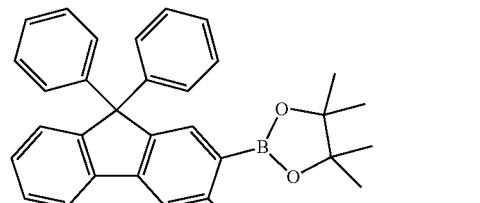

+

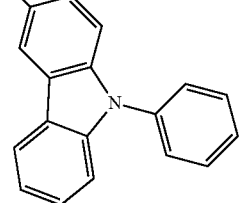

N-(4-bromophenyl)-N-phenyl-[1,1'-biphenyl]-4-amine

Pd(PPh₃)₄, K₂CO₃
THF/H₂O, Reflux

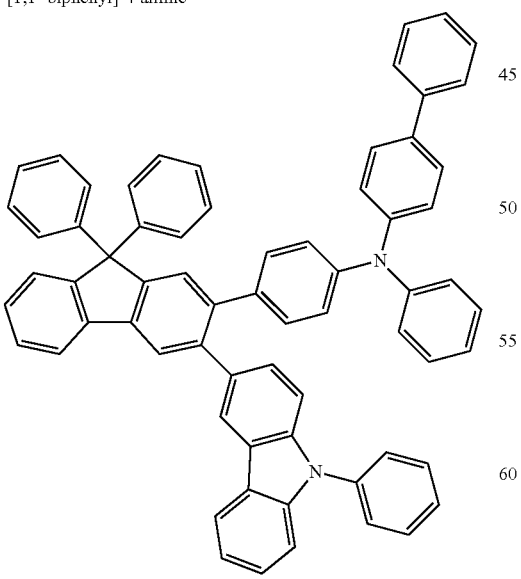

Compound A (6.97 g, 10.17 mmol) and N-(4-bromophenyl)-N-phenyl-(1,1'-biphenyl)-4-amine (3.14 g, 9.68 mmol)

were completely dissolved in 260 ml of tetrahydrofuran in a 500-ml round bottom flask under a nitrogen atmosphere, and then an aqueous 2 M potassium carbonate solution (130 ml) was added thereto, tetrakis-(triphenylphosphine)palladium (0.34 g, 0.29 mmol) was put thereinto, and then the resulting mixture was heated and stirred for 5 hours. The temperature was lowered to room temperature, the aqueous layer was removed, and the residue was dried over anhydrous magnesium sulfate, and then concentrated under reduced pressure, and recrystallized with 210 ml of ethyl acetate to prepare Compound 14 (5.11 g, 60%).
MS[M+H]+=880

Preparation Example 15

Compound 15

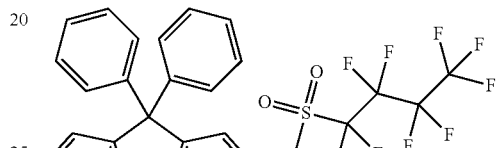

+

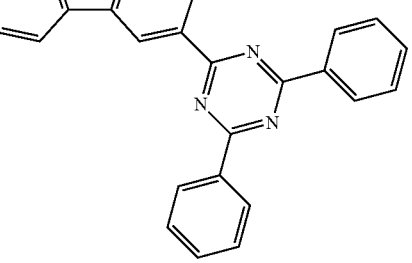

D

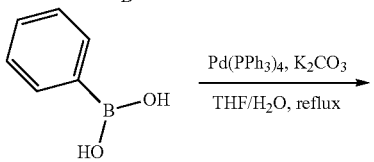

phenylboronic acid

Pd(PPh₃)₄, K₂CO₃
THF/H₂O, reflux

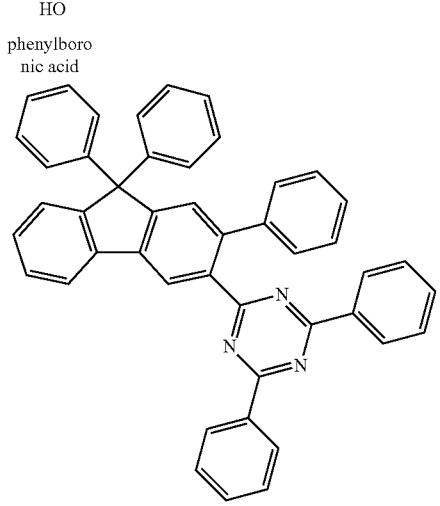

Compound D (20.58 g, 24.30 mmol) and phenylboronic acid (3.12 g, 25.57 mmol) were completely dissolved in 260 ml of tetrahydrofuran in a 500-ml round bottom flask under a nitrogen atmosphere, and then an aqueous 2 M potassium carbonate solution (130 ml) was added thereto, tetrakis- (triphenylphosphine)palladium (0.89 g, 0.77 mmol) was put thereinto, and then the resulting mixture was heated and stirred for 5 hours. The temperature was lowered to room temperature, the aqueous layer was removed, and the residue was dried over anhydrous magnesium sulfate, and then concentrated under reduced pressure, and recrystallized with 260 ml of ethyl acetate to prepare Compound 15 (7.28 g, 53%).

MS[M+H]$^+$=626

Preparation Example 16

Compound 16

Compound B (11.45 g, 15.90 mmol) and 2-(4-bromophenyl)-4,6-diphenyl-1,3,5-triazine (5.35 g, 13.82 mmol) were completely dissolved in 240 ml of tetrahydrofuran in a 500-ml round bottom flask under a nitrogen atmosphere, and then an aqueous 2 M potassium carbonate solution (120 ml) was added thereto, tetrakis-(triphenylphosphine)palladium (0.48 g, 0.41 mmol) was put thereinto, and then the resulting mixture was heated and stirred for 5 hours. The temperature was lowered to room temperature, the aqueous layer was removed, and the residue was dried over anhydrous magnesium sulfate, and then concentrated under reduced pressure, and recrystallized with 450 ml of acetone to prepare Compound 16 (8.64 g, 69%).

MS[M+H]$^+$=902

Preparation Example 17

Compound 17

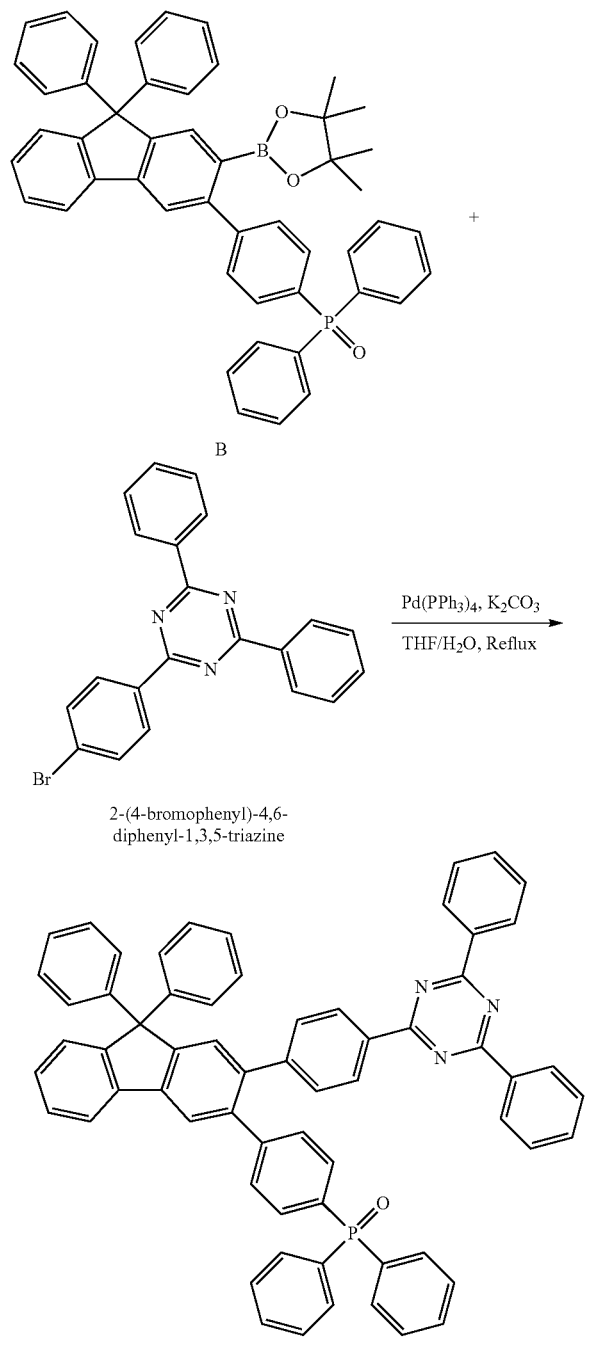

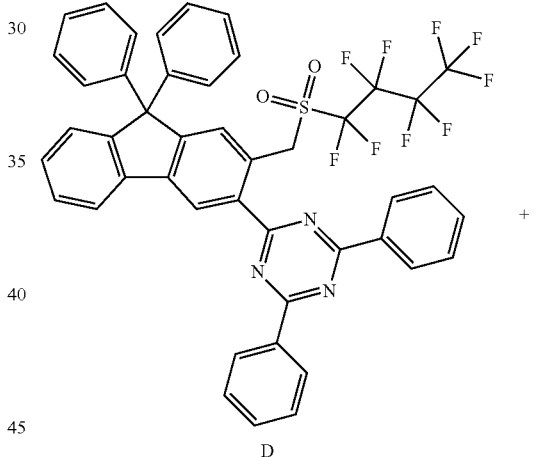

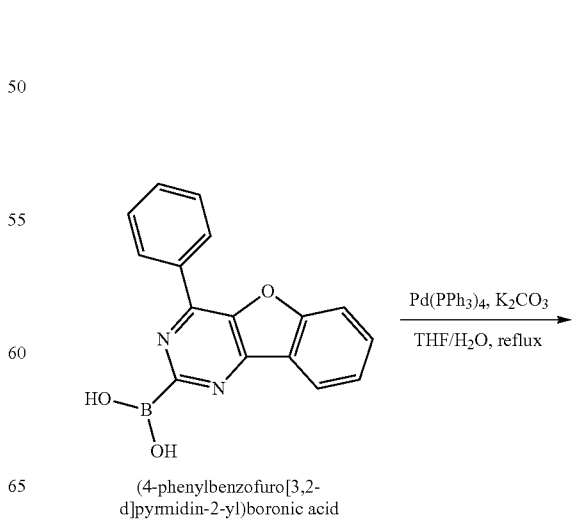

(4-phenylbenzofuro[3,2-d]pyrimidin-2-yl)boronic acid

-continued

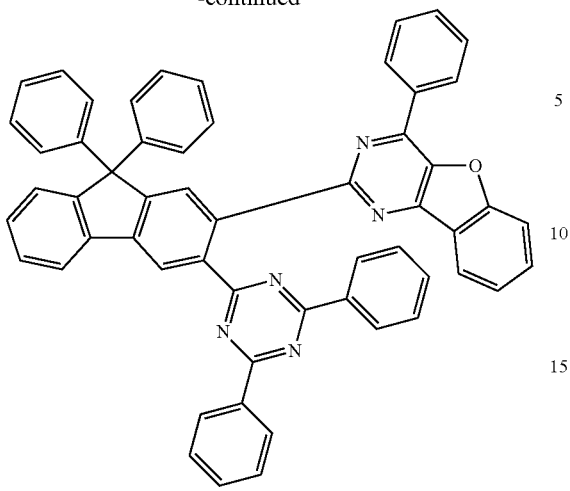

Compound D (13.46 g, 15.89 mmol) and (4-phenylbenzofuro[3,2-d]pyrimidin-2-yl)boronic acid (4.85 g, 16.72 mmol) were completely dissolved in 220 ml of tetrahydrofuran in a 500-ml round bottom flask under a nitrogen atmosphere, and then an aqueous 2 M potassium carbonate solution (110 ml) was added thereto, tetrakis-(triphenylphosphine)palladium (0.58 g, 0.50 mmol) was put thereinto, and then the resulting mixture was heated and stirred for 8 hours. The temperature was lowered to room temperature, the aqueous layer was removed, and the residue was dried over anhydrous magnesium sulfate, and then concentrated under reduced pressure, and recrystallized with 210 ml of ethyl acetate to prepare Compound 17 (6.29 g, 47%).
MS[M+H]$^+$=794

Experimental Example 1

Experimental Example 1-1

A glass substrate thinly coated with indium tin oxide (ITO) to have a thickness of 1,000 Å was put into distilled water in which a detergent was dissolved, and ultrasonically washed. At this time, a product manufactured by Fischer Co., was used as the detergent, and distilled water twice filtered using a filter manufactured by Millipore Co., was used as the distilled water. After the ITO was washed for 30 minutes, ultrasonic washing was repeated twice by using distilled water for 10 minutes. After the washing using distilled water was completed, ultrasonic washing was conducted by using isopropyl alcohol, acetone, and methanol solvents, and the resultant product was dried and then transported to a plasma washing machine. Furthermore, the substrate was washed by using an oxygen plasma for 5 minutes, and then was transported to a vacuum deposition machine.

Hexanitrile hexaazatriphenylene (HAT) of the following Chemical Formula was thermally vacuum deposited to have a thickness of 500 Å on the thus prepared ITO transparent electrode, thereby forming a hole injection layer.

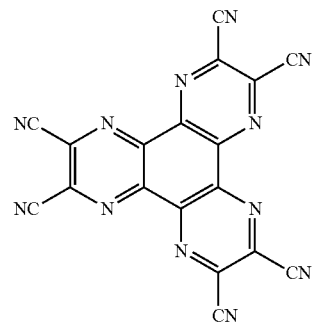

[HAT]

The following compound N4,N4,N4',N4'-tetra([1,1'-biphenyl]-4-yl)-[1,1'-biphenyl]-4,4'-diamine [HT1] (300 Å) being a material for transporting holes was vacuum deposited on the hole injection layer, thereby forming a hole transporting layer.

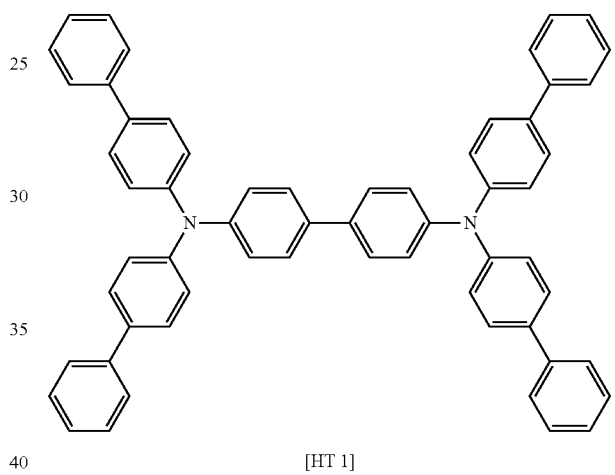

[HT 1]

Subsequently, the following Compound 7 was vacuum deposited to have a film thickness of 100 Å on the hole transporting layer, thereby forming an electron blocking layer.

Compound 7

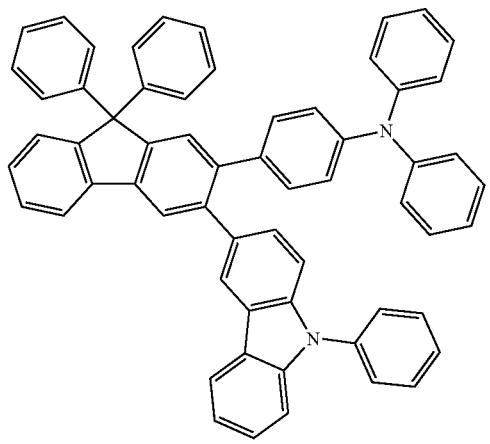 [SMILES: c1ccc(N(c2ccccc2)c2ccc(-c3cc4c(cc3-c3ccc5c(c3)c3ccccc3n5-c3ccccc3)-c3ccccc3C4(c3ccccc3)c3ccccc3)cc2)cc1]

Subsequently, BH and BD described below were vacuum deposited at a weight ratio of 25:1 to have a film thickness of 300 Å on the electron blocking layer, thereby forming a light emitting layer.

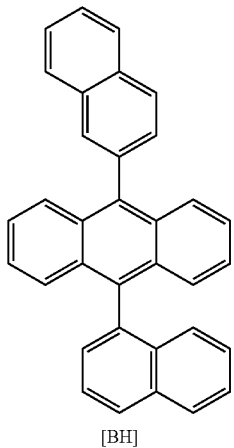

[BH]

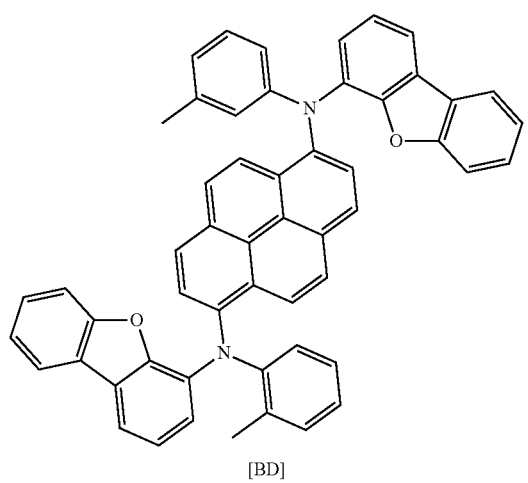

[BD]

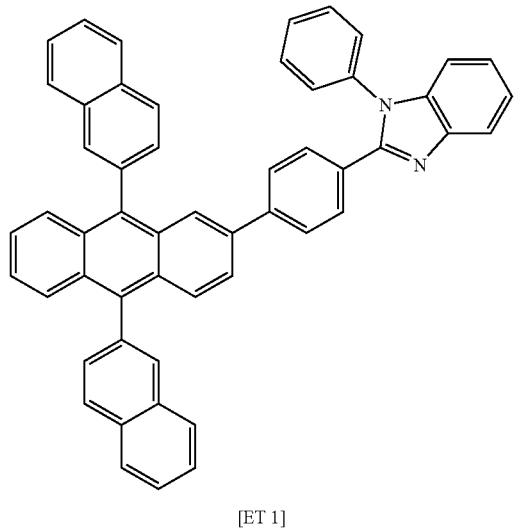

[ET 1]

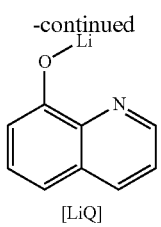

[LiQ]

Compound ET1 and Compound LiQ (lithium quinolate) were vacuum deposited at a weight ratio of 1:1 on the light emitting layer, thereby forming an electron injection and transporting layer having a thickness of 300 Å. Lithium fluoride (LiF) and aluminum were sequentially deposited on the electron injection and transporting layer to have a thickness of 12 Å and 2,000 Å, respectively, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2\times10^{-7}$ to $5\times10^{-6}$ torr, thereby manufacturing an organic light emitting device.

Experimental Example 1-2

An organic light emitting device was manufactured in the same manner as in Experimental Example 1-1, except that Compound 9 was used instead of Compound 7 in Experimental Example 1-1.

Experimental Example 1-3

An organic light emitting device was manufactured in the same manner as in Experimental Example 1-1, except that Compound 13 was used instead of Compound 7 in Experimental Example 1-1.

Experimental Example 1-4

An organic light emitting device was manufactured in the same manner as in Experimental Example 1-1, except that Compound 14 was used instead of Compound 7 in Experimental Example 1-1.

Comparative Example 1

An organic light emitting device was manufactured in the same manner as in Experimental Example 1-1, except that the compound of the following EB 1 was used instead of Compound 7 in Experimental Example 1-1.

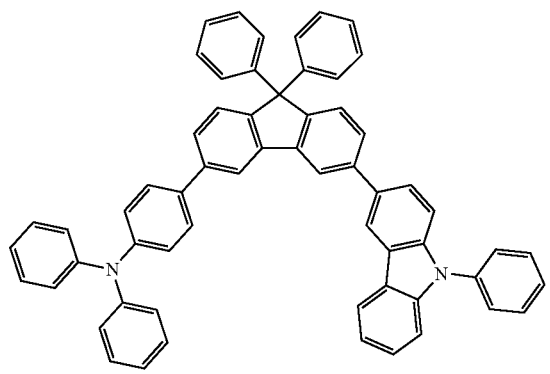

[EB 1]

Comparative Example 2

An organic light emitting device was manufactured in the same manner as in Experimental Example 1-1, except that the compound of the following EB 2 was used instead of Compound 7 in Experimental Example 1-1.

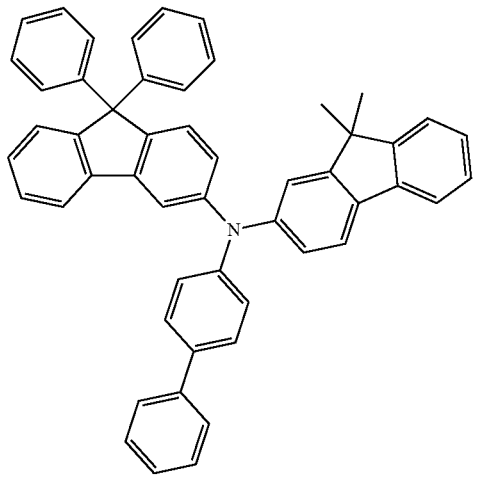

[EB 3]

Comparative Example 4

An organic light emitting device was manufactured in the same manner as in Experimental Example 1-1, except that the compound of the following EB 4 was used instead of Compound 7 in Experimental Example 1-1.

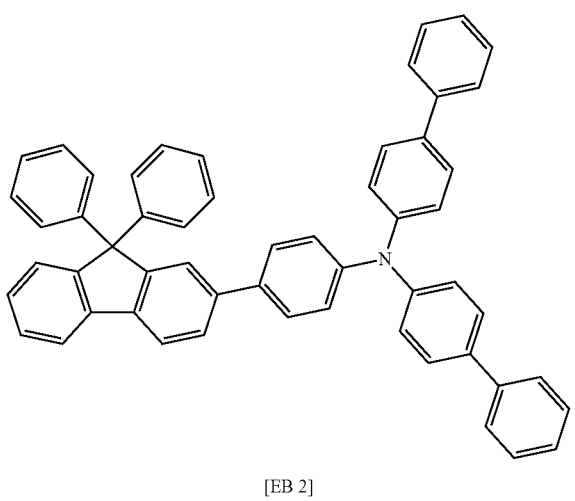 [SMILES: c1ccc(-c2ccc(N(c3ccc(-c4ccccc4)cc3)c3ccc(-c4ccc5c(c4)C(c4ccccc4)(c4ccccc4)c4ccccc4-5)cc3)cc2)cc1]

[EB 2]

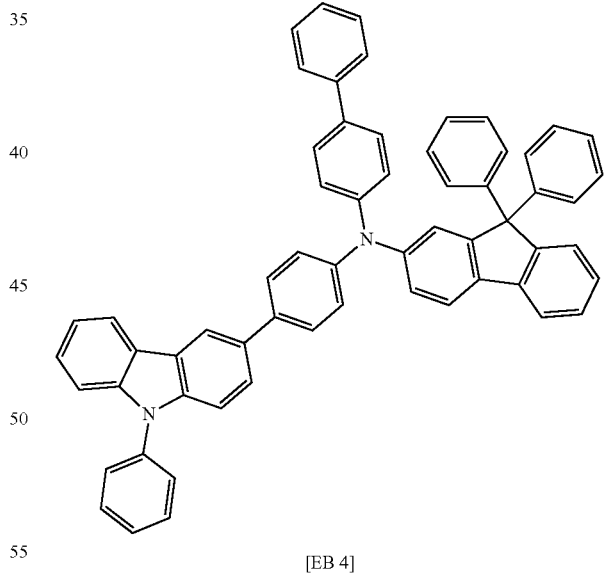

[EB 4]

Comparative Example 3

An organic light emitting device was manufactured in the same manner as in Experimental Example 1-1, except that the compound of the following EB 3 was used instead of Compound 7 in Experimental Example 1-1.

Comparative Example 5

An organic light emitting device was manufactured in the same manner as in Experimental Example 1-1, except that the compound of the following EB 5 was used instead of Compound 7 in Experimental Example 1-1.

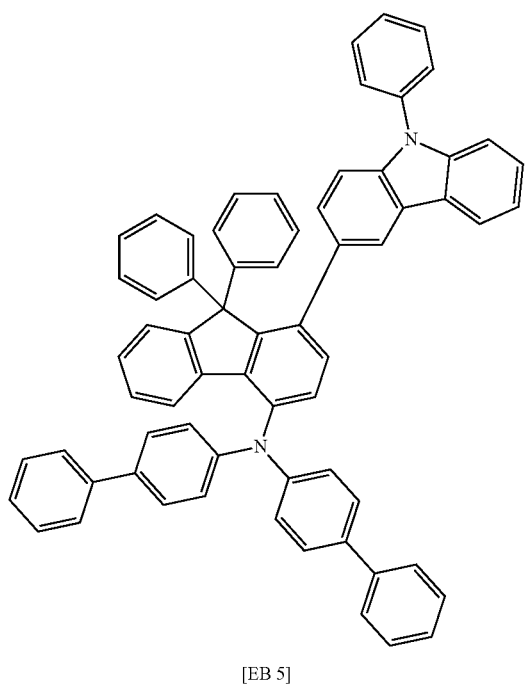 [SMILES: c1ccc(-c2ccc(N(c3ccc(-c4ccccc4)cc3)c3ccc(-c4ccc5c(c4)c4ccccc4n5-c4ccccc4)c4c3-c3ccccc3C4(c3ccccc3)c3ccccc3)cc2)cc1]

[EB 5]

When current was applied to the organic light emitting devices manufactured in Experimental Examples 1-1 to 1-4 and Comparative Examples 1 to 5, the voltages, efficiencies, color coordinates, and service lives were measured, and the results are shown in the following [Table 1]. T95 means the time taken for the luminance to be reduced to 95% of the initial luminance (1,300 nit).

TABLE 1

| | Compound (Electron blocking layer) | Voltage (V@10 Ma/cm$^2$) | Efficiency (cd/A@10 mA/cm$^2$) | Color coordinate (x, y) | T95 (hr) |
|---|---|---|---|---|---|
| Experimental Example 1-1 | Compound 7 | 4.42 | 6.44 | (0.141, 0.045) | 185 |
| Experimental Example 1-2 | Compound 9 | 4.50 | 6.32 | (0.142, 0.046) | 170 |
| Experimental Example 1-3 | Compound 13 | 4.38 | 6.49 | (0.141, 0.045) | 190 |
| Experimental Example 1-4 | Compound 14 | 4.46 | 6.38 | (0.141, 0.044) | 175 |
| Comparative Example 1 | EB 1 | 4.81 | 5.94 | (0.143, 0.048) | 155 |
| Comparative Example 2 | EB 2 | 4.72 | 6.11 | (0.143, 0.047) | 140 |
| Comparative Example 3 | EB 3 | 4.83 | 5.92 | (0.141, 0.047) | 145 |
| Comparative Example 4 | EB 4 | 4.80 | 5.95 | (0.142, 0.046) | 150 |
| Comparative Example 5 | EB 5 | 4.91 | 5.78 | (0.142, 0.049) | 85 |

As seen in Table 1, the organic light emitting device manufactured by using the compound of the present invention as an electron blocking layer exhibits excellent characteristics in terms of efficiency, driving voltage, and/or stability of the organic light emitting device.

Furthermore, a molecule having steric hindrance, in which two substituents made by a synthesis method recently developed by our company are disposed adjacent to each other, has a twisted structure as compared to a material having one substituent or two substituents disposed far away from each other, and exhibits characteristics in which the efficiency and service life are generally significantly increased in changing the morphology while the materials are accumulated during the deposition.

Referring to Comparative Examples 1 to 5, the organic light emitting devices manufactured by using the compounds of the present invention, in which the substituent is linked adjacent to Nos. 2 and 3 positions, exhibit characteristics in that the efficiency becomes high by 5% or more and the service life is increased by 10 to 30%, as compared to those of the organic light emitting devices manufactured by using, as an electron blocking layer, the compounds in which the substituents are away from each other and linked to both sides of 9,9-diphenylfluorene, or only one substituent is linked to Nos. 2 and 3 positions. Further, the compounds in Comparative Example 5, in which substituents are away from each other and linked to Nos. 1 and 4 positions, exhibited a result that the voltage is increased, the service life significantly deteriorates, there is no effect of an increase in efficiency, and the efficiency rather deteriorates.

As in the result in Table 1, it could be confirmed that the compound according to the present invention has an excellent electron blocking capability and thus can be applied to an organic light emitting device.

Experimental Example 2

Experimental Example 2-1

The compounds synthesized in the Synthesis Examples were subjected to high-purity sublimation purification by a typically known method, and then green organic light emitting devices were manufactured by the following method.

A glass substrate (Corning 7059 glass) thinly coated with indium tin oxide (ITO) to have a thickness of 1,000 Å was put into distilled water in which a dispersant was dissolved, and ultrasonically washed. A product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents in this order, and drying was then conducted. Hexanitrile hexaazatriphenylene was thermally vacuum deposited to have a thickness of 500 Å on the thus prepared ITO transparent electrode, thereby forming a hole injection layer. HT1 (300 Å) being a material for transporting holes was vacuum deposited thereon. The following Compound EB1 (100 Å) was vacuum deposited on the hole transporting layer, thereby forming an electron blocking layer. Compound 1 synthesized in Preparation Example 1 as a host and an Ir(ppy)3 dopant were vacuum deposited to have a thickness of 200 Å at a concentration of 10% as a light emitting layer. Next, the ET1 compound (300 Å) was thermally vacuum deposited sequentially as an electron injection and transporting layer. A negative electrode was formed by sequentially depositing lithium fluoride (LiF) and aluminum to have a thickness of 12 Å and 2,000 Å, respectively, on the electron transporting layer, thereby manufacturing an organic light emitting device. In the aforementioned procedure, the deposition rates of the organic material, lithium fluoride, and aluminum were maintained at 1 Å/sec, 0.2 Å/sec, and 3 to 7 Å/sec, respectively.

The structures of HAT, HT1, EB1, ET1, and Compound 1 are as follows.

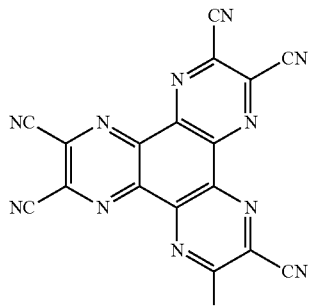

[HAT]

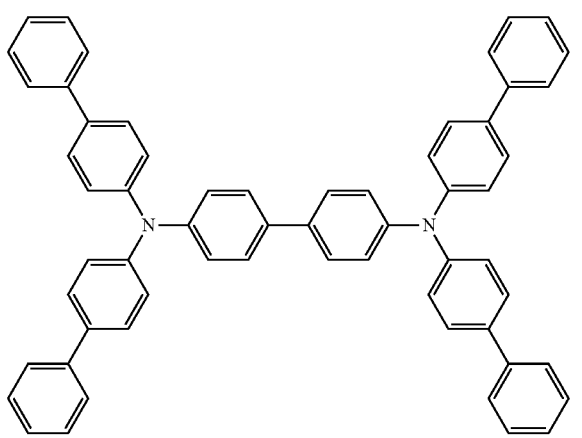

[HT1]

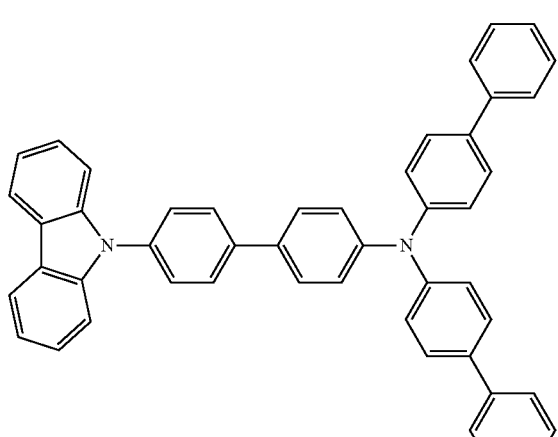

[EB1]

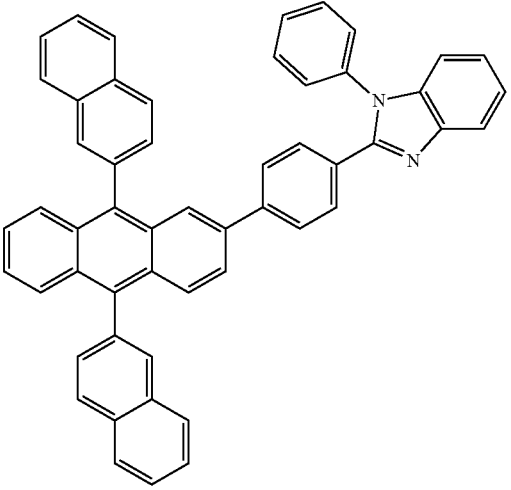

[ET1]

[Compound 1]

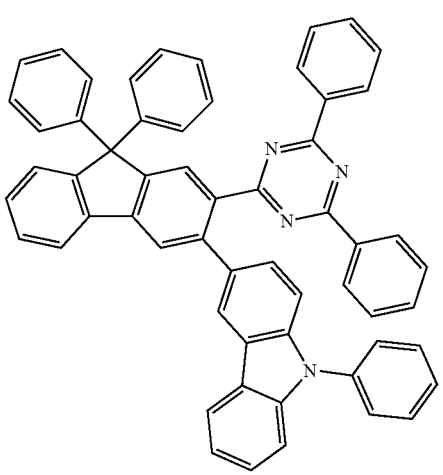

Experimental Example 2-2

An organic light emitting device was manufactured in the same manner as in Experimental Example 2-1, except that Compound 2 was used instead of Compound 1 in Experimental Example 2-1.

Experimental Example 2-3

An organic light emitting device was manufactured in the same manner as in Experimental Example 2-1, except that Compound 4 was used instead of Compound 1 in Experimental Example 2-1.

Experimental Example 2-4

An organic light emitting device was manufactured in the same manner as in Experimental Example 2-1, except that Compound 5 was used instead of Compound 1 in Experimental Example 2-1.

Experimental Example 2-5

An organic light emitting device was manufactured in the same manner as in Experimental Example 2-1, except that Compound 10 was used instead of Compound 1 in Experimental Example 2-1.

Experimental Example 2-6

An organic light emitting device was manufactured in the same manner as in Experimental Example 2-1, except that Compound 11 was used instead of Compound 1 in Experimental Example 2-1.

Experimental Example 2-7

An organic light emitting device was manufactured in the same manner as in Experimental Example 2-1, except that Compound 15 was used instead of Compound 1 in Experimental Example 2-1.

Experimental Example 2-8

An organic light emitting device was manufactured in the same manner as in Experimental Example 2-1, except that Compound 16 was used instead of Compound 1 in Experimental Example 2-1.

Experimental Example 2-9

An organic light emitting device was manufactured in the same manner as in Experimental Example 2-1, except that Compound 17 was used instead of Compound 1 in Experimental Example 2-1.

Comparative Example 6

An organic light emitting device was manufactured in the same manner as in Experimental Example 2-1, except that the following Compound GH 1 was used instead of Compound 1 in Experimental Example 2-1.

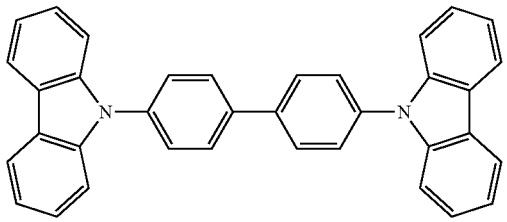

[GH 1]

Comparative Example 7

An organic light emitting device was manufactured in the same manner as in Experimental Example 2-1, except that the following Compound GH 2 was used instead of Compound 1 in Experimental Example 2-1.

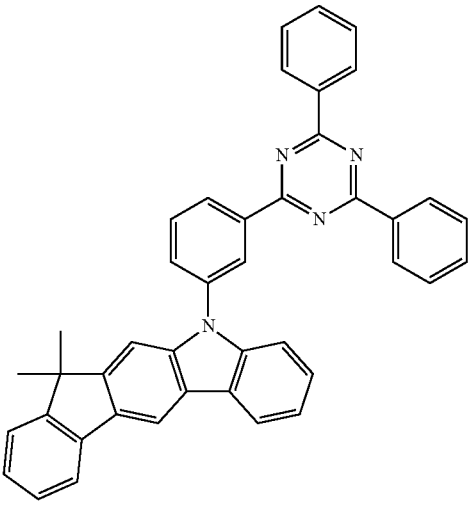

[GH 2]

Comparative Example 8

An organic light emitting device was manufactured in the same manner as in Experimental Example 2-1, except that the following Compound GH 3 was used instead of Compound 1 in Experimental Example 2-1.

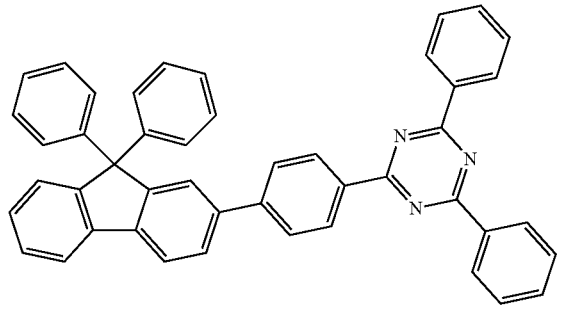

[GH 3]

Comparative Example 9

An organic light emitting device was manufactured in the same manner as in Experimental Example 2-1, except that the following Compound GH 4 was used instead of Compound 1 in Experimental Example 2-1.

[GH 4]

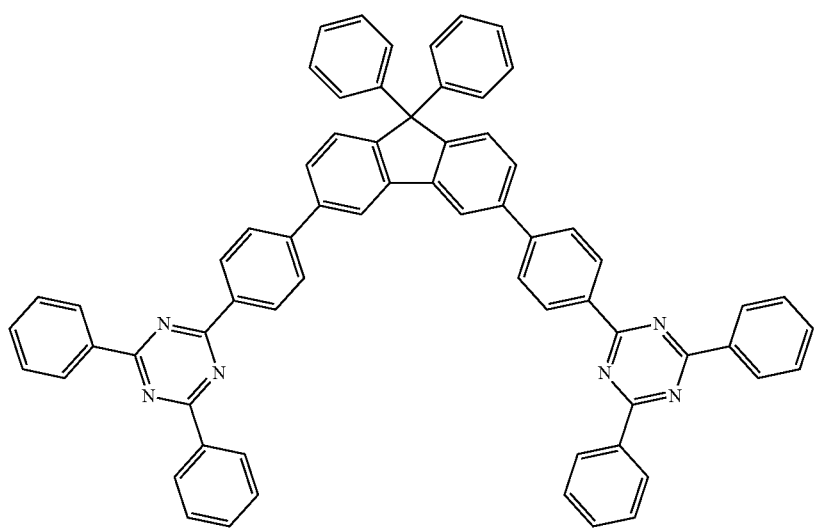

When current was applied to the organic light emitting devices manufactured in Experimental Examples 2-1 to 2-6 and Comparative Examples 6 to 9, the voltages, efficiencies, color coordinates, and service lives were measured, and the results are shown in the following [Table 2]. T95 means the time taken for the luminance to be reduced to 95% of the initial luminance (6,000 nit).

TABLE 2

|  | Compound (Host) | Voltage (V@10 mA/cm$^2$) | Efficiency (cd/A@10 mA/cm$^2$) | EL peak (nm) | T95 (h) |
| --- | --- | --- | --- | --- | --- |
| Experimental Example 2-1 | Compound 1 | 6.35 | 44.23 | 517 | 320 |
| Experimental Example 2-2 | Compound 2 | 6.42 | 43.81 | 517 | 335 |
| Experimental Example 2-3 | Compound 4 | 6.40 | 43.88 | 516 | 315 |
| Experimental Example 2-4 | Compound 5 | 6.49 | 43.65 | 517 | 315 |
| Experimental Example 2-5 | Compound 10 | 6.31 | 44.52 | 518 | 325 |
| Experimental Example 2-6 | Compound 11 | 6.29 | 44.84 | 518 | 320 |
| Experimental Example 2-7 | Compound 15 | 6.39 | 43.65 | 517 | 300 |
| Experimental Example 2-8 | Compound 16 | 6.37 | 44.52 | 518 | 355 |
| Experimental Example 2-9 | Compound 17 | 6.32 | 46.35 | 518 | 295 |
| Comparative Example 6 | GH 1 | 7.43 | 34.57 | 517 | 220 |
| Comparative Example 7 | GH 2 | 7.05 | 38.24 | 517 | 240 |
| Comparative Example 8 | GH 3 | 7.22 | 37.33 | 516 | 265 |
| Comparative Example 9 | GH 4 | 7.34 | 35.45 | 519 | 180 |

As a result of the experiments, it could be confirmed that the green organic EL devices in Experimental Examples 2-1 to 2-9 in which the compound of the present invention was used as the host material of the green light emitting layer, exhibited excellent performances in terms of current efficiency, driving voltage, and service life on the whole, as compared to the organic light emitting devices manufactured by using, as the host material, the compound in Comparative Example 6 in which CBP in the related art was used, the compound in Comparative Example 7 which was frequently used as a green light emitting layer, the compound in Comparative Example 8 in which only one substituent is linked to No. 2 position, and the compound in Comparative Example 9 in which two triazines were substituted at both sides of the fluorene core.

Experimental Example 3

Experimental Example 3-1

An experiment was performed in the same manner as in Experimental Example 2-1, except that as the electron transporting layer, Compound 1 was used instead of ET1.

Experimental Example 3-2

An experiment was performed in the same manner as in Experimental Example 3-1, except that as the electron transporting layer, Compound 2 was used instead of Compound 1.

Experimental Example 3-3

An experiment was performed in the same manner as in Experimental Example 3-1, except that as the electron transporting layer, Compound 3 was used instead of Compound 1.

Experimental Example 3-4

An experiment was performed in the same manner as in Experimental Example 3-1, except that as the electron transporting layer, Compound 4 was used instead of Compound 1.

Experimental Example 3-5

An experiment was performed in the same manner as in Experimental Example 3-1, except that as the electron transporting layer, Compound 5 was used instead of Compound 1.

Experimental Example 3-6

An experiment was performed in the same manner as in Experimental Example 3-1, except that as the electron transporting layer, Compound 6 was used instead of Compound 1.

Experimental Example 3-7

An experiment was performed in the same manner as in Experimental Example 3-1, except that as the electron transporting layer, Compound 8 was used instead of Compound 1.

Experimental Example 3-8

An experiment was performed in the same manner as in Experimental Example 3-1, except that as the electron transporting layer, Compound 10 was used instead of Compound 1.

Experimental Example 3-9

An experiment was performed in the same manner as in Experimental Example 3-1, except that as the electron transporting layer, Compound 11 was used instead of Compound 1.

Experimental Example 3-10

An experiment was performed in the same manner as in Experimental Example 3-1, except that as the electron transporting layer, Compound 12 was used instead of Compound 1.

Experimental Example 3-11

An experiment was performed in the same manner as in Experimental Example 3-1, except that as the electron transporting layer, Compound 15 was used instead of Compound 1.

Experimental Example 3-12

An experiment was performed in the same manner as in Experimental Example 3-1, except that as the electron transporting layer, Compound 16 was used instead of Compound 1.

Experimental Example 3-13

An experiment was performed in the same manner as in Experimental Example 3-1, except that as the electron transporting layer, Compound 17 was used instead of Compound 1.

Comparative Example 10

An organic light emitting device was manufactured in the same manner as in Experimental Example 3-1, except that the compound of the following ET2 was used instead of Compound 1 in Experimental Example 3-1.

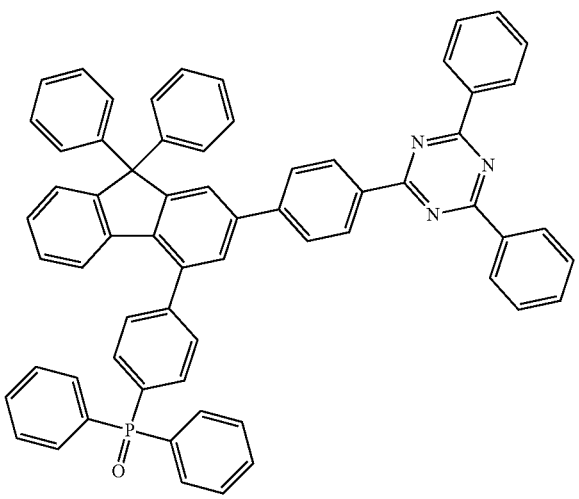

[ET 2]

When current was applied to the organic light emitting devices manufactured in Experimental Examples 3-1 to 3-13 and Comparative Example 10, the voltages, efficiencies, color coordinates, and service lives were measured, and the results are shown in the following [Table 3]. T95 means the time taken for the luminance to be reduced to 95% of the initial luminance (6,000 nit).

TABLE 3

| | Compound | Voltage (V@10 mA/cm$^2$) | Efficiency (cd/A@10 mA/cm$^2$) | Color coordinate (x, y) | T95 (h) |
|---|---|---|---|---|---|
| Experimental Example 3-1 | Compound 1 | 4.10 | 6.58 | (0.141, 0.045) | 320 |
| Experimental Example 3-2 | Compound 2 | 4.19 | 6.54 | (0.142, 0.046) | 335 |
| Experimental Example 3-3 | Compound 3 | 3.92 | 6.53 | (0.142, 0.046) | 315 |
| Experimental Example 3-4 | Compound 4 | 4.04 | 6.40 | (0.142, 0.046) | 315 |
| Experimental Example 3-5 | Compound 5 | 4.08 | 6.46 | (0.142, 0.046) | 325 |
| Experimental Example 3-6 | Compound 6 | 4.07 | 6.37 | (0.141, 0.045) | 320 |
| Experimental Example 3-7 | Compound 8 | 4.16 | 6.29 | (0.141, 0.045) | 350 |
| Experimental Example 3-8 | Compound 10 | 4.11 | 6.31 | (0.138, 0.045) | 330 |
| Experimental Example 3-9 | Compound 11 | 4.12 | 6.42 | (0.139, 0.046) | 345 |
| Experimental Example 3-10 | Compound 12 | 4.08 | 6.77 | (0.139, 0.045) | 340 |
| Experimental Example 3-11 | Compound 15 | 4.03 | 6.75 | (0.141, 0.045) | 315 |
| Experimental Example 3-12 | Compound 16 | 4.14 | 6.32 | (0.142, 0.045) | 320 |
| Experimental Example 3-13 | Compound 17 | 4.25 | 6.82 | (0.141, 0.045) | 305 |
| Comparative Example 10 | ET 2 | 5.16 | 5.75 | (0.139, 0.044) | 350 |

As a result of the experiments, it could be confirmed that the organic light emitting devices in Experimental Examples 3-2 to 3-13 in which the compound prepared according to the present invention was used as the electron transporting layer exhibited excellent performances in terms of current efficiency, driving voltage, and service life.

The result showed that the service life of the material in Comparative Example 10 in which the phosphine oxide group and the triazine group are substituted so as not to be adjacent to each other was maintained to some degree, but a very high voltage was measured, and the efficiency was also decreased by 10% or more.

Although the preferred exemplary embodiments (a hole transporting layer, a green light emitting layer, and an electron transporting layer) of the present invention have been described above, the present invention is not limited thereto, and various modifications can be made and carried out within the scope of the claims and the detailed description of the invention, and also fall within the scope of the invention.

EXPLANATION OF REFERENCE NUMERALS AND SYMBOLS

1: Substrate
2: Positive electrode
3: Light emitting layer
4: Negative electrode
5: Hole injection layer
6: Hole transporting layer
7: Electron transporting layer

The invention claimed is:

1. A compound represented by the following Chemical Formula 1:

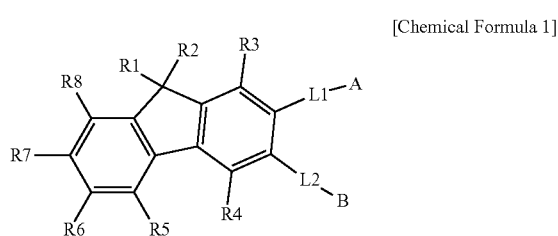

[Chemical Formula 1]

in Chemical Formula 1,

R1 and R2 are a phenyl group,

R3 to R8 are the same as or different from each other, and are each independently hydrogen or deuterium, L1 and L2 are the same as or different from each other, and are each independently a single bond or a phenylene group, and A and B are the same as or different from each other, and are each independently a phenyl group which is unsubstituted or substituted with a nitrile group; a naphthyl group; a N-phenyl carbazole group; a triazine group which is substituted with a phenyl group or a biphenyl group; a pyrimidine group which is substituted with a phenyl group or a biphenyl group; a benzofuropyrimidine group which is substituted with a phenyl group; an amine group which is substituted with a phenyl group, a biphenyl group, or a dimethylfluorene group; or a phosphine oxide group which is substituted with a phenyl group, wherein A and B are not a N-phenyl carbazole group at the same time.

2. The compound of claim 1, wherein Chemical Formula 1 is any one of the following compounds:

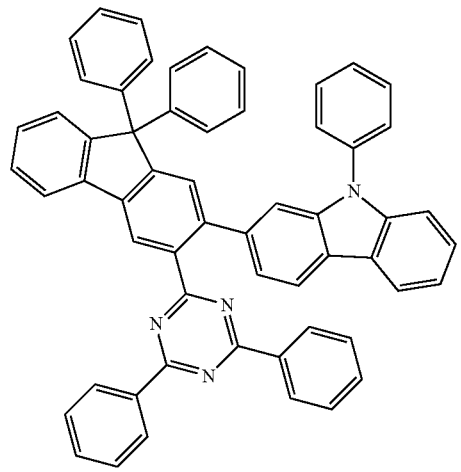

1-7

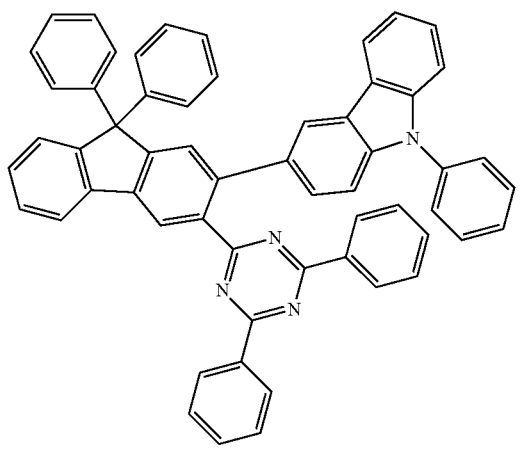

1-8

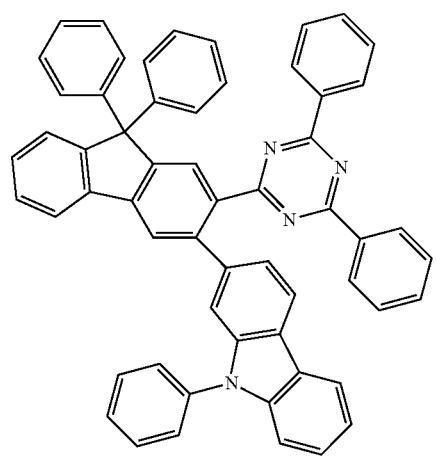

1-11

-continued
1-12
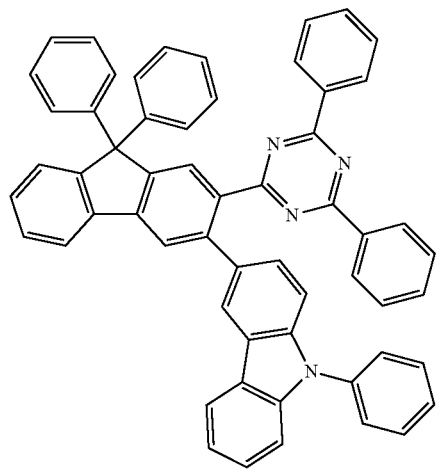
1-27
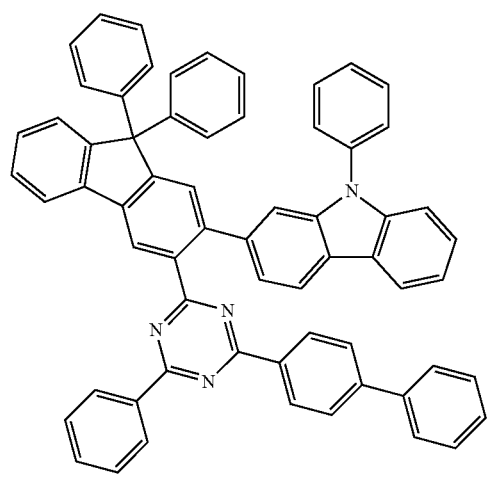
1-28
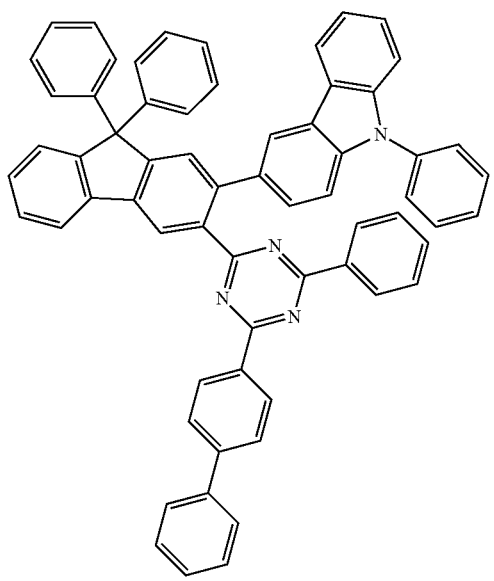
-continued
1-31
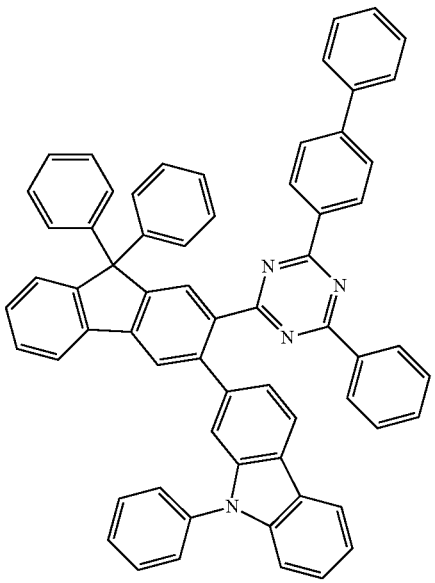
1-32
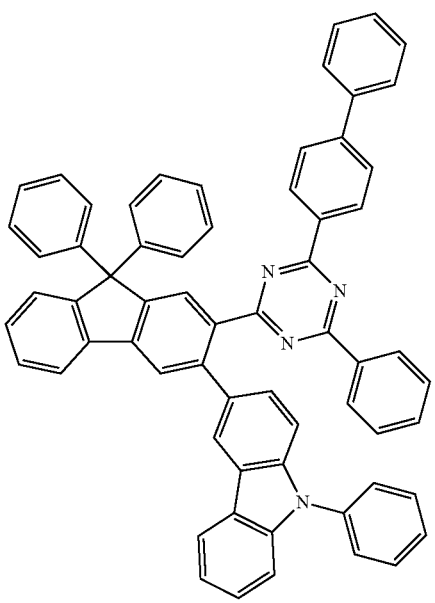
1-47
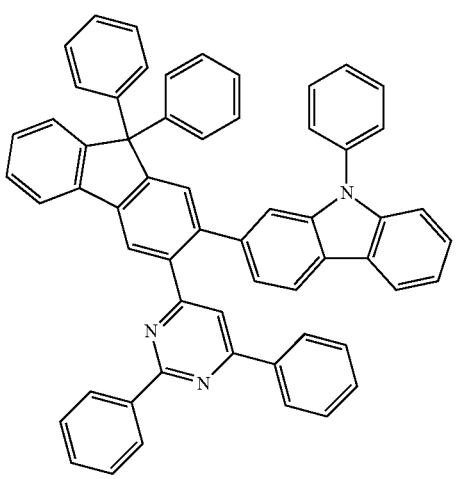

-continued
1-48
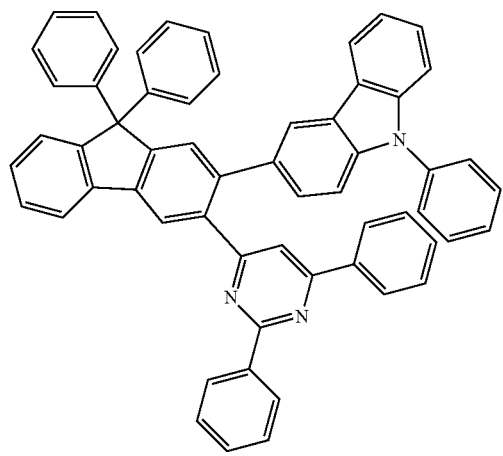
1-51
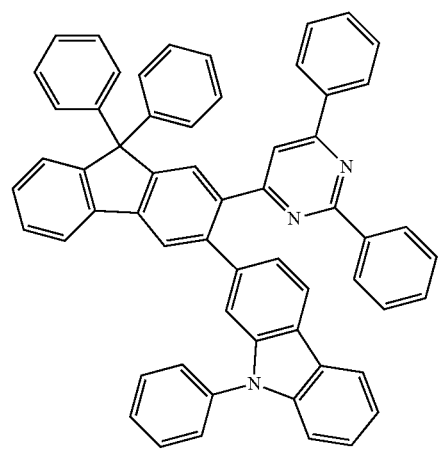
1-52
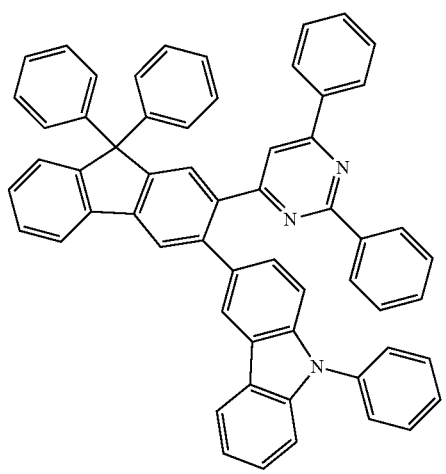
-continued
1-67
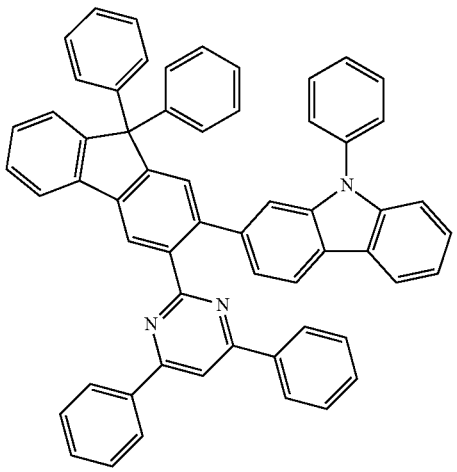
1-68
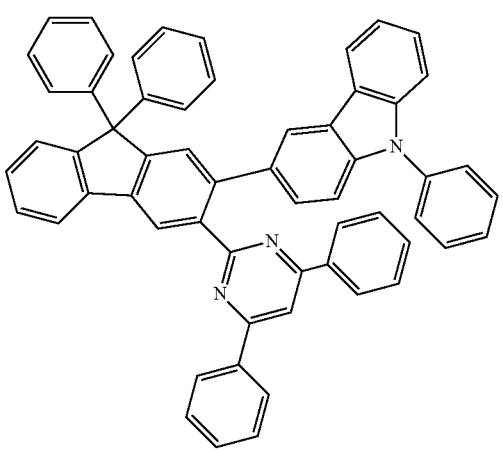
1-71
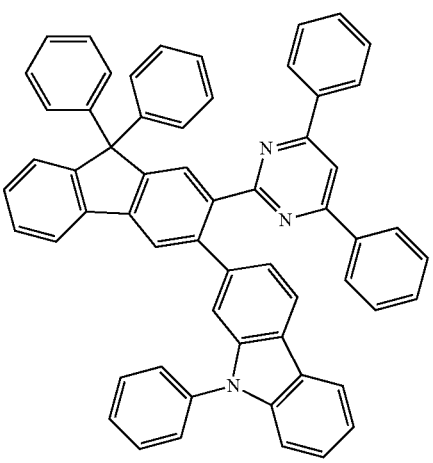

-continued
1-72
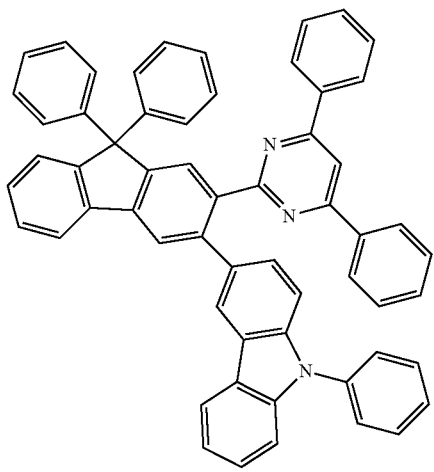
1-101
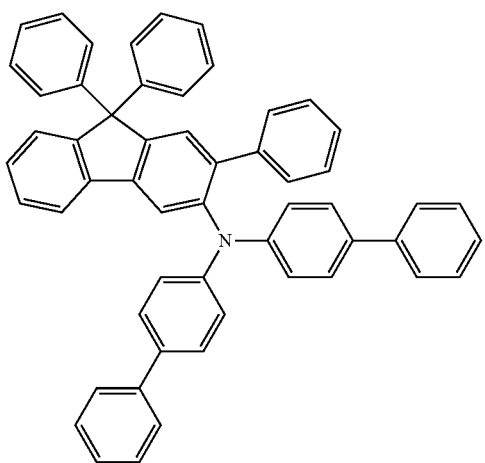
1-102
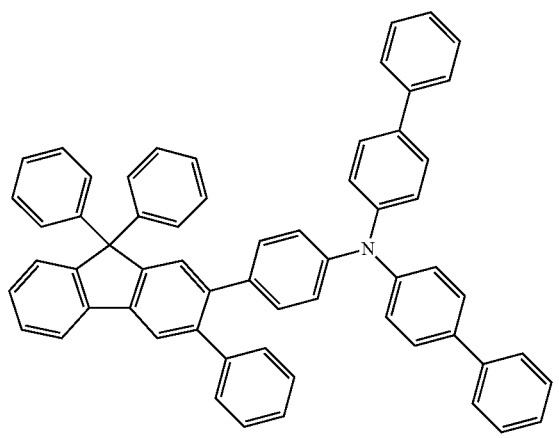
-continued
1-103
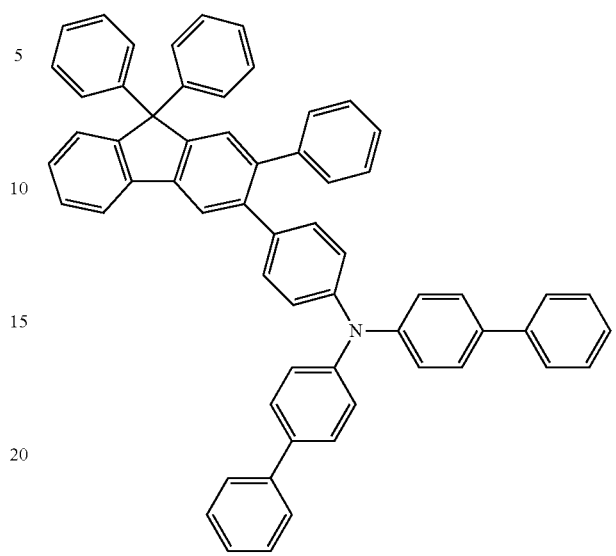
1-105
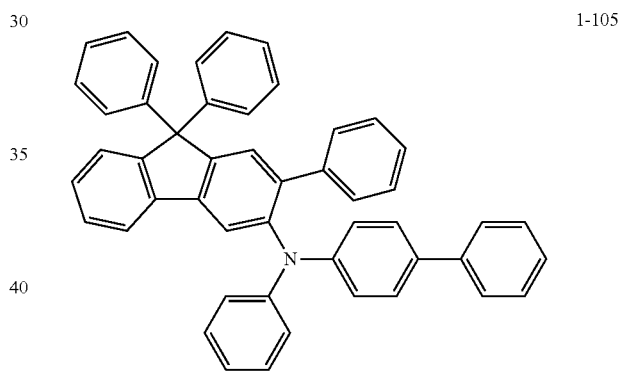
1-106
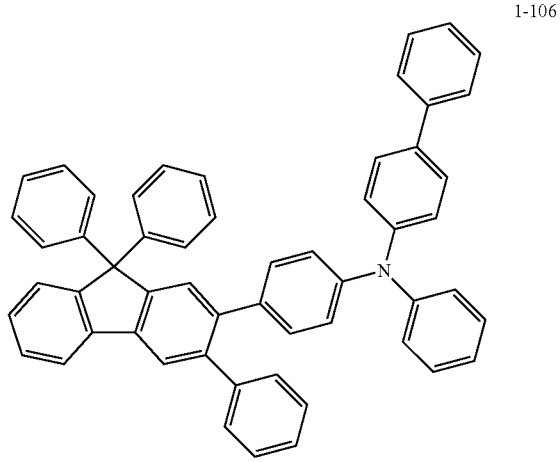

1-107
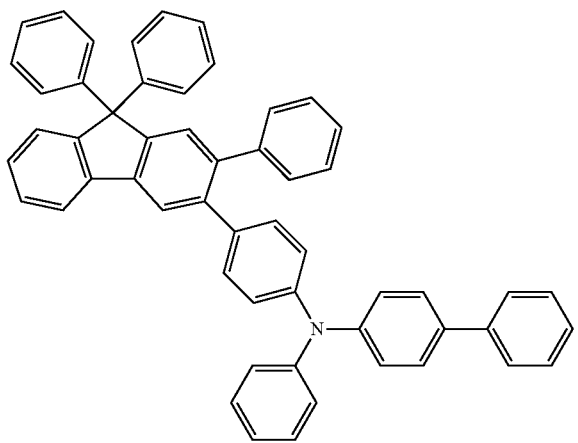
1-108
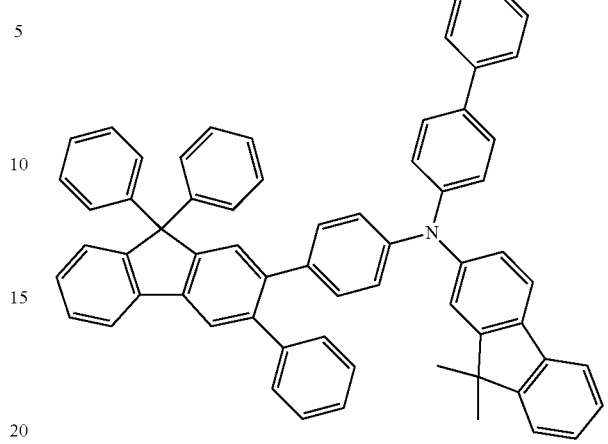
1-110
1-111
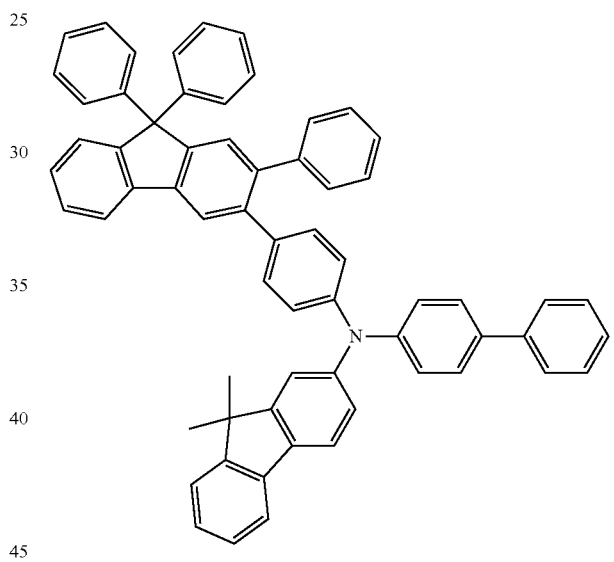
1-109
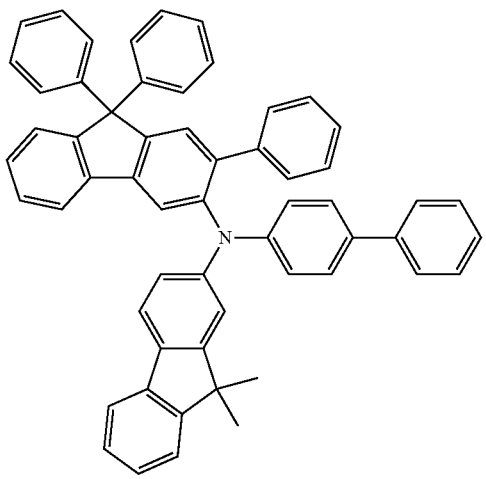
1-112
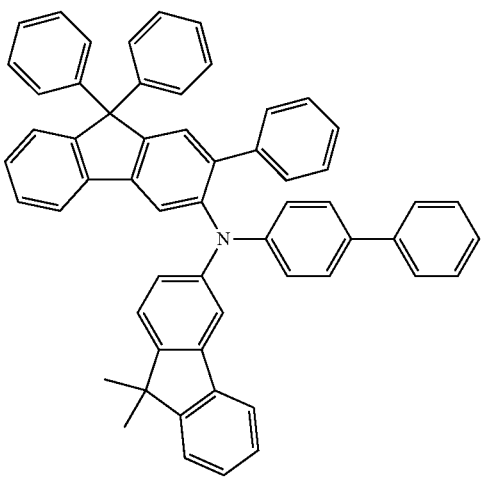

1-113
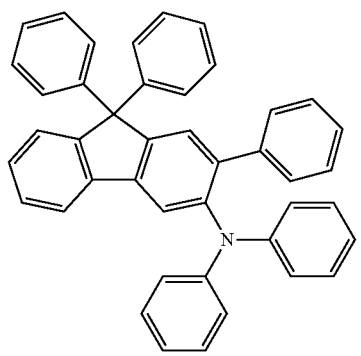
1-114
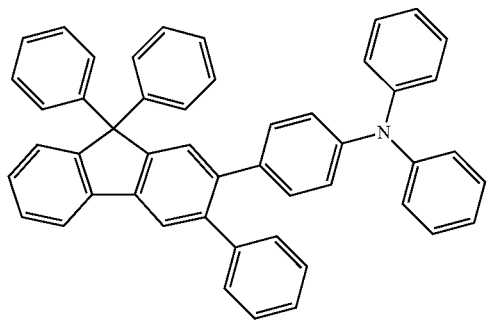
1-117
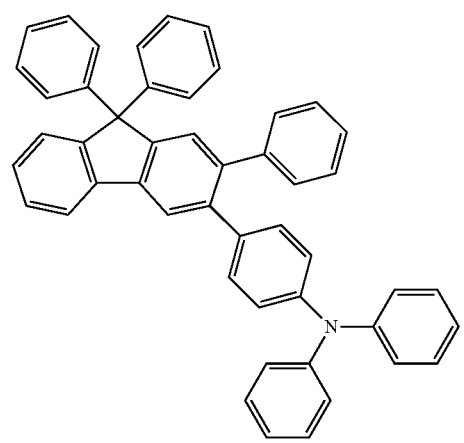
1-118
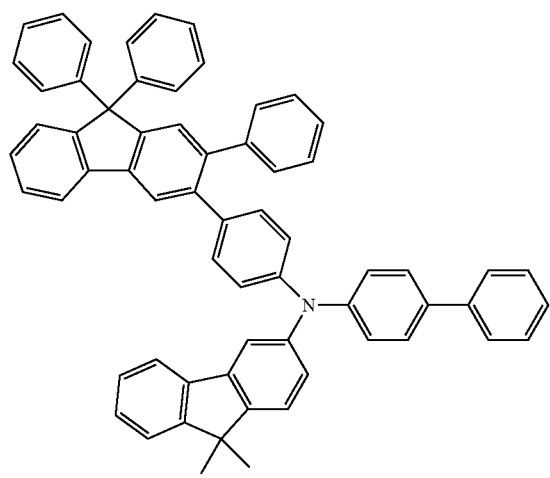
1-137
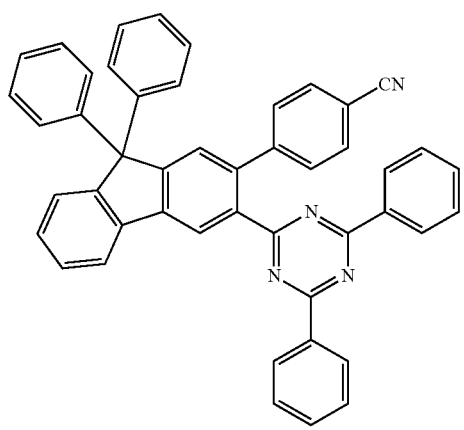
1-138
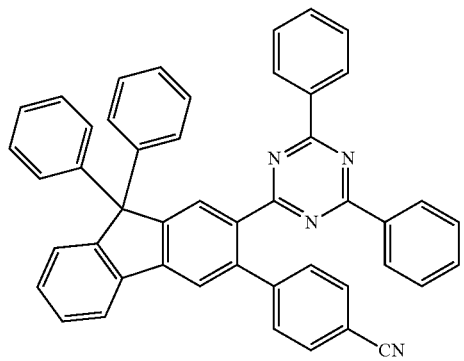
1-139
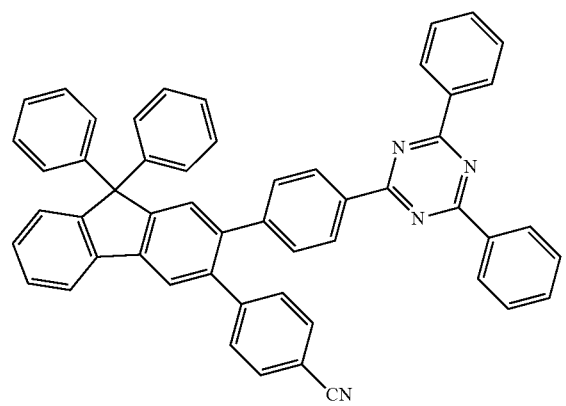

-continued
1-140
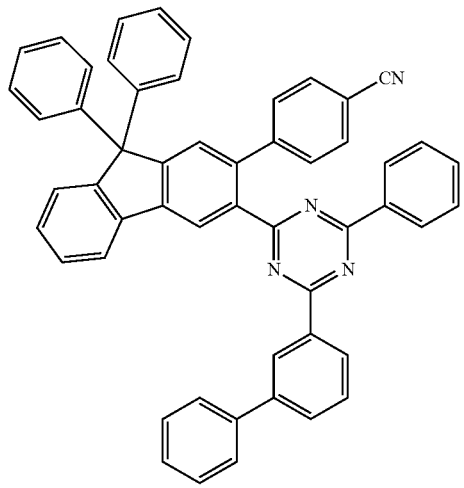
1-141
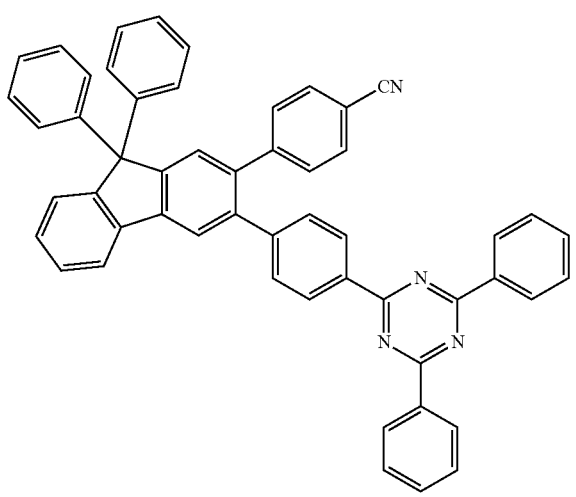
1-142
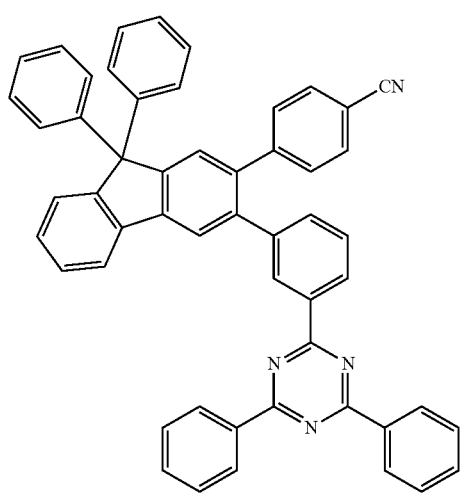
-continued
1-143
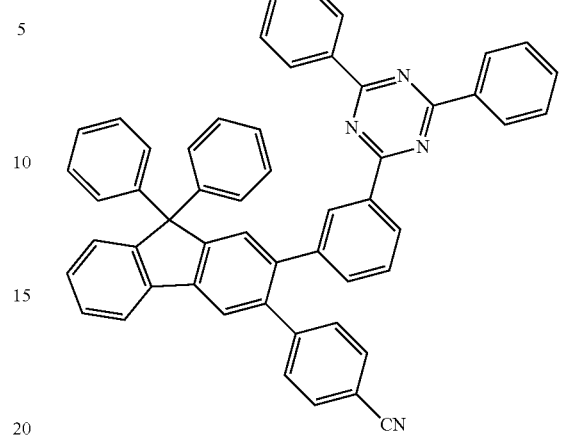
1-144
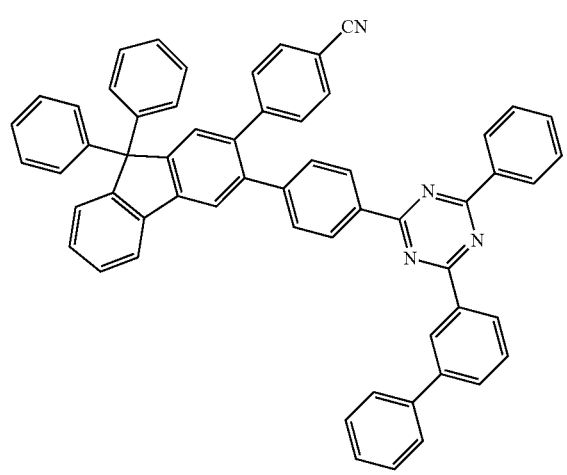
1-145
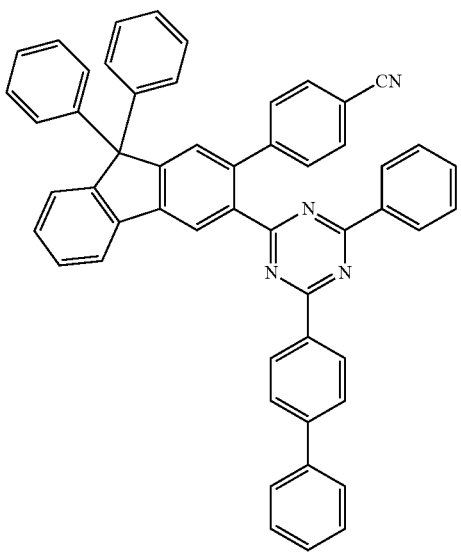

1-146
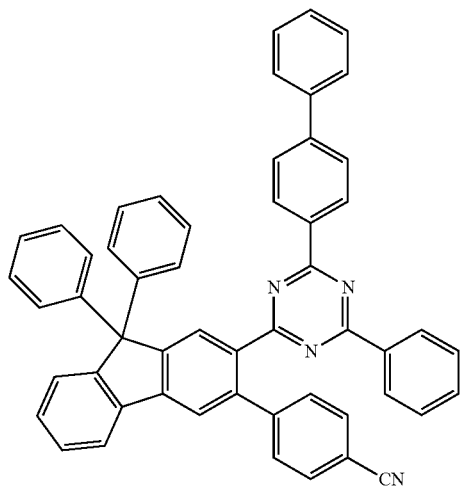
1-147
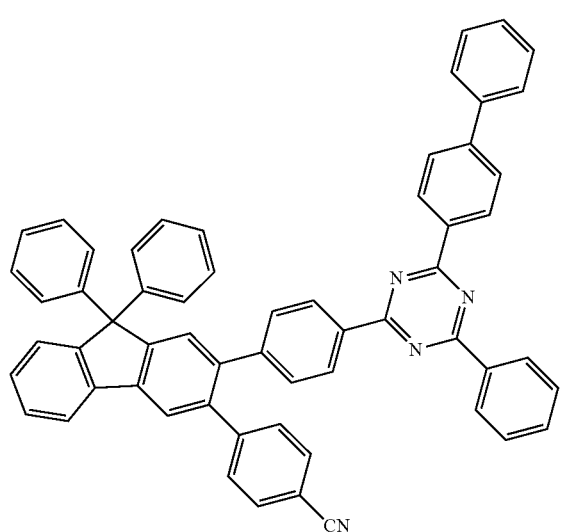
1-148
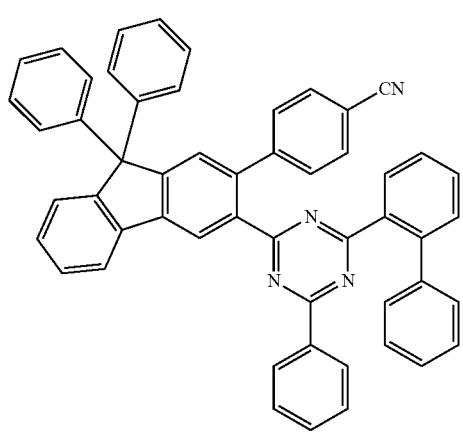
1-149
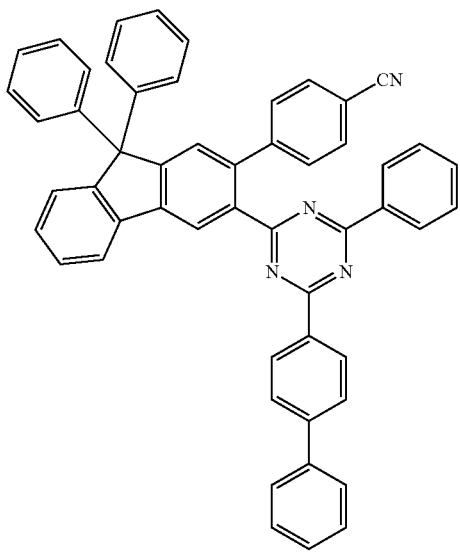
1-150
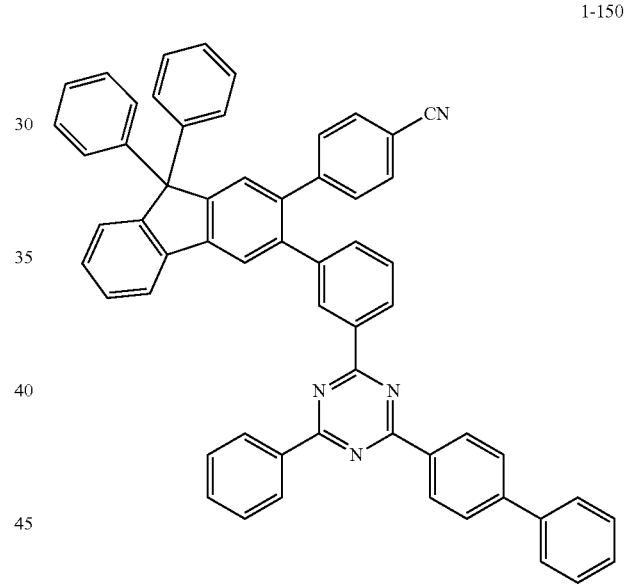
1-151
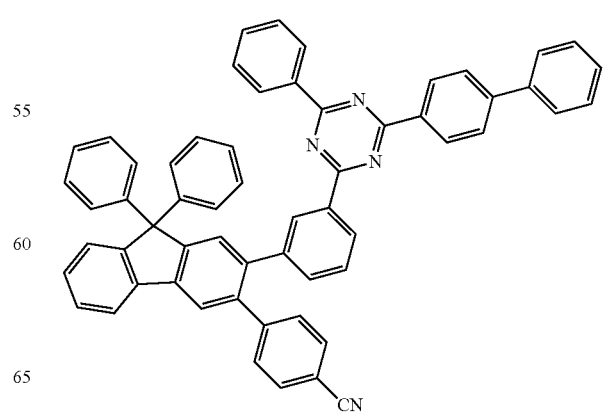

1-152
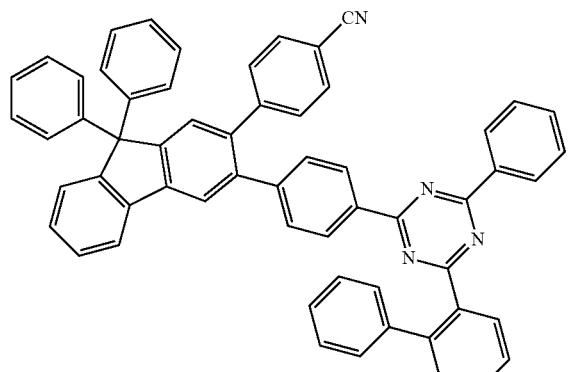
1-153
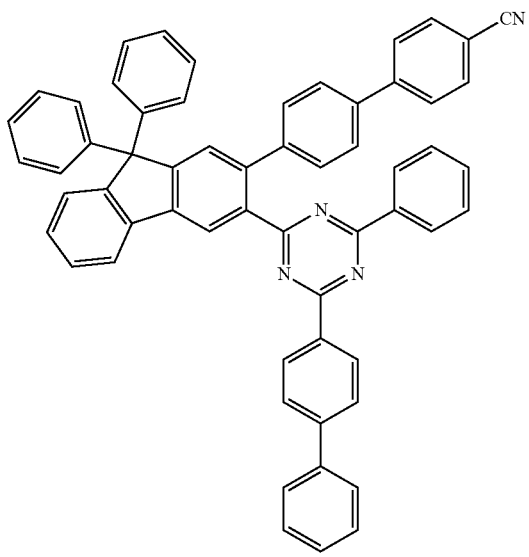
1-154
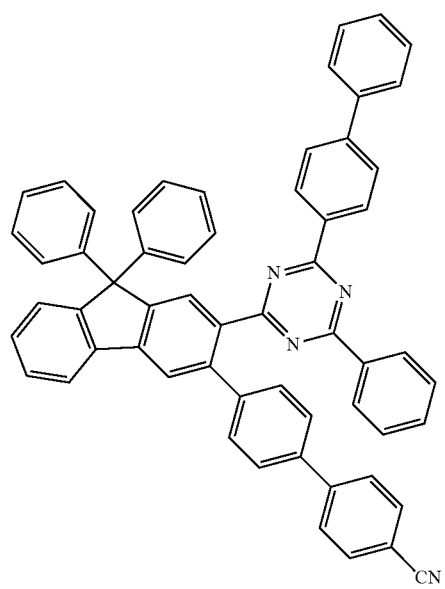
1-155
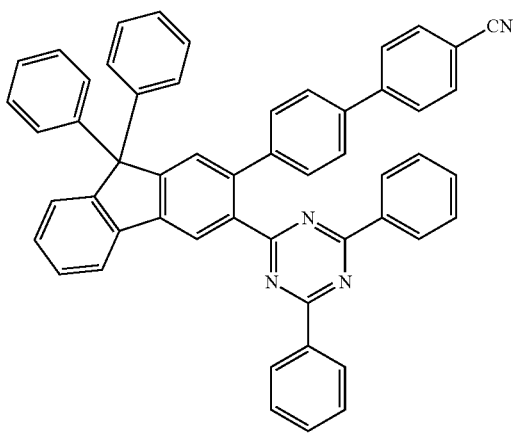
1-156
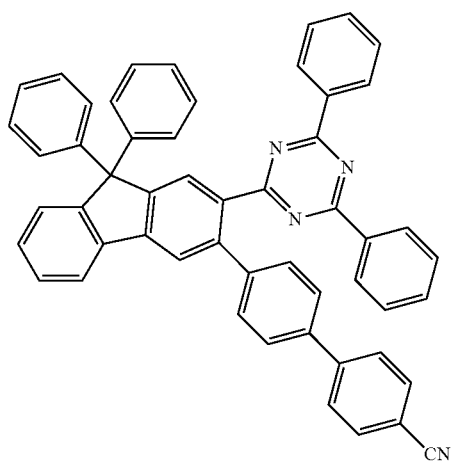
1-157
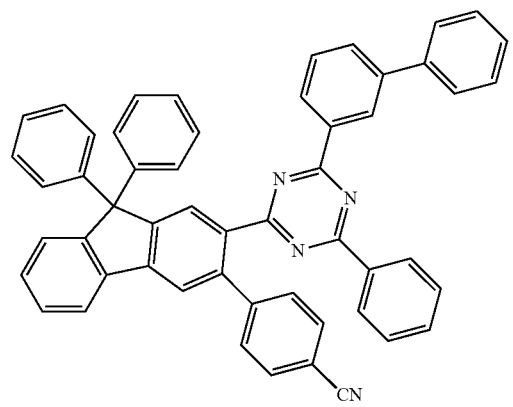

-continued
1-158
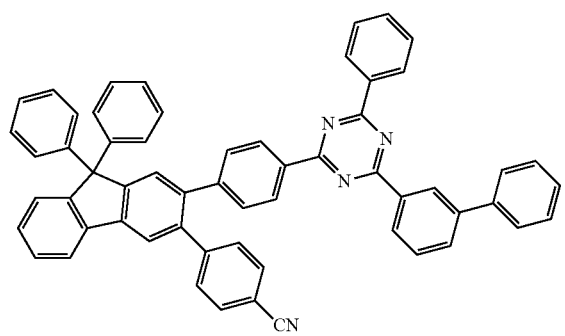
1-159
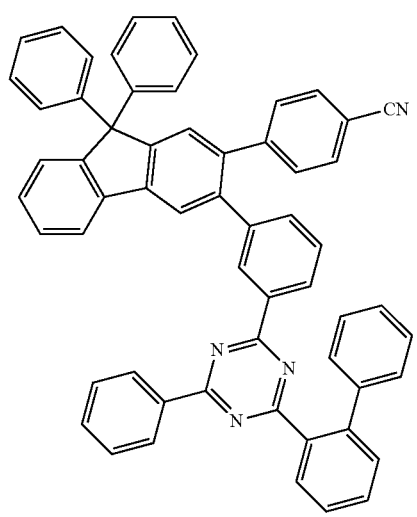
1-160
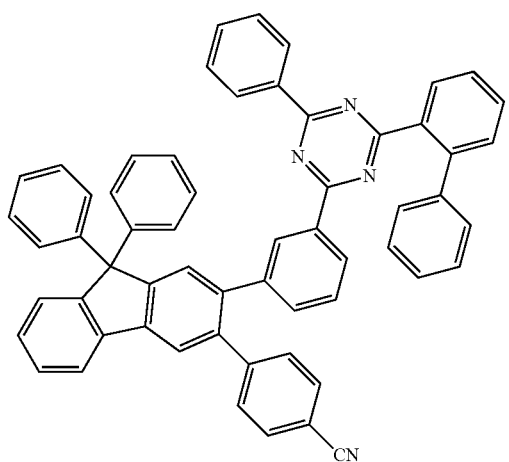
1-161
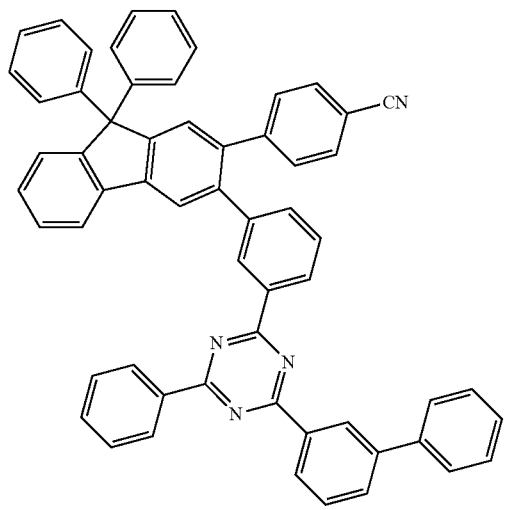
1-162
1-163
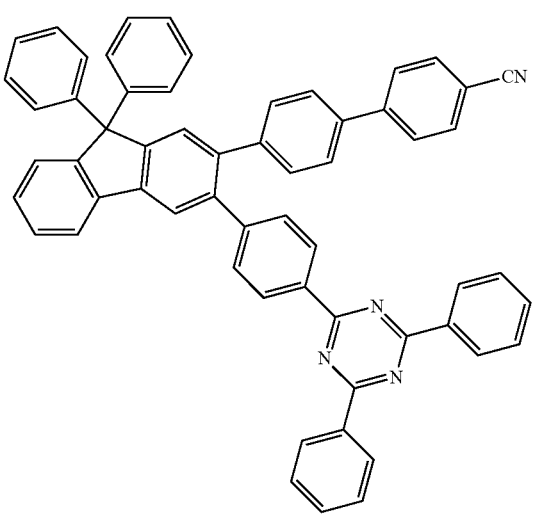

1-164
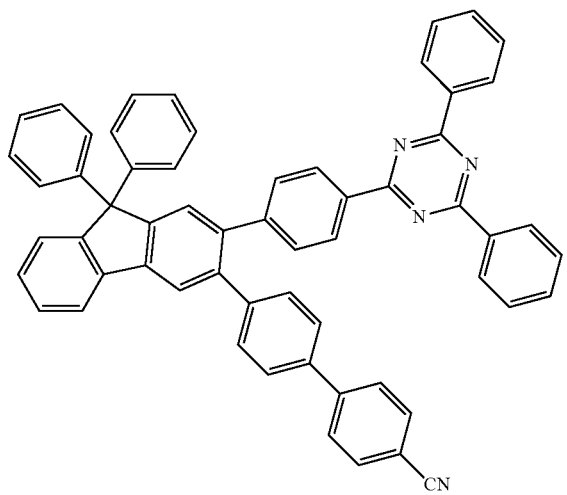
1-167
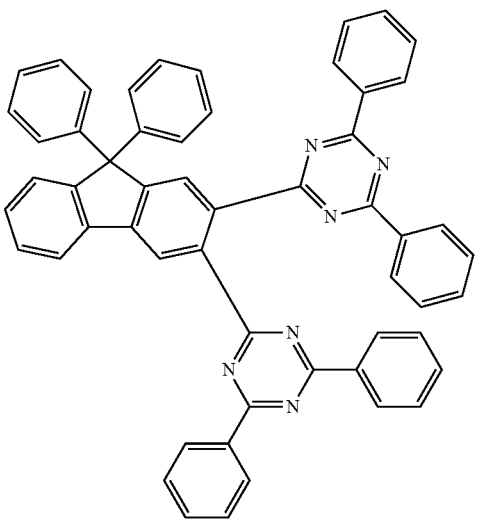
1-165
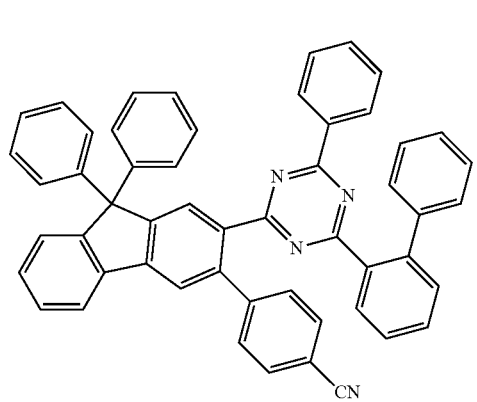
1-168
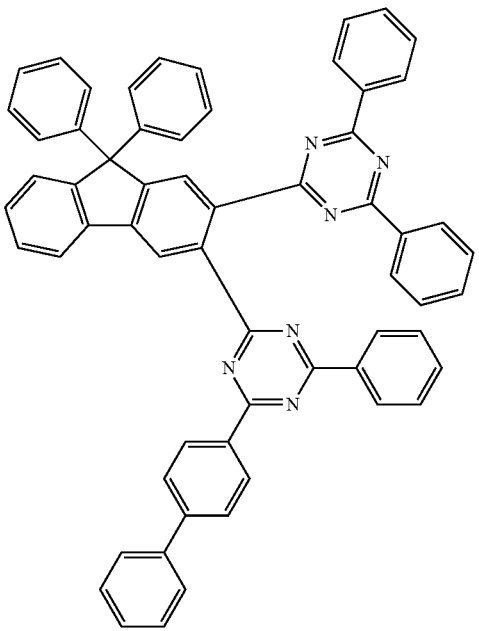
1-166
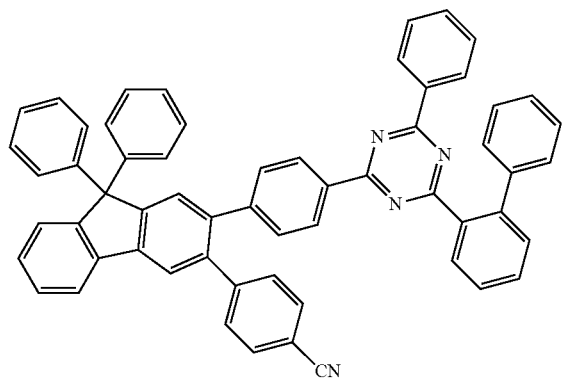

1-169
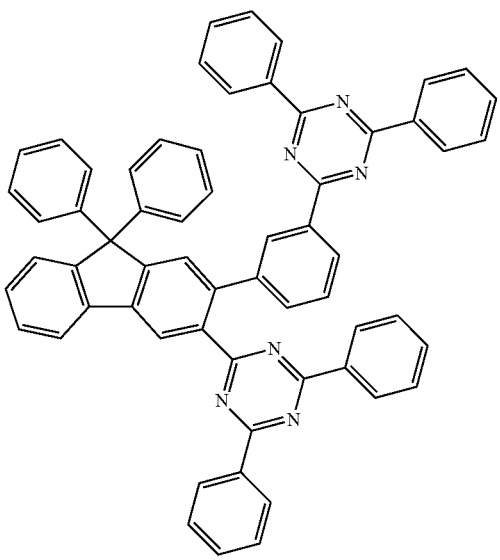
1-170
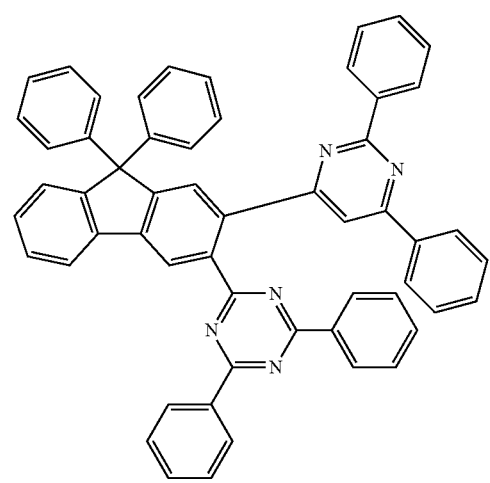
1-171
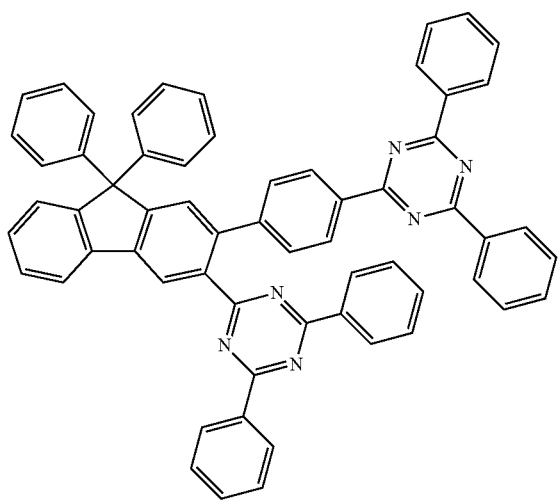
1-172
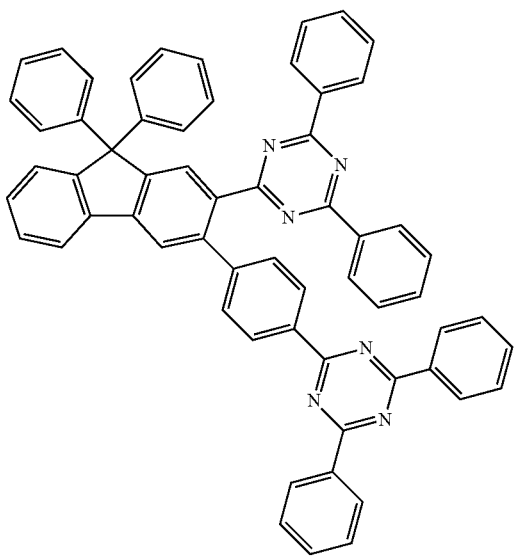
1-173
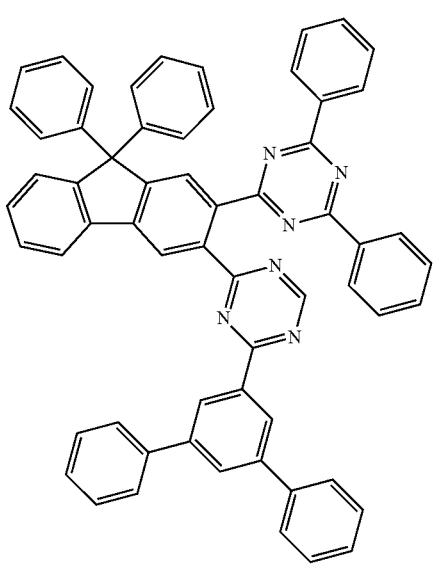
1-174
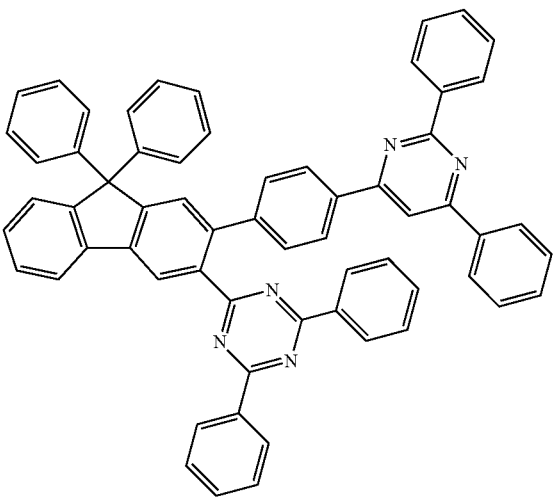

1-175
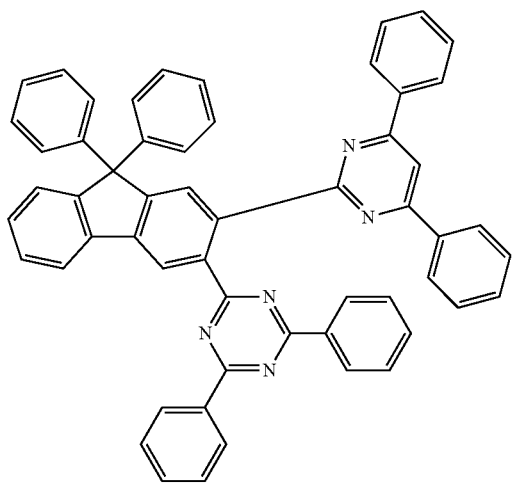
1-177
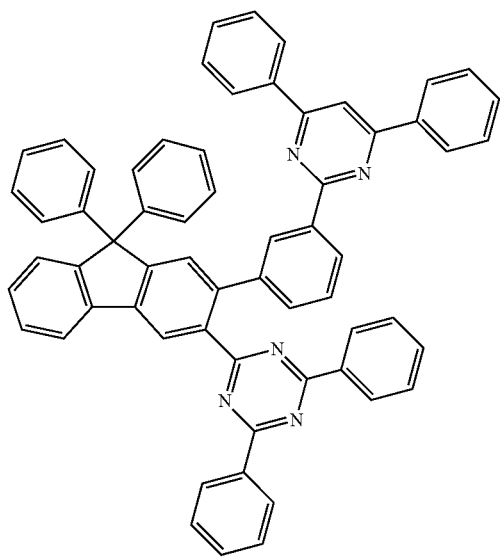
1-180
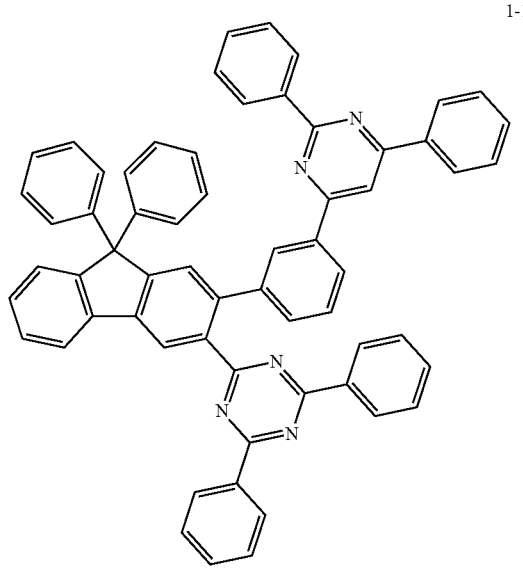
1-181
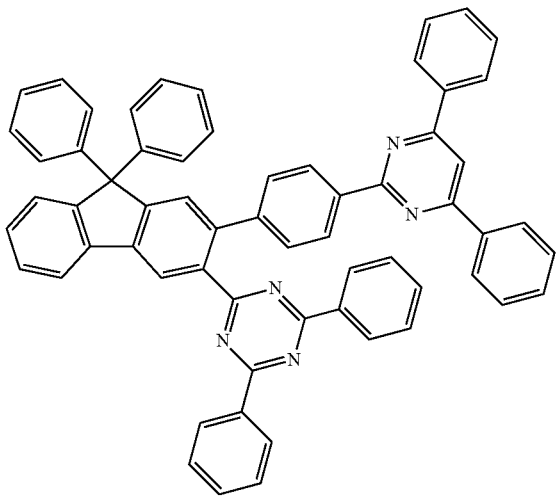
1-182
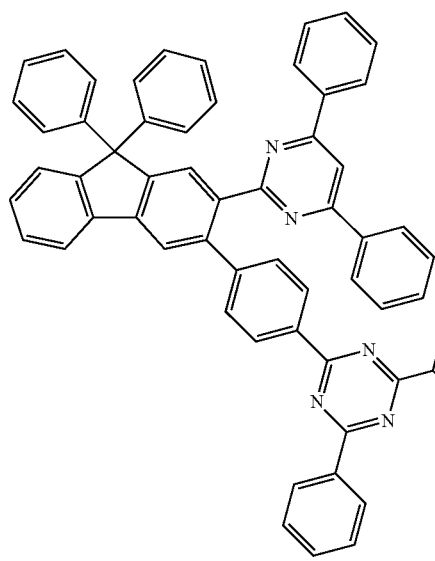
1-183
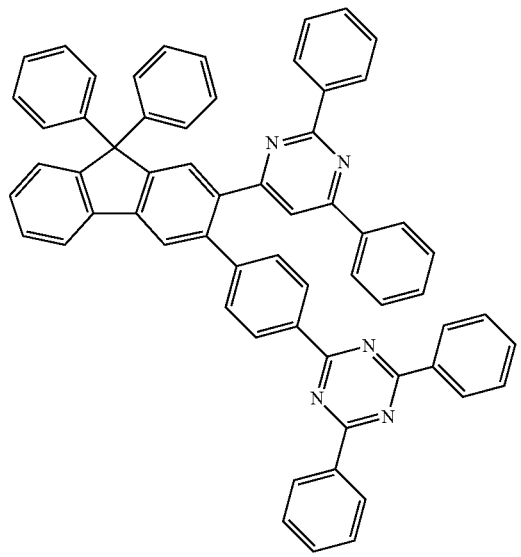

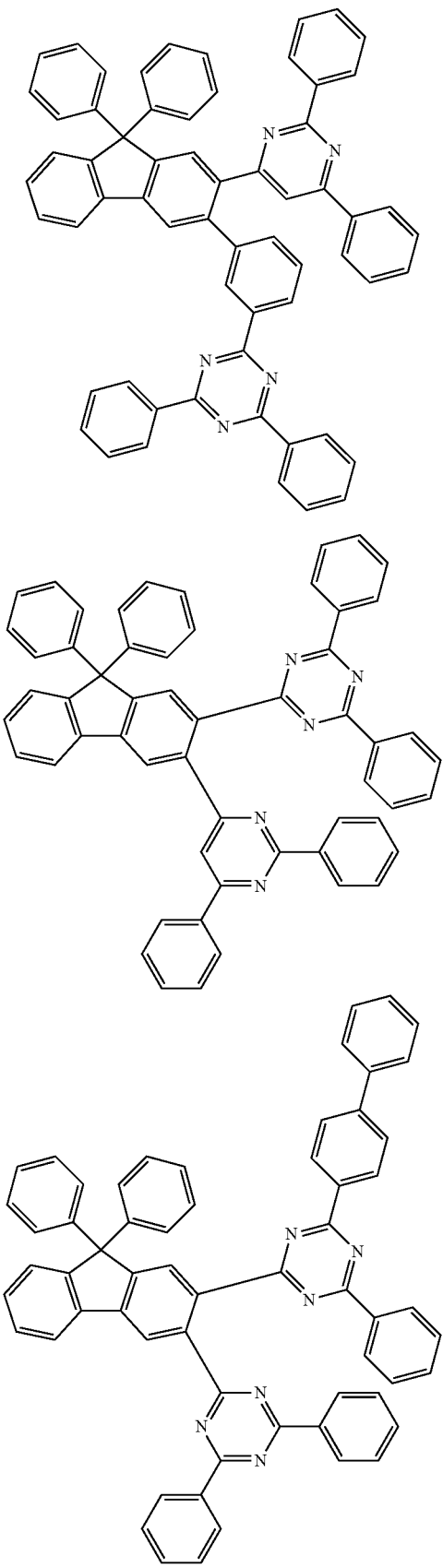
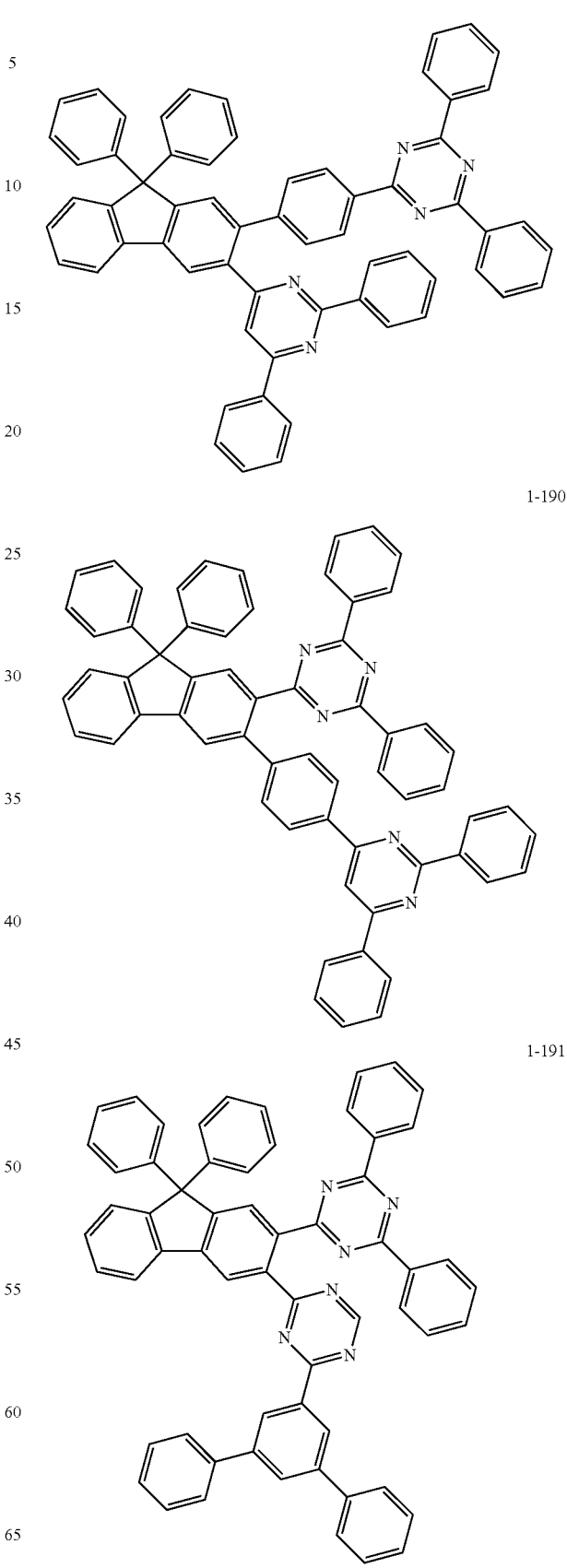

1-195
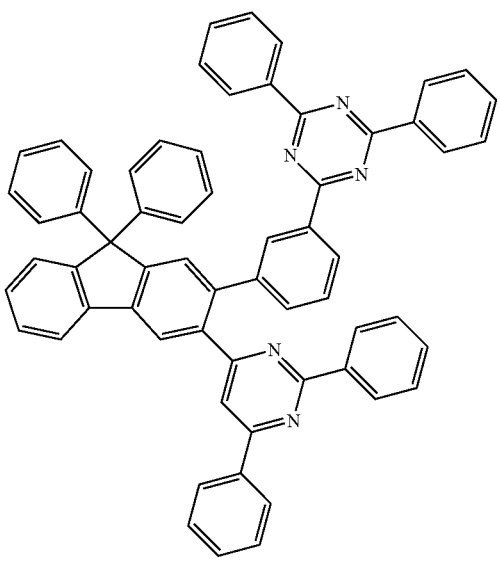
1-196
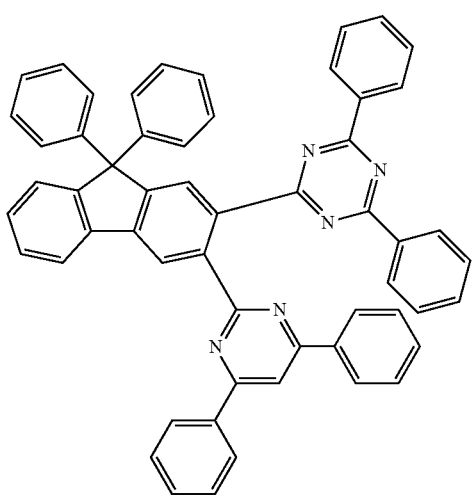
1-197
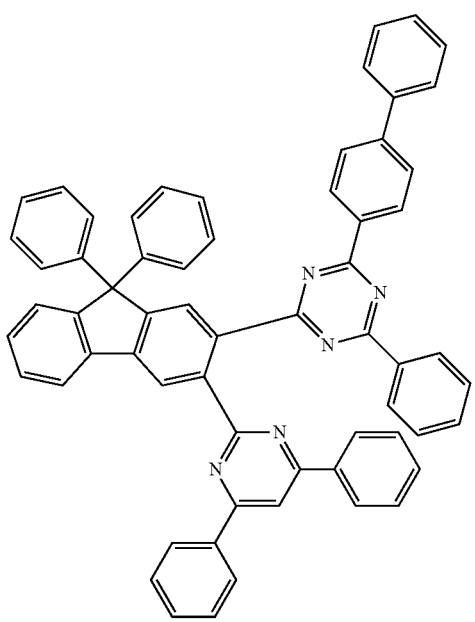
1-198
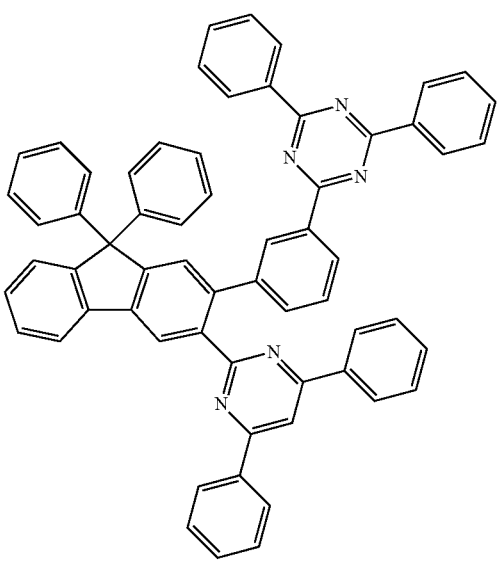
1-199
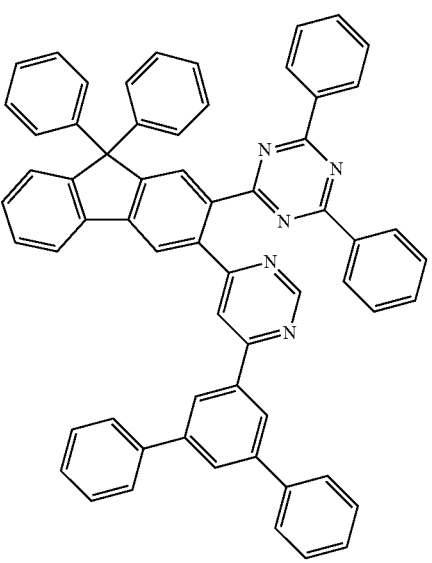
1-200
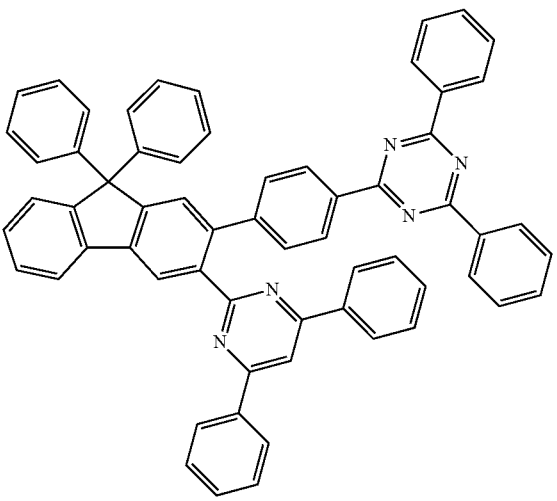

1-201
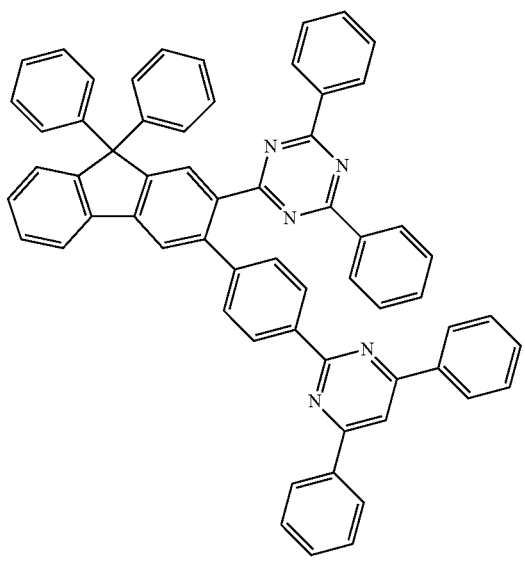
1-202
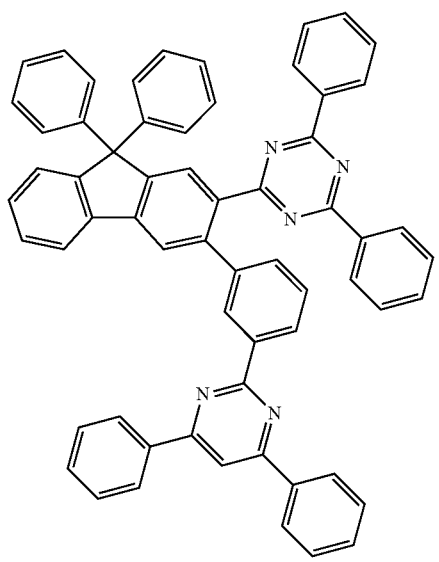
1-203
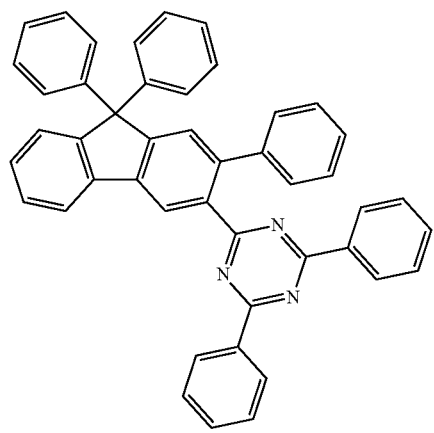
1-204
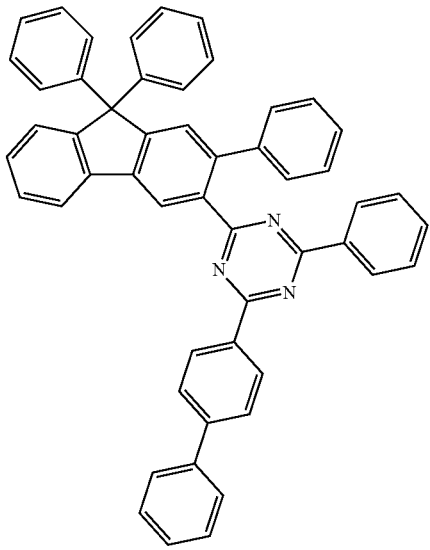
1-205
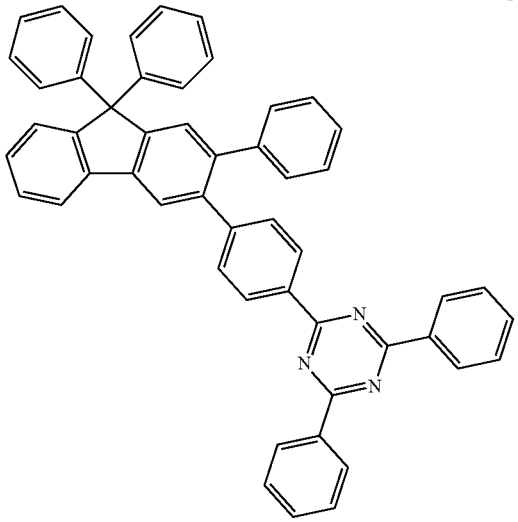
1-206
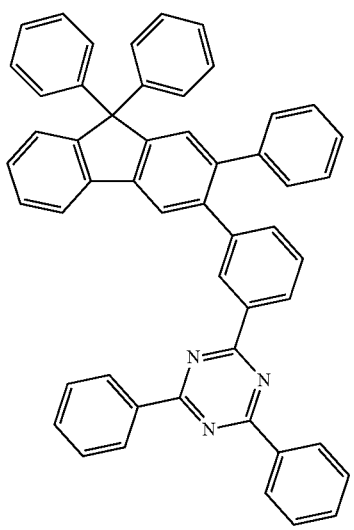

1-207
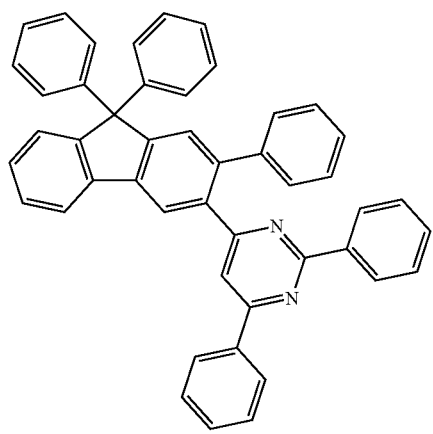
1-208
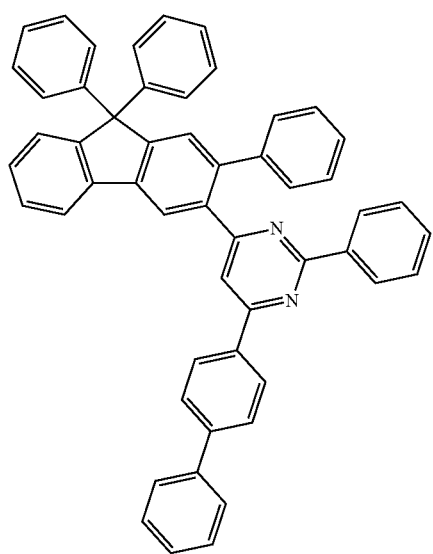
1-209
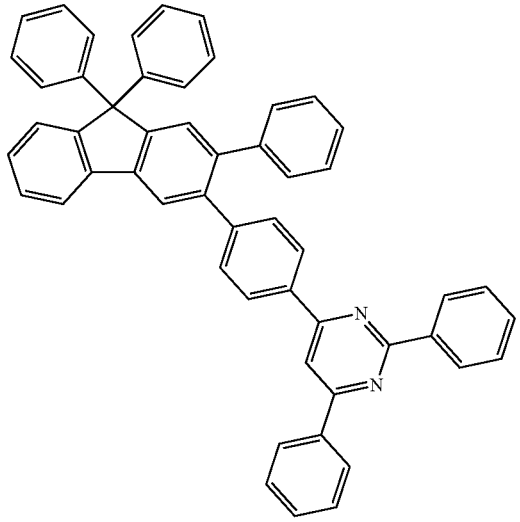
1-210
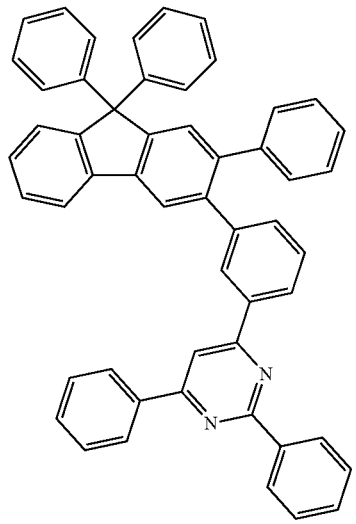
1-211
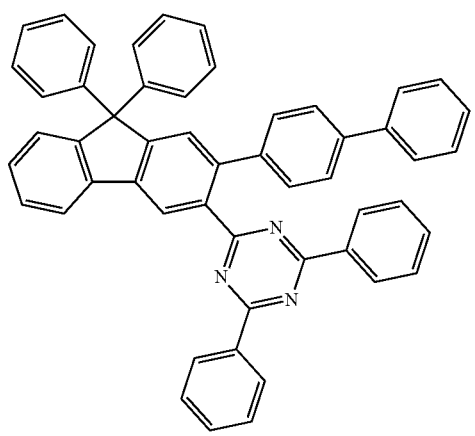
1-212
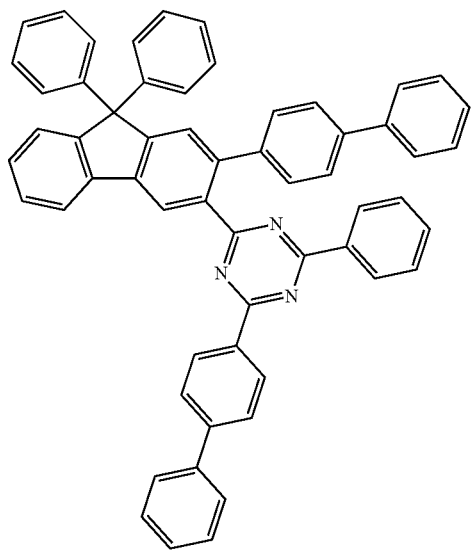

1-213
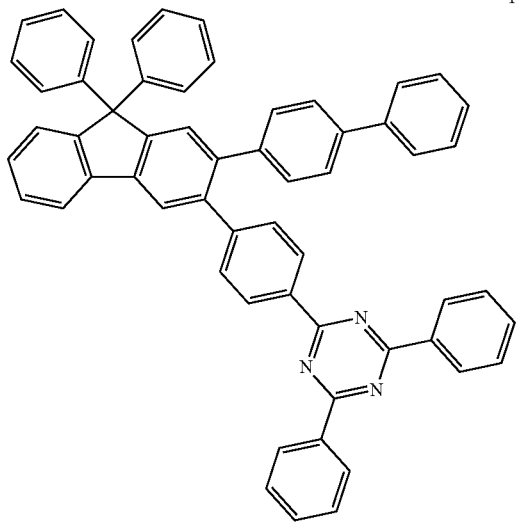
1-214
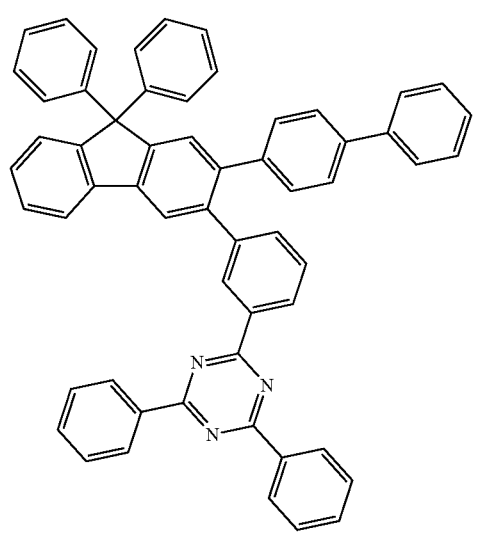
1-215
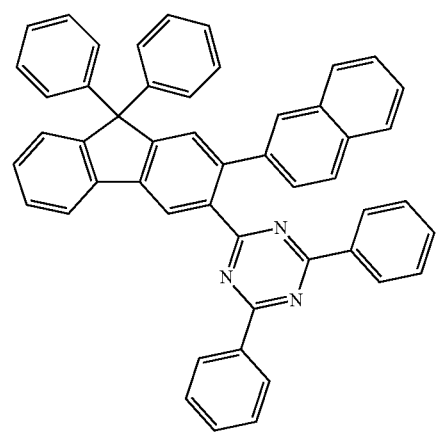
1-216
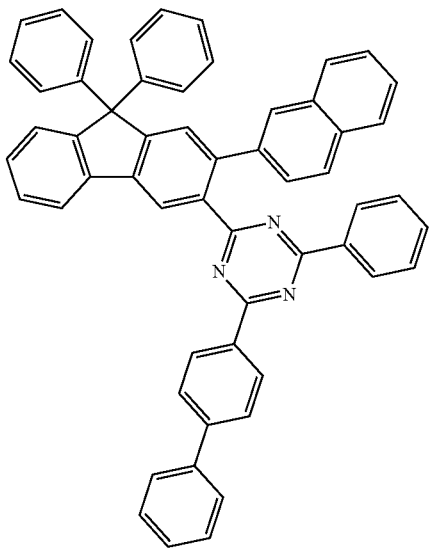
1-217
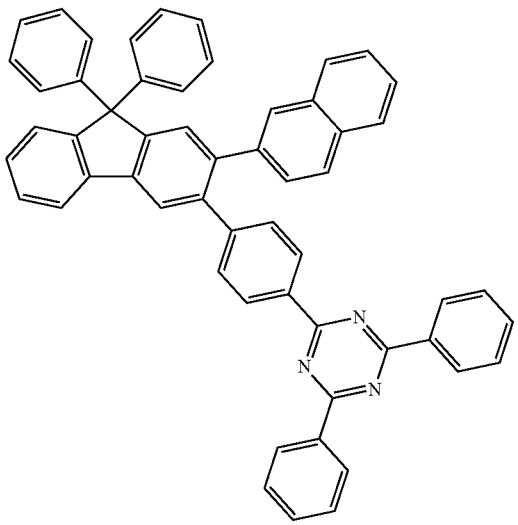
1-218
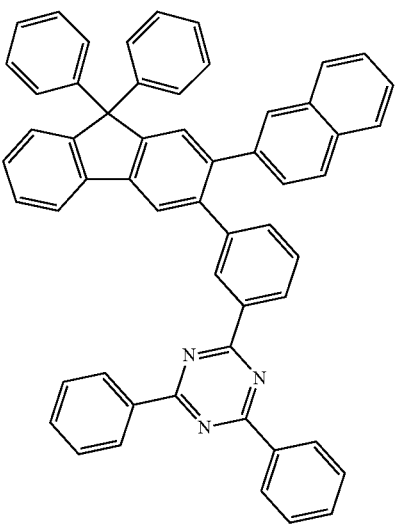

1-219
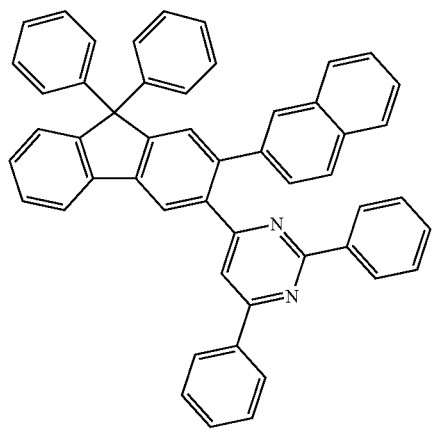
1-220
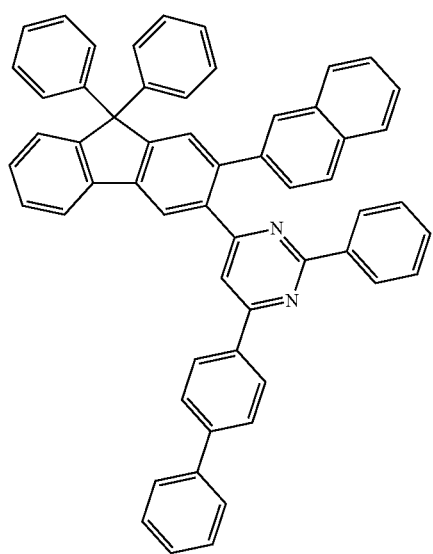
1-221
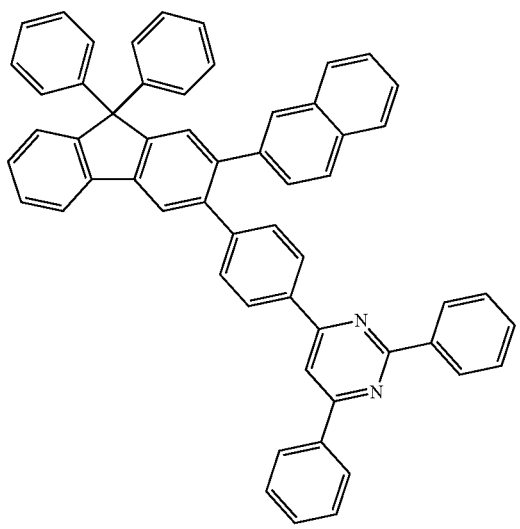
1-222
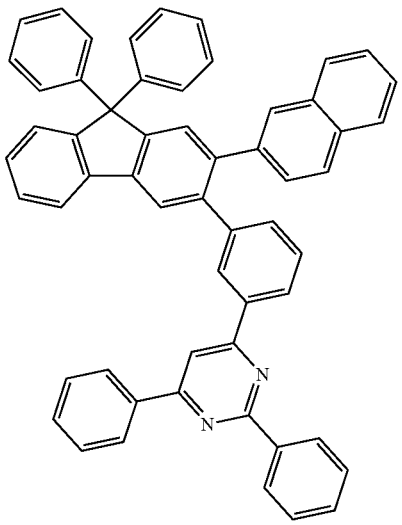
1-223
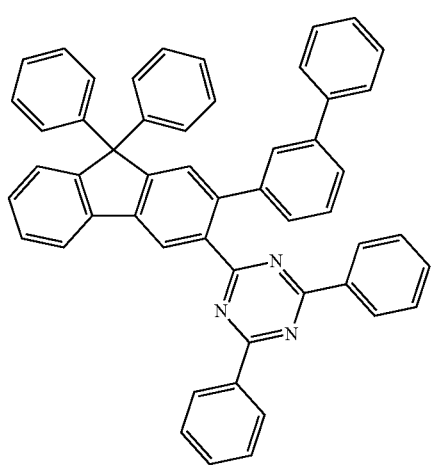
1-224
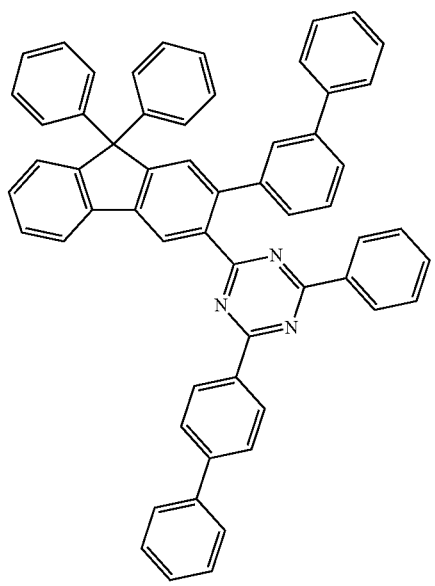

-continued
1-225
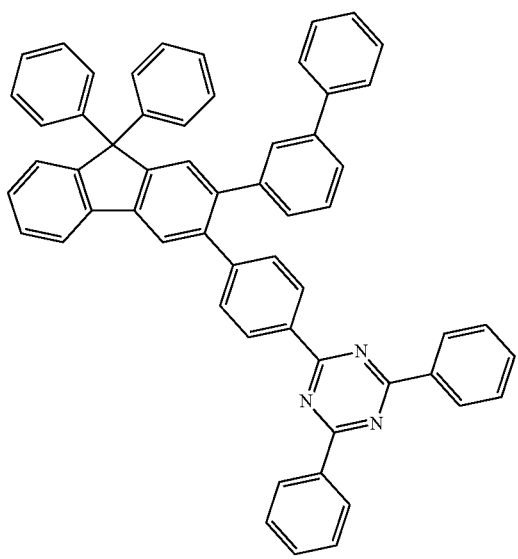
1-226
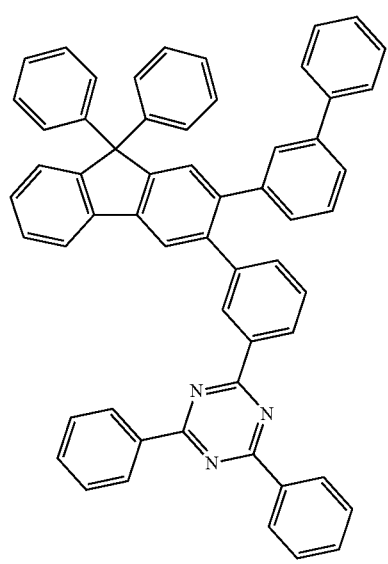
1-227
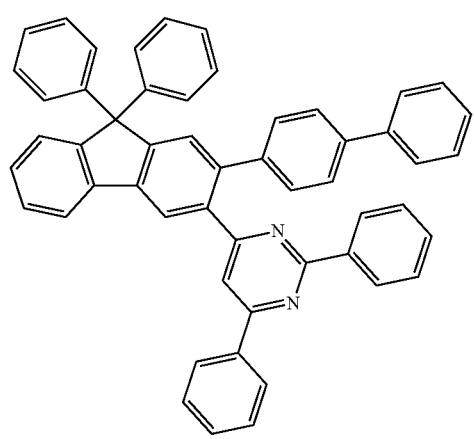
-continued
1-228
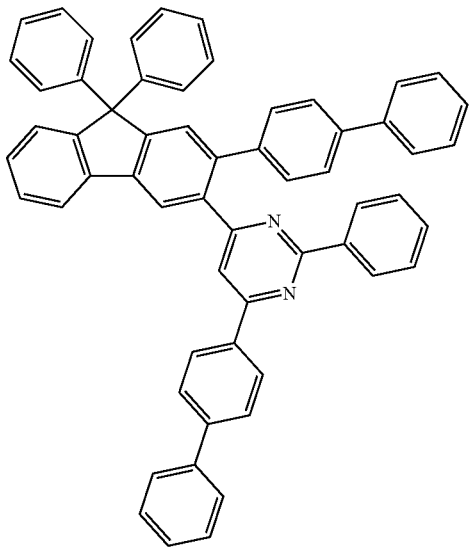
1-229
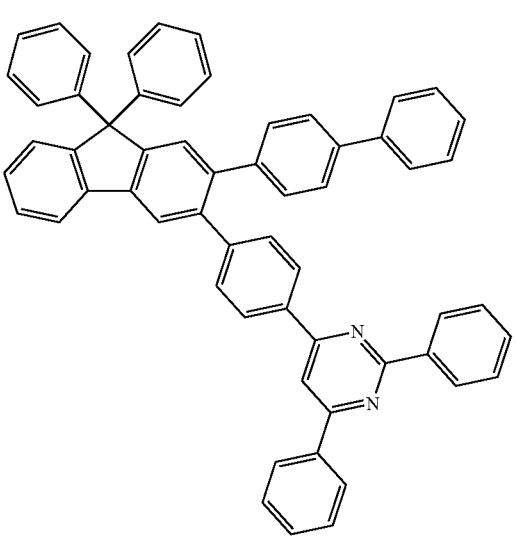
1-230
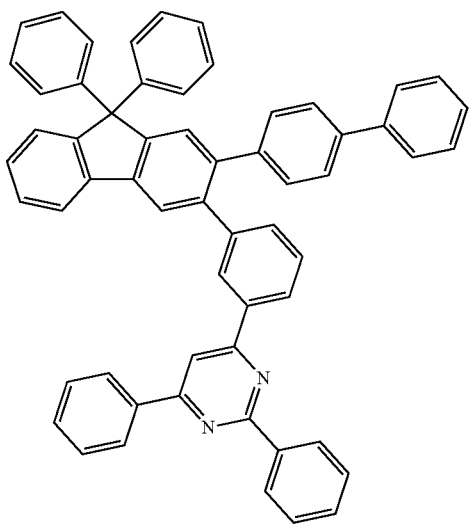

1-231
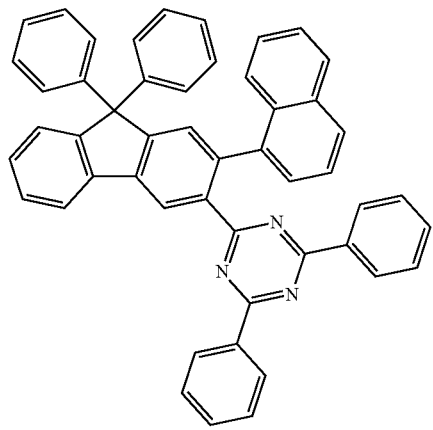
1-232
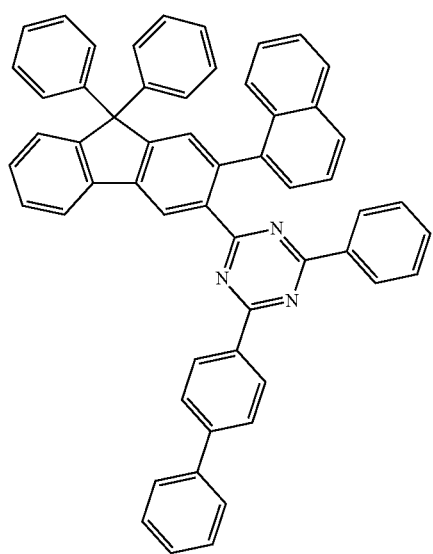
1-233
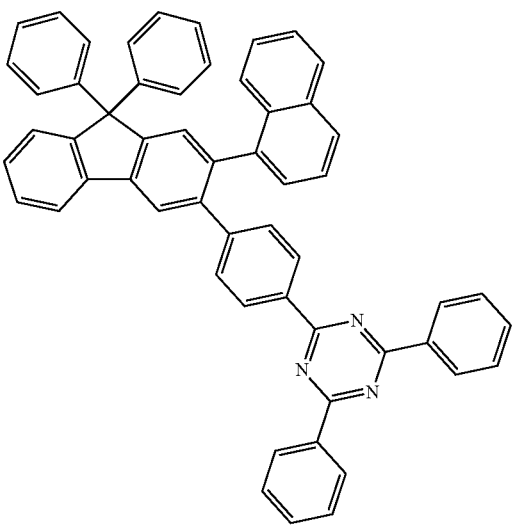
1-234
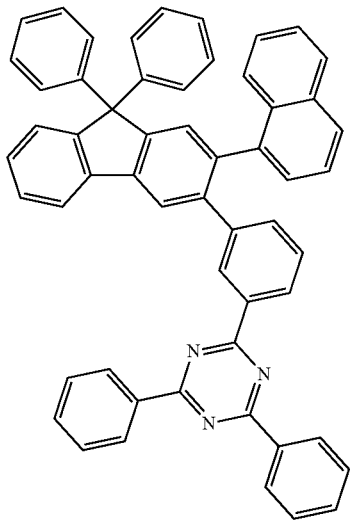
1-235
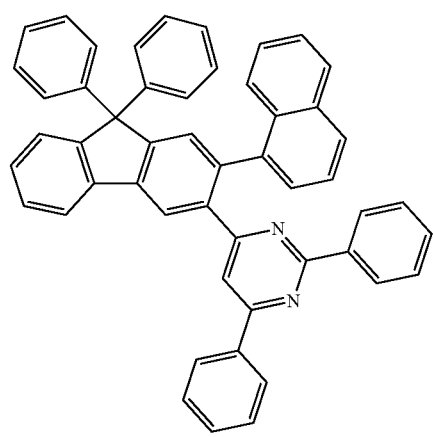
1-236
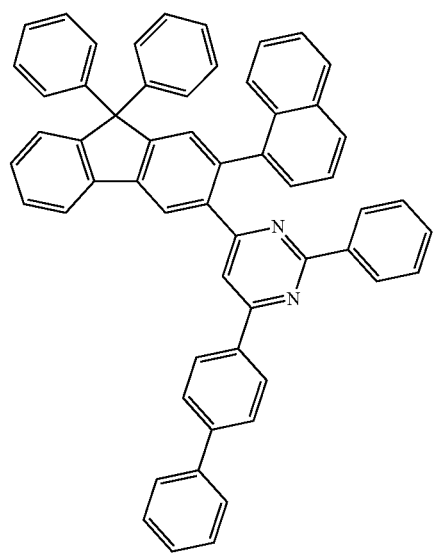

-continued
1-237
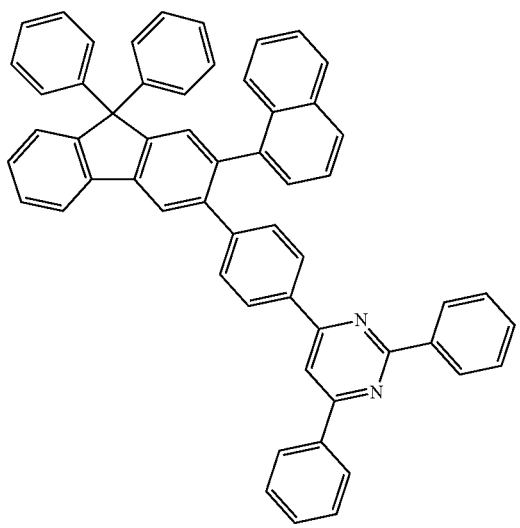
1-238
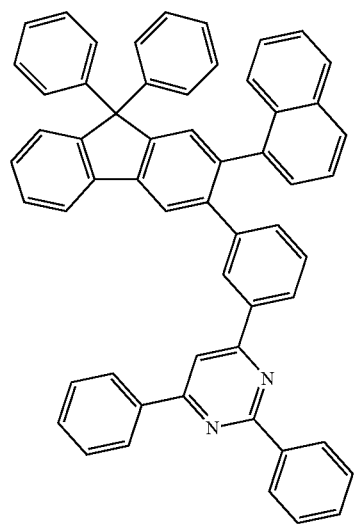
1-239
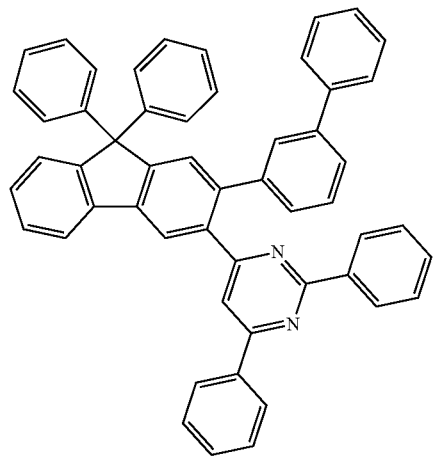
-continued
1-240
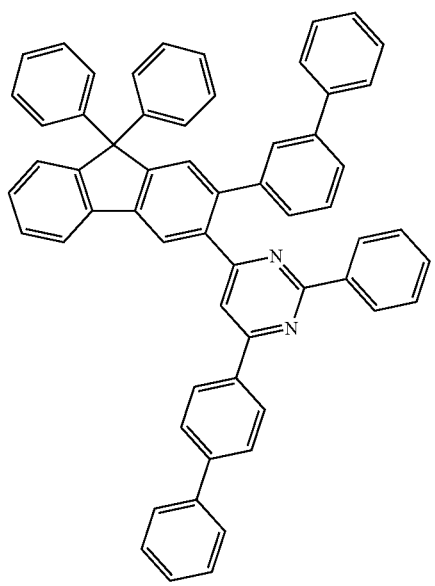
1-241
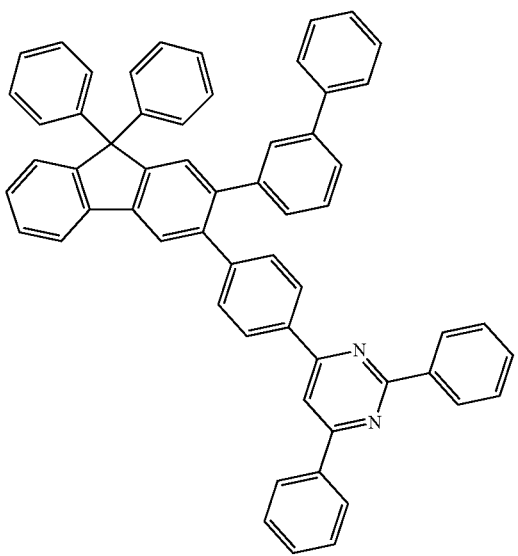

1-242
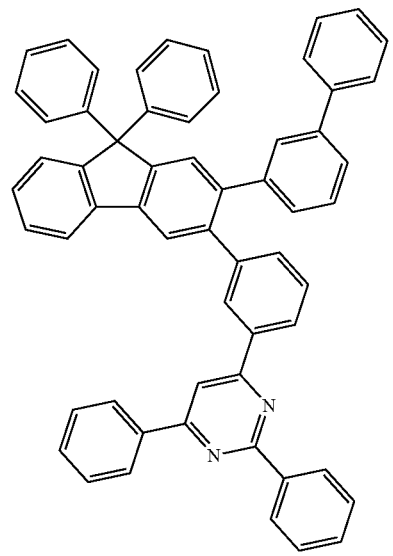
1-303
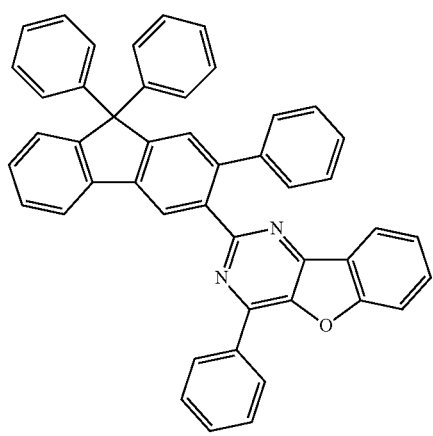
1-304
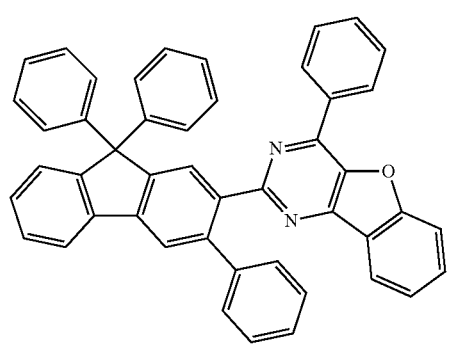
1-305
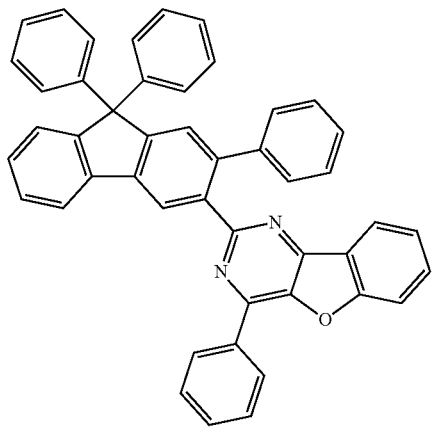
1-306
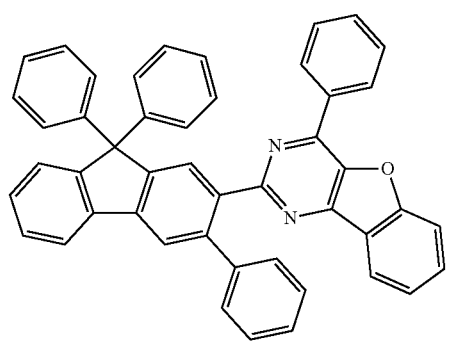
1-323
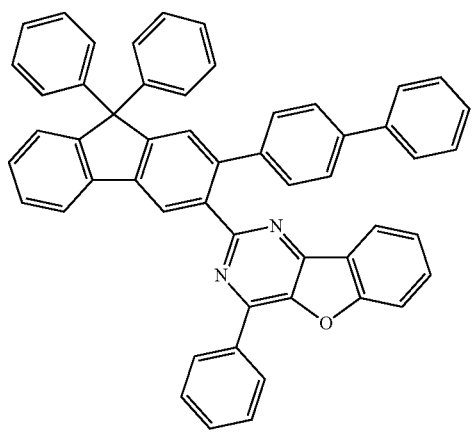
1-324
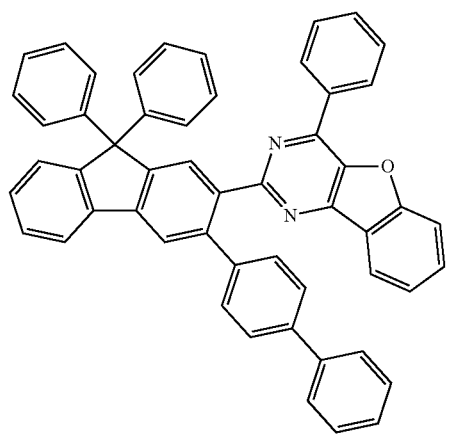

1-325
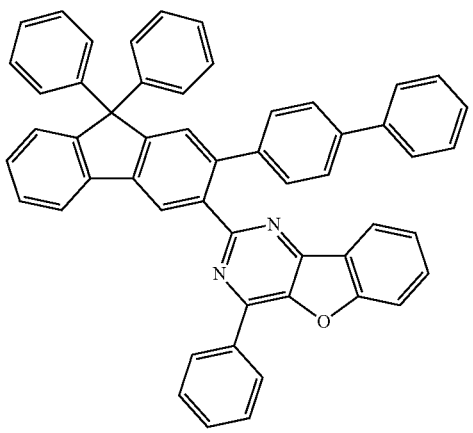
1-326
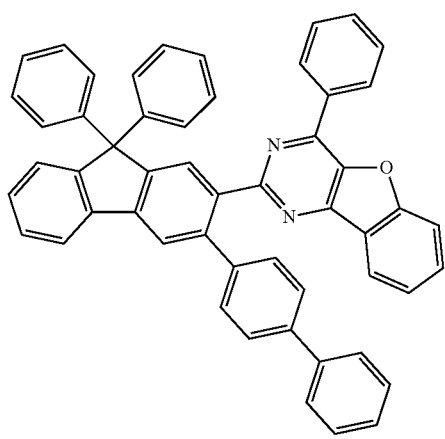
1-331
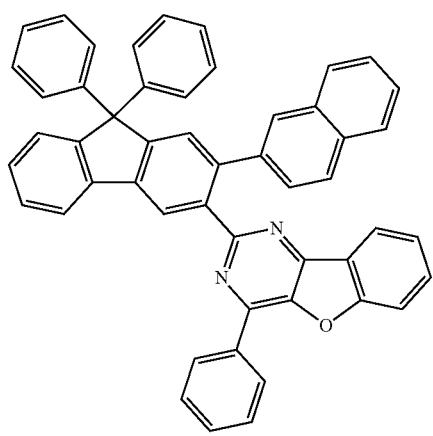
1-332
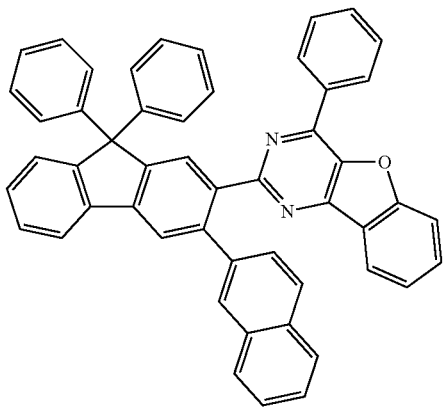
1-333
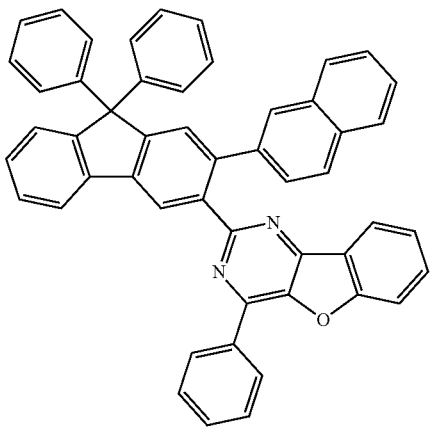
1-334
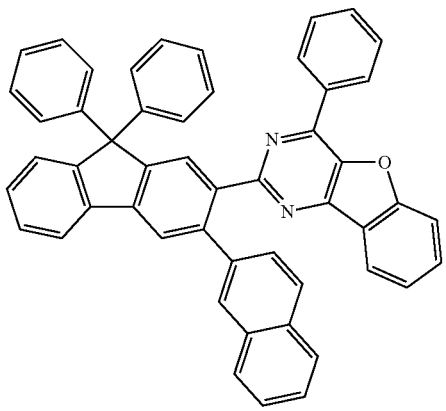

1-359
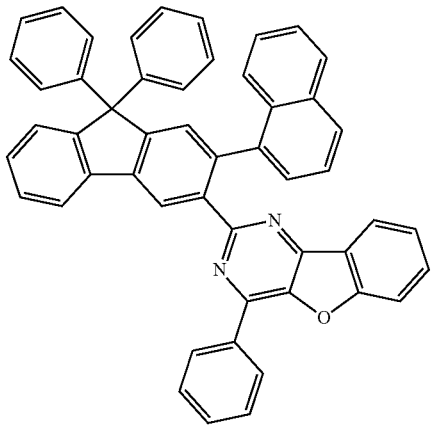
1-360
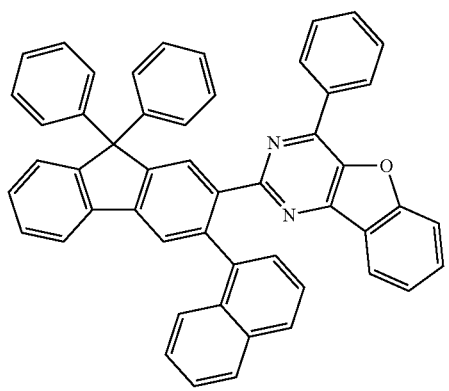
1-361
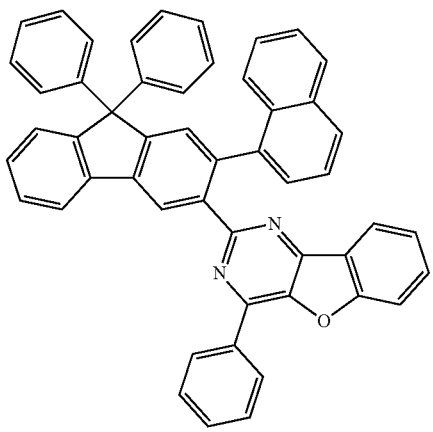
1-362
1-367
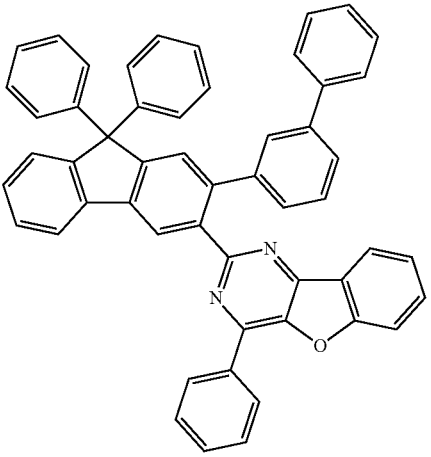
1-368
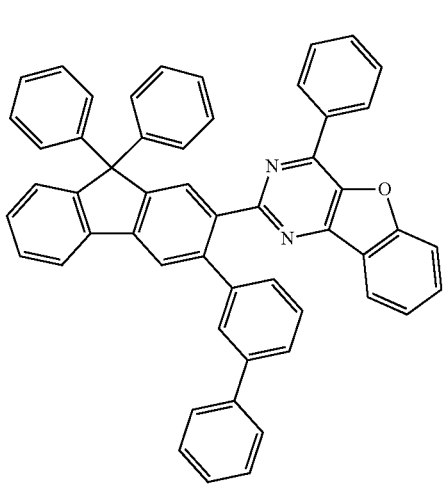
1-369
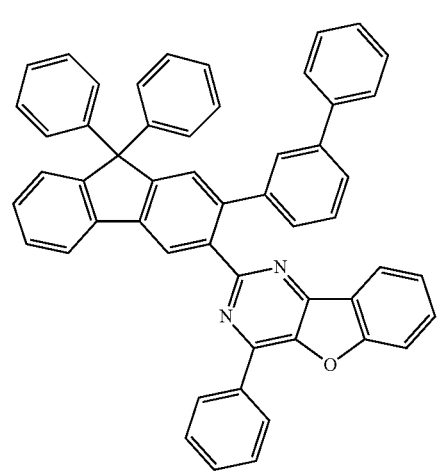

1-370
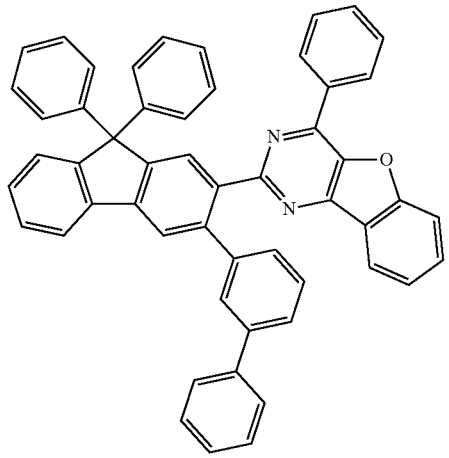
1-376
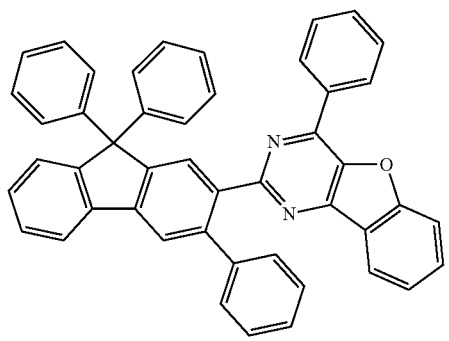
1-379
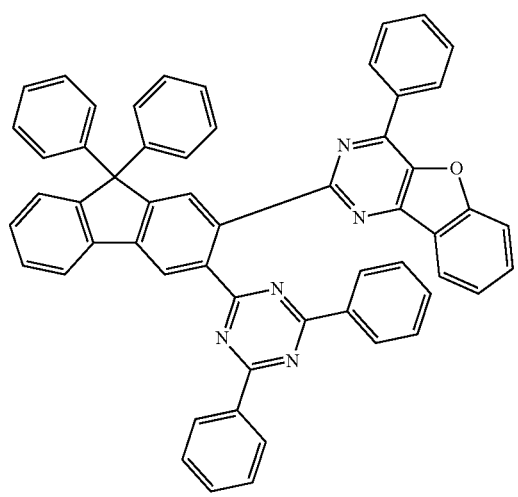
1-380
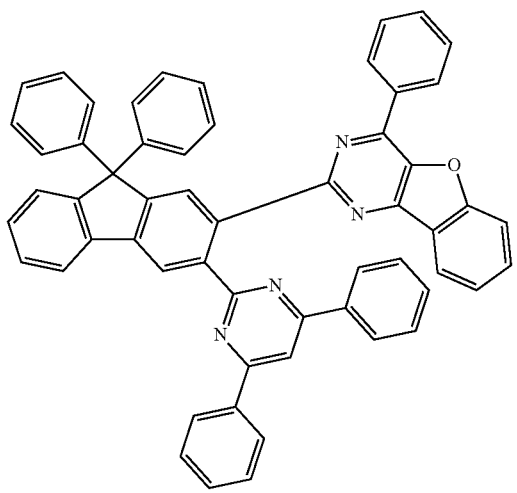
1-381
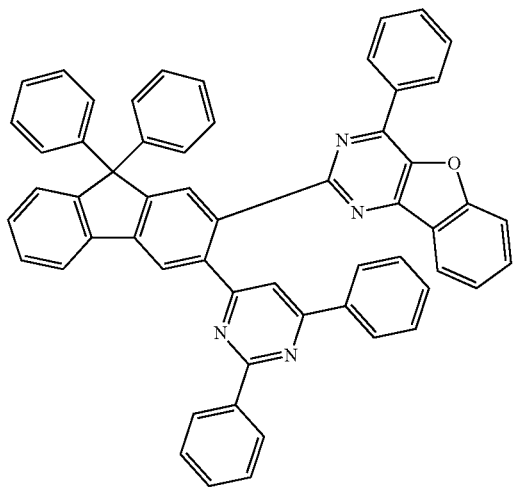
1-387
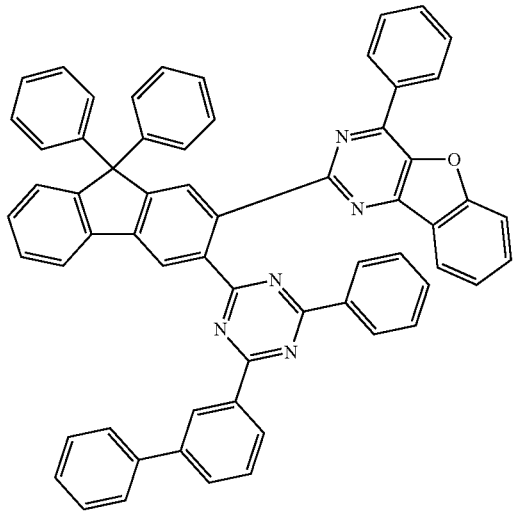

1-388
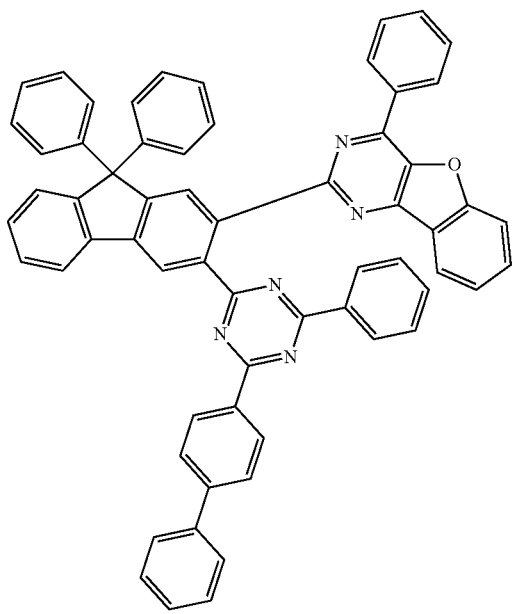
1-391
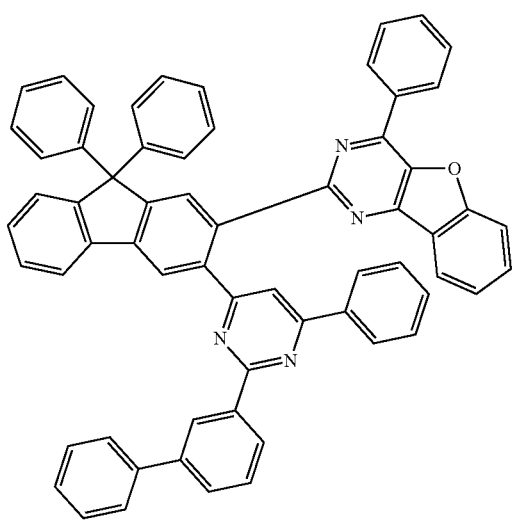
1-392
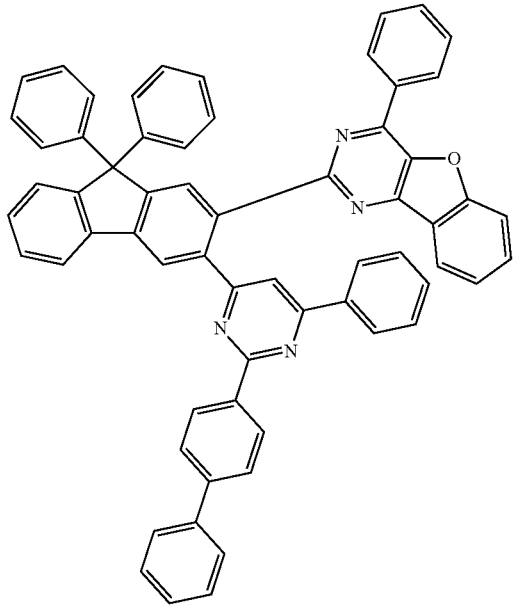
3. An organic light emitting device comprising:
a first electrode;
a second electrode disposed to face the first electrode; and
an organic material layer having one or two or more layers disposed between the first electrode and the second electrode, wherein one or more layers of the organic material layer comprise the compound of claim 1.

4. The organic light emitting device of claim 3, wherein the organic material layer comprises a light emitting layer, and the light emitting layer comprises the compound.

5. The organic light emitting device of claim 3, wherein the organic material layer comprises a hole injection layer, a hole transporting layer, or an electron blocking layer, and the hole injection layer, the hole transporting layer, or the electron blocking layer comprises the compound.

6. The organic light emitting device of claim 3, wherein the organic material layer comprises a hole blocking layer, an electron transporting layer, or an electron injection layer, and the hole blocking layer, the electron transporting layer, or the electron injection layer comprises the compound.

7. The organic light emitting device of claim 3, wherein the organic material layer comprises a light emitting layer, and the light emitting layer comprises a compound of the following Chemical Formula 2:

[Chemical Formula 2]

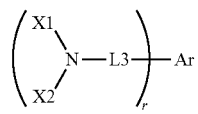

in Chemical Formula 2,

Ar is a benzofluorene skeleton, a fluoranthene skeleton, a pyrene skeleton, or a chrysene skeleton, L3 is a single bond, a $C_6$ to $C_{30}$ aryl group, or a $C_5$ to $C_{30}$ heterocyclic group, X1 and X2 are the same as or different from each other, and are each independently selected from the group consisting of a substituted or unsubstituted $C_6$ to $C_{30}$ aryl group, a substituted or unsubstituted $C_5$ to $C_{30}$ heterocyclic group, a substituted or unsubstituted $C_1$ to $C_{30}$ alkyl group, and a substituted or unsubstituted $C_7$ to $C_{30}$ arylalkyl group, and X1 and X2 are optionally bonded to each other to form a saturated or unsaturated ring, r is an integer of 1 or more, and when r is 2 or more, X1s are the same as or different from each other, and X2s are the same as or different from each other.

8. The organic light emitting device of claim 7, wherein Ar is a pyrene skeleton, L3 is a single bond, and X1 and X2 are the same as or different from each other, and are each independently an aryl group which is unsubstituted or substituted with an alkyl group; or a $C_5$ to $C_{30}$ heterocyclic group, and r is 2.

9. The organic light emitting device of claim 3, wherein the organic material layer comprises a light emitting layer, and the light emitting layer comprises a compound represented by the following Chemical Formula 3:

[Chemical Formula 3]

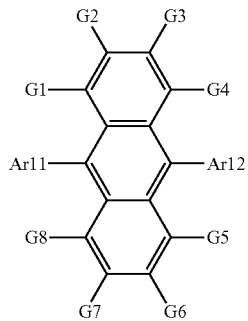

in Chemical Formula 3,

Ar11 and Ar12 are the same as or different from each other, and are each independently a substituted or unsubstituted monocyclic aryl group; or a substituted or unsubstituted polycyclic aryl group, and G1 to G8 are the same as or different from each other, and are each independently hydrogen; a substituted or unsubstituted monocyclic aryl group; or a substituted or unsubstituted polycyclic aryl group.

10. The organic light emitting device of claim 9, wherein Ar11 is a 1-naphthyl group, Ar12 is a 2-naphthyl group, and G1 to G8 are hydrogen.

11. The organic light emitting device of claim 7, wherein the light emitting layer comprises a compound represented by the following Chemical Formula 3:

[Chemical Formula 3]

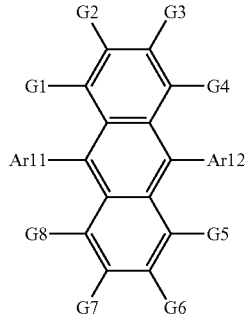

in Chemical Formula 3,

Ar11 and Ar12 are the same as or different from each other, and are each independently a substituted or unsubstituted monocyclic aryl group; or a substituted or unsubstituted polycyclic aryl group, and G1 to G8 are the same as or different from each other, and are each independently hydrogen; a substituted or unsubstituted monocyclic aryl group; or a substituted or unsubstituted polycyclic aryl group.

* * * * *